US012698320B2

(12) United States Patent
Lepak et al.

(10) Patent No.: US 12,698,320 B2
(45) Date of Patent: Aug. 4, 2026

(54) HEMOGLOBIN-BASED OXYGEN CARRIER COMPOSITIONS

(71) Applicant: 20BLOC, INC., Thousand Oaks, CA (US)

(72) Inventors: Alex Lepak, Thousand Oaks, CA (US); David Rozzell, Thousand Oaks, CA (US); Sky Ferrara, Thousand Oaks, CA (US); Kai Lu, Thousand Oaks, CA (US); Martin Michael Dcona, Thousand Oaks, CA (US); Nitin Pawar, Thousand Oaks, CA (US); Erik Goebel, Oakdale, MN (US)

(73) Assignee: 20BLOC, INC., Thousand Oaks, CA (US)

( * ) Notice: Subject to any disclaimer, the term of this patent is extended or adjusted under 35 U.S.C. 154(b) by 0 days.

(21) Appl. No.: 19/209,549

(22) Filed: May 15, 2025

(65) Prior Publication Data

US 2025/0353897 A1 Nov. 20, 2025

Related U.S. Application Data

(60) Provisional application No. 63/647,813, filed on May 15, 2024.

(51) Int. Cl.
*C07K 14/805* (2006.01)
*C07K 1/107* (2006.01)

(52) U.S. Cl.
CPC .......... *C07K 14/805* (2013.01); *C07K 1/1077* (2013.01)

(58) Field of Classification Search
CPC ............................ C07K 14/805; C07K 1/1077
See application file for complete search history.

(56) References Cited

U.S. PATENT DOCUMENTS

| | | |
|---|---|---|
| 5,399,671 A | 3/1995 | Kluger et al. |
| 9,351,980 B2 | 5/2016 | Perry et al. |
| 2004/0116293 A1 | 6/2004 | Silverman et al. |
| 2013/0035317 A1 | 2/2013 | Perry et al. |
| 2020/0016242 A1 | 1/2020 | Kluger et al. |
| 2025/0243148 A1 | 7/2025 | Lepak |

FOREIGN PATENT DOCUMENTS

| | | |
|---|---|---|
| CA | 2309236 A1 | 11/2001 |

OTHER PUBLICATIONS

Carey, Organic Chemistry, 2nd edition, McGraw-Hill Book Company, 1992, 6 pages.

Delaney et al., "Alternative Diaspirins for Modification of Hemoglobin and Sickle Hemoglobin" Archives of Biochemistry and Biophysics, Feb. 1, 1984, vol. 228, No. 2, pp. 627-638.

International Search Report and Written Opinion for PCT Application No. PCT/US2025/012981 mailed May 20, 2025, 11 pages.

Invitation to Pay Additional fees for International Application No. PCT/US2025/012981, mailed Mar. 19, 2025, 2 pages.

Kluger et al., "Trimesoyltris(3,5-dibromosalicylate): Specificity of Reactions of a Trifunctional Acylating Agent with Hemoglobin" J. Am. Chem. Soc., 1992, 114, pp. 9275-9279.

Lima M.C.P., et al., "Stroma-Free Hemoglobin from Bovine Blood" Artificial Cells, Blood Substitutes, and Biotechnology, 2007, vol. 35, pp. 431-447.

Neises et al., "Simple Method for the Esterification of Carboxylic Acids" Angew. Chem. Int. Ed, Jul. 1978, vol. 17, Issue 7, pp. 522-524.

Walder et al., "Diaspirins That Cross-Link Beta Chains of Hemoglobin: Bis(3,5- dibromosalicyl) Succinate and Bis(3,5-dibromosalicyl) Fumarate" Biochemistry, Oct. 2, 1979, vol. 18, No. 20, 6 pages.

Wood et al. Structural Specificities in Acylation of Hemoglobin and Sickle Hemoglobin by Diaspirins. Journal of Biological Chemistry , vol. 256, No. 13, 7046-7052. (Year: 1981).

Yu Z, et al., "Structural Characterization of Human Hemoglobin Crosslinked by Bis(3,5-dibromosalicyl) Fumarate Using Mass Spectrometric Techniques" Protein Science, Dec. 6, 1997(12), pp. 2568-2577.

Zaugg et al., "Modification of Hemoglobin with Analogs of Aspirin" The Journal of Biological Chemistry, 1980, vol. 255, No. 7, pp. 2816-2821.

PCT Application No. PCT/US2025/029570, International Search Report and Written Opinion mailed Aug. 19, 2025, Applicant 20BLOC, Inc.; 13 pages.

PCT Application No. PCT/US2025/029570, Invitation to Pay Additional fees mailed Jun. 24, 2025, Applicant 20BLOC, Inc.; 3 pages.

Singh, S "Strain-promoted azide-alkyne cycloaddition for protein-protein coupling in the formation of a bis-hemoglobin as a copper-free oxygen carrier", Organic & Biomolecular Chemistry, Sep. 27, 2016, vol. 14; [Retrieved from the Internet on Jun. 16, 2025 at URL: https://pubs.rsc.org/en/content/articlehtml/2016/ob/c6ob01817c], pp. 10011-10017.

(Continued)

*Primary Examiner* — Sikarl A Witherspoon
(74) *Attorney, Agent, or Firm* — COOLEY LLP

(57) ABSTRACT

Provided herein are modified hemoglobin (Hb) comprising at least two subunits of a Hb intramolecularly crosslinked with a compound of formula (I), (I)

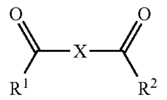

or salt, stereoisomer, or deuterated form thereof, wherein X, $R^1$, and $R^2$ are defined herein. The modified Hb can further comprise residues functionalized with reactive groups. Also provided herein are multimerized hemoglobin (Hb) compositions comprising a reaction product of: the modified Hb comprising a residue functionalized with one or more first reactive groups for click reaction and a reactant molecule comprising second reactive groups complementary to the first reactive group for the click reaction.

28 Claims, 18 Drawing Sheets

Specification includes a Sequence Listing.

(56) References Cited

OTHER PUBLICATIONS

Singh, S "Subunit-directed click coupling via doubly cross-linked hemoglobin efficiently produces readily purified functional bis-tetrameric oxygen carriers", Org Biomol Chem., Sep. 14, 2015, vol. 13; [Retrieved from Internet on Jun. 19, 2025 at URL: https://pubs.rsc.org/en/content/articlehtml/2015/ob/c5ob01755f], pp. 11118-11128.

Step 1 Acylation: HPLC comparison with bHb

Conjugation rate with bHb using1.05 equivalent NHSE-PEG4_N3 in MOPS PH 7.0, 4C, 18h

| Area | α | α-N3 1 | α-N3 2 | α-N3 3 | α-N3 4 | α-N3 5 | α-N3 6 | α-N3 7 | Total α-N3 | Total α + α-N3 |
|---|---|---|---|---|---|---|---|---|---|---|
| Peaks | 2.2188 | 0 | 0.1777 | 0.0466 | 0.0716 | 0.0415 | 0 | 0 | 0.3374 | 2.5562 |
| % α-modification | | | | | | | | | 13.19928018 | |

| Area | β | β-N3 1 | β-N3 2 | β-N3 3 | β-N3 4 | β-N3 5 | β-N3 6 | β-N3 7 | Total β-N3 | Total β + β-N3 |
|---|---|---|---|---|---|---|---|---|---|---|
| Peaks | 2.8357 | 0.123 | 0.2363 | 0.2547 | 0.0479 | 0.0415 | 0.064 | 0.0504 | 0.8178 | 3.6535 |
| % β-modification | | | | | | | | | 22.38401533 | |
| | | | | | | | | Total | 35.58329551 | |
| | | | | | | | | % attachements | 71.16659102 | |

✓ Results: Step 1: Showed 71% linker attachment per tetramer

1 – DBSF-bHb + 0.5 eq. 1,4-PBG at pH 6.5 150mM MOPS
2 – DBSF-bHb + 0.5 eq. 1,4-PBG at pH 7.3 150mM MOPS
3 – DBSF-bHb + 0.5 eq. 1,4-PBG at pH 7.6 150mM MOPS
4 – DBSF-bHb + 0.5 eq. 1,4-PBG at pH 8.2 150mM NaPO4

SEQUENCE LISTING

```
Sequence total quantity: 2
SEQ ID NO: 1            moltype = AA  length = 141
FEATURE                 Location/Qualifiers
source                  1..141
                        mol_type = protein
                        organism = Bos taurus
SEQUENCE: 1
VLSAADKGNV KAAWGKVGGH AAEYGAEALE RMFLSFPTTK TYFPHFDLSH GSAQVKGHGA  60
KVAAALTKAV EHLDDLPGAL SELSDLHAHK LRVDPVNFKL LSHSLLVTLA SHLPSDFTPA  120
VHASLDKFLA NVSTVLTSKY R                                            141

SEQ ID NO: 2            moltype = AA  length = 145
FEATURE                 Location/Qualifiers
source                  1..145
                        mol_type = protein
                        organism = Bos taurus
SEQUENCE: 2
MLTAEEKAAV TAFWGKVKVD EVGGEALGRL LVVYPWTQRF FESFGDLSTA DAVMNNPKVK  60
AHGKKVLDSF SNGMKHLDDL KGTFAALSEL HCDKLHVDPE NFKLLGNVLV VVLARNFGKE  120
FTPVLQADFQ KVVAGVANAL AHRYH                                        145
```

HEMOGLOBIN-BASED OXYGEN CARRIER COMPOSITIONS

CROSS-REFERENCE TO RELATED APPLICATIONS

This application claims priority to U.S. Provisional Patent Application No. 63/647,813, filed on May 15, 2024, the content of which is hereby incorporated by reference in its entirety for all purposes.

REFERENCE TO AN ELECTRONIC SEQUENCE LISTING

The contents of the electronic sequence listing (20BL_002_01US_SeqList_ST26.xml; Size: 3,047 bytes; and Date of Creation: May 14, 2025) are herein incorporated by reference in its entirety.

BACKGROUND

Efforts to develop safe blood substitutes have been ongoing for almost four decades. Although encouraging prototype products have been created, including several that entered clinical trials, none have achieved FDA approval due to various toxicity and efficacy issues. Despite the lack of success to date, there continues to be an unmet need for a blood substitute that (1) performs similarly to red blood cells in delivering oxygen to tissues without accompanying toxicity, (2) can be universally applied without a requirement for blood-type matching, (3) displays a prolonged shelf-life at room temperature, and (4) is available at a reasonable cost. Such a product could be carried in emergency vehicles and on the battlefield to stabilize victims of acute trauma and blood loss, as well as kept in hospitals and clinics as a blood extender when supplies of type-matched blood are limited or unavailable.

One of the most promising types of blood substitute is the hemoglobin-based oxygen carrier (HBOC), a product based on a modified hemoglobin protein. HBOCs are free of other red blood cell components, thus require no blood-typing and are universally compatible. Positive performance results have been obtained using HBOCs generated from hemoglobin from both human and non-human sources, but problems with stability, toxicity, efficacy, and cost remain. As such, there is a need to develop novel HBOCs having lower toxicity, improved stability, and extended shelf-life.

SUMMARY

The present disclosure provides in part, a modified hemoglobin (Hb), a multimerized Hb composition, and methods thereof. The modified Hbs and multimerized Hb compositions disclosed herein can be useful as HBOCs.

In one aspect, the present disclosure provides a modified hemoglobin (Hb), comprising: at least two subunits of a Hb intramolecularly crosslinked with a compound of formula (I)

(I)

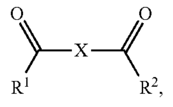

or a salt, a stereoisomer, or a deuterated form thereof, wherein:

X is $C_{1-24}$ alkylene, $C_{2-24}$ alkenylene, $C_{2-24}$ alkynylene, $C_{3-9}$ cycloalkylene, $C_{3-9}$ cycloalkenylene, 5-12 membered heterocyclylene containing 1 or 2 heteroatoms selected from N, S, or O, arylene, heteroarylene, or $-L^1-NR^4-L^2-$, wherein X is optionally substituted with 1-6 $R^3$ as permitted by valency;

$R^1$ and $R^2$ are each independently —OH, halogen, or a leaving group;

each $R^3$ is independently —OH, —CN, $—NO_2$, halogen, oxo, $—C_{1-6}$ alkyl, $—C_{1-6}$ haloalkyl, $—O(C_1$-6 alkyl), $—S(C_{1-6}$ alkyl), $—SO(C_{1-6}$ alkyl), $—SO_2(C_{1-6}$ alkyl), $—(C_{1-12}$ alkylene)-$N_3$, $—(C_{1-12}$ alkylene)-$(OCH_2CH_2)_m—(CH_2)_n—N_3$, —C(O)NH—$(C_{1-12}$ alkylene)-$(OCH_2CH_2)_m—(CH_2)_n—N_3$, —NHC(O)—$(C_{1-12}$ alkylene)-$(OCH_2CH_2)_m—(CH_2)_n—N_3$, —O—$(C_{1-12}$ alkylene)-$(OCH_2CH_2)_m—(CH_2)_n—N_3$, —S—$(C_{1-12}$ alkylene)-$(OCH_2CH_2)_m—(CH_2)_n—N_3$, or $—C(O)—R^1$, wherein each alkyl or alkylene is optionally and independently substituted with $—C_{1-6}$ alkyl, —OH, —CN, $—NO_2$, or halogen;

$R^4$ is H, $—C_{1-6}$ alkyl, aryl, —C(O)-aryl, $—SO_2(C_{1-6}$ alkyl), $—SO_2$-aryl, or $—(C_{1-6}$ alkylene)-$(OCH_2CH_2)_m—(CH_2)_n—N_3$, wherein each alkyl, aryl, or alkylene is optionally and independently substituted with $—C_{1-6}$ alkyl, —OH, —CN, $—NO_2$, or halogen;

$L^1$ and $L^2$ are each independently $C_{1-12}$ alkylene, $C_{2-12}$alkenylene, $C_{2-12}$alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each m is independently an integer of 1-200; and each n is independently an integer of 0-50.

In embodiments, the Hb intramolecularly crosslinked with the compound of formula (I) comprises:

(I-A)

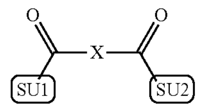

wherein SU1 is a residue on a first subunit of the Hb, and SU2 is a residue on a second subunit of the Hb.

In embodiments, the modified Hb comprises a first residue functionalized with a first reactive group. In embodiments, the first reactive group is suitable to react with a second reactive group to form linker using click chemistry. In embodiments, the first reactive group is azido, and the second reactive group is cycloalkynyl; or the first reactive group is cycloalkynyl, and the second reactive group is azido. In embodiments, the first reactive group is azido, and the second reactive group is propargyl; or the first reactive group is propargyl, and the second reactive group is azido. In embodiments, the first reactive group is tetrazine, and the second reactive group is trans-cyclooctene (TCO); or the first reactive group is TCO, and the second reactive group is tetrazine.

In embodiments, the at least two subunits are intramolecularly crosslinked with the compound of formula (I) at a residue selected from the group consisting of Lys (K), Cys (C), Arg (R), and an N-termini. In embodiments, the at least two subunits are intramolecularly crosslinked at residues Lys.

In embodiments, the two beta subunits of the Hb are intramolecularly crosslinked by the compound of formula (I). In embodiments, amino groups of lysine residues of the beta subunits are intramolecularly crosslinked by the compound of formula (I). In embodiments, the lysine residues of the beta subunits are Lys-81 and Lys-81 of SEQ ID NO: 2, Lys-81 and Lys-94 of SEQ ID NO: 2, or Lys-75 and Lys-81 of SEQ ID NO: 2. In embodiments, the lysine residues of the beta subunits are Lys-81 and Lys-81 of SEQ ID NO: 2.

In embodiments, the two alpha subunits of the Hb are intramolecularly crosslinked by the compound of formula (I). In embodiments, amino groups of lysine residues or N-terminus of the alpha subunits are intramolecularly crosslinked by the compound of formula (I). In embodiments, the lysine residues of the alpha subunits are Lys-99 and Lys-99 of SEQ ID NO: 1, Lys-7 and Lys-139 of SEQ ID NO: 1, Lys-90 and Lys-139 of SEQ ID NO: 1, or Lys-90 and Lys-127 of SEQ ID NO: 1.

In embodiments, the alpha and the beta subunits of the Hb are intramolecularly crosslinked by the compound of formula (I). In embodiments, amino groups of lysine residues of the alpha and the beta subunits are intramolecularly crosslinked by the compound of formula (I). In embodiments, the lysine residues of the alpha and the beta subunits are Lys-99 of SEQ ID NO: 1 and Lys-103 of SEQ ID NO: 2, respectively.

In embodiments, the Hb is bovine, human, equine, porcine, ovine, simian, or fish hemoglobin. In embodiments, the Hb is bovine hemoglobin (bHb).

In embodiments, the modified Hb has a molecular weight of about 63 kDa to about 70 kDa.

In another aspect, the present disclosure provides a multimerized hemoglobin (Hb) composition comprising two or more modified Hb, wherein each modified Hb independently comprises: at least two subunits of a Hb intramolecularly crosslinked with a compound of formula (I)

(I)

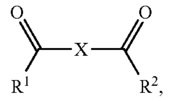

or a salt, a stereoisomer, or a deuterated form thereof, wherein:

X is $C_{1-24}$ alkylene, $C_{2-24}$ alkenylene, $C_{2-24}$ alkynylene, $C_{3-9}$ cycloalkylene, $C_{3-9}$ cycloalkenylene, 5-12 membered heterocyclylene containing 1 or 2 heteroatoms selected from N, S, or O, arylene, heteroarylene, or $-L^1-NR^A-L^2-$, wherein X is optionally substituted with 1-6 $R^3$ as permitted by valency;

$R^1$ and $R^2$ are each independently —OH, halogen, or a leaving group;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-12}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen;

$R^A$ is H, —$C_{1-6}$ alkyl, aryl, —C(O)-aryl, —$SO_2$($C_{1-6}$ alkyl), —$SO_2$-aryl, or —($C_{1-6}$ alkylene)-$(OCH_2CH_2)_m$—$(CH_2)_n$—$N_3$, wherein each alkyl, aryl, or alkylene is optionally and independently substituted with —$C_{1-6}$ alkyl, —OH, —CN, —$NO_2$, or halogen;

$L^1$ and $L^2$ are each independently $C_{1-12}$ alkylene, $C_{2-12}$ alkenylene, $C_{2-12}$ alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each m is independently an integer of 1-200; and each n is independently an integer of 0-50.

In embodiments, the Hb intramolecularly crosslinked with the compound of formula (I) comprises:

(I-A)

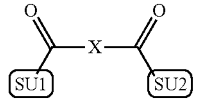

wherein SU1 is a residue on a first subunit of the Hb, and SU2 is a residue on a second subunit of the Hb.

In embodiments, the multimerized Hb composition comprises a reaction product of:

a first modified Hb comprising a first residue functionalized with a first reactive group for a click reaction; and a reactant molecule comprising a second reactive group that is complementary to the first reactive group for the click reaction.

In one embodiment, the reactant molecule is a second modified Hb comprising a second residue functionalized with the second reactive group.

In another embodiment, the reactant molecule is a scaffold compound comprising the second reactive group.

In embodiments, the first reactive group is azido, and the second reactive group is cycloalkynyl; or the first reactive group is cycloalkynyl, and the second reactive group is azido. In embodiments, the first reactive group is azido, and the second reactive group is propargyl; or the first reactive group is propargyl, and the second reactive group is azido. In embodiments, the first reactive group is tetrazine, and the second reactive group is TCO; or the first reactive group is TCO, and the second reactive group is tetrazine.

In embodiments, the at least two subunits of each modified Hb are intramolecularly crosslinked with the compound of formula (I) at a residue selected from the group consisting of Lys, Cys, Arg, and an N-termini. In embodiments, the at least two subunits are intramolecularly crosslinked at residues Lys.

In embodiments, the two beta subunits of the Hb are intramolecularly crosslinked by the compound of formula (I). In embodiments, amino groups of lysine residues of the beta subunits are intramolecularly crosslinked by the compound of formula (I). In embodiments, the lysine residues of the beta subunits are Lys-81 and Lys-81 of SEQ ID NO: 2, Lys-81 and Lys-94 of SEQ ID NO: 2, or Lys-75 and Lys-81 of SEQ ID NO: 2. In embodiments, the lysine residues of the beta subunits are Lys-81 and Lys-81 of SEQ ID NO: 2.

In embodiments, the two alpha subunits of the Hb are intramolecularly crosslinked by the compound of formula (I). In embodiments, amino groups of lysine residues or N-terminus of the alpha subunits are intramolecularly crosslinked by the compound of formula (I). In embodiments, the lysine residues of the alpha subunits are Lys-99 and Lys-99 of SEQ ID NO: 1, Lys-7 and Lys-139 of SEQ ID NO: 1, Lys-90 and Lys-139 of SEQ ID NO: 1, or Lys-90 and Lys-127 of SEQ ID NO: 1.

In embodiments, the alpha and the beta subunits of the Hb are intramolecularly crosslinked by the compound of formula (I). In embodiments, amino groups of lysine residues of the alpha and the beta subunits are intramolecularly crosslinked by the compound of formula (I). In embodiments, the lysine residues of the alpha and the beta subunits are Lys-99 of SEQ ID NO: 1 and Lys-103 of SEQ ID NO: 2, respectively.

In embodiments, the Hb is bovine, human, equine, porcine, ovine, simian, or fish hemoglobin. In embodiments, the Hb is bovine hemoglobin (bHb).

In embodiments, the first reactive group is azido, and the second reactive group is cycloalkynyl; or the first reactive group is cycloalkynyl, and the second reactive group is azido.

(II)

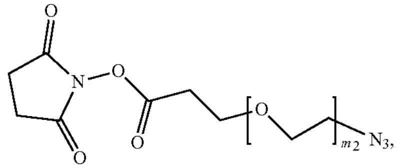

(III)

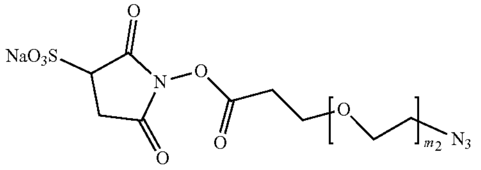

wherein $m_2$ and $m_3$ are each independently an integer of 1-5000. In embodiments, the scaffold compound is a compound of formula (IV) or (V)

(IV)

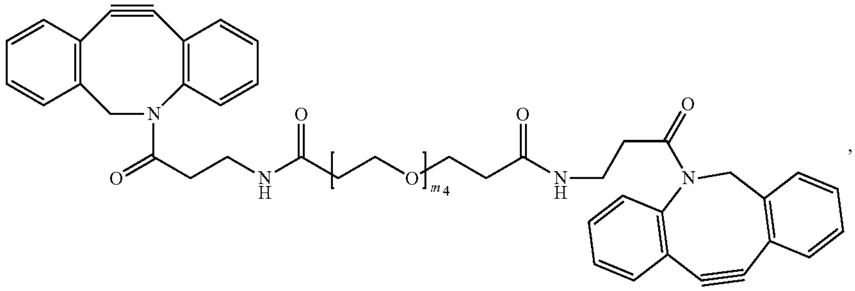

, (V)

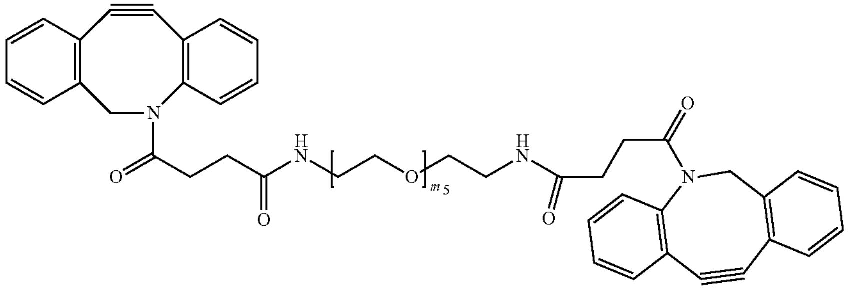

In embodiments, the scaffold compound has two, three, or four second reactive groups.

wherein $m_4$ and $m_5$ are each independently an integer of 1-5000.

In embodiments, the first reactive group is azido, and the second reactive groups are cycloalkynyl. In embodiments, the cycloalkynyl is a $C_{6-9}$ heterocycloalkynyl. In embodiments, the first modified Hb comprising a first residue functionalized with the first reactive group for a click reaction is obtained by:

reacting the compound of formula (I) and a Hb to form a crosslinked Hb, and reacting the crosslinked Hb and an azido compound; or reacting an azido compound and a Hb to form an azido-functionalized Hb, and reacting the azido-functionalized Hb and the compound of formula (I), wherein the azido compound is 4-azidophenylglyoxal (4-APG), 6-azidomethyl pyridine carboxaldehyde (6-AMPC), or a compound of formula (II) or (III)

In embodiments, the first reactive group is cycloalkynyl, and the second reactive groups are azido. In embodiments, the first modified Hb comprising a first residue functionalized with the first reactive group for a click reaction is obtained by:

reacting the compound of formula (I) and a Hb to form a crosslinked Hb, and reacting the crosslinked Hb and a cycloalkynyl compound; or reacting a cycloalkynyl compound and a Hb to form an alkynyl-functionalized Hb, and reacting the alkynyl-functionalized Hb and the compound of formula (I), wherein the cycloalkynyl compound is a compound of formula (VI), (VII), (VIII), or (IX)

(VI)

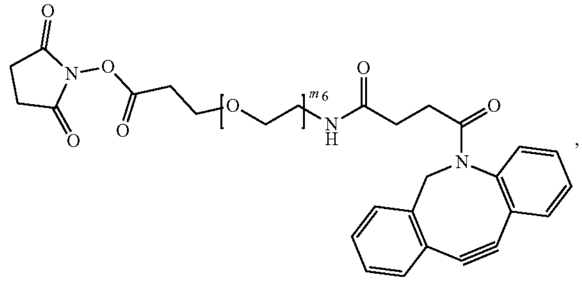

(VII)

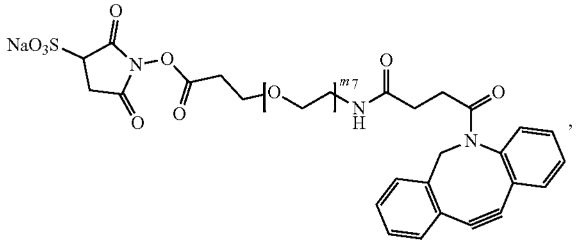

(VIII)

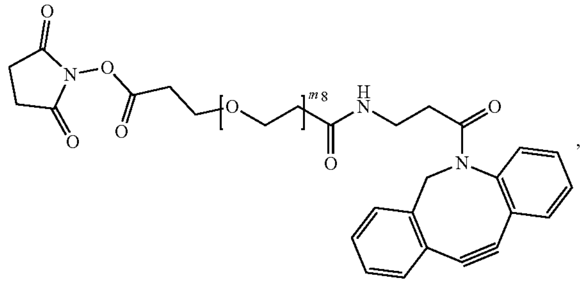

-continued (IX)

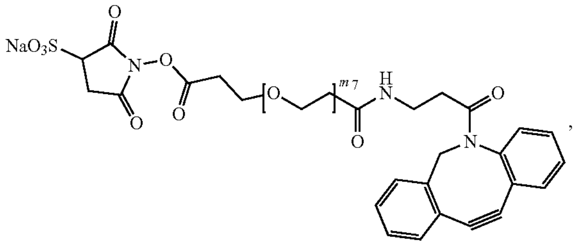

wherein $m_6$, $m_7$, $m_8$, and $m_9$ are each independently an integer of 1-5000. In embodiments, the scaffold compound is a compound of formula (X) or (XI)

(X)

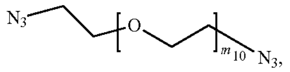

or (XI)

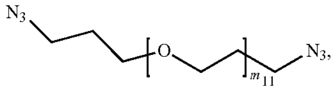

wherein $m_{10}$ and $m_{11}$ are each independently an integer of 1-5000.

In embodiments, the first modified Hb comprising a first residue functionalized with a first reactive group for a click reaction comprises at least one azido or at least one cycloalkynyl that is covalently linked to alpha subunits of the Hb.

In another embodiment, the two or more modified Hb are connected by a bifunctional linker selected from 1,4-bis-phenylglyoxal (1,4-PBG) and $(PEG)_{m12}$-bis-phenylglyoxal:

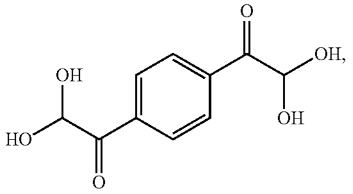

(1,4-PBG)

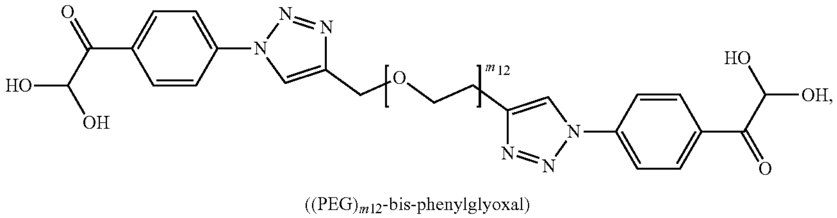

($(PEG)_{m12}$-bis-phenylglyoxal)

wherein $m_{12}$ is an integer of 1-5000. In embodiments, arginine (Arg) residues of the two or more modified Hb are connected by the bifunctional linker. In embodiments, arginine (Arg) residues of the beta subunits of the two or more modified Hb are connected by the bifunctional linker.

In embodiments of the aforementioned multimerized Hb composition,

X is $C_{1-24}$ alkylene, $C_{2-24}$ alkenylene, $C_{2-24}$ alkynylene, $C_{3-9}$ cycloalkylene, $C_{3-9}$ cycloalkenylene, 5-12 membered heterocyclylene containing 1 or 2 heteroatoms selected from N, S, or O, arylene, heteroarylene, or $-L^1-NR^A-L^2-$, wherein X is optionally substituted with 1-6 $R^3$ as permitted by valency;

$R^1$ and $R^2$ are each independently —OH, halogen, or a leaving group;

each $R^3$ is independently —OH, —CN, $—NO_2$, halogen, oxo, $—C_{1-6}$ alkyl, $—C_{1-6}$ haloalkyl, $—O(C_{1-6}$ alkyl), $—S(C_{1-6}$ alkyl), $—SO(C_{1-6}$ alkyl), $—SO_2(C_{1-6}$ alkyl), or $—C(O)—R^1$, wherein each alkyl or alkylene is optionally and independently substituted with $—C_{1-6}$ alkyl, —OH, —CN, $—NO_2$, or halogen;

$R^A$ is H, $—C_{1-6}$ alkyl, aryl, —C(O)-aryl, $—SO_2(C_{1-6}$ alkyl), or $—SO_2$-aryl, wherein each alkyl, aryl, or alkylene is optionally and independently substituted with $—C_{1-6}$ alkyl, —OH, —CN, $—NO_2$, or halogen;

$L^1$ and $L^2$ are each independently $C_{1-12}$ alkylene, $C_{2-12}$alkenylene, $C_{2-12}$alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each m is independently an integer of 1-200; and each n is independently an integer of 0-50.

In a further aspect, the present disclosure provides a multimerized Hb composition, comprising a reaction product of: a modified Hb comprising a residue functionalized with a first reactive group for a click reaction; and a reactant molecule comprising a second reactive group that is complementary to the first reactive group for the click reaction, wherein the modified Hb comprises:

at least two subunits of a Hb intramolecularly crosslinked with a compound of formula (I)

(I)

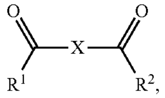

or a salt, a stereoisomer, or a deuterated form thereof, wherein:

X is $C_{1-24}$ alkylene, $C_{2-24}$alkenylene, $C_{2-24}$alkynylene, $C_{3-9}$cycloalkylene, $C_{3-9}$ cycloalkenylene, 5-12 membered heterocyclylene containing 1 or 2 heteroatoms selected from N, S, or O, arylene, heteroarylene, or $-L^1-NR^A-L^2-$, wherein X is optionally substituted with 1-6 $R^3$ as permitted by valency;

$R^1$ and $R^2$ are each independently —OH, halogen, or a leaving group;

each $R^3$ is independently $—(C_{1-12}$ alkylene)-$N_3$, $—(C_{1-12}$ alkylene)-$(OCH_2CH_2)_m—(CH_2)_n—N_3$, $—C(O)NH—(C_{1-12}$ alkylene)-$(OCH_2CH_2)_m—(CH_2)_n—N_3$, $—NHC(O)—(C_{1-12}$ alkylene)-$(OCH_2CH_2)_m—(CH_2)_n—N_3$, $—O—(C_{1-12}$ alkylene)-$(OCH_2CH_2)_m—(CH_2)_n—N_3$, or $—S—(C_{1-12}$ alkylene)-$(OCH_2CH_2)_m—(CH_2)_n—N_3$, wherein each alkylene is optionally and independently substituted with $—C_{1-6}$ alkyl, —OH, —CN, $—NO_2$, or halogen;

$R^A$ is $—(C_{1-6}$ alkylene)-$(OCH_2CH_2)_m—(CH_2)_n—N_3$, wherein each alkylene is optionally and independently substituted with $—C_{1-6}$ alkyl, —OH, —CN, $—NO_2$, or halogen;

$L^1$ and $L^2$ are each independently $C_{1-12}$ alkylene, $C_{2-12}$ alkenylene, $C_{2-12}$ alkynylene, $C_{3-9}$cycloalkylene, $C_{3-9}$cycloalkenylene, arylene, or heteroarylene, wherein $L^1$ and $L^2$ are optionally and independently substituted with 1-3 $R^3$ as permitted by valency;

each m is independently an integer of 1-200; and each n is independently an integer of 0-50.

In embodiments, the reactant molecule is a scaffold compound comprising two or more second reactive groups, which are cycloalkynyl. In embodiments, the scaffold compound comprises two, three, or four second reactive groups, which are cycloalkynyl. In embodiments, the scaffold compound is a compound of formula (IV) or (V)

(IV)

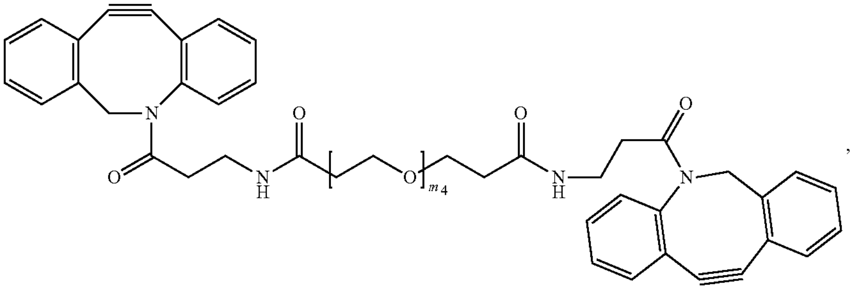

,

-continued (V)

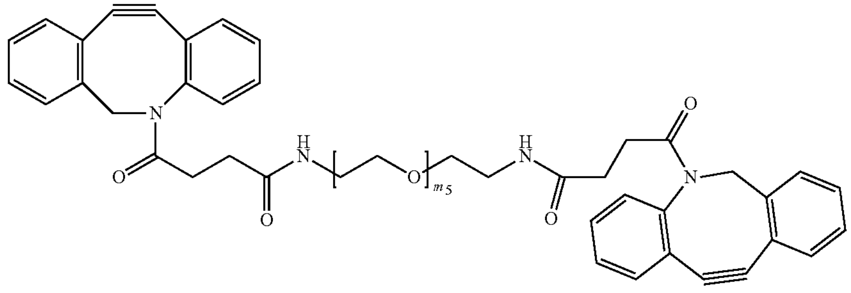

wherein $m_4$ and $m_5$ are each independently an integer of 1-5000.

In embodiments, the Hb intramolecularly crosslinked with the compound of formula (I) comprises:

(I-A)

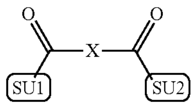

wherein SU1 is a residue on a first subunit of the Hb, and SU2 is a residue on a second subunit of the Hb.

In embodiments, the at least two subunits of each modified Hb are intramolecularly crosslinked with the compound of formula (I) at a residue selected from the group consisting of Lys, Cys, Arg, and an N-termini. In embodiments, the at least two subunits are intramolecularly crosslinked at residues Lys.

In embodiments, the two beta subunits of the Hb are intramolecularly crosslinked by the compound of formula (I). In embodiments, amino groups of lysine residues of the beta subunits are intramolecularly crosslinked by the compound of formula (I). In embodiments, the lysine residues of the beta subunits are Lys-81 and Lys-81 of SEQ ID NO: 2, Lys-81 and Lys-94 of SEQ ID NO: 2, or Lys-75 and Lys-81 of SEQ ID NO: 2. In embodiments, the lysine residues of the beta subunits are Lys-81 and Lys-81 of SEQ ID NO: 2.

In embodiments, the two alpha subunits of the Hb are intramolecularly crosslinked by the compound of formula (I). In embodiments, amino groups of lysine residues or N-terminus of the alpha subunits are intramolecularly crosslinked by the compound of formula (I). In embodiments, the lysine residues of the alpha subunits are Lys-99 and Lys-99 of SEQ ID NO: 1, Lys-7 and Lys-139 of SEQ ID NO: 1, Lys-90 and Lys-139 of SEQ ID NO: 1, or Lys-90 and Lys-127 of SEQ ID NO: 1.

In embodiments, the alpha and the beta subunits of the Hb are intramolecularly crosslinked by the compound of formula (I). In embodiments, amino groups of lysine residues of the alpha and the beta subunits are intramolecularly crosslinked by the compound of formula (I). In embodiments, the lysine residues of the alpha and the beta subunits are Lys-99 of SEQ ID NO: 1 and Lys-103 of SEQ ID NO: 2, respectively.

In embodiments, the Hb is bovine, human, equine, porcine, ovine, simian, or fish hemoglobin. In embodiments, the Hb is bovine hemoglobin (bHb).

In embodiments, the multimerized Hb composition in any of the above embodiments has a molecular weight of about 64 kDa to about 10 MDa.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION

Figure 1A:
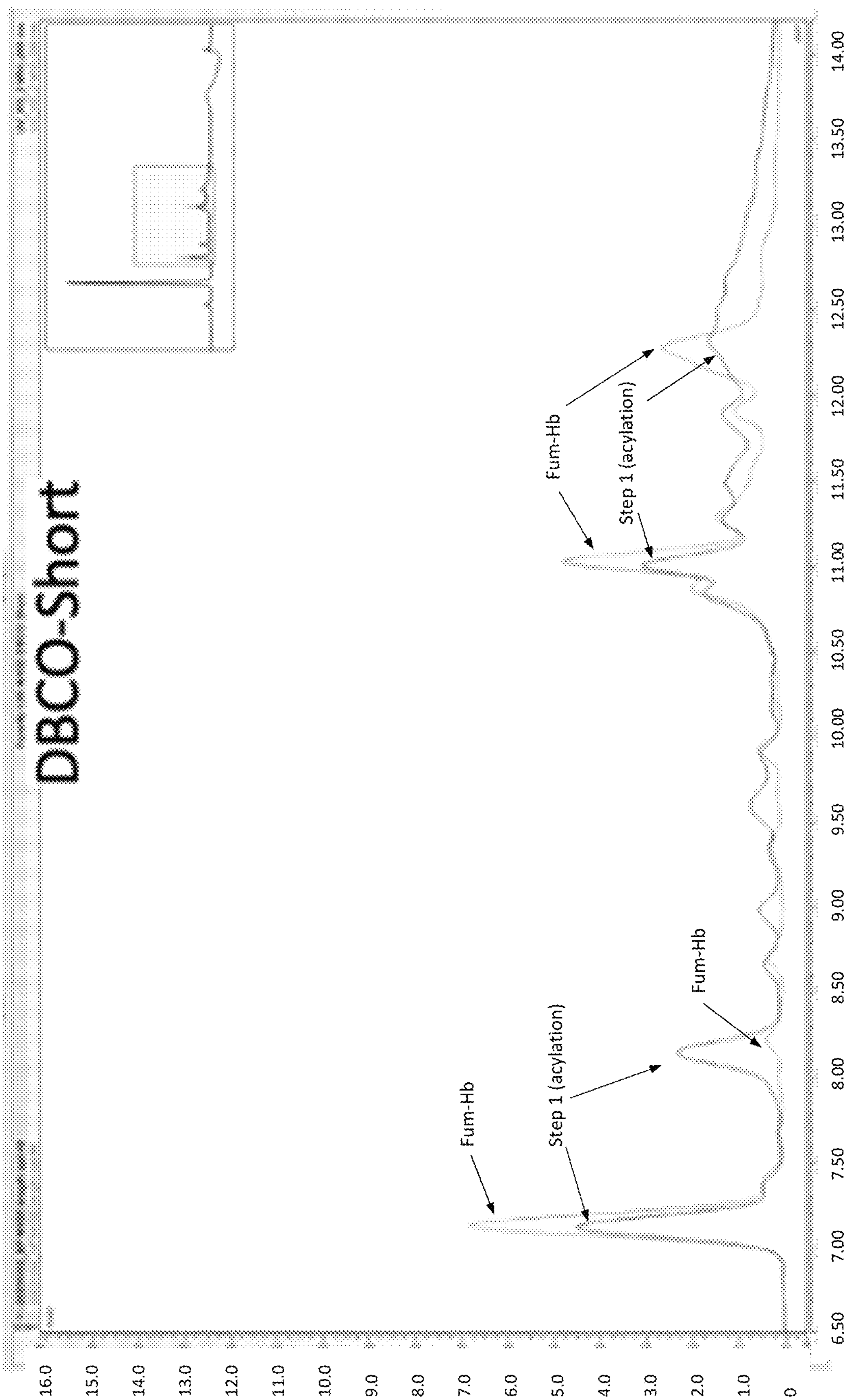
FIG. 1A shows analysis by High-performance liquid chromatography (HPLC) comparison of Fum-Hb (starting material) and step 1 (acylation) of Exp. 1 of Example 1.
Figure 1B:
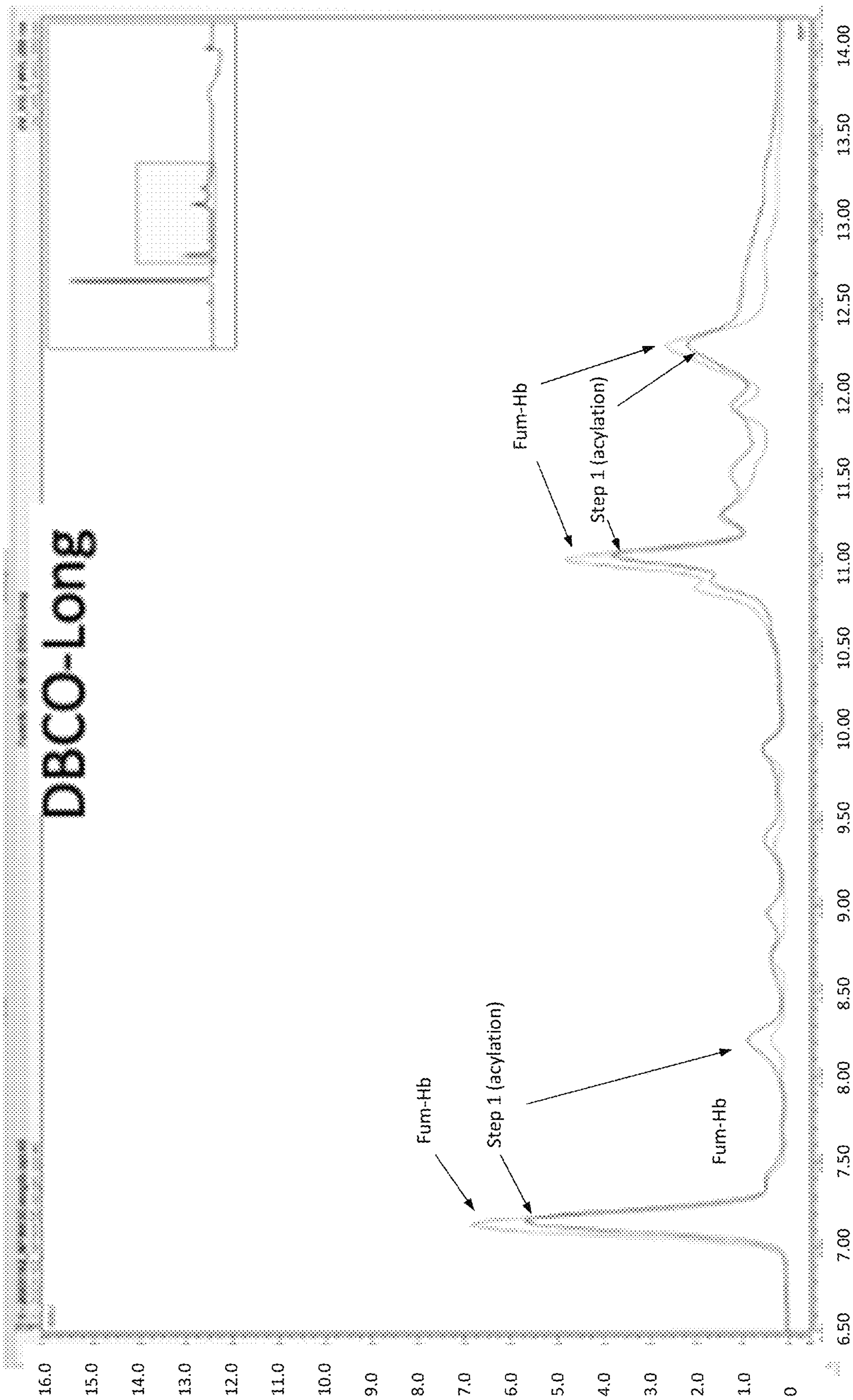
FIG. 1B shows analysis by HPLC comparison of Fum-Hb (starting material) and step 1 (acylation reaction) of Exp. 3 of Example 1.
Figure 1C:
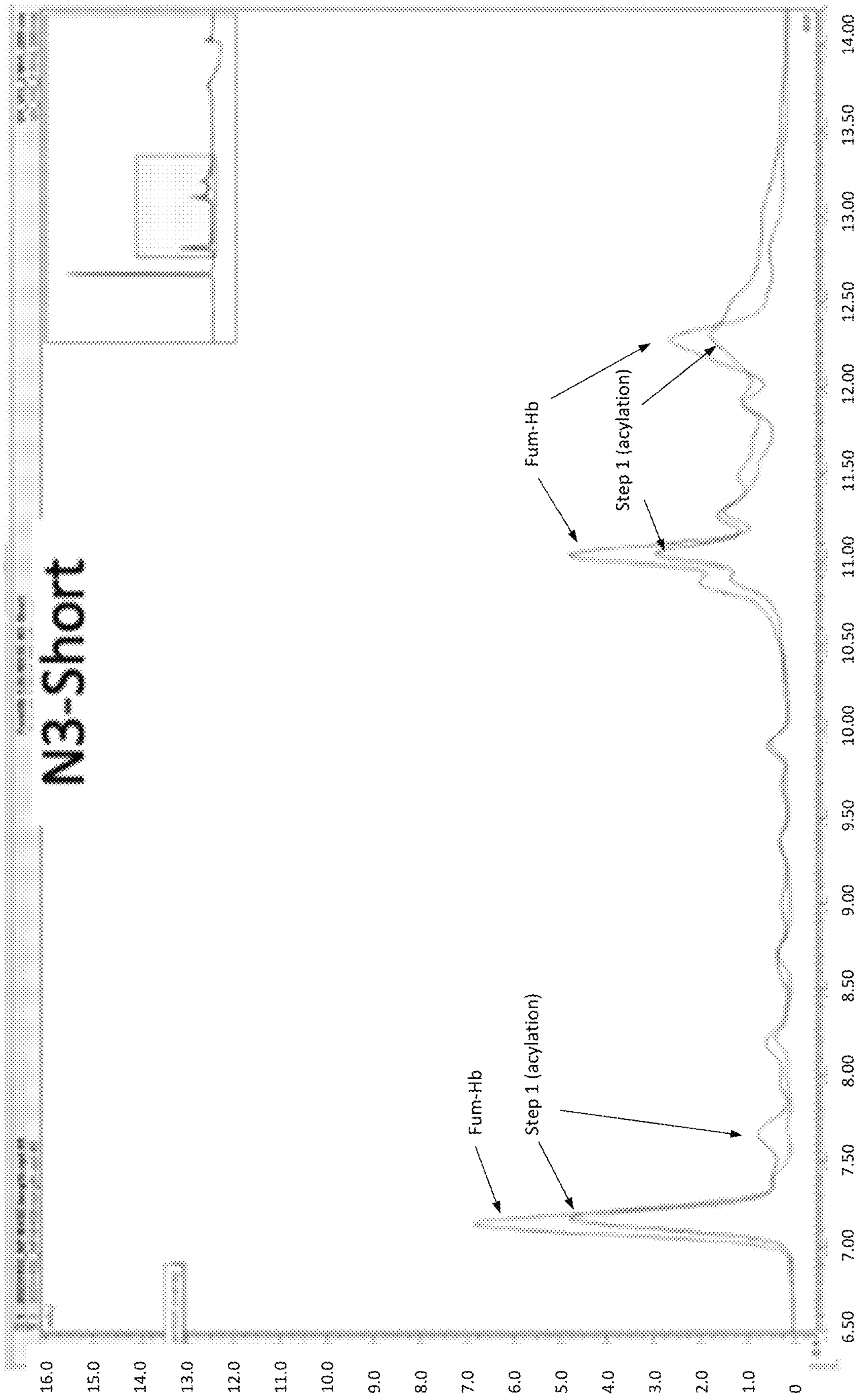
FIG. 1C shows analysis by HPLC comparison of Fum-Hb (starting material) and step 1 (acylation) of Exp. 5 of Example 1.
Figure 1D:
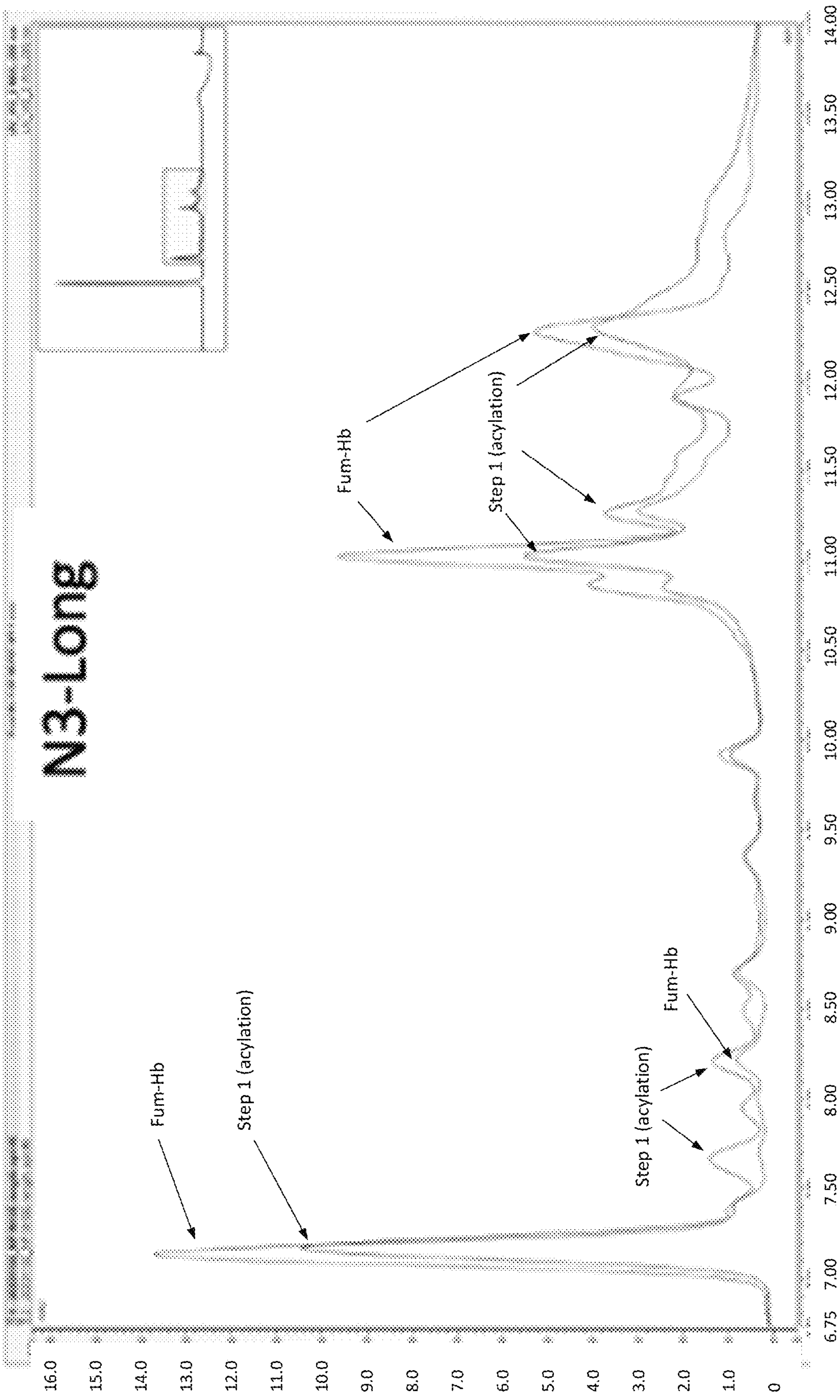
FIG. 1D shows analysis by HPLC comparison of Fum-Hb (starting material) and step 1 (acylation) of Exp. 7 of Example 1.
Figure 2A:
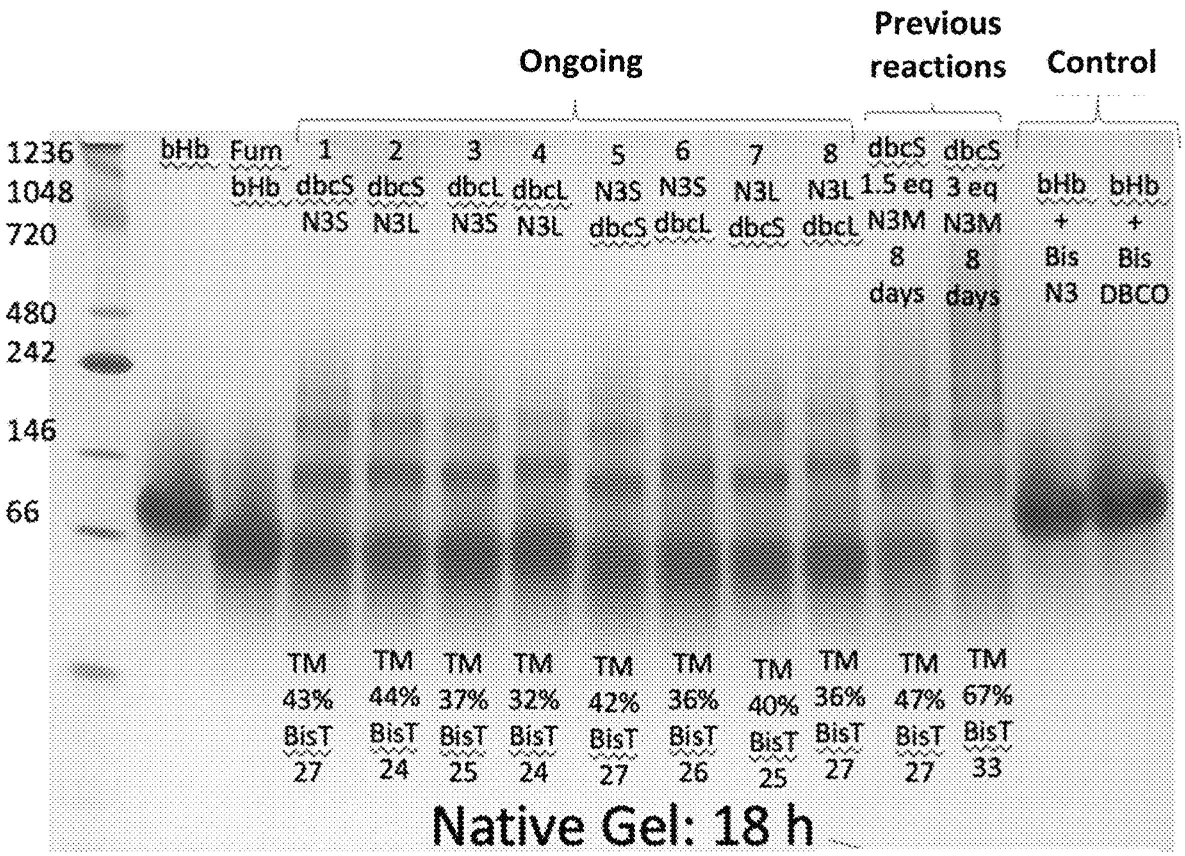
FIG. 2A shows progress of click reactions in Example 1 at 18 h monitored by native gel.
Figure 2B:
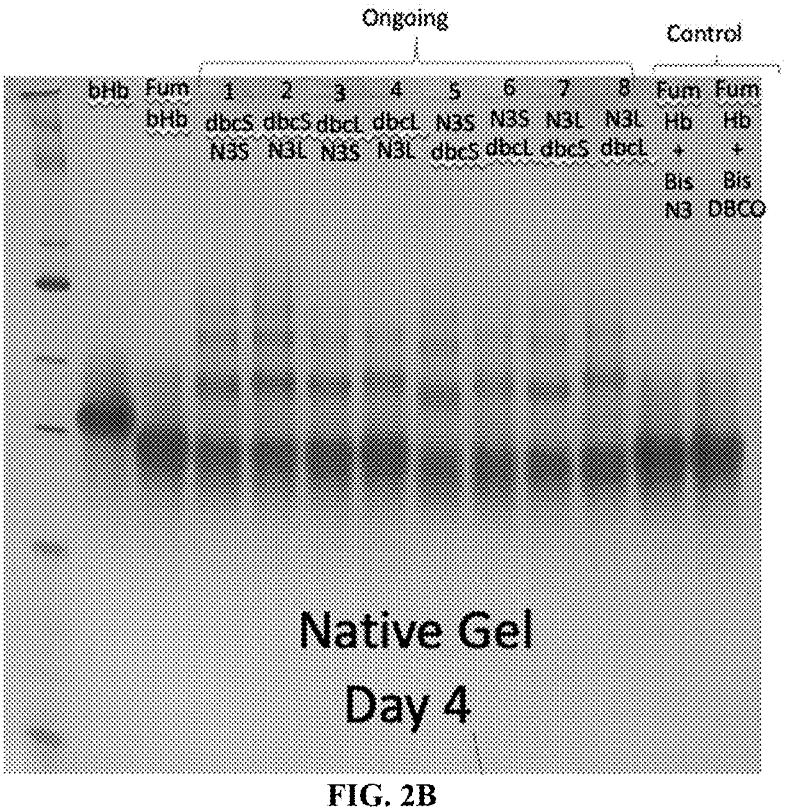
FIG. 2B shows progress of click reactions in Example 1 at day 4 monitored by native gel.
Figure 2C:
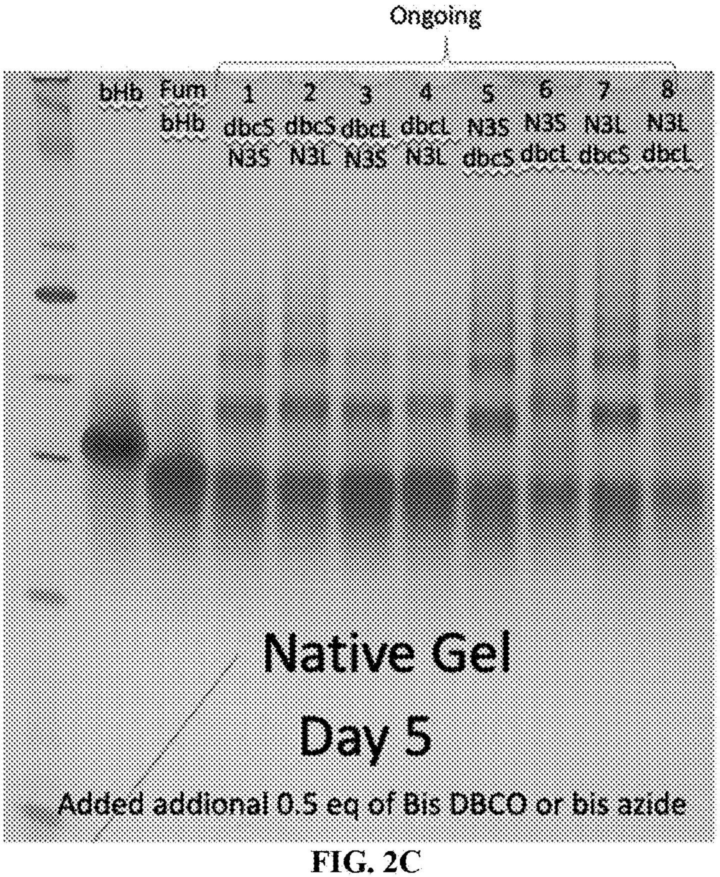
FIG. 2C shows progress of click reactions in Example 1 at day 5 monitored by native gel.
Figure 3:
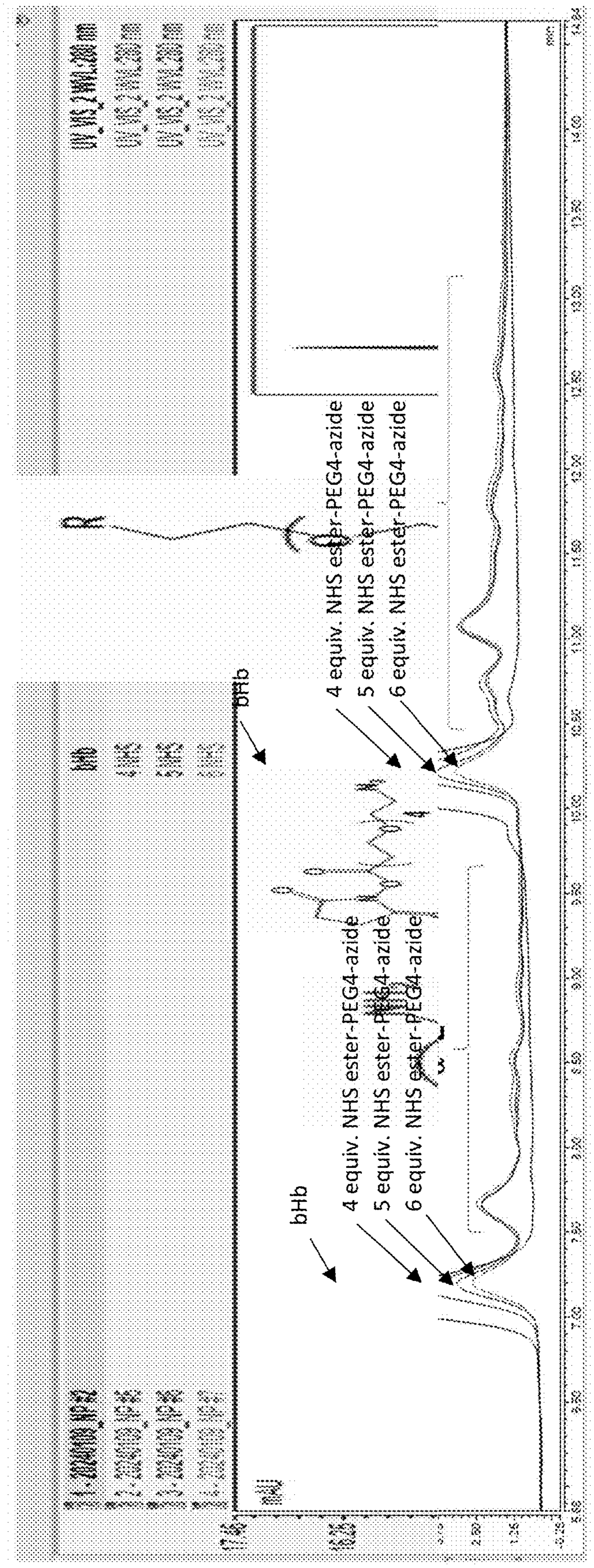
FIG. 3 is a HPLC spectrum (collected using C4 column) of the reaction mixture of Example 2 at 4 h.
Figure 4:
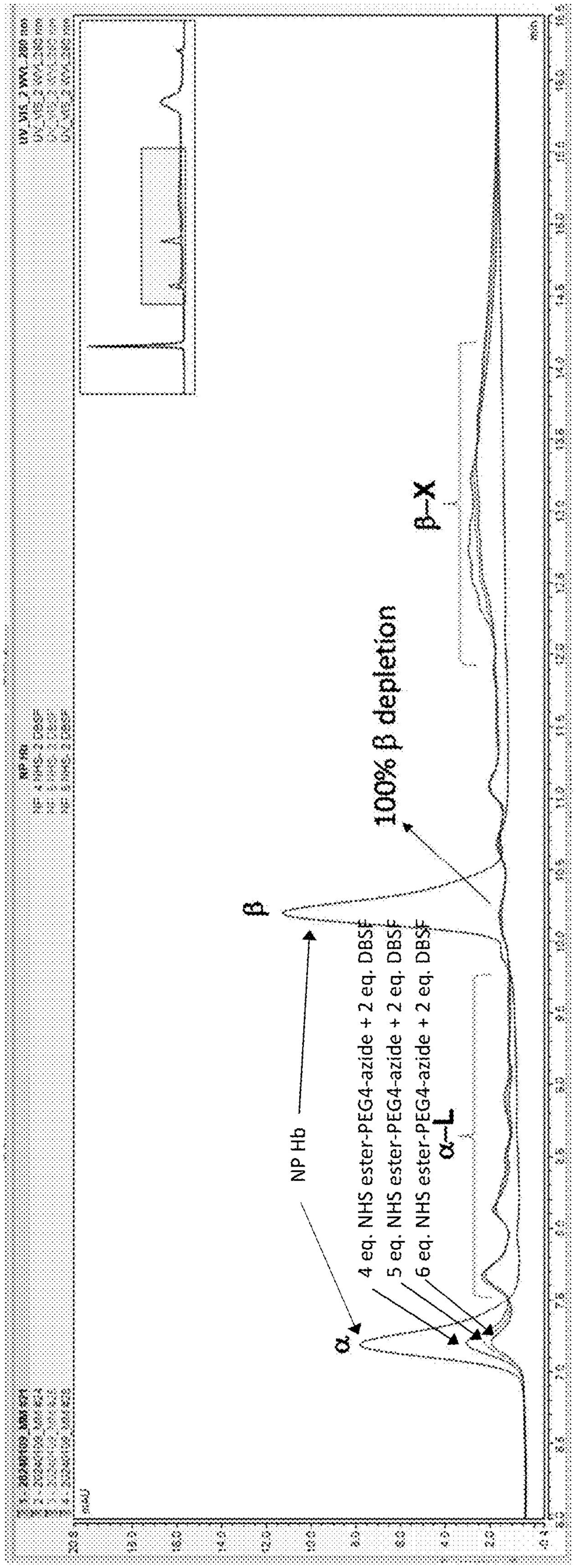
FIG. 4 is a HPLC spectrum of the reaction mixture of Example 3 at 4 h.
Figure 5:
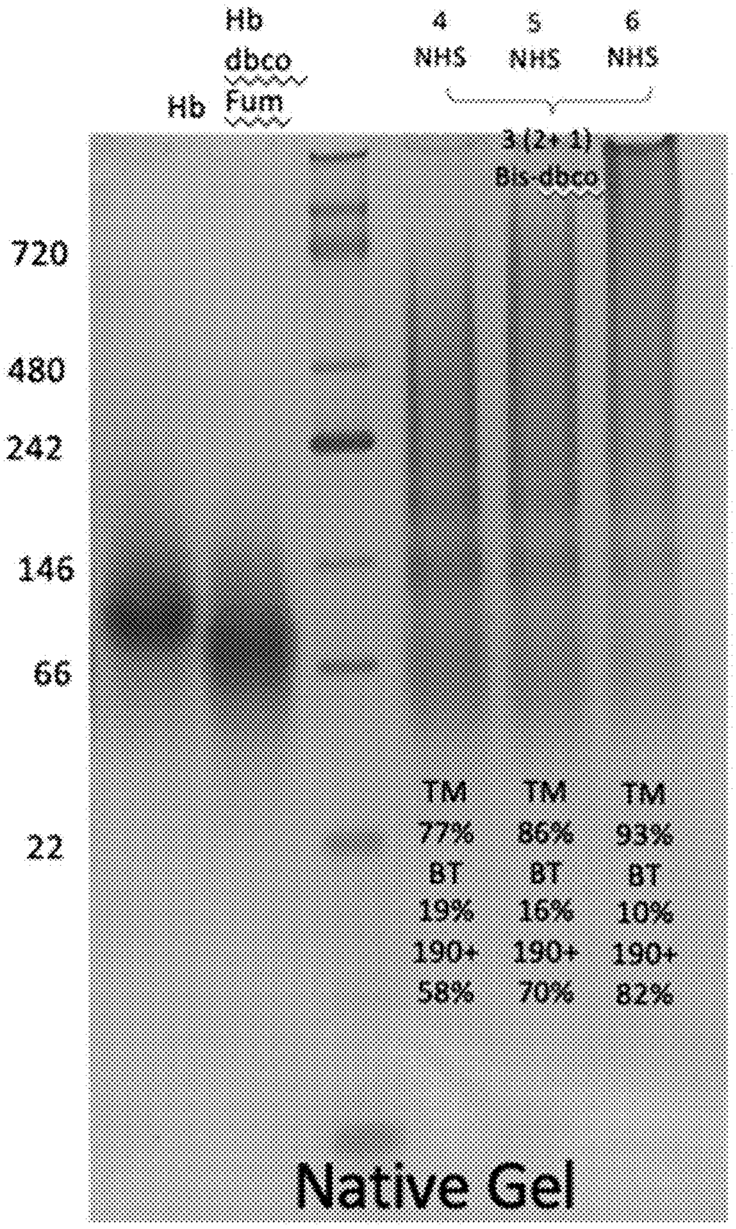
FIG. 5 shows progress of multimer formation reactions in Example 4 monitored by native gel.
Figure 6:
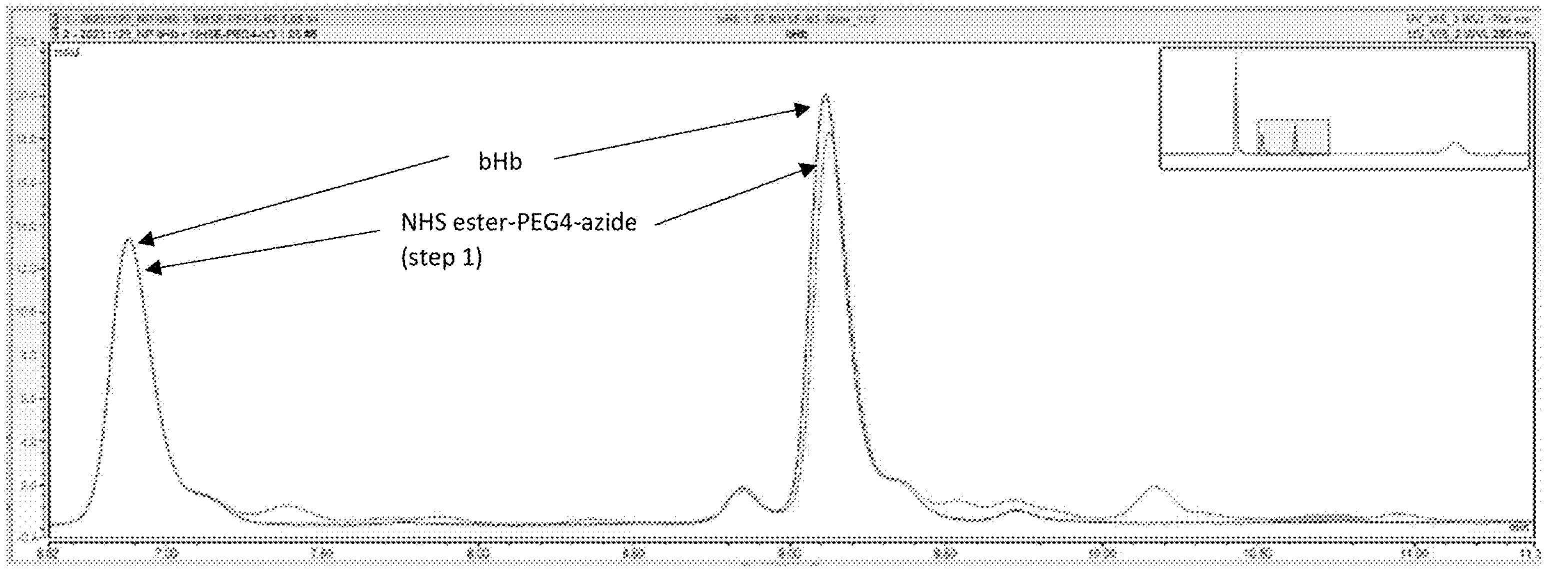
FIG. 6 shows analysis by HPLC comparison of bHb (starting material) and step 1 (acylation) of Example 5.
Figure 7:
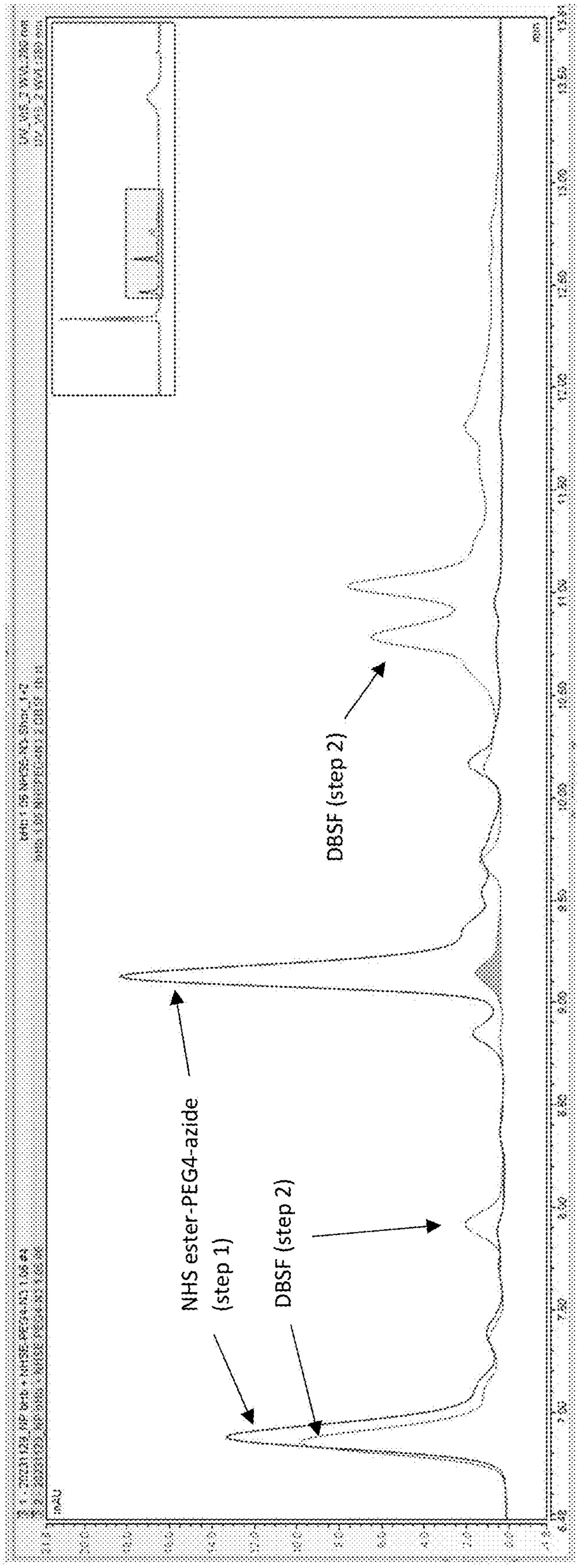
FIG. 7 is a HPLC spectrum of the reaction mixture of step 2 (crosslinking) in Example 5 at 18 h.
Figure 8:
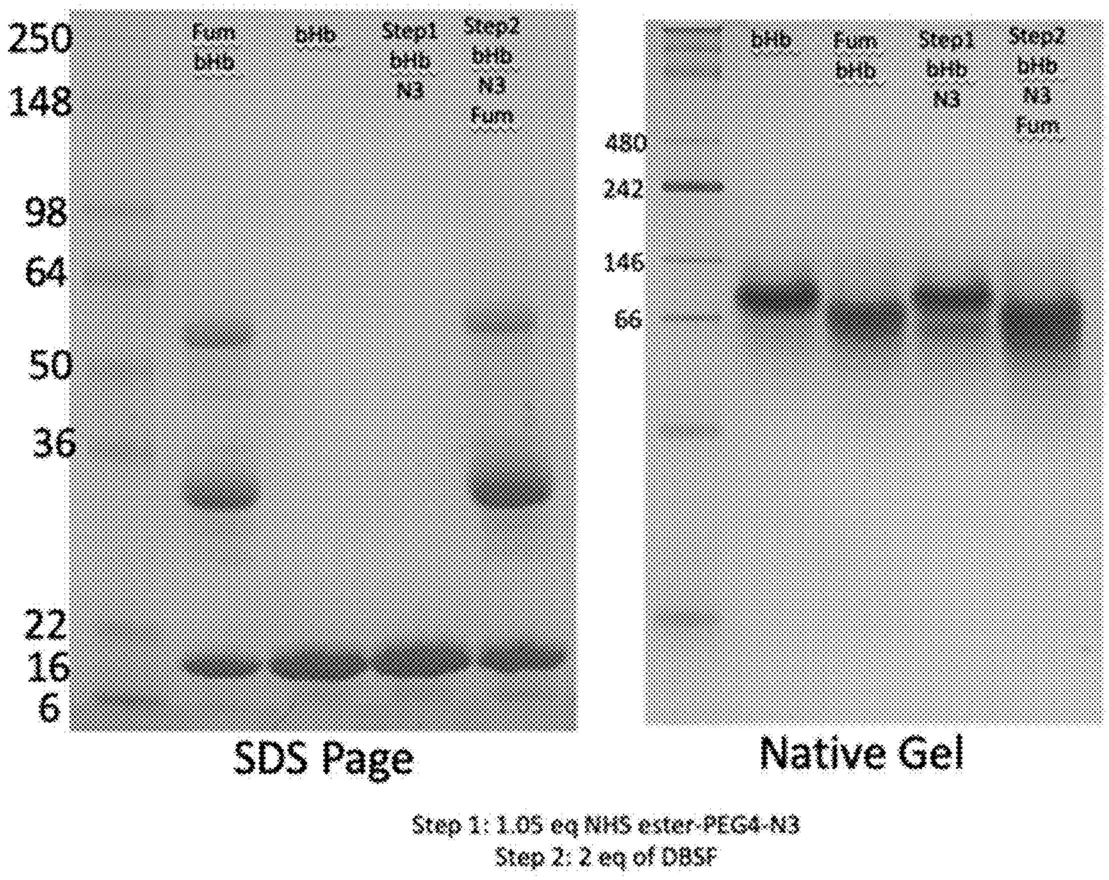
FIG. 8 shows progress of step 2 (crosslinking) in Example 5 at 18 h monitored by native gel and sodium dodecyl sulfate-polyacrylamide gel electrophoresis (SDS-PAGE), respectively.
Figure 9:
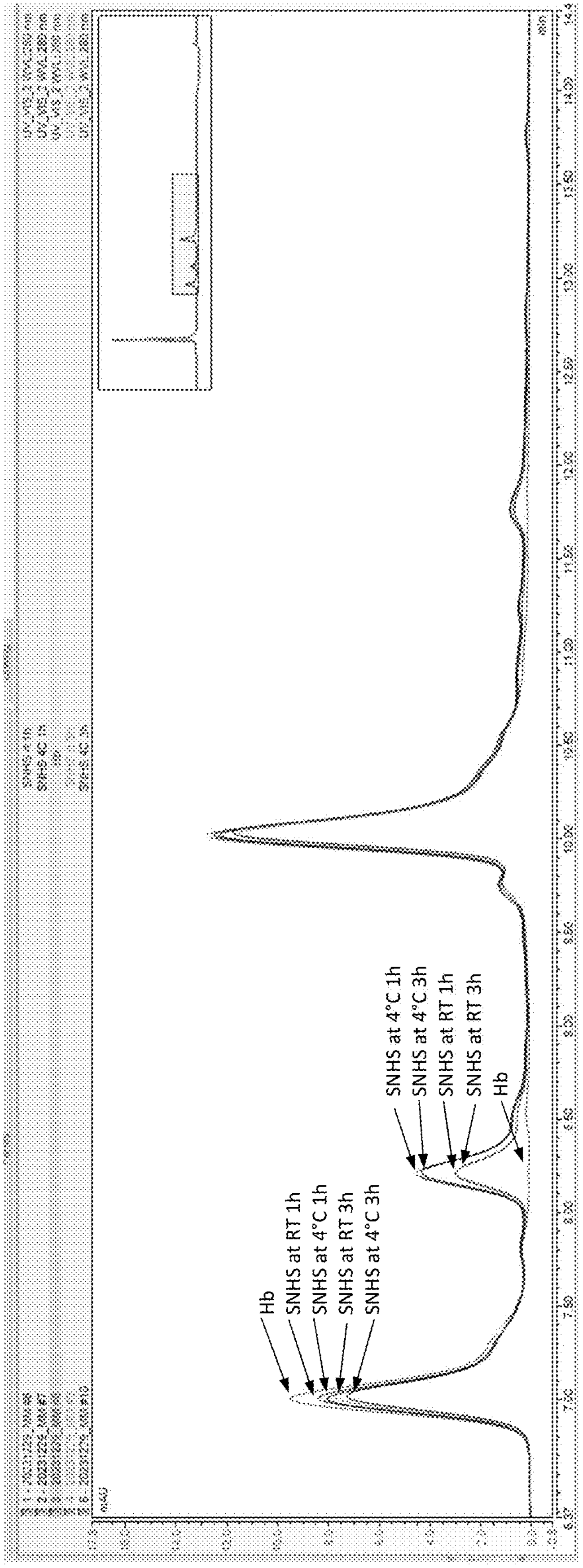
FIG. 9 is a HPLC spectrum (collected using C4 column) of the reaction mixture of Example 6 at 1 h and 4 h.
Figure 10:
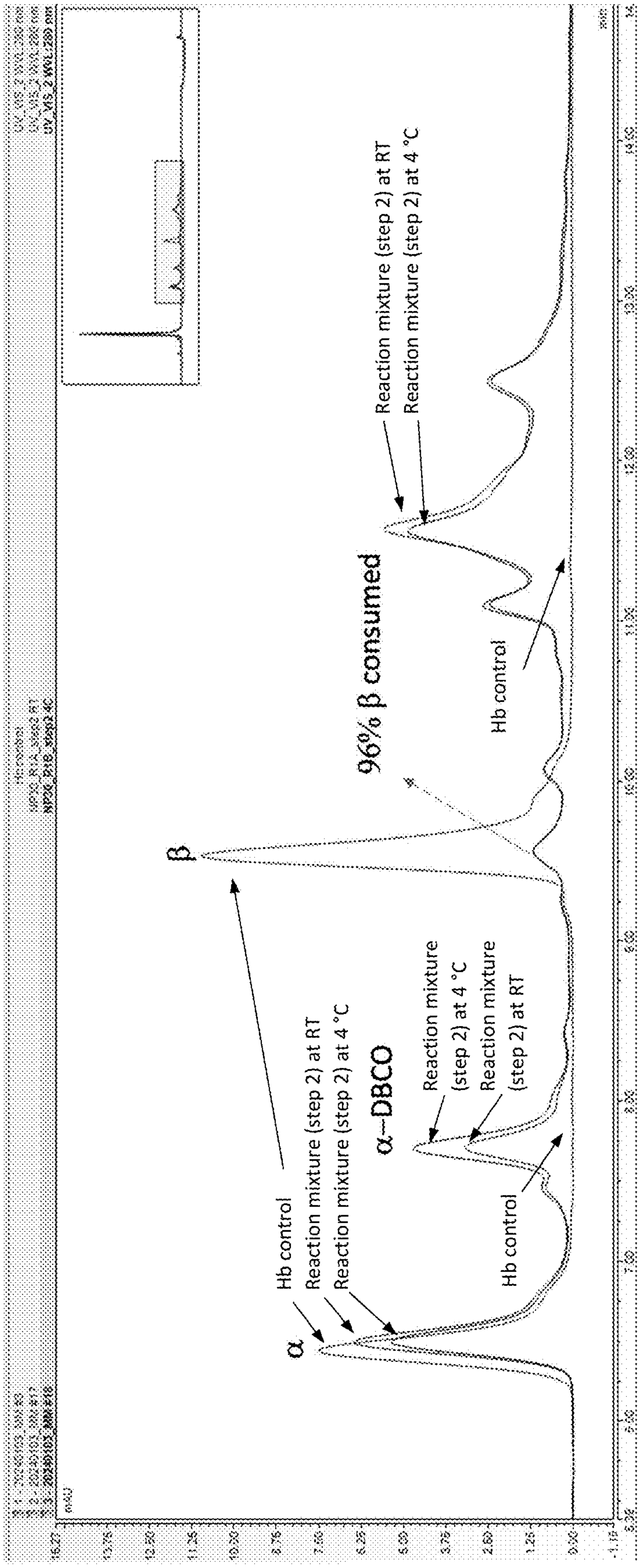
FIG. 10 is a HPLC spectrum of the reaction mixture of Example 7 at 2 h.
Figure 11:
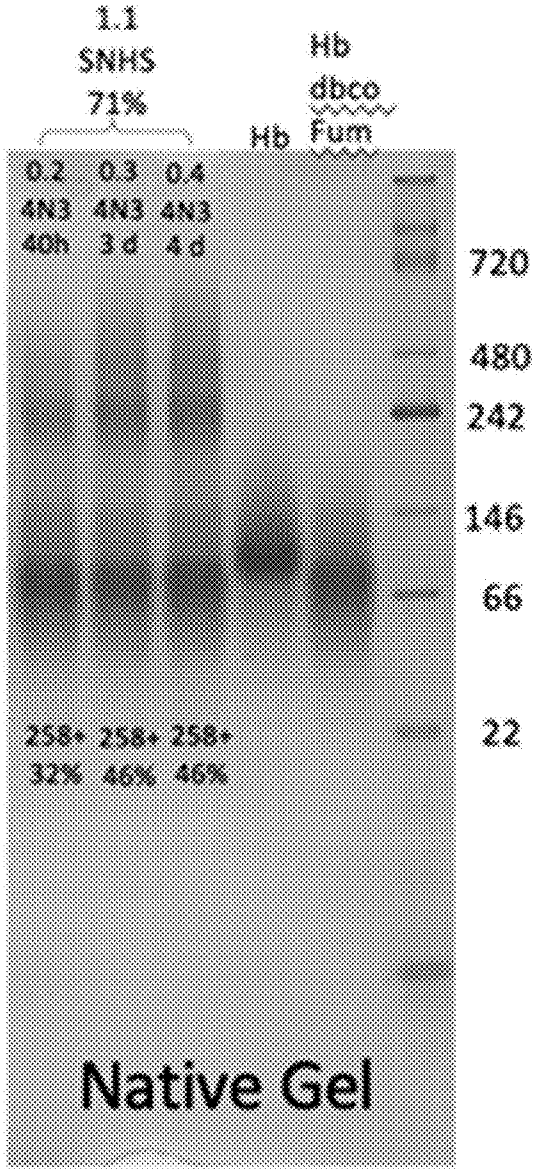
FIG. 11 shows progress of multimerization reactions in Example 8 at 40 h, day 3, and day 4 monitored by native gel.
Figure 12:
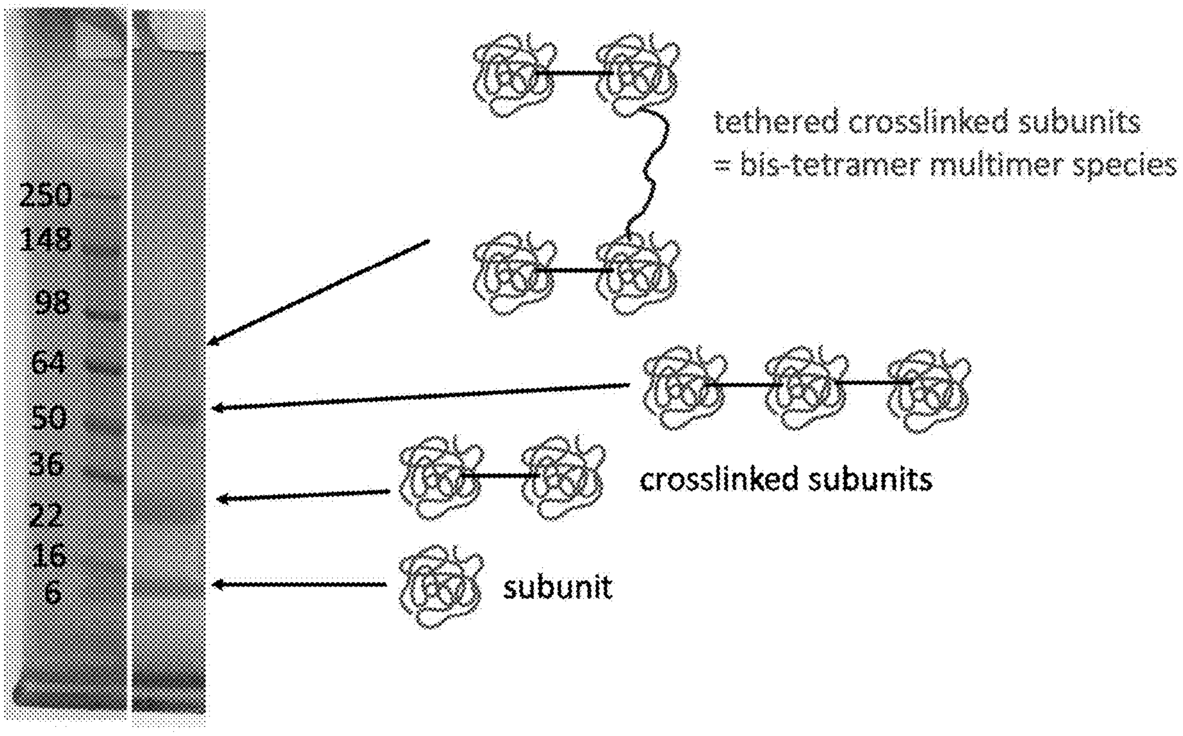
FIG. 12 illustrates an SDS-PAGE gel containing multimer product of Example 13, which is formed from the reaction between 1 mM DBSF-crosslinked bHb (150 mM sodium phosphate buffer, pH 8) with 0.5 eq. 1,4-PBG over 24 hours at 35° C.
Figure 13:
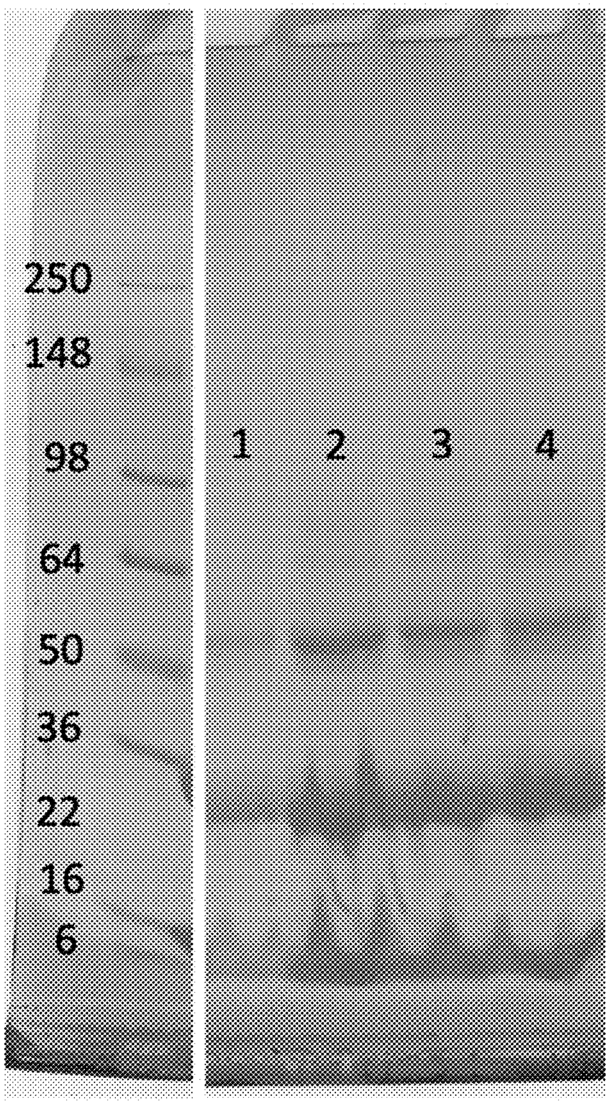
FIG. 13 illustrates SDS-PAGE analysis of the reactions between DBSF-crosslinked bHb and 0.5 eq. 1,4-PBG over a range of pH values in Example 13. Differences in yields are essentially negligible. Note: Lane 1 containing the reaction at pH 6.5 appears fainter than the rest of the lanes due to smaller total protein loading, however, densitometry reveals a similar yield of multimeric product over the entire protein contents of the lane.
Figure 13:
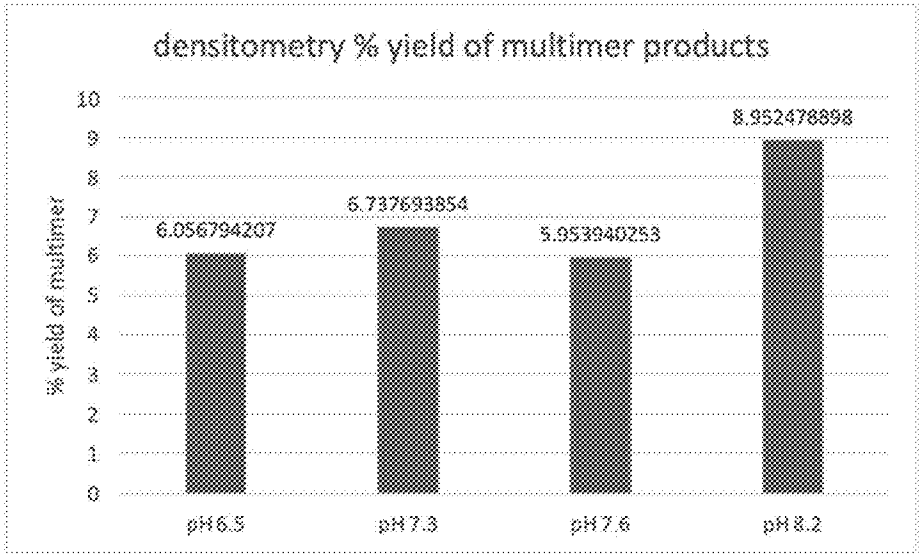

Throughout this disclosure, various patents, patent applications and publications are referenced. The disclosures of these patents, patent applications and publications in their entireties are incorporated into this disclosure by reference for all purposes in order to more fully describe the state of the art as known to those skilled therein as of the date of this disclosure. This disclosure will govern in the instance that there is any inconsistency between the patents, patent applications and publications cited and this disclosure.

Definitions

Listed below are definitions of various terms used in the specification and claims to describe the present disclosure.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, exemplary methods, and materials are described herein.

As used herein, the term "and/or" includes any and all combinations of one or more of the associated listed items. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

As used in the specification and the appended claims, the singular forms "a," "an" and "the" include plural referents unless the context clearly dictates otherwise.

The term "about" when immediately preceding a numerical value means a range of plus or minus an acceptable degree of variation in the art. In some embodiments, the term "about" encompasses 10% of that value, e.g., "about 50" means 45 to 55, "about 25,000" means 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 50.5. Furthermore, the phrases "less than about" a value or "greater than about" a value should be understood in view of the definition of the term "about" provided herein.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The terms below, as used herein, have the following meanings, unless indicated otherwise:

"Azido" or "azide" refers to $—N_3$ group.

"Cyano" refers to the —CN radical.

"Hydroxy" or "hydroxyl" refers to the —OH radical.

"Oxo" refers to the =O substituent.

"Halo" or "halogen" refers to fluorine (fluoro, —F), chlorine (chloro, —Cl), bromine (bromo, —Br), or iodine (iodo, —I).

"Alkyl" or "alkyl group" refers to a fully saturated, straight or branched hydrocarbon chain group, which is attached to the rest of the molecule by a single bond. Alkyls comprising any number of carbon atoms, including but not limited to from 1 to 12 are included. For example, "$C_1$ to $C_6$ alkyl" or "$C_{1-6}$ alkyl" denotes alkyl chain having 1 to 6 carbon atoms. The alkyl groups typically include $C_1$ to $C_{21}$, for example $C_1$, $C_2$, $C_3$, $C_4$, $C_5$, $C_6$, $C_7$, $C_8$, $C_9$, $C_{10}$, $C_{11}$, $C_{12}$, and specifically includes, but is not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, 2,3-dimethylbutyl, 2-ethylhexyl, n-heptyl, n-octyl, n-nonyl, 3,7-dimethyloctyl, n-decyl, n-undecyl, n-dodecyl, n-tridecyl, and 2-propylheptyl. Unless stated otherwise, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. The double bond of an alkenyl group can be unconjugated or conjugated to another unsaturated group. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Exemplary alkenyl groups include, but are not limited to, ethenyl, 1-propenyl, 2-propenyl (or "allyl"), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, butadienyl, pentadienyl, hexadienyl, 2-ethylhexenyl, 2-propyl-2-butenyl, 4-(2-methyl-3-ethenyl)-pentenyl. Unless stated otherwise specifically in the specification, an alkenyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. The triple bond of an alkynyl group can be unconjugated or conjugated to another unsaturated group. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of alkynyl group include 1-propynyl, 2-propynyl (i.e., propargyl), 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonynyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, 2-ethylhexynyl, 4-(2-methyl-3-ethynyl)-pentynyl, and the like. In particular, "propargyl" refers to $—CH_2—C≡CH$ group. Unless stated otherwise specifically in the specification, an alkynyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula $—OR_a$ where $R_a$ is an alkyl, alkenyl or alkynyl radical as defined above containing one to twelve carbon atoms. Unless stated otherwise specifically in the specification, an alkoxy group can be optionally substituted.

"Aryl" refers to a substituent that is derived from an aromatic hydrocarbon (arene) that has had a hydrogen atom removed from a ring carbon atom. Non-limiting examples of aryl includes phenyl, biphenyl, naphthyl, anthracenyl, and the like. Unless stated otherwise specifically in the specification, the term "aryl" is meant to include aryl radicals that are optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include cycloalkyl, cycloalkenyl and cycloalkynyl as defined herein. Unless stated otherwise specifically in the specification, a carbocyclyl group can be optionally substituted.

"Cycloalkyl" refers to cyclized alkyl groups having from three to twenty carbon atoms, e.g., having from three to nine carbon atoms, which can include fused, bridged, or spiro ring systems. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused, bridged, or spiro ring systems, having from three to twenty carbon atoms, e.g., having from three to nine carbon atoms, and which is attached to the rest of the molecule by a single bond. Monocyclic cycloalkenyl radicals include, for example, cyclopentenyl, cyclohexenyl, cycloheptenyl, cycloctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Heterocyclyl" "heterocyclic ring" or "heterocycle" refers to a stable 3- to 20-membered non-aromatic, saturated or partially unsaturated ring radical which consists of two to twelve carbon ring atoms and from one to six heteroatoms as ring atoms selected from nitrogen, oxygen or sulfur, at least one non-aromatic, saturated or partially unsaturated ring containing at least one heteroatom as a ring atom. Unless stated otherwise specifically in the specification, the heterocyclyl radical can be a monocyclic, bicyclic, tricyclic or tetracyclic ring system, which can include fused, bridged, or spiro ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In embodiments where "L" is heterocyclyl, the heterocyclyl radical is a diradical. Unless stated otherwise specifically in the specification, a heterocyclyl group can be optionally substituted.

"Heterocyclyl" or "heterocyclic" or "heterocycle" as used by itself or as part of another group refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is on the heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like. Unless otherwise stated specifically in the specification, a heterocyclyl can be optionally substituted.

"Heteroaryl" refers to a 5- to 20-membered ring system radical comprising one to thirteen carbon ring atoms, one to six heteroatoms as ring atoms selected from nitrogen, oxygen and sulfur, and at least one aromatic ring containing at least one heteroatom as a ring atom. For purposes of this disclosure, the heteroaryl radical can be a monocyclic, bicyclic, tricyclic or tetracyclic ring system, which can include fused, bridged, or spiro ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophene), benzotriazolyl, benzo[4,6]imidazo[1,2-a]pyridinyl, carbazolyl, cinnolinyl, dibenzofuranyl, dibenzothiophene, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, I-oxidopyridinyl, 1-oxidopyrimidinyl, I-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophene (i.e. thienyl). In embodiments where "X" is heteroarylene, X is a heteroaryl diradical. In particular, "tetrazine" or "tetrazinyl" as used herein refers to 1,2,4,5-tetrazine, e.g.

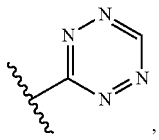
,
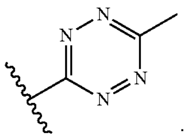
.

Unless stated otherwise specifically in the specification, a heteroaryl group can be optionally substituted.

"Leaving group" refers to a functional group that can be substituted by another functional group during a chemical reaction. Exemplary leaving groups can be found in e.g., *Organic Chemistry*, Francis Carey, $2^{nd}$ edition, pages 328-331, McGraw-Hill Book Company, 1992, incorporated by reference herein. Non-limiting examples of leaving group include

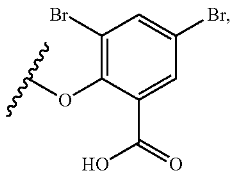
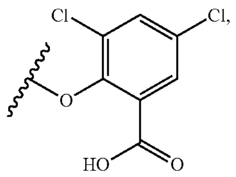

-continued

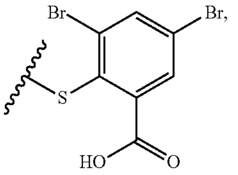

,

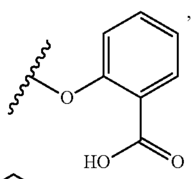

,

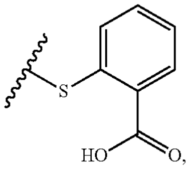

, halogens (e.g., Cl, Br, I), methanesulfonyl (mesyl, Ms), p-toluenesulfonyl (tosyl, Ts), fluoromethanesulfonyl, difluoromethanesulfonyl, trifluoromethylsulfonyl (triflate, Tf), ethanesulfonyl, and diazonium group.

The term "substituted" used herein means any of the above groups (i.e., alkyl, alkylene, alkenyl, alkenylene, alkynyl, alkynylene, alkoxy, alkylamino, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups.

"Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further includes any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group.

In addition, each of the foregoing substituents can also be optionally substituted with one or more of the above substituents.

As used herein, the symbol

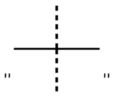

or

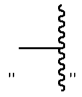

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

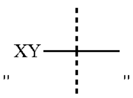

or

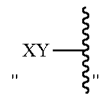

indicates that the chemical entity "XY" is bonded to another chemical entity via the point of attachment bond. Furthermore, the specific point of attachment to the non-depicted chemical entity can be specified by inference.

The term "salt" includes both acid and base addition salts. Salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

As used herein, the term "stereoisomer" refers to isomeric molecules that have the same molecular formula and sequence of bonded atoms (i.e., constitution), but differ in the three-dimensional orientations of their atoms in space. This contrasts with structural isomers, which share the same molecular formula, but the bond connection of their order differs. Molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans- (or E- and Z-) stereoisomers of the compounds of the present disclosure wherein rotation around the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

The present disclosure is intended to encompass deuterated forms of the compounds described herein, which include isotopes of atoms occurring in the compounds. Isotopes include those atoms having the same atomic number but different mass numbers. By way of general example, and without limitation, isotopes of hydrogen include deuterium and tritium, and isotopes of carbon include $^{13}C$ and $^{14}C$. Isotopically labeled compounds of the present disclosure can generally be prepared by conventional techniques known to those skilled in the art or by processes and methods analogous to those described herein, using an appropriate isotopically labeled reagent in place of the non-labeled reagent otherwise employed.

The terms "click chemistry" and "click reaction" are used interchangeably herein and refer to a cycloaddition, which can be 1,3-dipolar cycloaddition or [3+2]cycloaddition between an azide and an alkyne to form a 1,2,3-triazole, or a Diels-Alder reaction. The terms "1,3-dipolar cycloaddition" or "[3+2]cycloaddition" also encompasses "copper-less" 1,3-dipolar cycloadditions between azides and cyclooctynes. The Diels-Alder reaction also encompasses alkene and tetrazine inverse-demand Diels-Alder reaction.

Unless otherwise specified, the term "modified hemoglobin" or "modified Hb" refers to: (i) an intramolecularly crosslinked Hb (e.g., a crosslinked Hb that comprises at least two subunits of the Hb intramolecularly crosslinked with a compound of formula (I)), (ii) a Hb that is functionalized, or (iii) an intramolecularly crosslinked Hb that has been further functionalized (e.g., a crosslinked Hb that further comprises one or more residues functionalized with reactive groups).

As used herein, a reactive group (i.e., a first reactive group) is denoted as "complementary" to another reactive group (i.e., a second reactive group) when the first reactive group reacts with the second reactive group and forms one or more covalent bonds, for example, by oxidation, reduction, substitution, addition, or cycloaddition reaction. For example, "a second reactive group that is complementary to the first reactive group for the click chemistry" means the first and the second reactive groups are capable of reacting with each other via a click chemistry reaction.

As used herein, the term "functionalized" refers to chemically adding a new functional group to a Hb or a modified Hb.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Compounds

In one aspect of the present disclosure, a multifunctional linker compound is provided, and the linker compound is a compound of formula (I), (I-1), (I-2), (I-3), or (I-4), or Table A, or a salt, a stereoisomer, or a deuterated form thereof. These linker compounds can be used for conjugation with proteins including Hemoglobin protein (Hb) e.g., the modified hemoglobins and multimerized hemoglobin compositions disclosed herein, as well as amino acids and peptides, thereby providing crosslinked structures with enhanced stability.

Compounds of Formula (I)

In embodiments, the present disclosure provides a compound of formula (I):

(I)

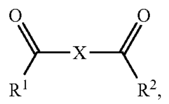

or a salt, a stereoisomer, or a deuterated form thereof, wherein:

X is $C_{1-24}$ alkylene, $C_{2-24}$ alkenylene, $C_{2-24}$ alkynylene, $C_{3-9}$ cycloalkylene, $C_{3-9}$ cycloalkenylene, 5-12 membered heterocyclylene containing 1 or 2 heteroatoms selected from N, S, or O, arylene, heteroarylene, or $-L^1-NR^A-L^2-$, wherein X is optionally substituted with 1-6 $R^3$ as permitted by valency;

$R^1$ and $R^2$ are each independently —OH, halogen, or a leaving group;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-6}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen;

$R^A$ is H, —$C_{1-6}$ alkyl, aryl, —C(O)-aryl, —$SO_2$($C_{1-6}$ alkyl), —$SO_2$-aryl, or —($C_{1-6}$ alkylene)-$(OCH_2CH_2)_m$—$(CH_2)_n$—$N_3$, wherein each alkyl, aryl, or alkylene is optionally and independently substituted with —$C_{1-6}$ alkyl, —OH, —CN, —$NO_2$, or halogen;

$L^1$ and $L^2$ are each independently $C_{1-12}$ alkylene, $C_{2-12}$ alkenylene, $C_{2-12}$ alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each m is independently an integer of 1-200; and each n is independently an integer of 0-50.

$R^1$ and $R^2$

In some embodiments of the compounds of formula (I), or a salt, stereoisomer, or deuterated form thereof, $R^1$ and $R^2$ are each independently —OH, halogen, or a leaving group. In some embodiments, $R^1$ and $R^2$ are each independently halogen (e.g., —F, —Cl, —Br, —I), or a leaving group. In some embodiments, $R^1$ and $R^2$ are each independently a leaving group. In some embodiments, $R^1$ and $R^2$ are the same. In some embodiments, $R^1$ and $R^2$ are different.

In some embodiments of the compounds of formula (I), or a salt, stereoisomer, or deuterated form thereof, $R^1$ and $R^2$ are each independently a leaving group, which is

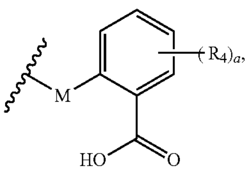

wherein M is O or S, each $R^4$ is independently halogen or $—C_{1-6}$ alkyl, and a is an integer of 0-4. In some embodiments, M is O, and a is 0, and the leaving group is

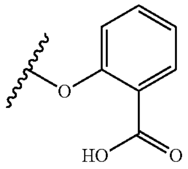 [SMILES: *Oc1ccccc1C(=O)O]

In some embodiments, M is S, and a is 0, and the leaving group is

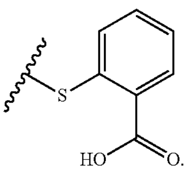 [SMILES: *Sc1ccccc1C(=O)O]

In some embodiments, a is 1, 2, or 3. In some embodiments, each $R^4$ is halogen (—F, —Cl, —Br, —I). In some embodiments, each $R^4$ is independently —F, $—C_1$, or —Br. In some embodiments, a is 2 and each $R^4$ is —Br, and the leaving group is

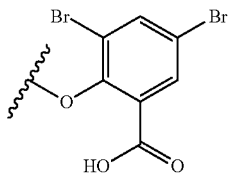

or

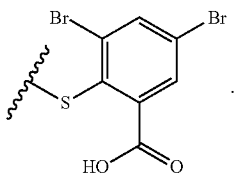 [SMILES: *Sc1c(Br)cc(Br)cc1C(=O)O]

In some embodiments, a is 2 and each $R^4$ is —Cl, and the leaving group is

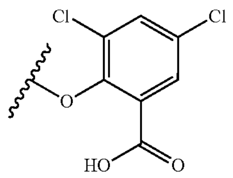

or

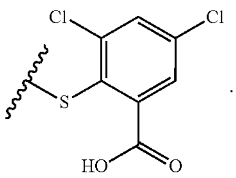

In some embodiments, a is 1, and $R^4$ is —Br, and the leaving group is

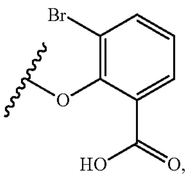

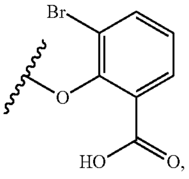

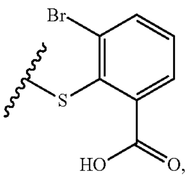

or

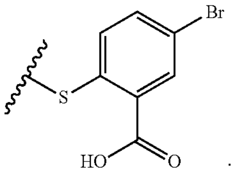

In some embodiments of the compounds of formula (I), or a salt, stereoisomer, or deuterated form thereof, $R^1$ and $R^2$ are

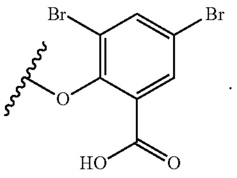

In some embodiments of the compounds of formula (I), or a salt, stereoisomer, or deuterated form thereof, $R^1$ and $R^2$ are

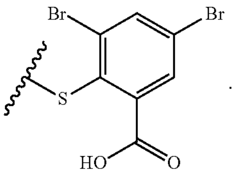

In some embodiments of the compounds of formula (I), or a salt, stereoisomer, or deuterated form thereof, $R^1$ and $R^2$ are

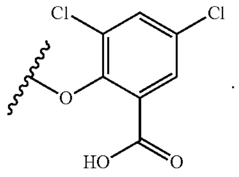 [SMILES: *Oc1c(Cl)cc(Cl)cc1C(=O)O]

In some embodiments of the compounds of formula (I), or a salt, stereoisomer, or deuterated form thereof, $R^1$ and $R^2$ are

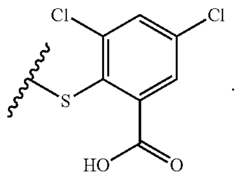

In some embodiments of the compounds of formula (I), or a salt, stereoisomer, or deuterated form thereof, $R^1$ and $R^2$ are

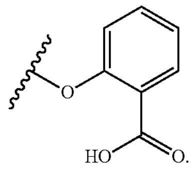 [SMILES: *Oc1ccccc1C(=O)O]

In some embodiments of the compounds of formula (I), or a salt, stereoisomer, or deuterated form thereof, $R^1$ and $R^2$ are

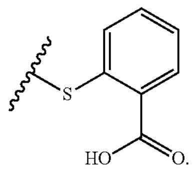 [SMILES: *Sc1ccccc1C(=O)O]

In some embodiments of the compounds of formula (I), or a salt, stereoisomer, or deuterated form thereof, $R^1$ and $R^2$ are each independently a leaving group, which is —O—($C_{1-6}$ alkylene)-$SO_3H$. In some embodiments, $R^1$ and $R^2$ are each independently a leaving group selected from the group consisting of —O—($CH_2$)—$SO_3H$, —O—($CH_2CH_2$)—$SO_3H$, —O—($CH_2CH_2CH_2$)—$SO_3H$, and —O—($CH_2CH_2CH_2CH_2$)—$SO_3H$. In some embodiments, the leaving group is —O—($CH_2CH_2$)—$SO_3H$. In some embodiments of the compounds of formula (I), or a salt, stereoisomer, or deuterated form thereof, $R^1$ and $R^2$ are —O—($CH_2CH_2$)—$SO_3H$.

X

In some embodiments of the compounds of formula (I), or a salt, stereoisomer, or deuterated form thereof, X is $C_{1-24}$ alkylene, $C_{2-24}$ alkenylene, $C_{2-24}$ alkynylene, $C_{3-9}$ cycloalkylene, $C_{3-9}$ cycloalkenylene, 5-12 membered heterocyclylene containing 1 or 2 heteroatoms selected from N, S, or O, arylene, heteroarylene, or -$L^1$-$NR^A$-$L^2$-, wherein X is optionally substituted; $R^A$ is H, —$C_{1-6}$ alkyl, aryl, —C(O)-aryl, —$SO_2$($C_{1-6}$ alkyl), —$SO_2$-aryl, or —($C_{1-6}$ alkylene)-($OCH_2CH_2$)$_m$—($CH_2$)$_n$—$N_3$, wherein each alkyl, aryl, or alkylene is optionally and independently substituted; and $L^1$ and $L^2$ are each independently $C_{1-12}$ alkylene, $C_{2-12}$ alkenylene, $C_{2-12}$ alkynylene, $C_{3-9}$ cycloalkylene, $C_{3-9}$ cycloalkenylene, arylene, or heteroarylene, wherein $L^1$ and $L^2$ are optionally and independently substituted.

In some embodiments, X is optionally substituted with 1-6 $R^3$ as permitted by valency, wherein each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-6}$ alkylene)-$N_3$, —($C_{1-12}$ alkylene)-($OCH_2CH_2$)$_m$—($CH_2$)$_n$—$N_3$, —C(O)NH—($C_{1-12}$ alkylene)-($OCH_2CH_2$)$_m$—($CH_2$)$_n$—$N_3$, —NHC(O)—($C_{1-12}$ alkylene)-($OCH_2CH_2$)$_m$—($CH_2$)$_n$—$N_3$, —O—($C_{1-12}$ alkylene)-($OCH_2CH_2$)$_m$—($CH_2$)$_n$—$N_3$, —S—($C_{1-12}$ alkylene)-($OCH_2CH_2$)$_m$—($CH_2$)$_n$—$N_3$, or —C(O)—$R^1$, wherein each alkyl or alkylene is optionally and independently substituted with —$C_{1-6}$ alkyl, —OH, —CN, —$NO_2$, or halogen. In some embodiments, $R^1$ is —OH, halogen, or a leaving group. In some embodiments, each m is independently an integer in a range of 1-200, 2-175, 3-150, 4-125, 5-100, 6-75, 7-50, 8-45, 9-40, 10-35, 11-30, 12-25, 13-22, 14-20, 15-18, or 16-17. In some embodiments, each n is independently an integer in a range of 0-50, 1-40, 2-35, 3-30, 4-25, 5-20, 6-18, 7-16, 8-14, 9-12, or 10-11.

In some embodiments, X is -$L^1$-$NR^A$-$L^2$-. In some embodiments, each alkyl, aryl, or alkylene of $R^A$ is optionally and independently substituted with —$C_{1-6}$ alkyl, —OH, —CN, —$NO_2$, or halogen. In some embodiments, $L^1$ and $L^2$ are optionally and independently substituted with 1-3 $R^3$ as permitted by valency, wherein each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-6}$ alkylene)-$N_3$, —($C_{1-12}$ alkylene)-($OCH_2CH_2$)$_m$—($CH_2$)$_n$—$N_3$, —C(O)NH—($C_{1-12}$ alkylene)-($OCH_2CH_2$)$_m$—($CH_2$)$_n$—$N_3$, —NHC(O)—($C_{1-12}$ alkylene)-($OCH_2CH_2$)$_m$—($CH_2$)$_n$—$N_3$, —O—($C_{1-12}$ alkylene)-($OCH_2CH_2$)$_m$—($CH_2$)$_n$—$N_3$, —S—($C_{1-12}$ alkylene)-($OCH_2CH_2$)$_m$—($CH_2$)$_n$—$N_3$, or —C(O)—$R^1$, wherein each alkyl or alkylene is optionally and independently substituted with —$C_{1-6}$ alkyl, —OH, —CN, —$NO_2$, or halogen. In some embodiments, $R^1$ is —OH, halogen, or a leaving group. In some embodiments, each m is independently an integer in a range of 1-200, 2-175, 3-150, 4-125, 5-100, 6-75, 7-50, 8-45, 9-40, 10-35, 11-30, 12-25, 13-22, 14-20, 15-18, or 16-17. In some embodiments, each n is independently an integer in a range of 0-100, 1-50, 2-40, 2-35, 3-30, 4-25, 5-20, 6-18, 7-16, 8-14, 9-12, or 10-11.

(i) Alkylene, Alkenylene, or Alkynylene as X

In some embodiments of the compounds of formula (I), or a salt, stereoisomer, or deuterated form thereof, X is $C_{1-12}$ alkylene, $C_{2-12}$ alkenylene, or $C_{2-12}$ alkynylene, each of which is optionally substituted with 1-6 $R^3$ as permitted by valency. In some embodiments, each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-6}$ alkylene)-$N_3$, —($C_{1-12}$ alkylene)-($OCH_2CH_2$)$_m$—($CH_2$)$_n$—$N_3$, —C(O)NH—($C_{1-12}$ alkylene)-($OCH_2CH_2$)$_m$—($CH_2$)$_n$—$N_3$, —NHC(O)—($C_{1-12}$ alkylene)-($OCH_2CH_2$)$_m$—($CH_2$)$_n$—$N_3$, —O—($C_{1-12}$ alkylene)-($OCH_2CH_2$)$_m$—($CH_2$)$_n$—$N_3$, —S—($C_{1-12}$ alkylene)-($OCH_2CH_2$)$_m$—($CH_2$)$_n$—$N_3$, or —C(O)—$R^1$, wherein each alkyl or alkylene is optionally and independently substituted with —$C_{1-6}$ alkyl, —OH, —CN, —$NO_2$, or halogen.

In some embodiments, X is $C_{1-12}$ alkylene, $C_{2-11}$ alkylene, $C_{3-10}$ alkylene, $C_{4-9}$ alkylene, $C_{5-8}$ alkylene, or $C_{6-7}$ alkylene, each of which is optionally substituted with 1-6, 2-5, or 3-4 $R^3$ as permitted by valency. In some embodiments, X is $C_{2-12}$ alkenylene, $C_{3-10}$ alkenylene, $C_{4-10}$ alkenylene, $C_{5-9}$ alkenylene, $C_{6-8}$ alkenylene, or $C_7$ alkenylene, each of which is optionally substituted with 1-6, 2-5, or 3-4 $R^3$ as permitted by valency. In some embodiments, X is $C_{2-12}$ alkynylene, $C_{3-11}$ alkynylene, $C_{4-10}$ alkynylene, $C_{5-9}$ alkynylene, $C_{6-8}$ alkynylene, or $C_7$ alkynylene, each of which is optionally substituted with 1-6, 2-5, or 3-4 $R^3$ as permitted by valency. In some embodiments, X is unsubstituted $C_{1-12}$ alkylene, $C_{2-12}$ alkenylene, or $C_{2-12}$ alkynylene. In some embodiments, X is straight (i.e., unbranched) $C_{1-12}$ alkylene, $C_{2-12}$ alkenylene, or $C_{2-12}$ alkynylene.

In some embodiments of the compounds of formula (I), or a salt, stereoisomer, or deuterated form thereof, X is $C_{1-6}$ alkylene, $C_{2-6}$ alkenylene, or $C_{2-6}$ alkynylene, each of which is optionally substituted with 1 or 2 $R^3$ as permitted by valency. In some embodiments, X is unsubstituted $C_{1-6}$ alkylene, $C_{2-6}$ alkenylene, or $C_{2-6}$ alkynylene. In some embodiments, X is straight $C_{1-6}$ alkylene, $C_{2-6}$ alkenylene, or $C_{2-6}$ alkynylene.

In some embodiments of the compounds of formula (I), or a salt, stereoisomer, or deuterated form thereof, X is $C_{1-6}$ alkylene optionally substituted with 1 or 2 $R^3$ as permitted by valency. In some embodiments, X is unsubstituted $C_{1-6}$ alkylene. In some embodiments, X is straight $C_{1-6}$ alkylene. In some embodiments, X is

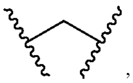,
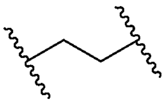,
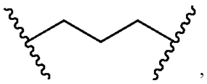,
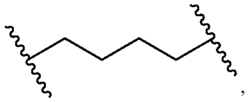,
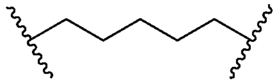, or
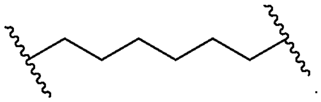.

In some embodiments, X is

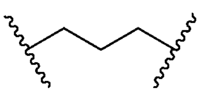.

In some embodiments of the compounds of formula (I), or a salt, stereoisomer, or deuterated form thereof, X is $C_{2-6}$ alkenylene optionally substituted with 1 or 2 $R^3$ as permitted by valency. In some embodiments, X is unsubstituted $C_{2-6}$ alkenylene. In some embodiments, X is straight $C_{2-6}$ alkenylene. In some embodiments, X is

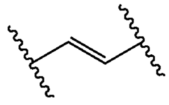 or 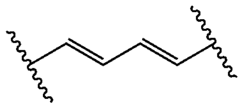.

In some embodiments, X is

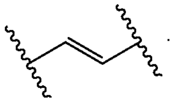.

In some embodiments of the compounds of formula (I), or a salt, stereoisomer, or deuterated form thereof, X is $C_{2-6}$ alkynylene optionally substituted with 1 or 2 $R^3$ as permitted by valency. In some embodiments, X is unsubstituted $C_{2-6}$ alkynylene. In some embodiments, X is straight $C_{2-6}$ alkynylene. In some embodiments, X is

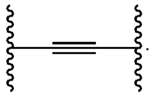.

In some embodiments of the compounds of formula (I), or a salt, stereoisomer, or deuterated form thereof, X is $C_{1-6}$ alkylene, $C_{2-6}$ alkenylene, or $C_{2-6}$ alkynylene, each of which is substituted with $—S—(C_{1-6}$ alkylene$)-(OCH_2CH_2)_m—(CH_2)_n—N_3$, $—O—(C_{1-6}$ alkylene$)-(OCH_2CH_2)_m—(CH_2)_n—N_3$, or $—(CH_2)_n—N_3$, and wherein each m is independently an integer of 1-50, 2-40, 3-30, 4-25, 5-20, 6-18, 7-16, 8-14, 9-12, or 10-11, and each n is independently an integer of 0-25, 1-20, 2-15, 3-10, 4-8, or 5-7.

In some embodiments, X is $C_{1-6}$ alkylene substituted with $—S—(C_{1-6}$ alkylene$)-(OCH_2CH_2)_m—(CH_2)_n—N_3$, and wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In some embodiments, X is

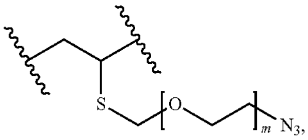, and wherein m is an integer of 1-25, 2-20, 3-15, 4-10, or 5-8. In some embodiments, m is 3-8, 4-7, or 5-6. In some embodiments, X is

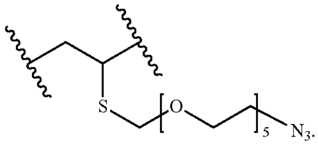.

In some embodiments, X is $C_{1-6}$ alkylene substituted with $—(CH_2)_n—N_3$, wherein n is an integer of 0-25, 1-20, 2-15, 3-10, 4-8, or 5-7. In some embodiments, n is 7, and X is

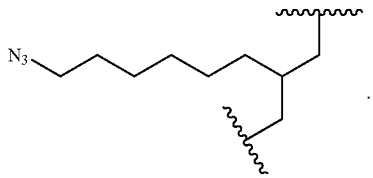 [SMILES: *CC(C*)CCCCCCN=[N+]=[N-]].

(ii) Cycloalkylene, Cycloalkenylene, or Heterocyclylene as X

In some embodiments of the compounds of formula (I), or a salt, stereoisomer, or deuterated form thereof, X is $C_{3-9}$ cycloalkylene, $C_{3-9}$ cycloalkenylene, or 5-12 membered heterocyclylene, each of which is optionally substituted with 1 or 2 $R^3$ as permitted by valency. In some embodiments, each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-6}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen. In some embodiments, X is unsubstituted $C_{3-9}$ cycloalkylene, $C_{3-9}$ cycloalkenylene, or 5-12 membered heterocyclylene.

In some embodiments, X is $C_{3-9}$ cycloalkylene, $C_{4-8}$ cycloalkylene, $C_{5-7}$ cycloalkylene, or $C_6$ cycloalkylene, each of which is optionally substituted with 1 or 2 $R^3$ as permitted by valency.

In some embodiments, X is $C_{3-9}$ cycloalkenylene, $C_{4-8}$ cycloalkenylene, $C_{5-7}$cycloalkenylene, or $C_6$ cycloalkenylene, each of which is optionally substituted with 1 or 2 $R^3$ as permitted by valency. In some embodiments, X is 5-12 membered, 6-11 membered, 7-10 membered, or 8-9 membered heterocyclylene containing a heteroatom which is S, O, or N, each of which is optionally substituted with 1 or 2 $R^3$ as permitted by valency.

In some embodiments of the compounds of formula (I), or a salt, stereoisomer, or deuterated form thereof, X is $C_{3-7}$ cycloalkylene or $C_{4-6}$ cycloalkylene optionally substituted with 1 or 2 $R^3$ as permitted by valency. In some embodiments, X is unsubstituted $C_{3-7}$ cycloalkylene or $C_{4-6}$ cycloalkylene. In some embodiments, X is

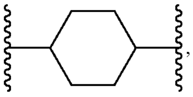,
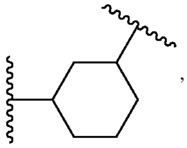, or
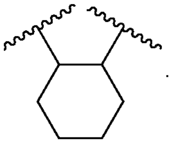.

In some embodiments of the compounds of formula (I), or a salt, stereoisomer, or deuterated form thereof, X is $C_{3-7}$ cycloalkenylene or $C_{4-6}$ cycloalkenylene optionally substituted with 1 or 2 $R^3$ as permitted by valency. In some embodiments, X is unsubstituted $C_{3-7}$cycloalkenylene or $C_{4-6}$ cycloalkenylene. In some embodiments, X is

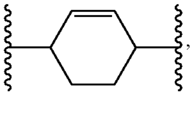,
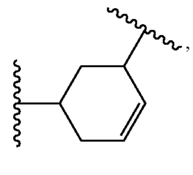,

-continued

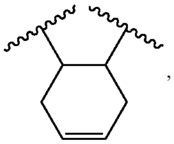,
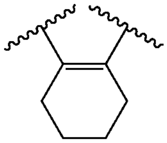, or
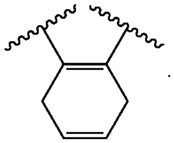.

In some embodiments of the compounds of formula (I), or a salt, stereoisomer, or deuterated form thereof, X is $C_{3-7}$ cycloalkenylene or $C_{4-6}$ cycloalkenylene substituted with —($C_{1-12}$ alkylene)-$N_3$, —($C_{1-9}$ alkylene)-$N_3$, —($C_{1-6}$ alkylene)-$N_3$, —($C_{2-5}$ alkylene)-$N_3$, or —($C_{3-4}$ alkylene)-$N_3$. In some embodiments, X is

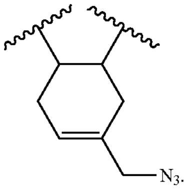 [SMILES: *C1CC=C(CN=[N+]=[N-])CC1*]

In some embodiments of the compounds of formula (I), or a salt, stereoisomer, or deuterated form thereof, X is a 5-12 membered, 6-11 membered, 7-10 membered, or 8-9 membered heterocyclylene containing a heteroatom which is S or O, and wherein the heterocyclylene is optionally substituted. In some embodiments, the heterocyclylene is optionally substituted with —($C_{1-6}$ alkylene)-$N_3$. In some embodiments, X is a 6-10 membered, or 7-9 membered heterocyclylene containing O, and wherein the heterocyclylene is substituted with —($C_{1-6}$ alkylene)-$N_3$. In some embodiments, X is

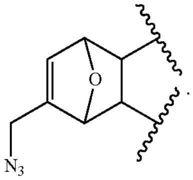 [SMILES: *C1C2C=C(CN=[N+]=[N-])C(O2)C1*]

(iii) Arylene or Heteroarylene as X

In some embodiments of the compounds of formula (I), or a salt, stereoisomer, or deuterated form thereof, X is arylene or heteroarylene, each of which is optionally substituted with 1 or 2 $R^3$ as permitted by valency.

In some embodiments of the compounds of formula (I), or a salt, stereoisomer, or deuterated form thereof, X is $C_{6-10}$ arylene that is optionally substituted. In some embodiments, X is $C_{6-10}$ arylene that is optionally substituted with 1 or 2 $R^3$ as permitted by valency.

In embodiments, X is unsubstituted $C_{6-10}$ arylene. In some embodiments, X is

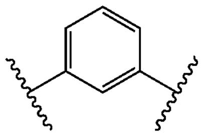

or

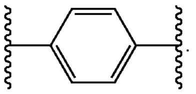

In embodiments, X is substituted $C_{6-10}$ arylene.

In embodiments, X is $C_{6-10}$ arylene substituted with —C(O)—$R^1$, and wherein $R^1$ is —OH, halogen, or a leaving group. In some embodiments, $R^1$ is a leaving group. In some embodiments, $R^1$ is a leaving group which is

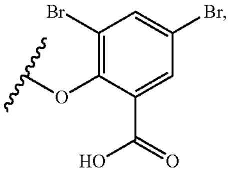

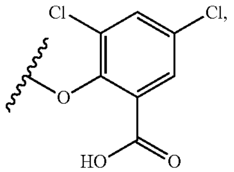

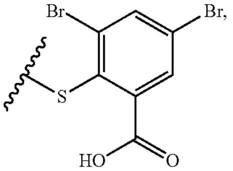

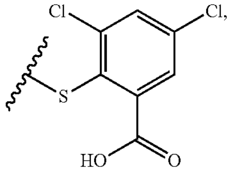

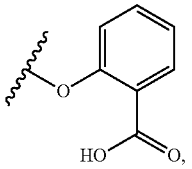

or

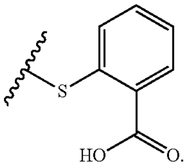

In some embodiments, X is

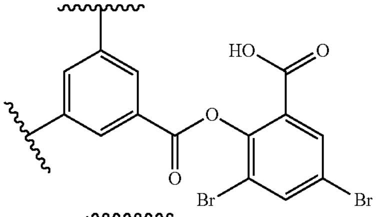

or

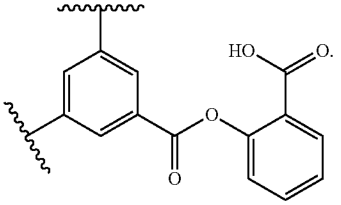

In embodiments, X is $C_{6-10}$ arylene substituted with —C(O)NH—($C_{1-12}$ alkylene)-$(OCH_2CH_2)_m$—$(CH_2)_n$—$N_3$, or —NHC(O)—($C_{1-12}$ alkylene)-$(OCH_2CH_2)_m$—$(CH_2)_n$—$N_3$, and wherein each m is independently an integer of 1-200, 2-175, 3-150, 4-125, 5-100, 6-75, 7-50, 8-45, 9-40, 10-35, 11-30, 12-25, 13-22, 14-20, 15-18, or 16-17, and each n is independently an integer of 0-100, 1-50, 2-40, 3-30, 4-25, 5-20, 6-18, 7-16, 8-14, 9-12, or 10-11.

In embodiments, X is $C_{6-10}$ arylene substituted with —C(O)NH—($C_{1-6}$ alkylene)-$(OCH_2CH_2)_m$—$N_3$, and wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In embodiments, X is

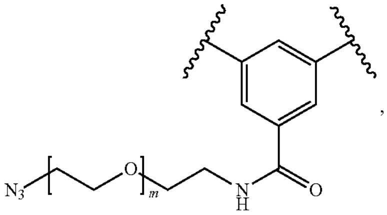

, and wherein m is an integer of 2-50, 3-25, or 4-10. In embodiments, X is

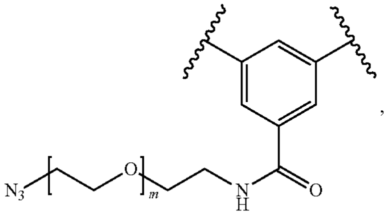

, and wherein m is 4. In embodiments, X is

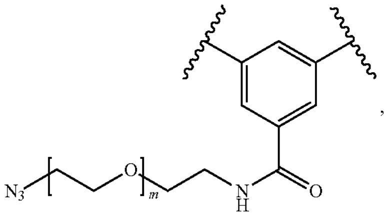

, and wherein m is 9.

In embodiments, X is $C_{6-10}$ arylene substituted with —NHC(O)—($C_{1-6}$ alkylene)-$(OCH_2CH_2)_m$—$N_3$, and wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In embodiments, X is

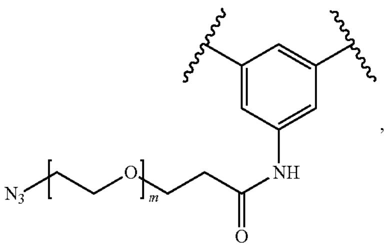

, and wherein m is an integer of 2-50, 3-25, or 4-10. In embodiments, X is

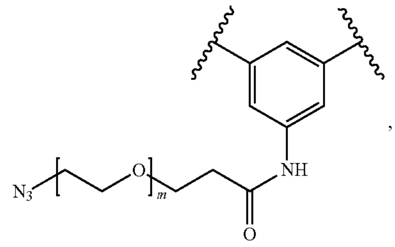

, and wherein m is 4. In embodiments, X is

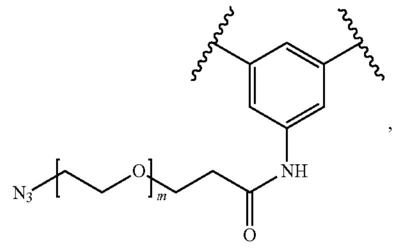

, and wherein m is 9.

(iv) $-L^1-NR^A-L^2-$ as X

In some embodiments of the compounds of formula (I), or a salt, stereoisomer, or deuterated form thereof, X is $-L^1-NR^A-L^2-$, and wherein: $R^A$ is H, $-C_{1-6}$ alkyl, aryl, $-C(O)$-aryl, $-SO_2(C_{1-6}$ alkyl), $-SO_2$-aryl, or $-(C_{1-12}$ alkylene)-$(OCH_2CH_2)_m-(CH_2)_n-N_3$, wherein m is an integer of 1-50, 2-40, 3-30, 4-25, 5-20, 6-18, 7-16, 8-14, 9-12, or 10-11, n is an integer of 0-25, 1-20, 2-15, 3-10, 4-8, or 5-7, and each alkyl, aryl, or alkylene is optionally and independently substituted; and $L^1$ and $L^2$ are each independently $C_{1-6}$ alkylene, $C_{2-6}$alkenylene, $C_{2-6}$alkynylene, $C_{3-6}$cycloalkylene, $C_{3-6}$cycloalkenylene, arylene, or heteroarylene, wherein $L^1$ and $L^2$ are optionally and independently substituted. In embodiments, each alkyl, aryl, or alkylene of $R^A$ is optionally and independently substituted with $-C_{1-6}$ alkyl. In embodiments, $L^1$ and $L^2$ are optionally and independently substituted with 1-3 $R^3$. In some embodiments, each $R^3$ is independently $-OH$, $-CN$, $-NO_2$, halogen, oxo, $-C_{1-6}$ alkyl, $-C_{1-6}$ haloalkyl, $-O(C_{1-6}$ alkyl), $-S(C_{1-6}$ alkyl), $-SO(C_{1-6}$ alkyl), $-SO_2(C_{1-6}$ alkyl), $-(C_{1-6}$ alkylene)-$N_3$, $-(C_{1-12}$ alkylene)-$(OCH_2CH_2)_m-(CH_2)_n-N_3$, $-C(O)NH-(C_{1-12}$ alkylene)-$(OCH_2CH_2)_m-(CH_2)_n-N_3$, $-NHC(O)-(C_{1-2}$ alkylene)-$(OCH_2CH_2)_m-(CH_2)_n-N_3$, $-O-(C_{1-12}$ alkylene)-$(OCH_2CH_2)_m-(CH_2)_n-N_3$, $-S-(C_{1-12}$ alkylene)-$(OCH_2CH_2)_m-(CH_2)_n-N_3$, or $-C(O)-R^1$, wherein each alkyl or alkylene is optionally and independently substituted with $-C_{1-6}$ alkyl, $-OH$, $-CN$, $-NO_2$, or halogen.

In embodiments, $L^1$ and $L^2$ are the same. In embodiments, $L^1$ and $L^2$ are different.

In embodiments, $R^A$ is H. In embodiments, $L^1$ and $L^2$ are each independently $C_{1-6}$ alkylene or $C_{2-6}$ alkenylene. In embodiments, $R^A$ is H, and $L^1$ and $L^2$ are each independently $C_{1-6}$ alkylene or $C_{2-6}$ alkenylene. In embodiments, $L^1$ and $L^2$ are $C_{1-6}$ alkylene, $C_{2-5}$ alkylene, or $C_{3-4}$ alkylene. In embodiments, $L^1$ and $L^2$ are $-CH_2-$. In embodiments, X is

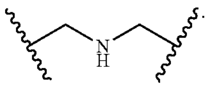 [SMILES: *CNC*]

In embodiments, $R^A$ is $C_{6-10}$ aryl, and wherein the aryl of $R^A$ is optionally substituted. In embodiments, the aryl of $R^A$ is optionally substituted with $-C_{1-6}$ alkyl. In embodiments, $L^1$ and $L^2$ are each independently $C_{1-6}$ alkylene, or $C_{2-6}$ alkenylene. In embodiments, $R^A$ is $C_{6-10}$ aryl, and $L^1$ and $L^2$ are each independently $C_{1-6}$ alkylene, or $C_{2-6}$ alkenylene, and wherein the aryl of $R^A$ is optionally substituted with $-C_{1-6}$ alkyl. In embodiments, $R^A$ is phenyl. In embodiments, $L^1$ and $L^2$ are $C_{1-6}$ alkylene, $C_{2-5}$ alkylene, or $C_{3-4}$ alkylene. In embodiments, $L^1$ and $L^2$ are $-CH_2-$. In embodiments, X is

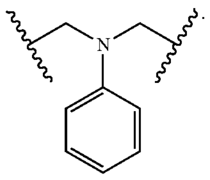 [SMILES: *CN(C*)c1ccccc1]

In embodiments, $R^A$ is $-SO_2-C_{1-6}$ alkyl. In embodiments, $L^1$ and $L^2$ are each independently $C_{1-6}$ alkylene, or $C_{2-6}$alkenylene. In embodiments, $R^A$ is $-SO_2-C_{1-6}$ alkyl, and $L^1$ and $L^2$ are each independently $C_{1-6}$ alkylene, or $C_{2-6}$ alkenylene. In embodiments, $R^A$ is $-SO_2-CH_3$. In embodiments, $L^1$ and $L^2$ are $C_{1-6}$ alkylene, $C_{2-5}$ alkylene, or $C_{3-4}$ alkylene. In embodiments, $L^1$ and $L^2$ are $-CH_2-$. In embodiments, X is

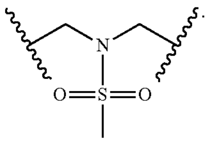 [SMILES: *CN(C*)S(C)(=O)=O]

In embodiments, $R^A$ is $-SO_2-C_{6-10}$ aryl, wherein the aryl of $R^A$ is optionally substituted. In embodiments, the aryl of $R^A$ is optionally substituted with $-C_{1-6}$ alkyl. In some embodiments, $L^1$ and $L^2$ are each independently $C_{1-6}$ alkylene, or $C_{2-6}$ alkenylene. In embodiments, $R^A$ is $-SO_2-C_{6-10}$ aryl, wherein the aryl of $R^A$ is optionally substituted with $-C_{1-6}$ alkyl, and $L^1$ and $L^2$ are each independently $C_{1-6}$ alkylene, or $C_{2-6}$ alkenylene. In embodiments, $R^A$ is

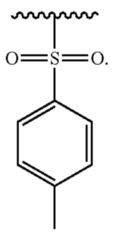

In embodiments, $L^1$ and $L^2$ are $C_{1-6}$ alkylene, $C_{2-5}$ alkylene, or $C_{3-4}$ alkylene. In embodiments, $L^1$ and $L^2$ are $-CH_2-$. In embodiments, X is

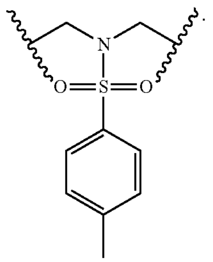 [SMILES: *CN(C*)S(=O)(=O)c1ccc(C)cc1]

In embodiments, $R^A$ is $-C(O)-C_{6-10}$ aryl, wherein the aryl of $R^A$ is optionally substituted. In some embodiments, the aryl of $R^A$ is optionally substituted with $-C_{1-6}$ alkyl. In embodiments, $L^1$ and $L^2$ are independently $C_{1-6}$ alkylene, or $C_{2-6}$ alkenylene. In embodiments, $R^A$ is $-C(O)-C_{6-10}$ aryl, wherein the aryl of $R^A$ is optionally substituted with $-C_{1-6}$ alkyl, and $L^1$ and $L^2$ are each independently $C_{1-6}$ alkylene, or $C_{2-6}$alkenylene. In embodiments, $R^A$ is

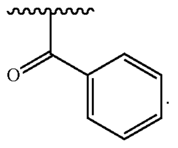 [SMILES: *C(=O)c1ccccc1]

In embodiments, $L^1$ and $L^2$ are $C_{1-6}$ alkylene, $C_{2-5}$ alkylene, or $C_{3-4}$ alkylene. In embodiments, $L^1$ and are $-CH_2-$. In embodiments, X is

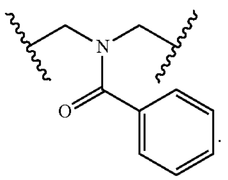 [SMILES: *CN(C*)C(=O)c1ccccc1]

In embodiments, $R^A$ is $-(C_{1-6}$ alkylene$)-(OCH_2CH_2)_m-(CH_2)_n$, $-N_3$, wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In embodiments, $L^1$ and $L^2$ are each independently $C_{1-6}$ alkylene, or $C_{2-6}$ alkenylene. In embodiments, $R^A$ is $-(C_{1-6}$ alkylene$)-(OCH_2CH_2)_m-(CH_2)_n-N_3$, and $L^1$ and $L^2$ are each independently $C_{1-6}$ alkylene, or $C_{2-6}$ alkenylene, wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In embodiments, n is 0. In embodiments, $R^A$ is

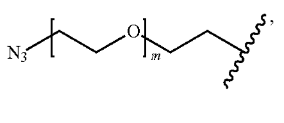

wherein m is 1-12, 2-6, or 3-5. In embodiments, $L^1$ and $L^2$ are $C_{1-6}$ alkylene, $C_{2-5}$ alkylene, or $C_{3-4}$ alkylene. In embodiments, $L^1$ and $L^2$ are $-CH_2-$. In embodiments, X is

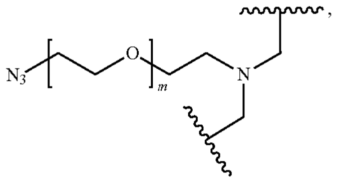

and m is 3.

Compounds of Formula (I-1)

In embodiments, the present disclosure provides a compound of formula (I-1):

(I-1)

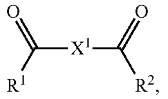

or a salt, a stereoisomer, or a deuterated form thereof, wherein:

$X^1$ is arylene or heteroarylene, wherein $X^1$ is optionally substituted with 1 or 2 $R^3$ as permitted by valency;

$R^1$ and $R^2$ are each independently a leaving group;

each $R^3$ is independently $-OH$, $-CN$, $-NO_2$, halogen, oxo, $-C_{1-6}$ alkyl, $-C_{1-6}$ haloalkyl, $-O(C_1$-6 alkyl), $-S(C_{1-6}$ alkyl), $-SO(C_{1-6}$ alkyl), $-SO_2(C_{1-6}$ alkyl), $-(C_{1-12}$ alkylene$)-N_3$, $-(C_{1-12}$ alkylene$)-(OCH_2CH_2)_m-(CH_2)_n-N_3$, $-C(O)NH-(C_{1-12}$ alkylene$)-(OCH_2CH_2)_m-(CH_2)_n-N_3$, $-NHC(O)-(C_{1-12}$ alkylene$)-(OCH_2CH_2)_m-(CH_2)_n-N_3$, $-O-(C_{1-12}$ alkylene$)-(OCH_2CH_2)_m-(CH_2)_n-N_3$, $-S-(C_{1-12}$ alkylene$)-(OCH_2CH_2)_m-(CH_2)_n-N_3$, or $-C(O)-R^1$, wherein each alkyl or alkylene is optionally and independently substituted with $-C_{1-6}$ alkyl, $-OH$, $-CN$, $-NO_2$, or halogen;

each m is independently an integer of 1-200; and each n is independently an integer of 0-50.

In embodiments of the compounds of formula (I-1), or a salt, stereoisomer, or deuterated form thereof, if $X^1$ is

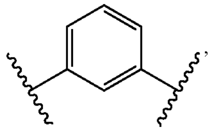 [SMILES: *c1cccc(*)c1]

then the leaving group is not

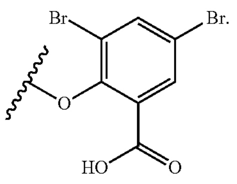 [SMILES: *Oc1c(Br)cc(Br)cc1C(=O)O]

In embodiments of the compounds of formula (I-1), or a salt, stereoisomer, or deuterated form thereof, if $X^1$ is an arylene substituted with 1 $R^3$, then $R^3$ is different from $-C(O)-R^1$ or $-C(O)-R^2$.

In embodiments, the compound of formula (I-1), or a salt, or a stereoisomer thereof, comprises one or more $^{13}C$ isotopes of carbon atoms occurring in the compound.

In embodiments of the compounds of formula (I-1), or a salt, stereoisomer, or deuterated form thereof, $X^1$ is $C_{6-10}$ arylene that is optionally substituted. In some embodiments, $X^1$ is $C_{6-10}$ arylene that is optionally substituted with 1 or 2 $R^3$ as permitted by valency.

In embodiments, $X^1$ is unsubstituted $C_{6-10}$ arylene. In some embodiments, $X^1$ is

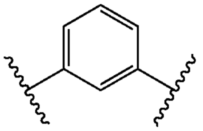

or

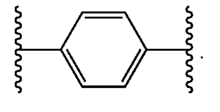

In embodiments, $X^1$ is substituted $C_{6-10}$ arylene. In embodiments, $X^1$ is $C_{6-10}$ arylene substituted with —C(O)—$R^1$, and wherein $R^1$ is —OH, halogen, or a leaving group. In some embodiments, $R^1$ is a leaving group. In some embodiments, $R^1$ is a leaving group which is

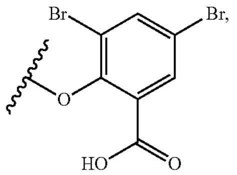

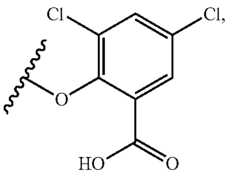

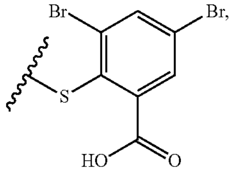

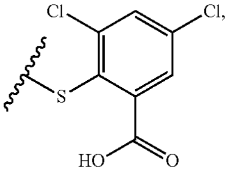

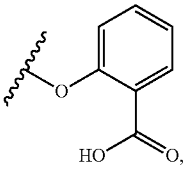

or

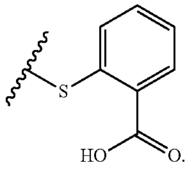

In some embodiments, $X^1$ is

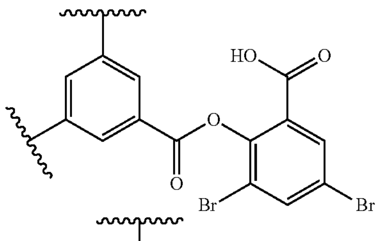

or

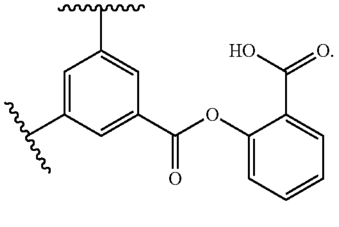

In embodiments, $X^1$ is $C_{6-10}$ arylene substituted with —C(O)NH—($C_{1-12}$ alkylene)-$(OCH_2CH_2)_m$—$(CH_2)_n$—$N_3$, or —NHC(O)—($C_{1-12}$ alkylene)-$(OCH_2CH_2)_m$—$(CH_2)_n$—$N_3$, and wherein each m is independently an integer of 1-200, and each n is independently an integer of 0-100. In embodiments, each m is independently an integer of 1-200, 2-175, 3-150, 4-125, 5-100, 6-75, 7-50, 8-45, 9-40, 10-35, 11-30, 12-25, 13-22, 14-20, 15-18, or 16-17. In embodiments, each n is independently an integer of 0-100, 1-50, 2-40, 3-30, 4-25, 5-20, 6-18, 7-16, 8-14, 9-12, or 10-11.

In embodiments, $X^1$ is $C_{6-10}$ arylene substituted with —C(O)NH—($C_{1-6}$ alkylene)-$(OCH_2CH_2)_m$—$N_3$, and wherein m is an integer of 1-50. In embodiments, m is an integer of 1-50, 2-50, 2-40, 3-30, 4-25, 5-20, 6-18, 7-16, 8-14, 9-12, or 10-11. In embodiments, $X^1$ is

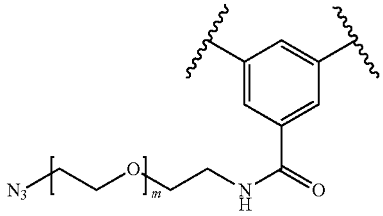

, and wherein m is an integer of 2-50, 3-25, or 4-10. In embodiments, $X^1$ is

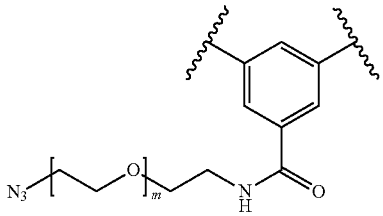

, and wherein m is 4. In embodiments, $X^1$ is

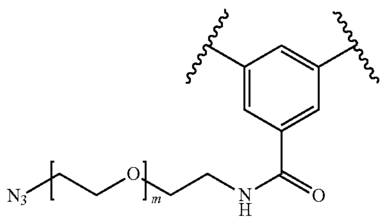

, and wherein m is 9.

In embodiments, $X^1$ is $C_{6-10}$ arylene substituted with —NHC(O)—($C_{1-6}$ alkylene)-$(OCH_2CH_2)_m$—$N_3$, and wherein m is an integer of 1-50. In embodiments, m is an integer of 1-50, 2-40, 3-30, 4-25, 5-20, 6-18, 7-16, 8-14, 9-12, or 10-11. In embodiments, $X^1$ is

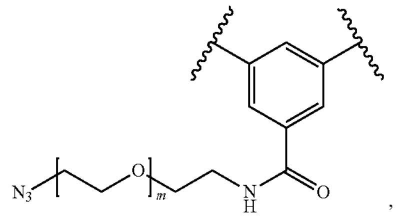

, and wherein m is an integer of 2-50, 3-25, or 4-10. In embodiments, $X^1$ is

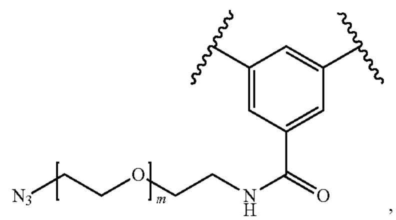

, and wherein m is 4. In embodiments, $X^1$ is

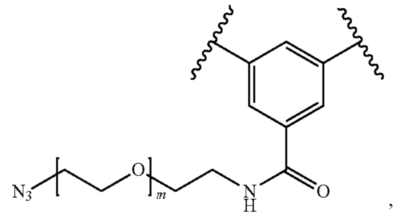

, and wherein m is 9.

Compounds of Formula (I-2)

In embodiments, the present disclosure provides a compound of formula (I-2):

(I-2)

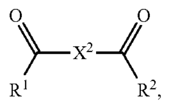

or a salt, a stereoisomer, or a deuterated form thereof, wherein:

$X^2$ is $-L^1-NR^A-L^2-$, $R^1$ and $R^2$ are each independently a leaving group;

$R^A$ is H, $-C_{1-6}$ alkyl, aryl, —C(O)-aryl, $-SO_2(C_{1-6}$ alkyl), $-SO_2$-aryl, or $-(C_{1-6}$ alkylene)-$(OCH_2CH_2)_m-(CH_2)_n-N_3$, wherein each alkyl, aryl, or alkylene is optionally and independently substituted with $-C_{1-6}$ alkyl, —OH, —CN, $-NO_2$, or halogen;

$L^1$ and $L^2$ are each independently $C_{1-12}$ alkylene, $C_{2-12}$alkenylene, $C_{2-12}$alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each $R^3$ is independently —OH, —CN, $-NO_2$, halogen, oxo, $-C_{1-6}$ alkyl, $-C_{1-6}$ haloalkyl, $-O(C_{1-6}$ alkyl), $-S(C_{1-6}$ alkyl), $-SO(C_{1-6}$ alkyl), $-SO_2(C_{1-6}$ alkyl), $-(C_{1-2}$ alkylene)-$N_3$, $-(C_{1-12}$ alkylene)-$(OCH_2CH_2)_m-(CH_2)_n-N_3$, $-C(O)NH-(C_{1-12}$ alkylene)-$(OCH_2CH_2)_m-(CH_2)_n-N_3$, $-NHC(O)-(C_{1-12}$ alkylene)-$(OCH_2CH_2)_m-(CH_2)_n-N_3$, $-O-(C_{1-12}$ alkylene)-$(OCH_2CH_2)_m-(CH_2)_n-N_3$, $-S-(C_{1-12}$ alkylene)-$(OCH_2CH_2)_m-(CH_2)_n-N_3$, or $-C(O)-R^1$, wherein each alkyl or alkylene is optionally and independently substituted with $-C_{1-6}$ alkyl, —OH, —CN, $-NO_2$, or halogen;

each m is independently an integer of 1-200; and each n is independently an integer of 0-50.

In embodiments, the compound of formula (I-2), or a salt, or a stereoisomer thereof, comprises one or more $^{13}C$ isotopes of carbon atoms occurring in the compound.

In embodiments of the compounds of formula (I-2), or a salt, a stereoisomer, or a deuterated form thereof, $R^A$ is H, $-C_{1-6}$ alkyl, aryl, —C(O)-aryl, $-SO_2(C_{1-6}$ alkyl), $-SO_2$-aryl, or $-(C_{1-12}$ alkylene)-$(OCH_2CH_2)_m-(CH_2)_n-N_3$, wherein m is an integer of 1-50, n is an integer of 0-25, and each alkyl, aryl, or alkylene is optionally and independently substituted with $-C_{1-6}$ alkyl; and $L^1$ and $L^2$ are each independently $C_{1-6}$ alkylene, $C_{2-6}$ alkenylene, $C_{2-6}$ alkynylene, $C_{3-6}$ cycloalkylene, $C_{3-6}$ cycloalkenylene, arylene, or heteroarylene, wherein $L^1$ and $L^2$ are optionally and independently substituted with 1-3 $R^3$.

In some embodiments of the compounds of formula (I-2), or a salt, stereoisomer, or deuterated form thereof, $X^2$ is $-L^1-NR^A-L^2-$, and wherein: $R^A$ is H, $-C_{1-6}$ alkyl, aryl, —C(O)-aryl, $-SO_2(C_{1-6}$ alkyl), $-SO_2$-aryl, or $-(C_{1-12}$ alkylene)-$(OCH_2CH_2)_m-(CH_2)_n-N_3$, wherein m is an integer of 1-50, 2-40, 3-30, 4-25, 5-20, 6-18, 7-16, 8-14, 9-12, or 10-11, n is an integer of 0-25, 1-20, 2-15, 3-10, 4-8, or 5-7, and each alkyl, aryl, or alkylene is optionally and independently substituted; and $L^1$ and $L^2$ are each independently $C_{1-6}$ alkylene, $C_{2-6}$ alkenylene, $C_{2-6}$ alkynylene, $C_{3-6}$cycloalkylene, $C_{3-6}$cycloalkenylene, arylene, or heteroarylene, wherein $L^1$ and $L^2$ are optionally and independently substituted. In embodiments, each alkyl, aryl, or alkylene of $R^A$ is optionally and independently substituted with $-C_{1-6}$ alkyl. In embodiments, $L^1$ and $L^2$ are optionally and independently substituted with 1-3 $R^3$. In some embodiments, each $R^3$ is independently —OH, —CN, $-NO_2$, halogen, oxo, $-C_{1-6}$ alkyl, $-C_{1-6}$ haloalkyl, $-O(C_{1-6}$ alkyl), $-S(C_{1-6}$ alkyl), $-SO(C_{1-6}$ alkyl), $-SO_2(C_{1-6}$ alkyl), $-(C_{1-6}$ alkylene)-$N_3$, $-(C_{1-12}$ alkylene)-$(OCH_2CH_2)_m-(CH_2)_n-N_3$, $-C(O)NH-(C_{1-12}$ alkylene)-$(OCH_2CH_2)_m-(CH_2)_n-N_3$, $-NHC(O)-(C_{1-12}$ alkylene)-$(OCH_2CH_2)_m-(CH_2)_n-N_3$, $-O-(C_{1-12}$ alkylene)-$(OCH_2CH_2)_m-(CH_2)_n-N_3$, $-S-(C_{1-12}$ alkylene)-$(OCH_2CH_2)_m-(CH_2)_n-N_3$, or $-C(O)-R^1$, wherein each alkyl or alkylene is optionally and independently substituted with $-C_{1-6}$ alkyl, —OH, —CN, $-NO_2$, or halogen.

In embodiments, $L^1$ and $L^2$ are the same. In embodiments, $L^1$ and $L^2$ are different.

In embodiments, $R^A$ is H. In embodiments, $L^1$ and $L^2$ are each independently $C_{1-6}$ alkylene or $C_{2-6}$ alkenylene. In embodiments, $R^A$ is H, and $L^1$ and $L^2$ are each independently $C_{1-6}$ alkylene or $C_{2-6}$ alkenylene. In embodiments, $L^1$ and $L^2$ are $C_{1-6}$ alkylene, $C_{2-5}$ alkylene, or $C_{3-4}$ alkylene. In embodiments, $L^1$ and $L^2$ are $-CH_2-$. In embodiments, $X^2$ is

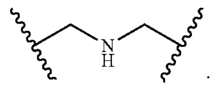

.

In embodiments, $R^A$ is $C_{6-10}$ aryl, and wherein the aryl of $R^A$ is optionally substituted. In embodiments, the aryl of $R^A$ is optionally substituted with —$C_{1-6}$ alkyl. In embodiments, $L^1$ and $L^2$ are each independently $C_{1-6}$ alkylene, or $C_{2-6}$ alkenylene. In embodiments, $R^A$ is $C_{6-10}$ aryl, and $L^1$ and $L^2$ are each independently $C_{1-6}$ alkylene, or $C_{2-6}$ alkenylene, and wherein the aryl of $R^A$ is optionally substituted with —$C_{1-6}$ alkyl. In embodiments, $R^A$ is phenyl. In embodiments, $L^1$ and $L^2$ are $C_{1-6}$ alkylene, $C_{2-5}$ alkylene, or $C_{3-4}$ alkylene. In embodiments, $L^1$ and $L^2$ are —$CH_2$—. In embodiments, $X^2$ is

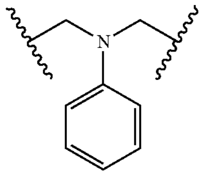

.

In embodiments, $R^A$ is —$SO_2$—$C_{1-6}$ alkyl. In embodiments, $L^1$ and $L^2$ are each independently $C_{1-6}$ alkylene, or $C_{2-6}$ alkenylene. In embodiments, $R^A$ is —$SO_2$—$C_{1-6}$ alkyl, and $L^1$ and $L^2$ are each independently $C_{1-6}$ alkylene, or $C_{2-6}$ alkenylene. In embodiments, $R^A$ is —$SO_2$—$CH_3$. In embodiments, $L^1$ and $L^2$ are $C_{1-6}$ alkylene, $C_{2-5}$ alkylene, or $C_{3-4}$ alkylene. In embodiments, $L^1$ and $L^2$ are —$CH_2$—. In embodiments, $X^2$ is

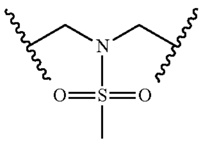

.

In embodiments, $R^A$ is —$SO_2$—$C_{6-10}$ aryl, wherein the aryl of $R^A$ is optionally substituted. In embodiments, the aryl of $R^A$ is optionally substituted with —$C_{1-6}$ alkyl. In some embodiments, $L^1$ and $L^2$ are each independently $C_{1-6}$ alkylene, or $C_{2-6}$ alkenylene. In embodiments, $R^A$ is —$SO_2$—$C_{6-10}$ aryl, wherein the aryl of $R^A$ is optionally substituted with —$C_{1-6}$ alkyl, and $L^1$ and $L^2$ are each independently $C_{1-6}$ alkylene, or $C_{2-6}$ alkenylene. In embodiments, $R^A$ is

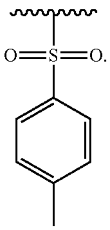 [SMILES: *S(=O)(=O)c1ccc(C)cc1]

In embodiments, $L^1$ and $L^2$ are $C_{1-6}$ alkylene, $C_{2-5}$ alkylene, or $C_{3-4}$ alkylene. In embodiments, $L^1$ and $L^2$ are —$CH_2$—. In embodiments, $X^2$ is

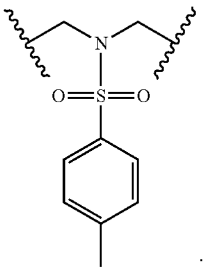 [SMILES: *CN(C*)S(=O)(=O)c1ccc(C)cc1]

.

In embodiments, $R^A$ is —C(O)—$C_{6-10}$ aryl, wherein the aryl of $R^A$ is optionally substituted. In some embodiments, the aryl of $R^A$ is optionally substituted with —$C_{1-6}$ alkyl. In embodiments, $L^1$ and $L^2$ are each independently $C_{1-6}$ alkylene, or $C_{2-6}$ alkenylene. In embodiments, $R^A$ is —C(O)—$C_{6-10}$ aryl, wherein the aryl of $R^A$ is optionally substituted with —$C_{1-6}$ alkyl, and $L^1$ and $L^2$ are each independently $C_{1-6}$ alkylene, or $C_{2-6}$ alkenylene. In embodiments, $R^A$ is

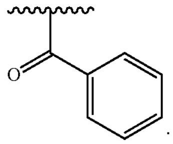 [SMILES: *C(=O)c1ccccc1]

.

In embodiments, $L^1$ and $L^2$ are $C_{1-6}$ alkylene, $C_{2-6}$ alkylene, or $C_{3-4}$ alkylene. In embodiments, $L^1$ and $L^2$ are —$CH_2$—. In embodiments, $X^2$ is

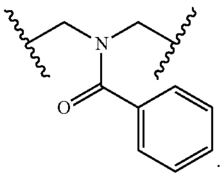 [SMILES: *CN(C*)C(=O)c1ccccc1]

.

In embodiments, $R^A$ is —($C_{1-6}$ alkylene)-($OCH_2CH_2$)$_m$—($CH_2$)$_n$—$N_3$, wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In embodiments, $L^1$ and $L^2$ are each independently $C_{1-6}$ alkylene, or $C_{2-6}$alkenylene. In embodiments, $R^A$ is —($C_{1-6}$ alkylene)-($OCH_2CH_2$)$_m$—($CH_2$)$_n$—$N_3$, and $L^1$ and $L^2$ are each independently $C_{1-6}$ alkylene, or $C_{2-6}$ alkenylene, wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In embodiments, n is 0. In embodiments, $R^A$ is

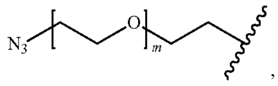

, wherein m is 1-12, 2-6, or 3-5. In embodiments, $L^1$ and $L^2$ are $C_{1-6}$ alkylene, $C_{2-5}$ alkylene, or $C_{3-4}$ alkylene. In embodiments, $L^1$ and $L^2$ are —$CH_2$—. In embodiments, $X^2$ is

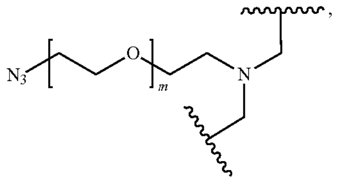

and m is 3.

Compounds of Formula (I-3)

In embodiments, the present disclosure provides a compound of formula (I-3):

(I-3)

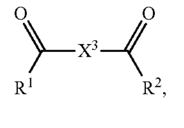

or a salt, a stereoisomer, or a deuterated form thereof, wherein:

$X^3$ is $C_{1-24}$ alkylene, $C_{2-24}$ alkenylene, or $C_{2-24}$ alkynylene, wherein $X^3$ is optionally substituted with 1-6 $R^3$ as permitted by valency;

$R^1$ and $R^2$ are each independently a leaving group;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_6$ alkyl), —$SO_2$($C_{1-6}$ alkyl), —($C_{1-12}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen;

each m is independently an integer of 1-200; and each n is independently an integer of 0-50.

In embodiments of the compounds of formula (I-3), when $X^3$ is unsubstituted, then the leaving group is not

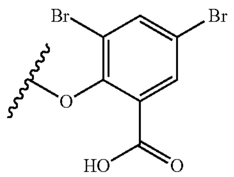

or

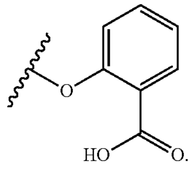

In embodiments, the compound of formula (I-3), or a salt, or a stereoisomer thereof, comprises one or more $^{13}C$ isotopes of carbon atoms occurring in the compound.

In some embodiments of the compounds of formula (I-3), or a salt, stereoisomer, or deuterated form thereof, $X^3$ is $C_{1-12}$ alkylene, $C_{2-12}$ alkenylene, or $C_{2-12}$ alkynylene, each of which is optionally substituted with 1-6 $R^3$ as permitted by valency. In some embodiments, each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-6}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen.

In some embodiments, $X^3$ is $C_{1-12}$ alkylene, $C_{2-12}$ alkylene, $C_{3-10}$ alkylene, $C_{4-9}$ alkylene, $C_{5-8}$ alkylene, or $C_{6-7}$ alkylene, each of which is optionally substituted with 1-6, 2-5, or 3-4 $R^3$ as permitted by valency. In some embodiments, $X^3$ is $C_{2-12}$ alkenylene, $C_{3-12}$ alkenylene, $C_{4-10}$ alkenylene, $C_{5-9}$ alkenylene, $C_{6-8}$ alkenylene, or $C_7$ alkenylene, each of which is optionally substituted with 1-6, 2-5, or 3-4 $R^3$ as permitted by valency. In some embodiments, $X^3$ is $C_{2-12}$ alkynylene, $C_{3-12}$ alkynylene, $C_{4-10}$ alkynylene, $C_{5-9}$ alkynylene, $C_{6-8}$ alkynylene, or $C_7$ alkynylene, each of which is optionally substituted with 1-6, 2-5, or 3-4 $R^3$ as permitted by valency. In some embodiments, $X^3$ is unsubstituted $C_{1-12}$ alkylene, $C_{2-12}$ alkenylene, or $C_{2-12}$ alkynylene. In some embodiments, $X^3$ is straight (i.e., unbranched) $C_{1-12}$ alkylene, $C_{2-12}$ alkenylene, or $C_{2-12}$ alkynylene.

In some embodiments of the compounds of formula (I-3), or a salt, stereoisomer, or deuterated form thereof, $X^3$ is $C_{1-6}$ alkylene, $C_{2-6}$ alkenylene, or $C_{2-6}$ alkynylene, each of which is optionally substituted with 1 or 2 $R^3$ as permitted by valency. In some embodiments, $X^3$ is unsubstituted $C_{1-6}$ alkylene, $C_{2-6}$ alkenylene, or $C_{2-6}$ alkynylene. In some embodiments, $X^3$ is straight $C_{1-6}$ alkylene, $C_{2-6}$ alkenylene, or $C_{2-6}$ alkynylene.

In some embodiments of the compounds of formula (I-3), or a salt, stereoisomer, or deuterated form thereof, $X^3$ is $C_{1-6}$ alkylene optionally substituted with 1 or 2 $R^3$ as permitted by valency. In some embodiments, $X^3$ is unsubstituted $C_{1-6}$ alkylene. In some embodiments, $X^3$ is straight $C_{1-6}$ alkylene. In embodiments, $X^3$ is

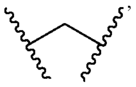,
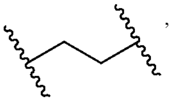,
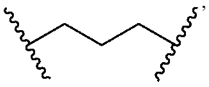,

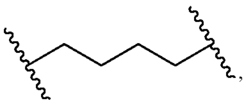,

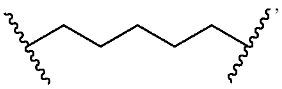, or

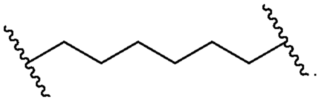.

In embodiments, $X^3$ is

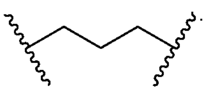 [SMILES: *CCC*].

In some embodiments of the compounds of formula (I-3), or a salt, stereoisomer, or deuterated form thereof, $X^3$ is $C_{2-6}$ alkenylene optionally substituted with 1 or 2 $R^3$ as permitted by valency. In some embodiments, $X^3$ is unsubstituted $C_{2-6}$ alkenylene. In some embodiments, $X^3$ is straight $C_{2-6}$ alkenylene. In some embodiments, $X^3$ is or

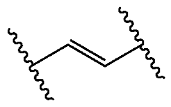

or

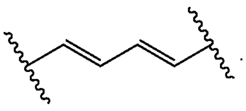

In some embodiments, $X^3$ is

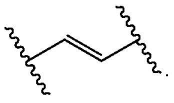 [SMILES: */C=C/*]

In some embodiments of the compounds of formula (I-3), or a salt, stereoisomer, or deuterated form thereof, $X^3$ is $C_{2-6}$ alkynylene optionally substituted with 1 or 2 $R^3$ as permitted by valency. In some embodiments, $X^3$ is unsubstituted $C_{2-6}$ alkynylene. In some embodiments, X is straight $C_{2-6}$ alkynylene. In embodiments, $X^3$ is

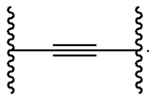

In some embodiments of the compounds of formula (I-3), or a salt, stereoisomer, or deuterated form thereof, $X^3$ is $C_{1-6}$ alkylene, $C_{2-6}$ alkenylene, or $C_{2-6}$ alkynylene, each of which is substituted with $-S-(C_{1-6}$ alkylene$)-(OCH_2CH_2)_m-(CH_2)_n-N_3$, or $-O-(C_{1-6}$ alkylene$)-(OCH_2CH_2)_m-(CH_2)_n-N_3$, and wherein each m is independently an integer of 1-50, 2-40, 3-30, 4-25, 5-20, 6-18, 7-16, 8-14, 9-12, or 10-11, and each n is independently an integer of 0-25, 1-20, 2-15, 3-10, 4-8, or 5-7. In some embodiments, $X^3$ is $C_{1-6}$ alkylene substituted with $-S-(C_{1-6}$ alkylene$)-(OCH_2CH_2)_m-(CH_2)_n-N_3$, and wherein m is an integer of 1-50, 2-40, 3-30, 4-25, 5-20, 6-18, 7-16, 8-14, 9-12, or 10-11, and n is an integer of 0-25, 1-20, 2-15, 3-10, 4-8, or 5-7. In some embodiments, $X^3$ is

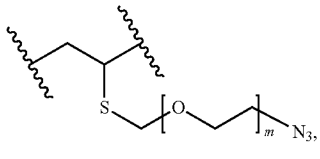

and wherein m is an integer of 1-25, 2-20, 3-15, 4-10, or 5-8. In some embodiments, m is 3-8, 4-7, or 5-6. In some embodiments, $X^3$ is

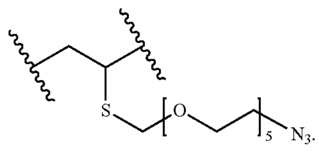

In embodiments, $X^3$ is $C_{1-6}$ alkylene substituted with $-S-(C_{1-6}$ alkylene$)-(OCH_2CH_2)_m-(CH_2)_n-N_3$, and wherein m is an integer of 1-50, and n is an integer of 0-25. In embodiments, $X^3$ is

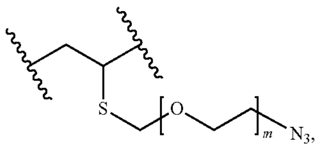

and wherein m is an integer of 1-25. In embodiments, $X^3$ is

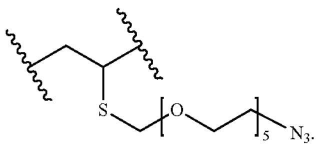

In embodiments, $X^3$ is $C_{1-24}$ alkylene $C_{2-20}$ alkylene, $C_{3-18}$ alkylene, $C_{414}$ alkylene, $C_{5-12}$ alkylene, or $C_{6-10}$ alkylene substituted with $-(C_{1-12}$ alkylene$)-N_3$, $-(C_{2-10}$ alkylene$)-N_3$, $-(C_{3-8}$ alkylene$)-N_3$, or $-(C_{4-6}$ alkylene$)-N_3$. In embodiments, $X^3$ is $C_{1-6}$ alkylene substituted with $-(C_{1-12}$ alkylene$)-N_3$. In embodiments, $X^3$ is $C_{1-6}$ alkylene substituted with $-(C_{2-8}$ alkylene$)-N_3$. In embodiments, $X^3$ is $C_{2-4}$ alkylene substituted with $-(C_2$ alkylene$)-N_3$, $-(C_3$ alkylene$)-N_3$, $-(C_4$ alkylene$)-N_3$, $-(C_5$ alkylene$)-N_3$, $-(C_6$ alkylene$)-N_3$, $-(C_7$ alkylene$)-N_3$, or $-(C_8$ alkylene$)-N_3$. In embodiments, $X^3$ is

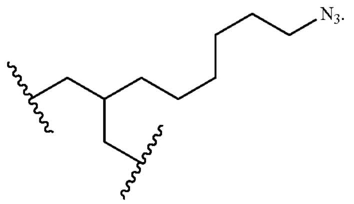 [SMILES: *CC(C*)CCCCCCN=[N+]=[N-]]

Compounds of Formula (I-4)

In embodiments, the present disclosure provides a compound of formula (I-4):

(I-4)

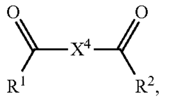

or a salt, a stereoisomer, or a deuterated form thereof, wherein:

$X^4$ is $C_{3-9}$ cycloalkylene, $C_{3-9}$ cycloalkenylene, 5-12 membered heterocyclylene containing 1 or 2 heteroatoms selected from N, S, or O, wherein $X^4$ is optionally substituted with 1-6 $R^3$ as permitted by valency;

$R^1$ and $R^2$ are each independently a leaving group;

each $R^3$ is independently $-OH$, $-CN$, $-NO_2$, halogen, oxo, $-C_{1-6}$ alkyl, $-C_{1-6}$ haloalkyl, $-O(C_{1-6}$ alkyl), $-S(C_{1-6}$ alkyl), $-SO(C_{1-6}$ alkyl), —$SO_2(C_{1-6}$ alkyl), —$(C_{1-12}$ alkylene)-$N_3$, —$(C_{1-12}$ alkylene)-$(OCH_2CH_2)_m$—$(CH_2)_n$—$N_3$, —C(O)NH—$(C_{1-12}$ alkylene)-$(OCH_2CH_2)_m$—$(CH_2)_n$—$N_3$, —NHC(O)—$(C_{1-12}$ alkylene)-$(OCH_2CH_2)_m$—$(CH_2)_n$—$N_3$, —O—$(C_{1-12}$ alkylene)-$(OCH_2CH_2)_m$—$(CH_2)_n$—$N_3$, —S—$(C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen;

each m is independently an integer of 1-200; and each n is independently an integer of 0-50.

In embodiments, the compound of formula (I-4), or a salt, or a stereoisomer thereof, comprises one or more $^{13}C$ isotopes of carbon atoms occurring in the compound.

In embodiments of the compound of formula (I-4), or a salt, a stereoisomer, or a deuterated form thereof, $X^4$ is $C_{3-9}$ cycloalkylene, $C_{3-9}$ cycloalkenylene, or 5-12 membered heterocyclylene, each of which is optionally substituted with 1 or 2 $R^3$ as permitted by valency. In some embodiments, each $R^3$ is independently —OH, —CN, —$NO_2$, halogen, oxo, —$C_{1-6}$ alkyl, —$C_{1-6}$ haloalkyl, —$O(C_{1-6}$ alkyl), —$S(C_{1-6}$ alkyl), —$SO(C_{1-6}$ alkyl), —$SO_2(C_{1-6}$ alkyl), —$(C_{1-6}$ alkylene)-$N_3$, —$(C_{1-12}$ alkylene)-$(OCH_2CH_2)_m$—$(CH_2)_n$—$N_3$, —C(O)NH—$(C_{1-12}$ alkylene)-$(OCH_2CH_2)_m$—$(CH_2)_n$—$N_3$, —NHC(O)—$(C_{1-12}$ alkylene)-$(OCH_2CH_2)_m$—$(CH_2)_n$—$N_3$, —O—$(C_{1-12}$ alkylene)-$(OCH_2CH_2)_m$—$(CH_2)_n$—$N_3$, —S—$(C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen. In some embodiments, $X^4$ is unsubstituted $C_{3-9}$ cycloalkylene, $C_{3-9}$ cycloalkenylene, or 5-12 membered heterocyclylene.

In some embodiments, $X^4$ is $C_{3-9}$ cycloalkylene, $C_{4-8}$ cycloalkylene, $C_{5-7}$ cycloalkylene, or $C_6$ cycloalkylene, each of which is optionally substituted with 1 or 2 $R^3$ as permitted by valency. In some embodiments, $X^4$ is $C_{3-9}$ cycloalkenylene, $C_{4-8}$ cycloalkenylene, $C_{5-7}$ cycloalkenylene, or $C_6$ cycloalkenylene, each of which is optionally substituted with 1 or 2 $R^3$ as permitted by valency. In some embodiments, $X^4$ is 5-12 membered, 6-11 membered, 7-10 membered, or 8-9 membered heterocyclylene containing a heteroatom which is S, O, or N, each of which is optionally substituted with 1 or 2 $R^3$ as permitted by valency.

In some embodiments of the compounds of formula (I-4), or a salt, stereoisomer, or deuterated form thereof, $X^4$ is $C_{3-7}$ cycloalkylene or $C_{4-6}$ cycloalkylene optionally substituted with 1 or 2 $R^3$ as permitted by valency. In some embodiments, $X^4$ is unsubstituted $C_{3-7}$ cycloalkylene or $C_{4-6}$ cycloalkylene. In embodiments, $X^4$ is

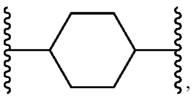,
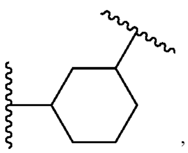, or
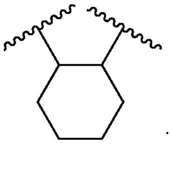.

In some embodiments of the compounds of formula (I-4), or a salt, stereoisomer, or deuterated form thereof, $X^4$ is $C_{3-7}$ cycloalkenylene or $C_{4-6}$ cycloalkenylene optionally substituted with 1 or 2 $R^3$ as permitted by valency. In some embodiments, $X^4$ is unsubstituted $C_{3-7}$ cycloalkenylene or $C_{4-6}$ cycloalkenylene. In embodiments, $X^4$ is

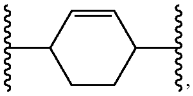,
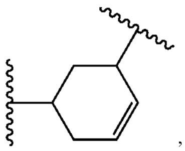,
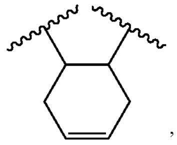,
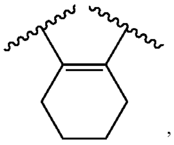, or
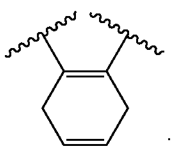.

In some embodiments of the compounds of formula (I-4), or a salt, stereoisomer, or deuterated form thereof, $X^4$ is $C_{3-7}$ cycloalkenylene or $C_{4-6}$ cycloalkenylene substituted with —$(C_{1-12}$ alkylene)-$N_3$, —$(C_{1-9}$ alkylene)-$N_3$, —$(C_{1-6}$ alkylene)-$N_3$, —$(C_{2-5}$ alkylene)-$N_3$, or —$(C_{3-4}$ alkylene)-$N_3$. In embodiments, $X^4$ is

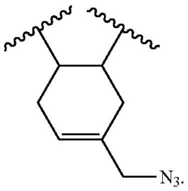 [SMILES: *C1CC=C(CN=[N+]=[N-])CC1*]

In embodiments, the $C_{3-9}$ cycloalkylene, $C_{3-9}$ cycloalkenylene, or 5-12 membered heterocyclylene is a bridged ring system, a fused ring system, or a spiro ring system.

In some embodiments of the compounds of formula (I-4), or a salt, stereoisomer, or deuterated form thereof, $X^4$ is a 5-12 membered, 6-11 membered, 7-10 membered, or 8-9 membered heterocyclylene containing a heteroatom which is S or O, and wherein the heterocyclylene is optionally substituted. In some embodiments, the heterocyclylene is optionally substituted with —$(C_{1-6}$ alkylene)-$N_3$. In some embodiments, $X^4$ is a 6-10 membered, or 7-9 membered heterocyclylene containing 0, and wherein the heterocyclylene is substituted with —$(C_{1-6}$ alkylene)-$N_3$. In embodiments, $X^4$ is

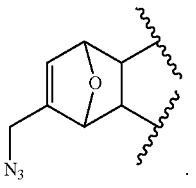 [SMILES: *C1C2C=C(CN=[N+]=[N-])C(O2)C1*]

R[1] and R[2] as Leaving Groups

In some embodiments of the compounds of formula (I), or a salt, stereoisomer, or deuterated form thereof, $R^1$ and $R^2$ are each independently —OH, halogen, or a leaving group. In some embodiments, $R^1$ and $R^2$ are each independently halogen (e.g., —F, —Cl, —Br, —I), or a leaving group. In some embodiments, $R^1$ and $R^2$ are each independently a leaving group. In some embodiments, $R^1$ and $R^2$ are the same. In some embodiments, $R^1$ and $R^2$ are different.

In embodiments of the compound of formula (I-1), (I-2), (I-3), or (I-4), or a salt, a stereoisomer, or a deuterated form thereof, $R^1$ and $R^2$ are each independently a leaving group, which is

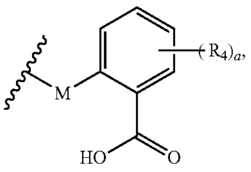

wherein M is O or S, each $R^4$ is independently halogen or —$C_{1-6}$ alkyl; and a is an integer of 0-4, or 1-3, or 2.

In embodiments, if $X^1$ of the compound of formula (I-1) is

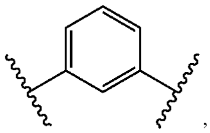 [SMILES: *c1cccc(*)c1]

then the leaving group is not

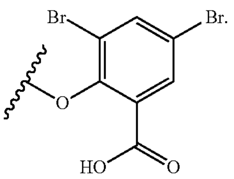 [SMILES: *Oc1c(Br)cc(Br)cc1C(=O)O]

In embodiments, if $X^1$ of the compound of formula (I-1) is an arylene substituted with 1 $R^3$, then $R^3$ is different from —C(O)—$R^1$ or —C(O)—$R^2$.

In embodiments, when $X^3$ of the compound of formula (I-3) is unsubstituted, then the leaving group is not

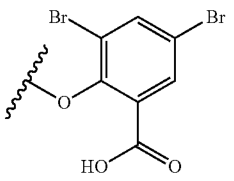

or

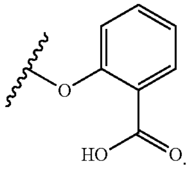

In some embodiments, M is O, and a is 0, and the leaving group is

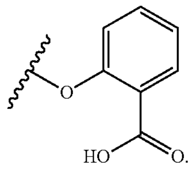

In some embodiments, M is S, and a is 0, and the leaving group is

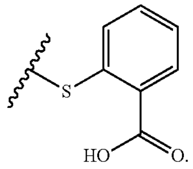

In some embodiments, a is 1, 2, or 3. In some embodiments, each $R^4$ is halogen (—F, —Cl, —Br, —I). In some embodiments, each $R^4$ is independently —F, —Cl, or —Br. In some embodiments, a is 2 and each $R^4$ is —Br, and the leaving group is

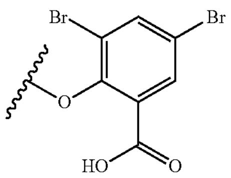

or

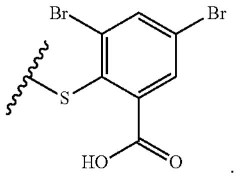

In some embodiments, a is 2 and each $R^4$ is —Cl, and the leaving group is

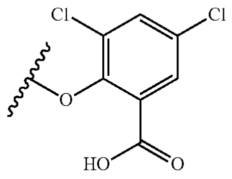

or

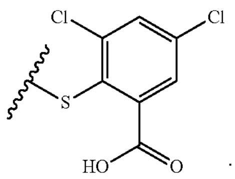

In some embodiments, a is 1, and $R^4$ is —Br, and the leaving group is

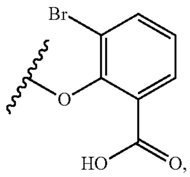
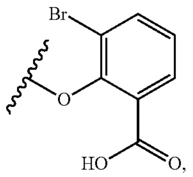
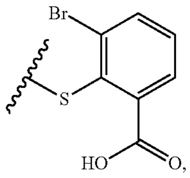
or
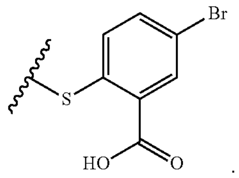
.

In some embodiments of the compounds of formula (I-1), (I-2), (I-3), or (I-4), or a salt, stereoisomer, or deuterated form thereof, $R^1$ and $R^2$ are

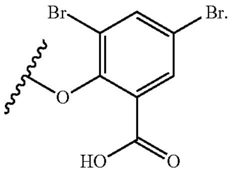 [SMILES: *Oc1c(Br)cc(Br)cc1C(=O)O]

In some embodiments of the compounds of formula (I-1), (I-2), (I-3), or (I-4), or a salt, stereoisomer, or deuterated form thereof, $R^1$ and $R^2$ are

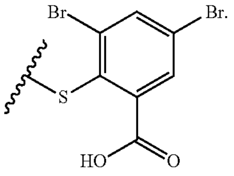

In some embodiments of the compounds of formula (I-1), (I-2), (I-3), or (I-4), or a salt, stereoisomer, or deuterated form thereof, $R^1$ and $R^2$ are

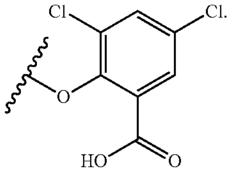 [SMILES: *Oc1c(Cl)cc(Cl)cc1C(=O)O]

In some embodiments of the compounds of formula (I-1), (I-2), (I-3), or (I-4), or a salt, stereoisomer, or deuterated form thereof, $R^1$ and $R^2$ are

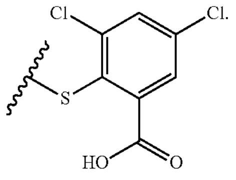 [SMILES: *Sc1c(Cl)cc(Cl)cc1C(=O)O]

In some embodiments of the compounds of formula (I-1), (I-2), (I-3), or (I-4), or a salt, stereoisomer, or deuterated form thereof, $R^1$ and $R^2$ are

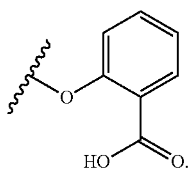

In some embodiments of the compounds of formula (I-1), (I-2), (I-3), or (I-4), or a salt, stereoisomer, or deuterated form thereof, $R^1$ and $R^2$ are

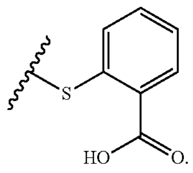

In embodiments of the compound of formula (I-1), (I-2), (I-3), or (I-4), or a salt, a stereoisomer, or a deuterated form thereof, the leaving group is

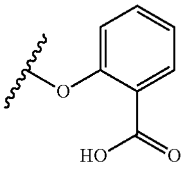
or
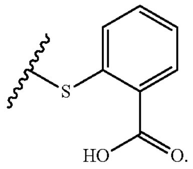

In embodiments of the compound of formula (I-1), (I-2), (I-3), or (I-4), or a salt, a stereoisomer, or a deuterated form thereof, the leaving group is

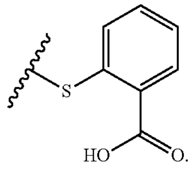

In embodiments of the compound of formula (I-1), (I-2), (I-3), or (I-4), or a salt, a stereoisomer, or a deuterated form thereof, each $R^4$ is halogen. In embodiments, each $R^4$ is independently —F, —Cl, or —Br. In embodiments, the leaving group is

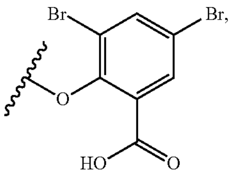

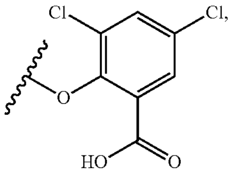

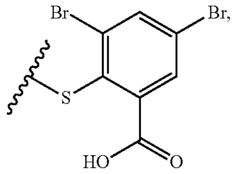 [SMILES: *Oc1c(Br)cc(Br)cc1C(=O)O]

or

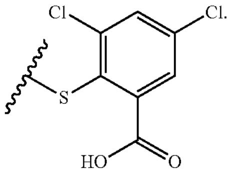

In embodiments, the leaving group is

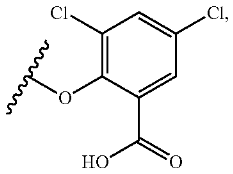

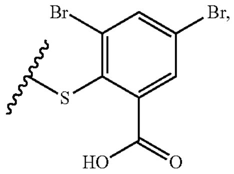

or

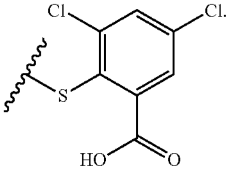

In some embodiments of the compounds of formula (I-1), (I-2), (I-3), or (I-4), or a salt, stereoisomer, or deuterated form thereof, $R^1$ and $R^2$ are each independently a leaving group, which is —O—($C_{1-6}$ alkylene)-$SO_3H$. In some embodiments, $R^1$ and $R^2$ are each independently a leaving group selected from the group consisting of —O—($CH_2$)—$SO_3H$, —O—($CH_2CH_2$)—$SO_3H$, —O—($CH_2CH_2CH_2$)—$SO_3H$, and —O—($CH_2CH_2CH_2CH_2$)—$SO_3H$. In some embodiments, the leaving group is —O—($CH_2CH_2$)—$SO_3H$. In some embodiments of the compounds of formula (I-1), (I-2), (I-3), or (I-4), or a salt, stereoisomer, or deuterated form thereof, $R^1$ and $R^2$ are —O—($CH_2CH_2$)—$SO_3H$.

TABLE A

Various exemplary compounds of the disclosure

| Comp. ID | Abbreviation | Structure |
|---|---|---|
| 1 | DBSF | 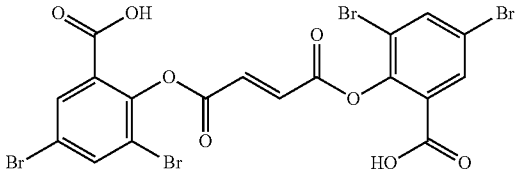 [SMILES: O=C(/C=C/C(=O)Oc1c(Br)cc(Br)cc1C(=O)O)Oc1c(Br)cc(Br)cc1C(=O)O] |
| 2 | DBSG | 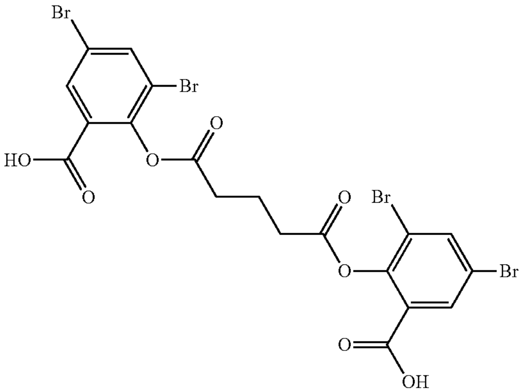 [SMILES: O=C(CCCC(=O)Oc1c(Br)cc(Br)cc1C(=O)O)Oc1c(Br)cc(Br)cc1C(=O)O] |
| 3 | DBSS | 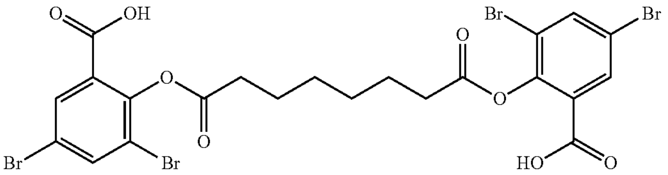 [SMILES: O=C(CCCCCCC(=O)Oc1c(Br)cc(Br)cc1C(=O)O)Oc1c(Br)cc(Br)cc1C(=O)O] |

TABLE A-continued
| Comp. ID | Abbreviation | Structure |
|---|---|---|
| Various exemplary compounds of the disclosure | | |
| 4 | TTDS | 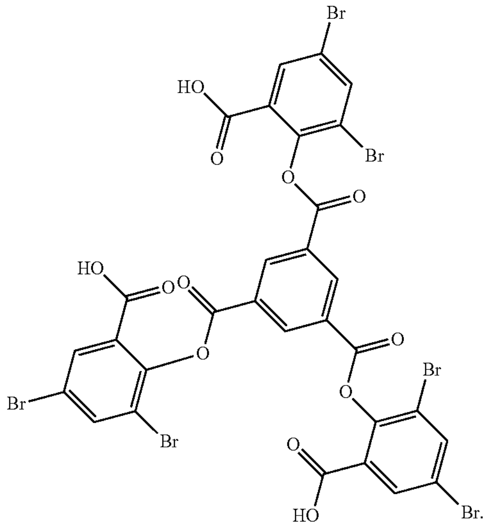 [SMILES: O=C(Oc1c(Br)cc(Br)cc1C(=O)O)c1cc(C(=O)Oc2c(Br)cc(Br)cc2C(=O)O)cc(C(=O)Oc2c(Br)cc(Br)cc2C(=O)O)c1] |
| 5 | TTS | 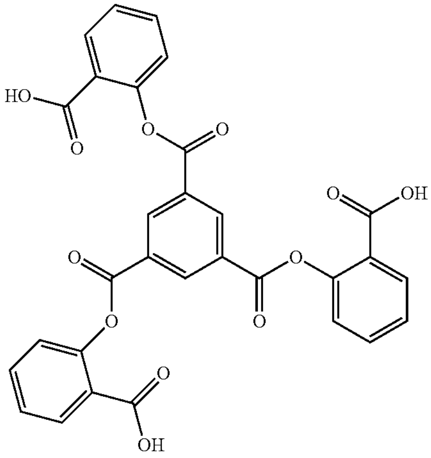 [SMILES: O=C(Oc1ccccc1C(=O)O)c1cc(C(=O)Oc2ccccc2C(=O)O)cc(C(=O)Oc2ccccc2C(=O)O)c1] |
| 6 | DBSM | 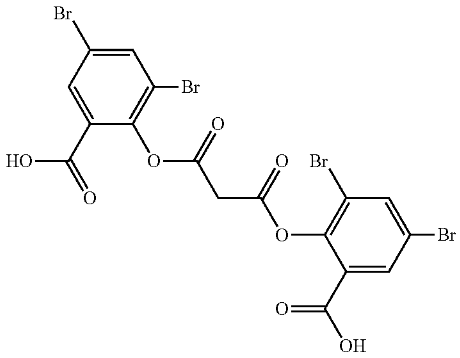 [SMILES: O=C(CC(=O)Oc1c(Br)cc(Br)cc1C(=O)O)Oc1c(Br)cc(Br)cc1C(=O)O] |
| 7 | DBST | 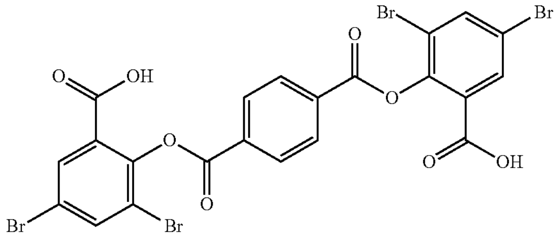 [SMILES: O=C(Oc1c(Br)cc(Br)cc1C(=O)O)c1ccc(C(=O)Oc2c(Br)cc(Br)cc2C(=O)O)cc1] |

TABLE A-continued
| Various exemplary compounds of the disclosure | | |
|---|---|---|
| Comp. ID | Abbreviation | Structure |
| 8 | DBSI | 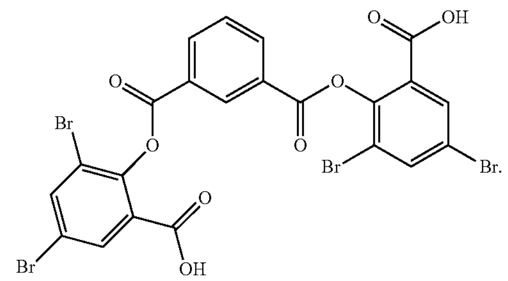 [SMILES: O=C(Oc1c(Br)cc(Br)cc1C(=O)O)c1cccc(C(=O)Oc2c(Br)cc(Br)cc2C(=O)O)c1] |
| 9 | BSI | 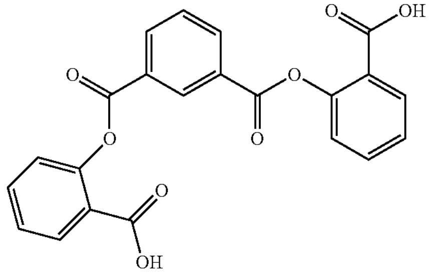 [SMILES: O=C(Oc1ccccc1C(=O)O)c1cccc(C(=O)Oc2ccccc2C(=O)O)c1] |
| 10 | BSAF | 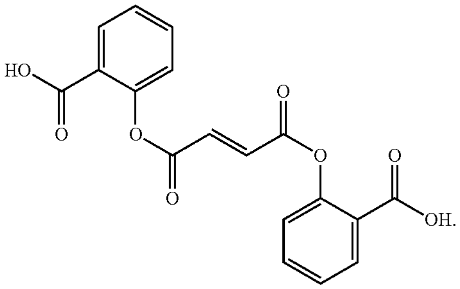 [SMILES: O=C(/C=C/C(=O)Oc1ccccc1C(=O)O)Oc1ccccc1C(=O)O] |
| 11 | BSEIA | 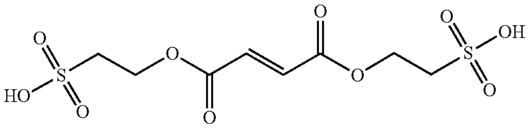 [SMILES: O=C(/C=C/C(=O)OCCS(=O)(=O)O)OCCS(=O)(=O)O] |
| 12 | BTASF | 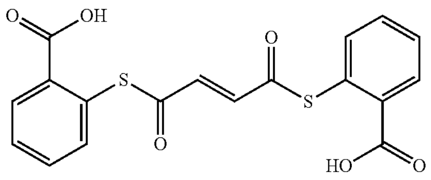 [SMILES: O=C(/C=C/C(=O)Sc1ccccc1C(=O)O)Sc1ccccc1C(=O)O] |
| 13 | DCSF | 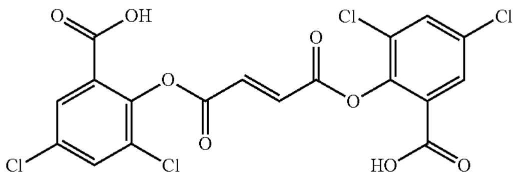 [SMILES: O=C(/C=C/C(=O)Oc1c(Cl)cc(Cl)cc1C(=O)O)Oc1c(Cl)cc(Cl)cc1C(=O)O] |

TABLE A-continued
| Various exemplary compounds of the disclosure | | |
|---|---|---|
| Comp. ID | Abbreviation | Structure |
| 14 | DCSIA | 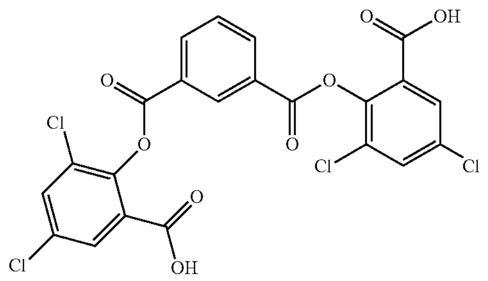 [SMILES: O=C(Oc1c(Cl)cc(Cl)cc1C(=O)O)c1cccc(C(=O)Oc2c(Cl)cc(Cl)cc2C(=O)O)c1] |
| 15 | DBSNP-4 | 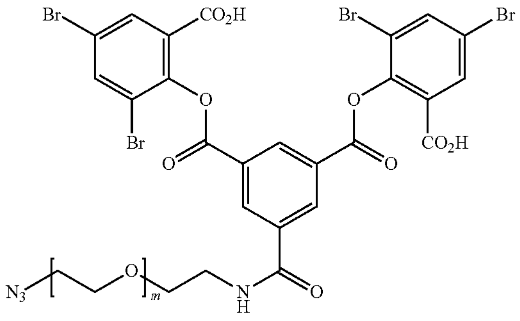<br>m = 4 |
| 16 | DBSNP-9 | 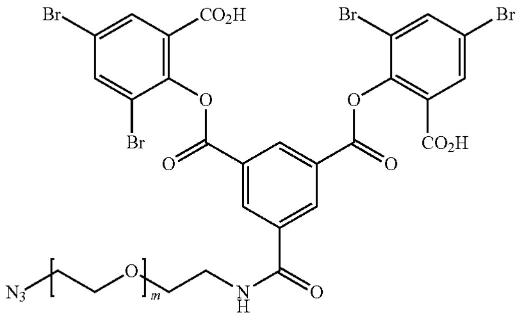<br>m = 9 |
| 17 | DBSNP-42 | 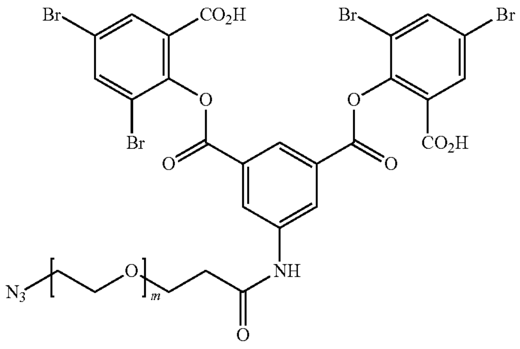<br>m = 4 |

TABLE A-continued
| Various exemplary compounds of the disclosure | | |
|---|---|---|
| Comp. ID | Abbreviation | Structure |
| 18 | DBSNP-92 | 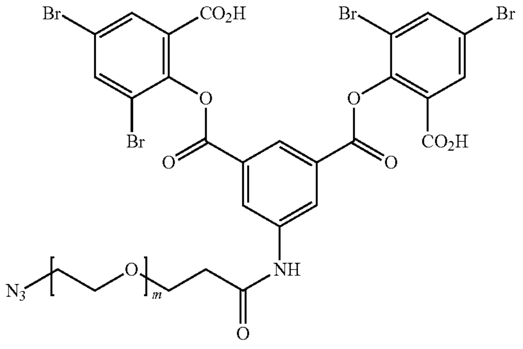 m = 9 |
| 19 | TIDA | 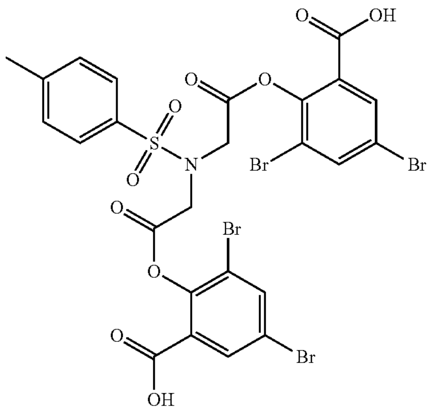 [SMILES: Cc1ccc(S(=O)(=O)N(CC(=O)Oc2c(Br)cc(Br)cc2C(=O)O)CC(=O)Oc2c(Br)cc(Br)cc2C(=O)O)cc1] |
| 20 | AIDA | 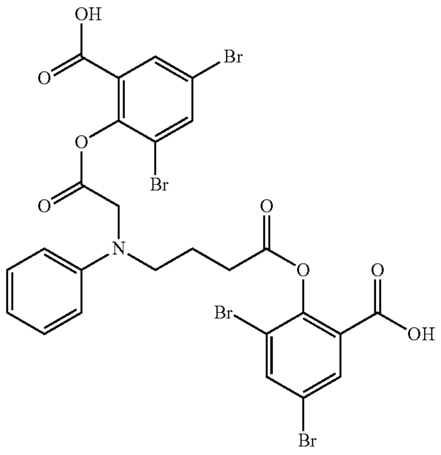 [SMILES: O=C(CCCN(CC(=O)Oc1c(Br)cc(Br)cc1C(=O)O)c1ccccc1)Oc1c(Br)cc(Br)cc1C(=O)O] |

TABLE A-continued
| Various exemplary compounds of the disclosure | | |
|---|---|---|
| Comp. ID | Abbreviation | Structure |
| 21 | MIDA | 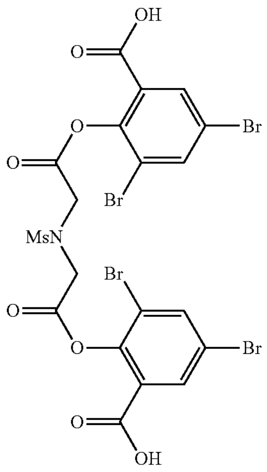 |
| 22 | IDDBSN | 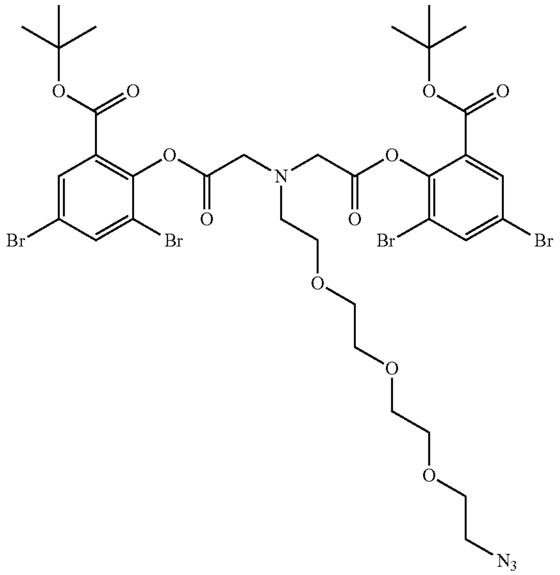 [SMILES: CC(C)(C)OC(=O)c1cc(Br)cc(Br)c1OC(=O)CN(CCOCCOCCOCCN=[N+]=[N-])CC(=O)Oc1c(Br)cc(Br)cc1C(=O)OC(C)(C)C] |
| 23 | AZS3 | 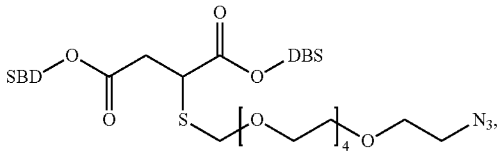 DBS represents 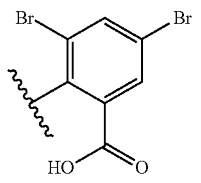 [SMILES: *c1c(Br)cc(Br)cc1C(=O)O] |

TABLE A-continued
| Various exemplary compounds of the disclosure | | |
|---|---|---|
| Comp. ID | Abbreviation | Structure |
| 24 | FuranDA | 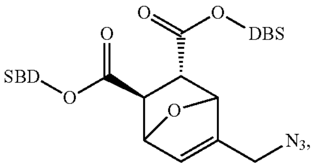 DBS represents 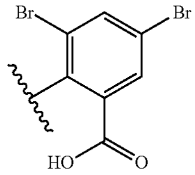 [SMILES: *c1c(Br)cc(Br)cc1C(=O)O] |
| 25 | | 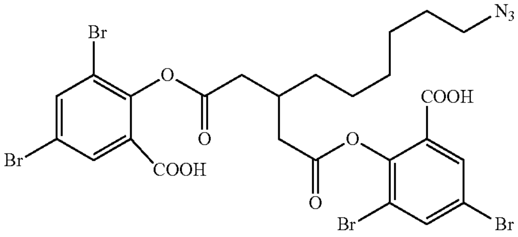 [SMILES: [N-]=[N+]=NCCCCCCC(CC(=O)Oc1c(Br)cc(Br)cc1C(=O)O)CC(=O)Oc1c(Br)cc(Br)cc1C(=O)O] |
In embodiments, the compound of formula (I) or (I-3) is not
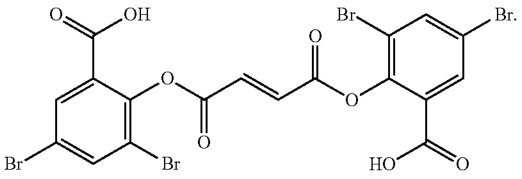 [SMILES: O=C(/C=C/C(=O)Oc1c(Br)cc(Br)cc1C(=O)O)Oc1c(Br)cc(Br)cc1C(=O)O]

In embodiments, the compound of formula (I) or (I-1) is not
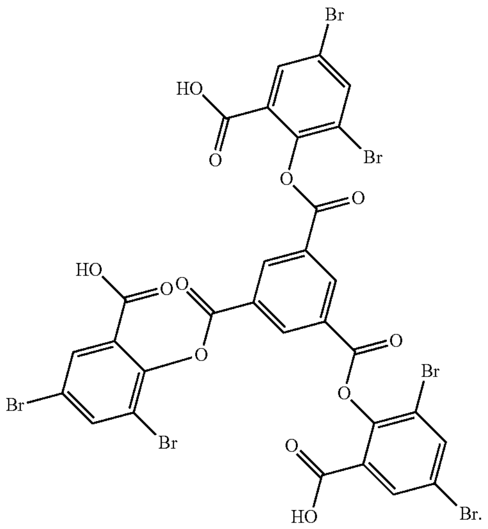 [SMILES: O=C(Oc1c(Br)cc(Br)cc1C(=O)O)c1cc(C(=O)Oc2c(Br)cc(Br)cc2C(=O)O)cc(C(=O)Oc2c(Br)cc(Br)cc2C(=O)O)c1]
In embodiments, the compound of formula (I) or (I-3) is not
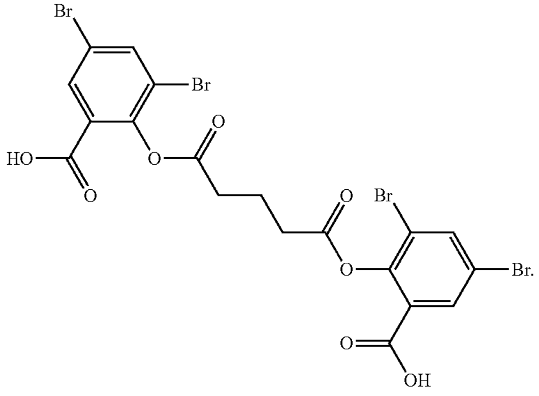 [SMILES: O=C(CCCC(=O)Oc1c(Br)cc(Br)cc1C(=O)O)Oc1c(Br)cc(Br)cc1C(=O)O]
In embodiments, the compound of formula (I) or (I-3) is not
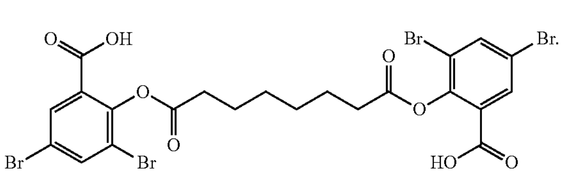 [SMILES: O=C(CCCCCCC(=O)Oc1c(Br)cc(Br)cc1C(=O)O)Oc1c(Br)cc(Br)cc1C(=O)O]
In embodiments, the compound of formula (I) or (I-1) is not
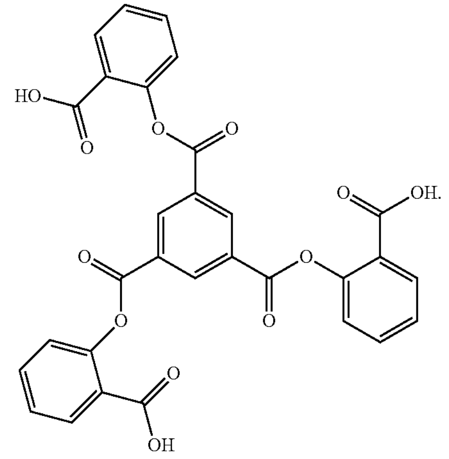 [SMILES: O=C(Oc1ccccc1C(=O)O)c1cc(C(=O)Oc2ccccc2C(=O)O)cc(C(=O)Oc2ccccc2C(=O)O)c1]
In embodiments, the compound of formula (I) or (I-3) is not
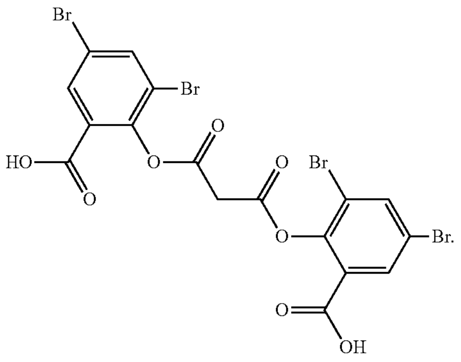 [SMILES: O=C(CC(=O)Oc1c(Br)cc(Br)cc1C(=O)O)Oc1c(Br)cc(Br)cc1C(=O)O]
In embodiments, the compound of formula (I) or (I-1) is not
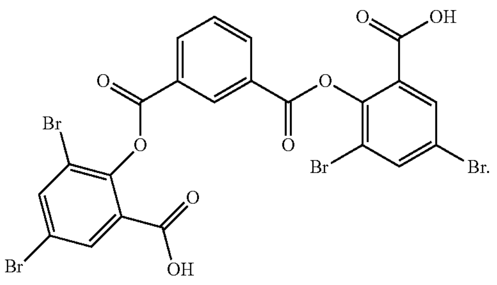 [SMILES: O=C(Oc1c(Br)cc(Br)cc1C(=O)O)c1cccc(C(=O)Oc2c(Br)cc(Br)cc2C(=O)O)c1]

In embodiments, the compound of formula (I) or (I-3) is not

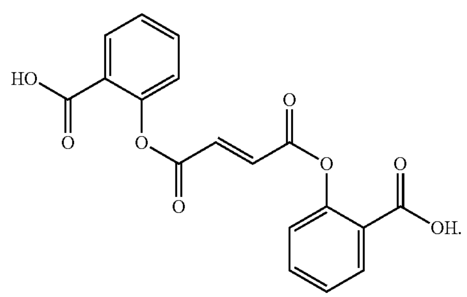 [SMILES: O=C(/C=C/C(=O)Oc1ccccc1C(=O)O)Oc1ccccc1C(=O)O]

The compounds of the present disclosure (e.g., a compound of formula (I), (I-1), (I-2), (I-3), or (I-4), or Table A, or a salt, stereoisomer, or deuterated form thereof) may be used on their own or used as a multifunctional linker compound to link a protein, a peptide, or an amino acid. In embodiments, the compound disclosed herein can act as a bifunctional or trifunctional crosslinker. In embodiments, the compound disclosed herein can act as a bifunctional linker (e.g.,

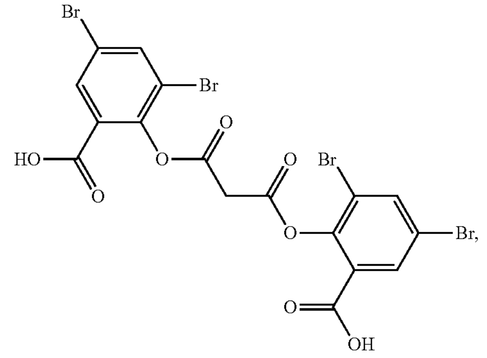

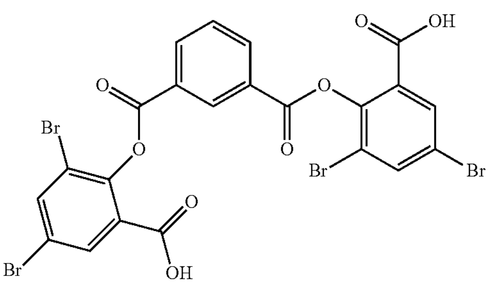

).

In embodiments, the compound disclosure herein can act as a trifunctional linker (e.g.,

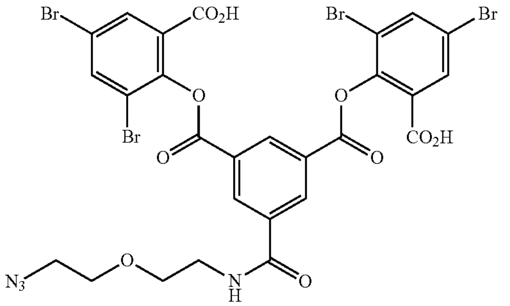

m = 4,

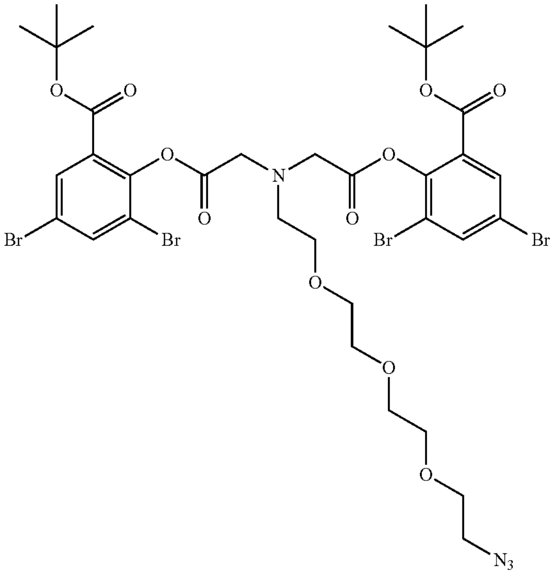

).

Bovine hemoglobin is a heterotetramer consisting of two alpha and two beta hemoglobin subunits. Each alpha monomer binds to a beta monomer forming an ab heterodimer. Two ab dimers associate to form the heterotetramer. These tetramers are relatively stable (although they can dissociate to alpha-beta dimers, which are toxic, see below) and can change between the relaxed oxygenated R-state and the deoxygenated T-state. For its native function, the hemoglobin transits through these two states to either release or bind oxygen. The ability of hemoglobin to cycle through these two states is described by the $P_{50}$ value. A high $P_{50}$ value correlates with an inability to bind oxygen efficiently while a low $P_{50}$ value correlates with tight oxygen binding but a reduced ability to release bound oxygen.

When the tetramer dissociates into its two heterodimers it can start to dissociate into the individual monomers, which are cleared through the kidney. Unfortunately, the clearance of larger hemoglobin amounts can cause severe distress in the kidneys and terminal kidney failure. Accordingly, there is a need to develop stabilized hemoglobin protein.

Click Chemistry

In embodiments, the modified hemoglobin (Hb), multimerized Hb composition, compounds, and formulas disclosed herein comprise a functional group capable of reacting through click chemistry and/or a linkage formed via click chemistry. As used herein, click chemistry refers to a copper-catalyzed 1,3-dipolar cycloaddition or [3+2]cycloaddition between an azide and an alkyne to form a 1,2,3- triazole, or a Diels-Alder reaction. The terms "1,3-dipolar cycloaddition" or "[3+2]cycloaddition" also encompasses "copper-less" 1,3-dipolar cycloadditions between azides and cyclooctynes. The Diels-Alder reaction also encompasses alkene and tetrazine inverse-demand Diels-Alder reaction. Other click reactions that may be used in addition to, or in lieu of the 1,3-dipolar cycloaddition or [3+2]cycloaddition and Diels-Alder reaction include, but are not limited to, thiol-ene reaction, [4+1]cycloadditions between isocyanides and tetrazine, and "photo-click" reaction between alkenes and tetrazoles.

In certain embodiments, the alkyne is a strained cycloalkynyl or heterocycloalkynyl, and the cycloaddition reaction may be performed in the presence or absence of a catalyst. In certain embodiments, for example, the cycloaddition reaction may occur spontaneously by a reaction called strain-promoted azide-alkyne cycloaddition (SPAAC), which is known in the art as "metal-free click chemistry" to form a triazole moiety. In certain embodiments, the strained cycloalkynyl or heterocycloalkynyl is as described herein.

Such catalyst-free [3+2]cycloadditions can be used in methods described herein to form multimerized Hb compositions of the present disclosure. Alkynes can be activated by ring strain such as, by way of example only, eight membered ring structures, appending electron-withdrawing groups to such alkyne rings, among others.

In certain embodiments, the alkyne is propargyl (i.e., not a strained cycloalkynyl). Cycloaddition of propargyl and an azido requires the presence of a metal catalyst (e.g., copper ions) to proceed.

An exemplary click chemistry utilizing a strained cycloalkynyl and an azide is illustrated below:

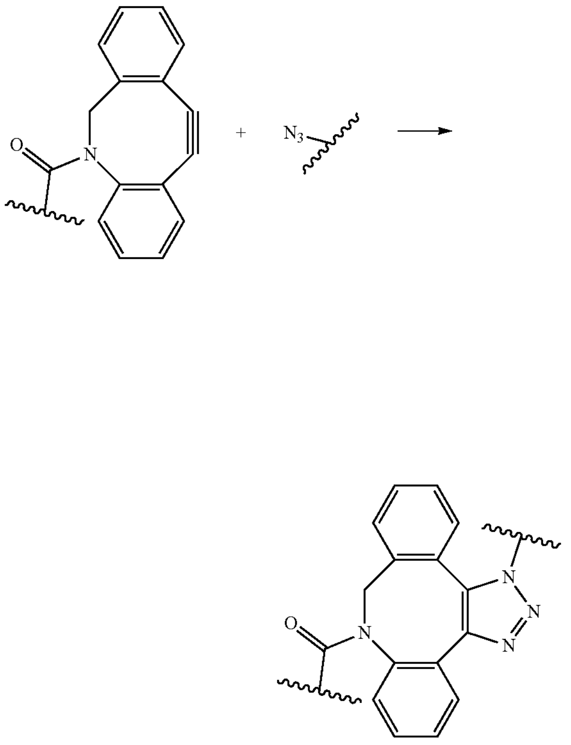

Exemplary triazole formed by an azide-alkyne cycloaddition include, but are not limited to,

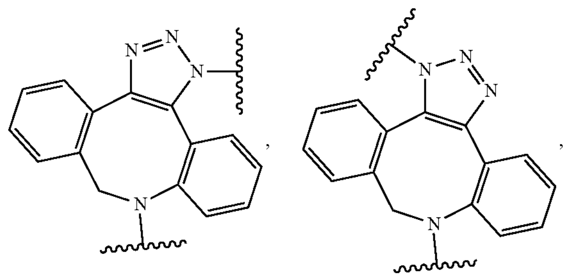

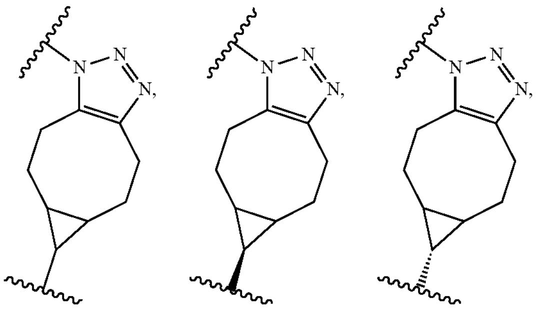

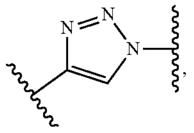

and

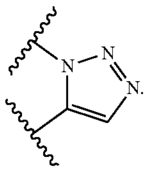

In certain embodiment, the alkenes in the Diels-Alder reaction are strained cyclooctenes e.g., trans-cyclooctene (TCO)) and other activated alkenes that readily react with tetrazines (e.g., 1,2,4,5-tetrazine,

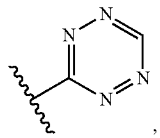

,

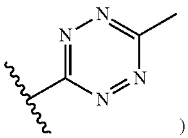

)

in an inverse electron-demand Diels-Alder followed by a retro [4+2]cycloaddition. In addition to TCO, three-membered, four-membered, and five-membered cycloalkenes can be used as the alkene herein due to their high ring strain. An exemplary Diels-Alder reaction is illustrated below:

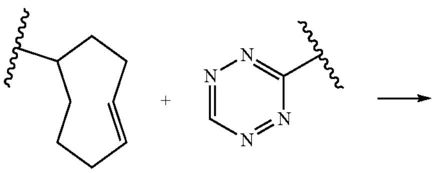

-continued

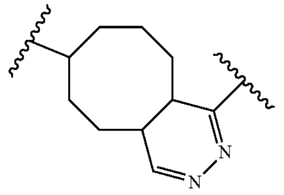

.

Unless otherwise indicated, the intramolecular crosslinking and functionalization steps described herein can be performed in either sequential order, i.e., crosslinking first followed by functionalization, or functionalization first followed by crosslinking.

Modified Hemoglobins

In one aspect, the present disclosure provides a modified hemoglobin (Hb), comprising at least two subunits of a Hb intramolecularly crosslinked with a compound of formula (I), (I-1), (I-2), (I-3), or (I-4), or Table A, or a salt, stereoisomer, or deuterated form thereof disclosed herein in any of the above embodiments.

In embodiments, the hemoglobin (Hb) is bovine, human, equine, porcine, ovine, simian, or fish hemoglobin. In embodiments, the Hb is bovine hemoglobin (bHb).

In embodiments, the Hb used herein, which is comprised of 2 alpha and 2 beta subunits, is represented by:

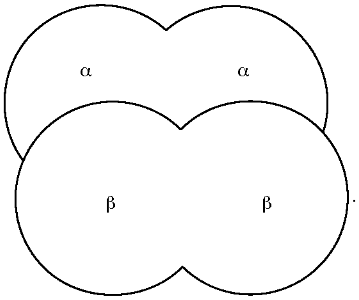

.

Each subunit of hemoglobin is well-characterized with known sequences. In embodiments, the alpha subunit of the Hb comprises an amino acid sequence of SEQ ID NO: 1. In embodiments, the alpha subunit of the Hb consists of an amino acid sequence of SEQ ID NO: 1. In embodiments, the alpha subunit of the Hb comprises Methionine (Met, M) on the N-terminus. In embodiments, the alpha subunit of the Hb has 80% or more, 90% or more, 95% or more, 96% or more, 97% or more, 98% or more, or 99% or more amino acid sequence similarity to the amino acid sequence of SEQ ID NO: 1. In embodiments, the beta subunit of the Hb comprises an amino acid sequence of SEQ ID NO: 2. In embodiments, the beta subunit of the Hb consists of an amino acid sequence of SEQ ID NO: 2. In embodiments, the beta subunit of the Hb has 80% or more, 90% or more, 95% or more, 96% or more, 97% or more, 98% or more, or 99% or more amino acid sequence similarity to the amino acid sequence of SEQ ID NO: 2.

In embodiments, the Hb intramolecularly crosslinked with the compound of formula (I) comprises:

(I-A)

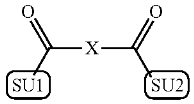

wherein SU1 is a residue on a first subunit of the Hb, and SU2 is a residue on a second subunit of the Hb. In embodiments, X is

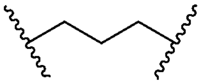

or

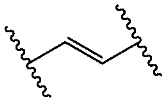

.

In embodiments, X is

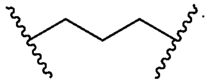 [SMILES: *CCC*]

.

In embodiments, the compound of formula (I) is

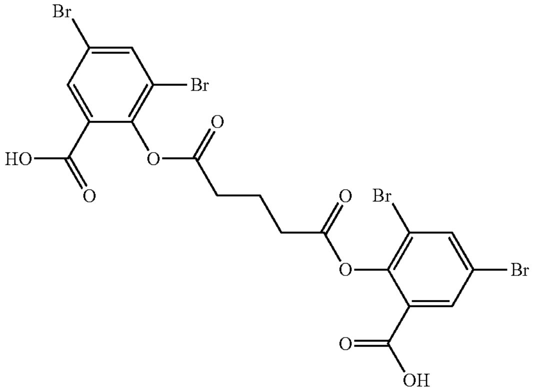 [SMILES: O=C(CCCC(=O)Oc1c(Br)cc(Br)cc1C(=O)O)Oc1c(Br)cc(Br)cc1C(=O)O]

(i.e., bis(3,5-dibromosalicyl)glutarate or "DBSG") or

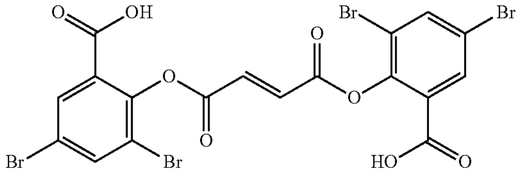 [SMILES: O=C(/C=C/C(=O)Oc1c(Br)cc(Br)cc1C(=O)O)Oc1c(Br)cc(Br)cc1C(=O)O]

(i.e., bis(3,5-dibromosalicyl)fumarate or "DBSF"). In embodiments, the compound of formula (I) is DBSG.

In embodiments, the Hb intramolecularly crosslinked with the compound of formula (I-1) comprises:

(I-1-A)

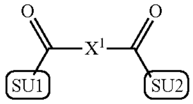

wherein SU1 is a residue on a first subunit of the Hb, and SU2 is a residue on a second subunit of the Hb.

In embodiments, the Hb intramolecularly crosslinked with the compound of formula (I-2) comprises:

(I-2-A)

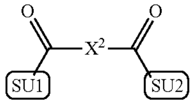

wherein SU1 is a residue on a first subunit of the Hb, and SU2 is a residue on a second subunit of the Hb.

In embodiments, the Hb intramolecularly crosslinked with the compound of formula (I-3) comprises:

(I-3-A)

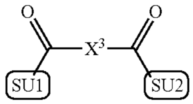

wherein SU1 is a residue on a first subunit of the Hb, and SU2 is a residue on a second subunit of the Hb. In embodiments, $X^3$ is

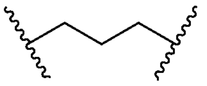

or

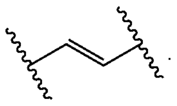

.

In embodiments, $X^3$ is

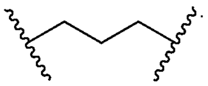 [SMILES: *CCC*]

.

In embodiments, the compound of formula (I-3) is DBSG or DBSF. In embodiments, the compound of formula (I-3) is DBSG.

In embodiments, the Hb intramolecularly crosslinked with the compound of formula (I-4) comprises:

(I-4-A)

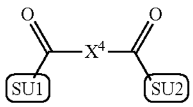

wherein SU1 is a residue on a first subunit of the Hb, and SU2 is a residue on a second subunit of the Hb.

In embodiments, at least two subunits are intramolecularly crosslinked with the compound of formula (I), (I-1), (I-2), (I-3), or (I-4) at a residue selected from the group consisting of Lys (K), Cys (C), Arg (R), and an N-termini. In embodiments, at least two subunits are intramolecularly crosslinked at residues Lys. In embodiments, the compound of formula (I) or (I-3) is DBSG or DBSF. In embodiments, the compound of formula (I) or (I-3) is DBSG.

In embodiments, the two beta subunits of the Hb are intramolecularly crosslinked by the compound of formula (I), (I-1), (I-2), (I-3), or (I-4). In embodiments, amino groups of lysine residues of the beta subunits are intramolecularly crosslinked by the compound of formula (I), (I-1), (I-2), (I-3), or (I-4). In embodiments, the lysine residues of the beta subunits are Lys-81 and Lys-81 of SEQ ID NO: 2, Lys-81 and Lys-94 of SEQ ID NO: 2, or Lys-75 and Lys-81 of SEQ ID NO: 2. In embodiments, the lysine residues of the beta subunits are Lys-81 and Lys-81 of SEQ ID NO: 2. In embodiments, the compound of formula (I) or (I-3) is DBSG or DBSF. In embodiments, the compound of formula (I) or (I-3) is DBSG.

In embodiments, the two alpha subunits of the Hb are intramolecularly crosslinked by the compound of formula (I), (I-1), (I-2), (I-3), or (I-4). In embodiments, amino groups of lysine residues or N-terminus of the alpha subunits are intramolecularly crosslinked by the compound of formula (I), (I-1), (I-2), (I-3), or (I-4). In embodiments, the lysine residues of the alpha subunits are Lys-99 and Lys-99 of SEQ ID NO: 1, Lys-7 and Lys-139 of SEQ ID NO: 1, Lys-90 and Lys-139 of SEQ ID NO: 1, or Lys-90 and Lys-127 of SEQ ID NO: 1. In embodiments, the compound of formula (I) or (I-3) is DBSG or DBSF. In embodiments, the compound of formula (I) or (I-3) is DBSG.

In embodiments, the alpha and the beta subunits of the Hb are intramolecularly crosslinked by the compound of formula (I), (I-1), (I-2), (I-3), or (I-4). In embodiments, amino groups of lysine residues of the alpha and the beta subunits are intramolecularly crosslinked by the compound of formula (I), (I-1), (I-2), (I-3), or (I-4). In embodiments, the lysine residues of the alpha and the beta subunits are Lys-99 of SEQ ID NO: 1 and Lys-103 of SEQ ID NO: 2, respectively. In embodiments, the compound of formula (I) or (I-3) is DBSG or DBSF. In embodiments, the compound of formula (I) or (I-3) is DBSG.

In embodiments, the modified Hb that is intramolecularly crosslinked by the compound of formula (I), (I-1), (I-2), (I-3), or (I-4) is obtained by reacting the compound of formula (I) and a Hb. In embodiments, the compound of formula (I) or (I-3) is DBSG or DBSF. In embodiments, the compound of formula (I) or (I-3) is DBSG.

A non-limiting example of a modified Hb (an intramolecularly crosslinked Hb) comprising amino groups of Lys-81 and Lys-81 of the beta subunits (SEQ ID NO: 2) of a Hb intramolecularly crosslinked with a compound of formula (I) is shown below, wherein X is defined previously:

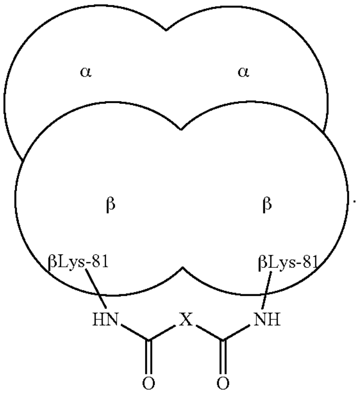

In embodiments, X is

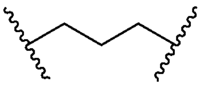

or

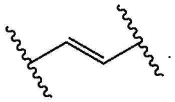

In embodiments, X is

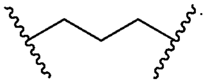 [SMILES: *CCC*]

In embodiments, the compound of formula (I) is DBSG or DBSF. In embodiments, the compound of formula (I) is DBSG.

A non-limiting example of a modified Hb (an intramolecularly crosslinked Hb) comprising amino groups of Lys-81 and Lys-81 of the beta subunits (SEQ ID NO: 2) of a Hb intramolecularly crosslinked with a compound of formula (I-3) is shown below, wherein $X^3$ is defined previously:

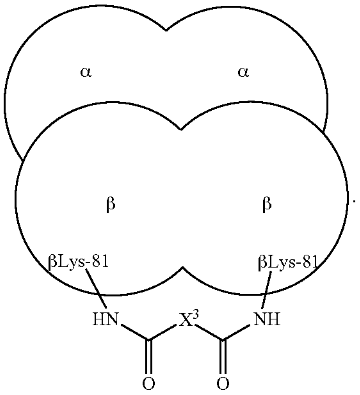

In embodiments, $X^3$ is

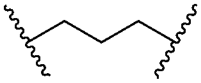

or

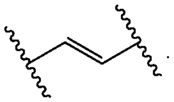

In embodiments, $X^3$ is

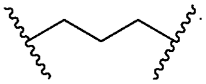 [SMILES: *CCC*]

In embodiments, the compound of formula (I-3) is DBSG or DBSF. In embodiments, the compound of formula (I-3) is DBSG.

In embodiments, the modified Hb comprises a first residue functionalized with a first reactive group. In embodiments, the first reactive group is suitable to react with a second reactive group to form linker using click chemistry. In embodiments, the first reactive group is azido, and the second reactive group is cycloalkynyl; or the first reactive group is cycloalkynyl, and the second reactive group is azido. In embodiments, the first reactive group is azido, and the second reactive group is propargyl; or the first reactive group is propargyl, and the second reactive group is azido. In embodiments, the first reactive group is tetrazine, and the second reactive group is trans-cyclooctene (TCO); or the first reactive group is TCO, and the second reactive group is tetrazine.

In embodiments, the first residue of the modified Hb is a residue of the alpha or the beta subunit. In embodiments, the first residue of the modified Hb is a residue of the alpha subunit. In embodiments, the first residue of the modified Hb is a lysine of the alpha subunit.

In embodiments, the modified Hb comprises at least 1, at least 2, at least 3, or at least 4 of the first residues.

In embodiments, the modified Hb comprises a first residue functionalized with a first reactive group which is azido (i.e., an azido-functionalized Hb). In embodiment, the modified Hb can be obtained by reacting an azido compound and a Hb to form an azido-functionalized Hb, wherein the azido compound is 4-azidophenylglyoxal (4-APG), 6-azidomethyl pyridine carboxaldehyde (6-AMPC), or a compound of formula (II) or (III)

(II)

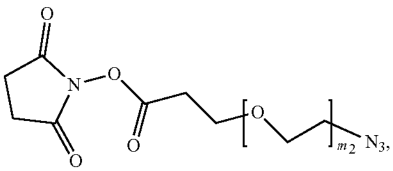

(III)

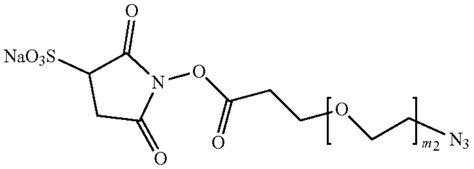

wherein $m_2$ and $m_3$ are each independently an integer of 1-5000, 2-4000, 3-3000, 4-2000, 5-1500, 6-1250, 7-1000, 8-900, 9-900, 10-800, 11-700, 12-600, 13-500, 14-400, 15-300, 16-250, 17-200, 18-175, 19-150, 20-125, 21-110, 22-100, 23-90, 24-80, 25-75, 26-70, 27-65, 28-60, 29-55, 30-50, or 35-40. In embodiments, $m_2$ and $m_3$ are each independently 4, or 12. In embodiments, $m_2$ is 4. In embodiments, $m_3$ is 4.

A non-limiting example of a modified Hb that is azido-functionalized obtained by reacting the compound of formula (II) and a Hb is illustrated below, where $m_2$ is defined previously:

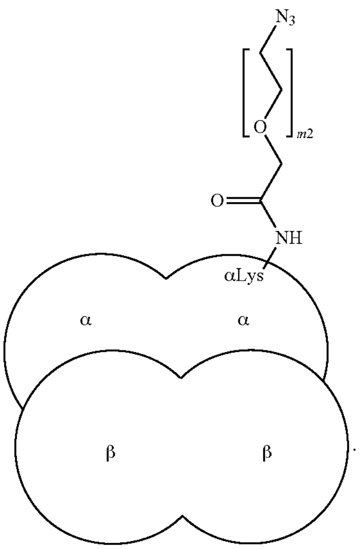

In embodiments, the modified Hb comprises a first residue functionalized with a first reactive group which is cycloalkynyl such as a $C_{6-9}$ heterocycloalkynyl, or a $C_{7-8}$ heterocycloalkynyl (i.e., a cycloalkynyl-functionalized Hb). In embodiments, the modified Hb can be obtained by reacting a cycloalkynyl compound and a Hb to form an alkynyl-functionalized Hb, wherein the cycloalkynyl compound is a compound of formula (VI), (VII), (VIII), or (IX)

(VI)

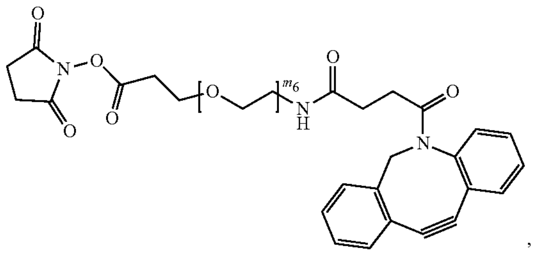

,

-continued (VII)

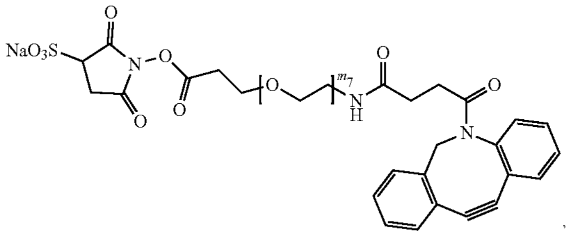

, (VIII)

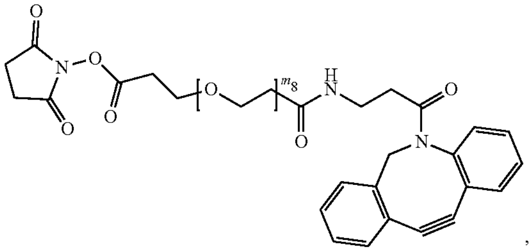

, (IX)

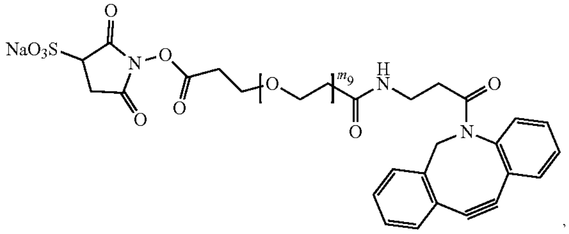

, wherein $m_6$, $m_7$, $m_8$, and $m_9$ are each independently an integer of 1-5000, 2-4000, 3-3000, 4-2000, 5-1500, 6-1250, 7-1000, 8-900, 9-900, 10-800, 11-700, 12-600, 13-500, 14-400, 15-300, 16-250, 17-200, 18-175, 19-150, 20-125, 21-110, 22-100, 23-90, 24-80, 25-75, 26-70, 27-65, 28-60, 29-55, 30-50, or 35-40. In embodiments, $m_6$, $m_7$, $m_8$, and $m_9$ are each independently 4, or 12.

A non-limiting example of a modified Hb that is alkynyl-functionalized obtained by reacting the compound of formula (VI) and a Hb is illustrated below, where $m_6$ is defined previously:

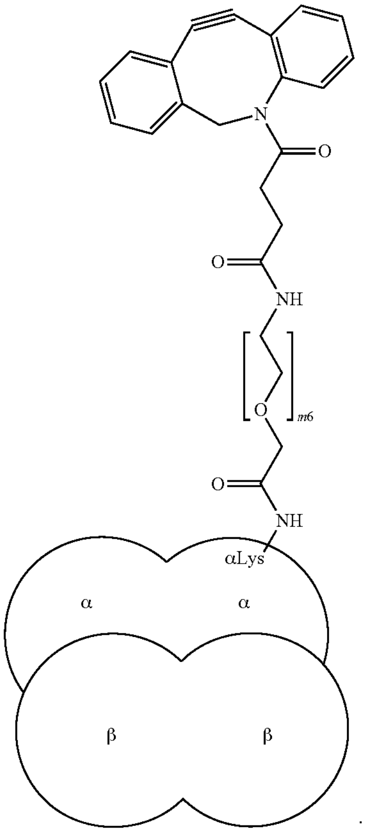

In embodiments, the modified Hb comprises: (i) at least two subunits of a Hb intramolecularly crosslinked with a compound of formula (I), (I-1), (I-2), (I-3), or (I-4), or Table A, or a salt, stereoisomer, or deuterated form thereof disclosed herein any of the above embodiments, and (ii) a first residue functionalized with a first reactive group disclosed above. In embodiments, the compound of formula (I) or (I-3) is DBSG or DBSF. In embodiments, the compound of formula (I) or (I-3) is DBSG.

In embodiments, the first reactive group is azido, and the modified Hb (crosslinked and functionalized) can be obtained by:

reacting the compound of formula (I), (I-1), (I-2), (I-3), or (I-4) and a Hb to form a crosslinked Hb, and reacting the crosslinked Hb and an azido compound; or reacting an azido compound and a Hb to form an azido-functionalized Hb, and reacting the azido-functionalized Hb and the compound of formula (I), (I-1), (I-2), (I-3), or (I-4), wherein the azido compound is 4-azidophenylglyoxal (4-APG), 6-azidomethyl pyridine carboxaldehyde (6-AMPC), or a compound of formula (II) or (III)

(II)

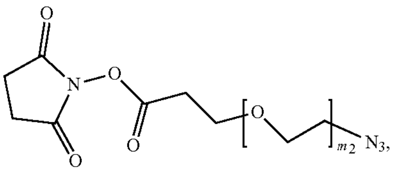

-continued (III)

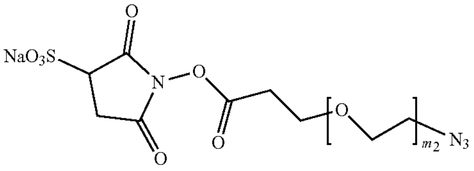

wherein $m_2$ and $m_3$ are each independently an integer of 1-5000, 2-4000, 3-3000, 4-2000, 5-1500, 6-1250, 7-1000, 8-900, 9-900, 10-800, 11-700, 12-600, 13-500, 14-400, 15-300, 16-250, 17-200, 18-175, 19-150, 20-125, 21-110, 22-100, 23-90, 24-80, 25-75, 26-70, 27-65, 28-60, 29-55, 30-50, or 35-40. In embodiments, $m_2$ and $m_3$ are each independently 4, or 12. In embodiments, the compound of formula (I) or (I-3) is DBSG or DBSF. In embodiments, the compound of formula (I) or (I-3) is DBSG.

A non-limiting example of a modified Hb that is (i) crosslinked with a compound of formula (I) and (ii) azido-functionalized using the compound of formula (II) is illustrated below, where X and $m_2$ are defined previously:

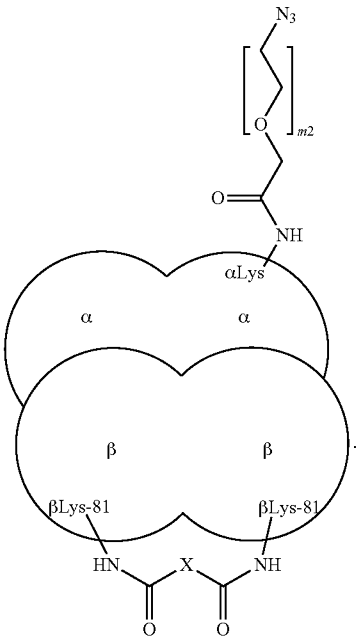

In embodiments, X is

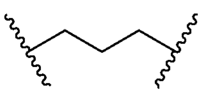

or

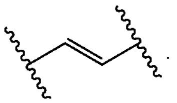

In embodiments, X

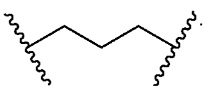 [SMILES: *CCC*]

In embodiments, the compound of formula (I) is DBSG or DBSF. In embodiments, the compound of formula (I) is DBSG.

A non-limiting example of a modified Hb that is (i) crosslinked with a compound of formula (I-3) and (ii) azido-functionalized using the compound of formula (II) is illustrated below, where $X^3$ and $m_2$ are defined previously:

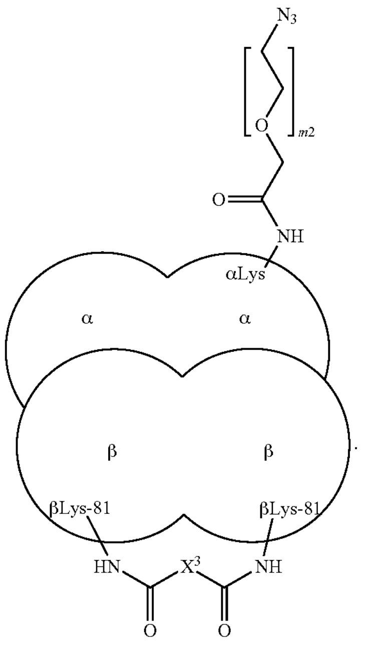

In embodiments, $X^3$ is

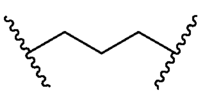

or

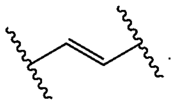

In embodiments, $X^3$ is

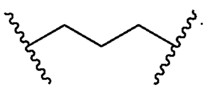

In embodiments, the compound of formula (I-3) is DBSG or DBSF. In embodiments, the compound of formula (I-3) is DBSG.

In embodiments, the first reactive group is cycloalkynyl, and the modified Hb (crosslinked and functionalized) can be obtained by:

reacting the compound of formula (I), (I-1), (I-2), (I-3), or (I-4) and a Hb to form a crosslinked Hb, and reacting the crosslinked Hb and a cycloalkynyl compound; or reacting a cycloalkynyl compound and a Hb to form an alkynyl-functionalized Hb, and reacting the alkynyl-functionalized Hb and the compound of formula (I), (I-1), (I-2), (I-3), or (I-4), wherein the cycloalkynyl compound is a compound of formula (VI), (VII), (VIII), or (IX)

(VI)

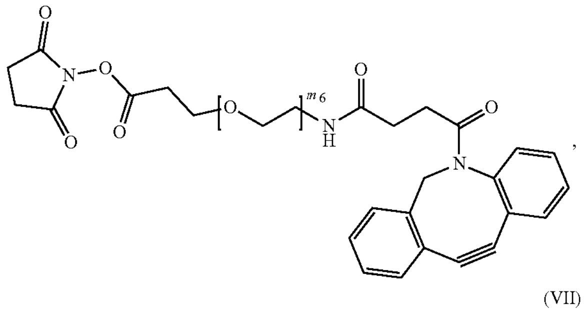

, (VII)

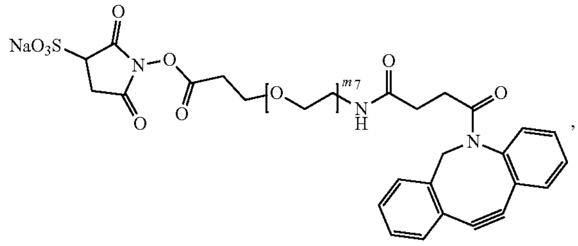

, (VIII)

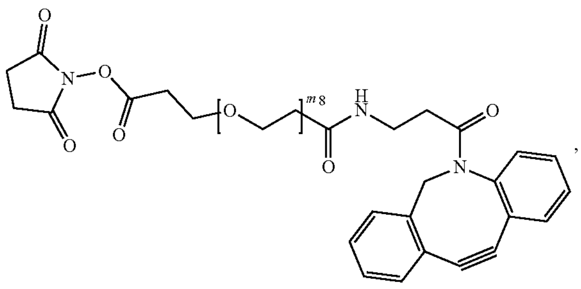

, (IX)

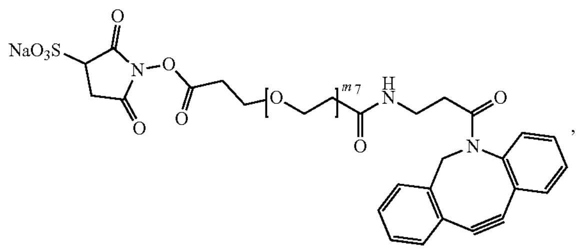

, wherein $m_6$, $m_7$, $m_8$, and $m_9$ are each independently an integer of 1-5000, 1-5000, 2-4000, 3-3000, 4-2000, 5-1500, 6-1250, 7-1000, 8-900, 9-900, 10-800, 11-700, 12-600, 13-500, 14-400, 15-300, 16-250, 17-200, 18-175, 19-150, 20-125, 21-110, 22-100, 23-90, 24-80, 25-75, 26-70, 27-65, 28-60, 29-55, 30-50, or 35-40. In embodiments, $m_6$, $m_7$, $m_8$, and $m_9$ are each independently 4, or 12. In embodiments, the compound of formula (I) or (I-3) is DBSG or DBSF. In embodiments, the compound of formula (I) or (I-3) is DBSG.

A non-limiting example of a modified Hb that is (i) crosslinked with a compound of formula (I) and (ii) cycloalkynyl-functionalized using the compound of formula (VI) is illustrated below, where X and $m_6$ are defined previously:

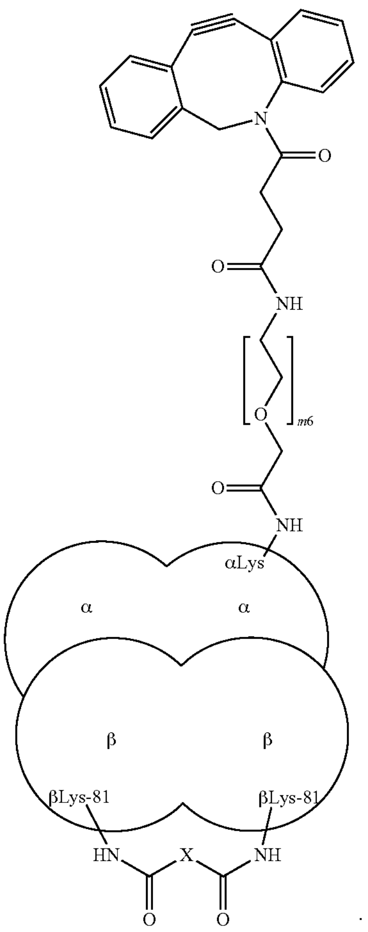

In embodiments, X is

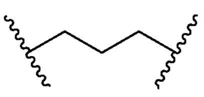

or

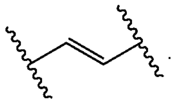

In embodiments, X is

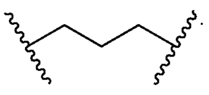 [SMILES: *CCC*]

In embodiments, the compound of formula (I) is DBSG or DBSF. In embodiments, the compound of formula (I) is DBSG.

A non-limiting example of a modified Hb that is (i) crosslinked with a compound of formula (I-3) and (ii) cycloalkynyl-functionalized using the compound of formula (VI) is illustrated below, where $X^3$ and $m_6$ are defined previously:

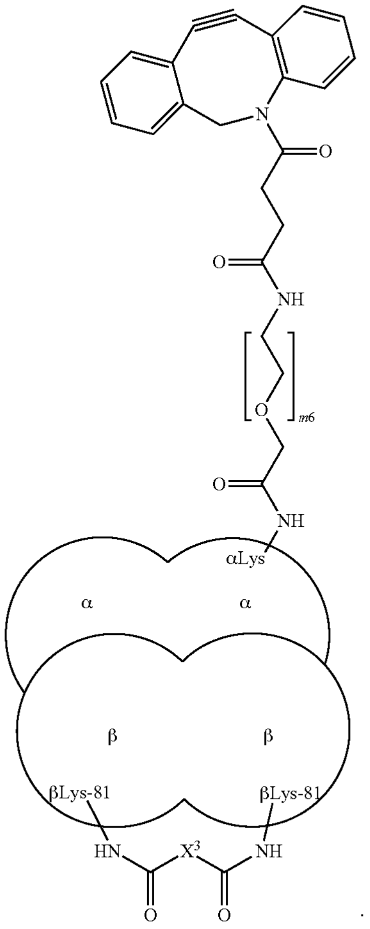

In embodiments, $X^3$ is

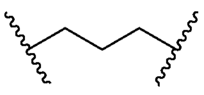

or

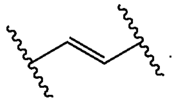

In embodiments, $X^3$ is

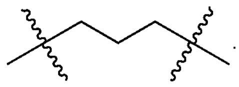 [SMILES: *CCC*]

In embodiments, the compound of formula (I-3) is DBSG or DBSF. In embodiments, the compound of formula (I-3) is DBSG.

In embodiments, the modified Hb disclosed herein in any of its embodiments has a molecular weight of about 60 kDa to about 100 kDa, about 62 kDa to about 80 kDa, about 63 kDa to about 70 kDa, about 64 kDa to about 69 kD, about 65 kDa to about 68 kDa, or about 66 kDa to about 67 kDa.

Multimerized Hemoglobin Compositions

In a further aspect, the present disclosure provides a multimerized hemoglobin (Hb) composition, comprising two or more of the modified Hb described herein in any of the above embodiments (i.e., each modified Hb independently comprises at least two subunits intramolecularly crosslinked with a compound of formula (I), (I-1), (I-2), (I-3), or (I-4), or a salt, stereoisomer, or deuterated form thereof disclosed herein in any of the above embodiments). In embodiments, the multimerized Hb composition comprises two or more of the modified Hb that are covalently linked. The two or more of the modified Hb of the multimerized Hb composition can be covalently linked (e.g., multimerized) according to descriptions further below.

In embodiments, the Hb is bovine, human, equine, porcine, ovine, simian, or fish hemoglobin. In embodiments, the Hb is bovine hemoglobin (bHb).

In embodiments, the Hb used herein, which is comprised of 2 alpha and 2 beta subunits, is represented by:

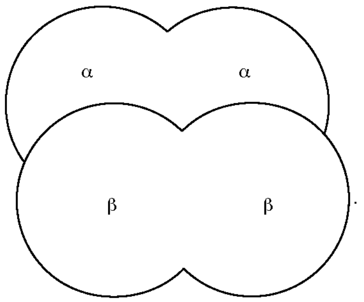

Each subunit of hemoglobin is well-characterized with known sequences. In embodiments, the alpha subunit of the Hb comprises an amino acid sequence of SEQ ID NO: 1. In embodiments, the alpha subunit of the Hb consists of an amino acid sequence of SEQ ID NO: 1. In embodiments, the alpha subunit of the Hb comprises Methionine (Met, M) on the N-terminus. In embodiments, the alpha subunit of the Hb has 80% or more, 90% or more, 95% or more, 96% or more, 97% or more, 98% or more, or 99% or more amino acid sequence similarity to the amino acid sequence of SEQ ID NO: 1. In embodiments, the beta subunit of the Hb comprises an amino acid sequence of SEQ ID NO: 2. In embodiments, the beta subunit of the Hb consists of an amino acid sequence of SEQ ID NO: 2. In embodiments, the beta subunit of the Hb has 80% or more, 90% or more, 95% or more, 96% or more, 97% or more, 98% or more, or 99% or more amino acid sequence similarity to the amino acid sequence of SEQ ID NO: 2.

A. Crosslinking

In embodiments, the Hb intramolecularly crosslinked with the compound of formula (I) comprises:

(I-A)

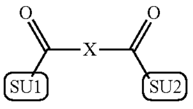

wherein SU1 is a residue on a first subunit of the Hb, and SU2 is a residue on a second subunit of the Hb. In embodiments, X is

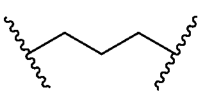
or
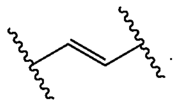

In embodiments, X is

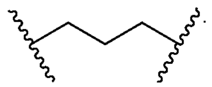

In embodiments, the compound of formula (I) is DBSG or DBSF. In embodiments, the compound of formula (I) is DBSG.

In embodiments, the Hb intramolecularly crosslinked with the compound of formula (I-1) comprises:

(I-1-A)

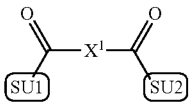

wherein SU1 is a residue on a first subunit of the Hb, and SU2 is a residue on a second subunit of the Hb.

In embodiments, the Hb intramolecularly crosslinked with the compound of formula (I-2) comprises:

(I-2-A)

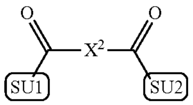

wherein SU1 is a residue on a first subunit of the Hb, and SU2 is a residue on a second subunit of the Hb.

In embodiments, the Hb intramolecularly crosslinked with the compound of formula (I-3) comprises:

(I-3-A)

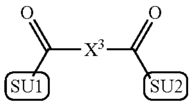

wherein SU1 is a residue on a first subunit of the Hb, and SU2 is a residue on a second subunit of the Hb. In embodiments, $X^3$ is

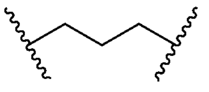
or
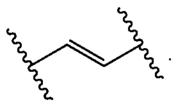

In embodiments, $X^3$ is

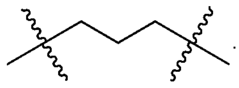 [SMILES: *CCC*]

In embodiments, the compound of formula (I-3) is DBSG or DBSF. In embodiments, the compound of formula (I-3) is DBSG.

In embodiments, the Hb intramolecularly crosslinked with the compound of formula (I-4) comprises:

(I-4-A)

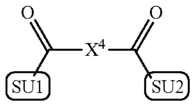

wherein SU1 is a residue on a first subunit of the Hb, and SU2 is a residue on a second subunit of the Hb.

In embodiments, at least two subunits of each modified Hb are intramolecularly crosslinked with the compound of formula (I), (I-1), (I-2), (I-3), or (I-4) at a residue selected from the group consisting of Lys, Cys, Arg, and an N-termini. In embodiments, at least two subunits are intramolecularly crosslinked at residues Lys. In embodiments, the compound of formula (I) or (I-3) is DBSG or DBSF. In embodiments, the compound of formula (I) or (I-3) is DBSG.

In embodiments, the two beta subunits of the Hb are intramolecularly crosslinked by the compound of formula (I), (I-1), (I-2), (I-3), or (I-4). In embodiments, amino groups of lysine residues of the beta subunits are intramolecularly crosslinked by the compound of formula (I), (I-1), (I-2), (I-3), or (I-4). In embodiments, the lysine residues of the beta subunits are Lys-81 and Lys-81 of SEQ ID NO: 2, Lys-81 and Lys-94 of SEQ ID NO: 2, or Lys-75 and Lys-81 of SEQ ID NO: 2. In embodiments, the lysine residues of the beta subunits are Lys-81 and Lys-81 of SEQ ID NO: 2. In embodiments, the compound of formula (I) or (I-3) is DBSG or DBSF. In embodiments, the compound of formula (I) or (I-3) is DBSG.

In embodiments, the two alpha subunits of the Hb are intramolecularly crosslinked by the compound of formula (I), (I-1), (I-2), (I-3), or (I-4). In embodiments, amino groups of lysine residues or N-terminus of the alpha subunits are intramolecularly crosslinked by the compound of formula (I), (I-1), (I-2), (I-3), or (I-4). In embodiments, the lysine residues of the alpha subunits are Lys-99 and Lys-99 of SEQ ID NO: 1, Lys-7 and Lys-139 of SEQ ID NO: 1, Lys-90 and Lys-139 of SEQ ID NO: 1, or Lys-90 and Lys-127 of SEQ ID NO: 1. In embodiments, the compound of formula (I) or (I-3) is DBSG or DBSF. In embodiments, the compound of formula (I) or (I-3) is DBSG.

In embodiments, the alpha and the beta subunits of the Hb are intramolecularly crosslinked by the compound of formula (I), (I-1), (I-2), (I-3), or (I-4). In embodiments, amino groups of lysine residues of the alpha and the beta subunits are intramolecularly crosslinked by the compound of formula (I), (I-1), (I-2), (I-3), or (I-4). In embodiments, the lysine residues of the alpha and the beta subunits are Lys-99 of SEQ ID NO: 1 and Lys-103 of SEQ ID NO: 2, respectively. In embodiments, the compound of formula (I) or (I-3) is DBSG or DBSF. In embodiments, the compound of formula (I) or (I-3) is DBSG.

In embodiments, the modified Hb described in any of the above embodiments is obtained with a bifunctional linker. In embodiments, the compound of formula (I) is a bifunctional linker, wherein:

X is $C_{1-24}$ alkylene, $C_{2-24}$ alkenylene, $C_{2-24}$ alkynylene, $C_{3-9}$ cycloalkylene, $C_{3-9}$ cycloalkenylene, 5-12 membered heterocyclylene containing 1 or 2 heteroatoms selected from N, S, or O, arylene, heteroarylene, or $-L^1-NR^A-L^2-$, wherein X is optionally substituted with 1-6 $R^3$ as permitted by valency;

$R^1$ and $R^2$ are each independently —OH, halogen, or a leaving group;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), or —C(O)—$R^1$, wherein each alkyl or alkylene is optionally and independently substituted with —$C_{1-6}$ alkyl, —OH, —CN, —$NO_2$, or halogen;

$R^A$ is H, —$C_{1-6}$ alkyl, aryl, —C(O)-aryl, —$SO_2$($C_{1-6}$ alkyl), or —$SO_2$-aryl, wherein each alkyl, aryl, or alkylene is optionally and independently substituted with —$C_{1-6}$ alkyl, —OH, —CN, —$NO_2$, or halogen;

$L^1$ and $L^2$ are each independently $C_{1-12}$ alkylene, $C_{2-12}$ alkenylene, $C_{2-12}$alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each m is independently an integer of 1-200; and each n is independently an integer of 0-50.

In embodiments, the modified Hb described in any of the above embodiments is obtained with a bifunctional linker. In embodiments, the compound of formula (I-1) is the bifunctional linker, wherein:

$X^1$ is arylene or heteroarylene, wherein $X^1$ is optionally substituted with 1 or 2 $R^3$ as permitted by valency;

$R^1$ and $R^2$ are each independently a leaving group;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), or —C(O)—$R^1$, wherein each alkyl or alkylene is optionally and independently substituted with —$C_{1-6}$ alkyl, —OH, —CN, —$NO_2$, or halogen;

each m is independently an integer of 1-200; and each n is independently an integer of 0-50.

In embodiments of the compounds of formula (I-1), or a salt, stereoisomer, or deuterated form thereof, if $X^1$ is

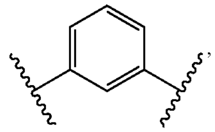 [SMILES: *c1cccc(*)c1]

then the leaving group is not

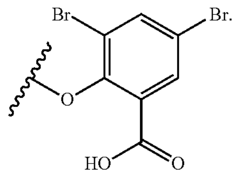 [SMILES: *Oc1c(Br)cc(Br)cc1C(=O)O]

In embodiments, the modified Hb described in any of the above embodiments is obtained with a bifunctional linker. In embodiments, the compound of formula (I-2) is the bifunctional linker, wherein:

$X^2$ is $-L^1-NR^A-L^2-$, $R^1$ and $R^2$ are each independently a leaving group;

$R^A$ is H, —$C_{1-6}$ alkyl, aryl, —C(O)-aryl, —$SO_2$($C_{1-6}$ alkyl), —$SO_2$-aryl, or —($C_{1-6}$ alkylene)-($OCH_2CH_2$)$_m$—($CH_2$)$_n$—$N_3$, wherein each alkyl, aryl, or alkylene is optionally and independently substituted with —$C_{1-6}$ alkyl, —OH, —CN, —$NO_2$, or halogen;

$L^1$ and $L^2$ are each independently $C_{1-12}$ alkylene, $C_{2-12}$ alkenylene, $C_{2-12}$ alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), or —C(O)—$R^1$, wherein each alkyl or alkylene is optionally and independently substituted with —$C_{1-6}$ alkyl, —OH, —CN, —$NO_2$, or halogen;

each m is independently an integer of 1-200; and each n is independently an integer of 0-50.

In embodiments, the modified Hb described in any of the above embodiments is obtained with a bifunctional linker. In embodiments, the compound of formula (I-3) is the bifunctional linker, wherein:

$X^3$ is $C_{1-24}$ alkylene, $C_{2-24}$ alkenylene, or $C_{2-24}$ alkynylene, wherein $X^2$ is optionally substituted with 1-6 $R^3$ as permitted by valency;

$R^1$ and $R^2$ are each independently a leaving group;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), or —C(O)—$R^1$, wherein each alkyl or alkylene is optionally and independently substituted with —$C_{1-6}$ alkyl, —OH, —CN, —$NO_2$, or halogen;

each m is independently an integer of 1-200; and each n is independently an integer of 0-50.

In embodiments of the compounds of formula (I-3), when $X^3$ is unsubstituted, then the leaving group is not

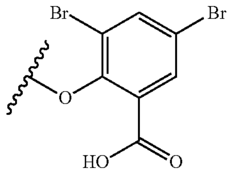

or

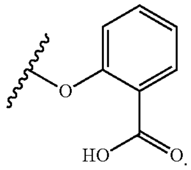

In embodiments, the modified Hb described in any of the above embodiments is obtained with a bifunctional linker. In embodiments, the compound of formula (I-4) is a bifunctional linker, wherein:

$X^4$ is $C_{3-9}$ cycloalkylene, $C_{3-9}$ cycloalkenylene, 5-12 membered heterocyclylene containing 1 or 2 heteroatoms selected from N, S, or O, wherein $X^4$ is optionally substituted with 1-6 $R^3$ as permitted by valency;

$R^1$ and $R^2$ are each independently a leaving group;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), or —C(O)—$R^1$, wherein each alkyl or alkylene is optionally and independently substituted with —$C_{1-6}$ alkyl, —OH, —CN, —$NO_2$, or halogen;

each m is independently an integer of 1-200; and each n is independently an integer of 0-50.

In embodiments, $R^1$ and $R^2$ of formula (I), (I-1), (I-2), (I-3), or (I-4) are a leaving group, and the leaving group is

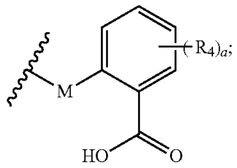

M is O or S;

each $R^4$ is independently halogen or —$C_{1-6}$ alkyl; and a is an integer of 0-4.

In embodiments, the leaving group is

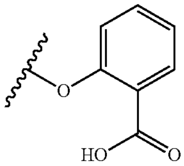

or

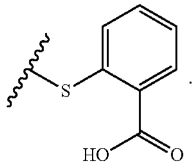

In embodiments, a is 1, 2, or 3. In embodiments, each $R^4$ is halogen. In embodiments, each $R^4$ is independently —F, —Cl, or —Br. In embodiments, the leaving group is

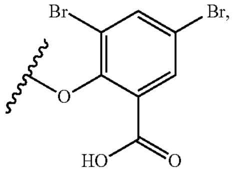

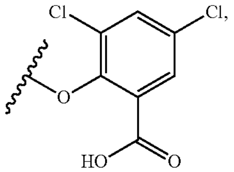

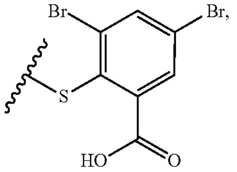

or

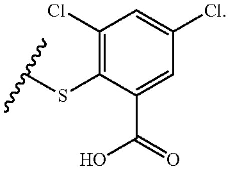

In embodiments, $R^1$ and $R^2$ of formula (I), (I-1), (I-2), (I-3), or (I-4) are a leaving group, and wherein the leaving group is —O—($C_{1-6}$ alkylene)-$SO_3H$. In embodiments, the leaving group is —O—($CH_2CH_2$)—$SO_3H$.

In embodiments, X of formula (I) or (I-3) is $C_{1-12}$ alkylene, $C_{2-12}$alkenylene, or $C_{2-12}$ alkynylene, each of which is optionally substituted with 1-6 $R^3$ as permitted by valency. In embodiments, X of formula (I) or (I-3) is $C_{1-6}$ alkylene, $C_{2-6}$ alkenylene, or $C_{2-6}$ alkynylene, each of which is optionally substituted with 1 or 2 $R^3$ as permitted by valency.

In embodiments, X of formula (I) or (I-3) is $C_{1-6}$ alkylene optionally substituted with 1 or 2 $R^3$ as permitted by valency. In embodiments, X is

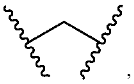

,

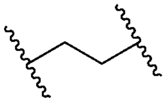

,

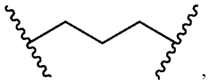

,

-continued

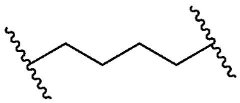

,

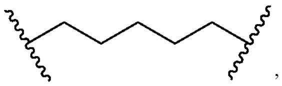

, or

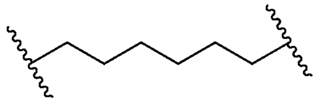

.

In embodiments, X is

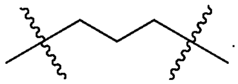 [SMILES: *CCC*]

.

In embodiments, X is $C_{2-6}$ alkenylene optionally substituted with 1 or 2 $R^3$ as permitted by valency. In embodiments, X is

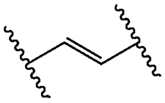

or

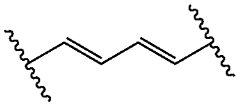

.

In embodiments, X is

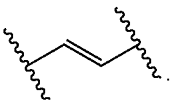 [SMILES: */C=C/*]

.

In embodiments, X is $C_{2-6}$ alkynylene optionally substituted with 1 or 2 $R^3$ as permitted by valency. In embodiments, X is

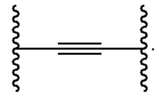 [SMILES: *C#C*]

.

In embodiments, X of formula (I) or (I-4) is $C_{3-9}$ cycloalkylene, $C_{3-9}$ cycloalkenylene, or 5-12 membered heterocyclylene, each of which is optionally substituted with 1 or 2 $R^3$ as permitted by valency.

In embodiments, X is $C_{3-7}$ cycloalkylene optionally substituted with 1 or 2 $R^3$ as permitted by valency. In embodiments, X is

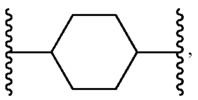

,

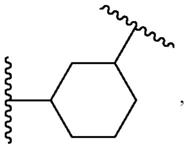

, or

-continued

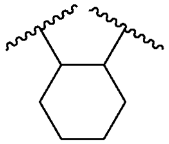

.

In embodiments, X is $C_{3-7}$ cycloalkenylene optionally substituted with 1 or 2 $R^3$ as permitted by valency. In embodiments, X is

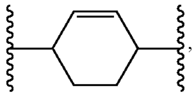

,

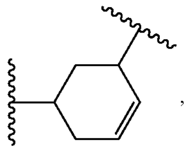

,

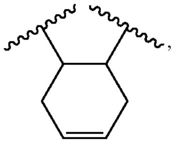

,

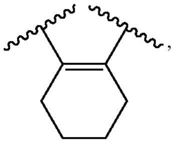

, or

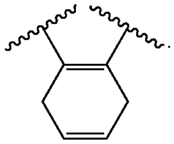

.

In embodiments, X of formula (I) or (I-1) is arylene or heteroarylene, each of which is optionally substituted with 1 or 2 $R^3$ as permitted by valency.

In embodiments, X is $C_{6-10}$ arylene optionally substituted with 1 or 2 $R^3$ as permitted by valency. In embodiments, X is

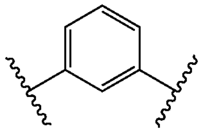

or

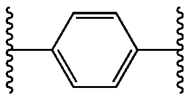

.

In embodiments, X is $C_{6-10}$ arylene substituted with —C(O)—$R^1$, and wherein $R^1$ is —OH, halogen, or a leaving group. In embodiments, $R^1$ is a leaving group. In embodiments, the leaving group is

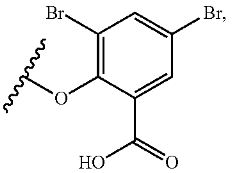

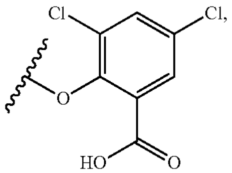

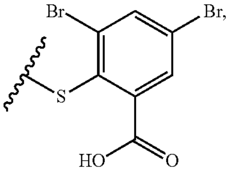

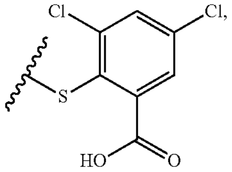

-continued

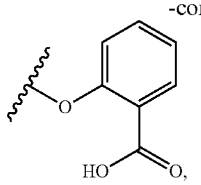

or

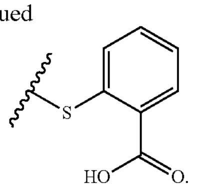

In embodiments, X is

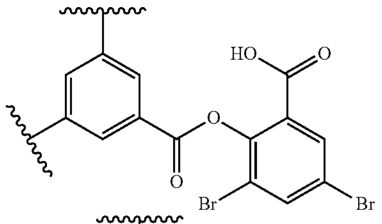

or

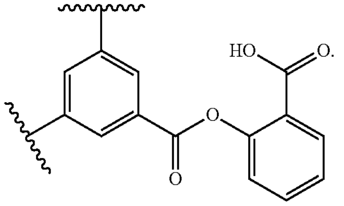

In embodiments, X of formula (I) or (I-2) is -$L^1$-$NR^A$-$L^2$-, and:

$R^A$ is H, —$C_{1-6}$ alkyl, aryl, —C(O)-aryl, —$SO_2$($C_{1-6}$ alkyl), —$SO_2$-aryl, wherein m is an integer of 1-50, n is an integer of 0-25, and each alkyl, aryl, or alkylene is optionally and independently substituted with —$C_{1-6}$ alkyl; and $L^1$ and $L^2$ are each independently $C_{1-6}$ alkylene, $C_{2-6}$ alkenylene, $C_{2-6}$ alkynylene, $C_{3-6}$ cycloalkylene, $C_{3-6}$ cycloalkenylene, arylene, or heteroarylene, wherein $L^1$ and $L^2$ are optionally and independently substituted with 1-3 $R^3$.

In embodiments, $R^A$ is H, and $L^1$ and $L^2$ are each independently $C_{1-6}$ alkylene or $C_{2-6}$ alkenylene. In embodiments, X is H

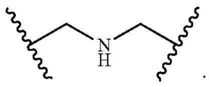

In embodiments, $R^A$ is $C_{6-10}$ aryl, and $L^1$ and $L^2$ are each independently $C_{1-6}$ alkylene, or $C_{2-6}$alkenylene, and wherein the aryl of $R^A$ is optionally substituted with —$C_{1-6}$ alkyl. In embodiments, X is

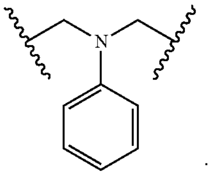 [SMILES: *CN(C*)c1ccccc1]

In embodiments, $R^A$ is —$SO_2$—$C_{1-6}$ alkyl, and $L^1$ and $L^2$ are each independently $C_{1-6}$ alkylene, or $C_{2-6}$alkenylene. In embodiments, X is

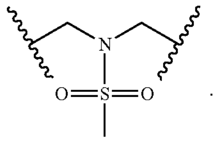 [SMILES: *CN(C*)S(C)(=O)=O]

In embodiments, $R^A$ is —$SO_2$—$C_{6-10}$ aryl, and $L^1$ and $L^2$ are each independently $C_{1-6}$ alkylene, or $C_{2-6}$ alkenylene, and wherein the aryl of $R^A$ is optionally substituted with —$C_{1-6}$ alkyl. In embodiments, X is

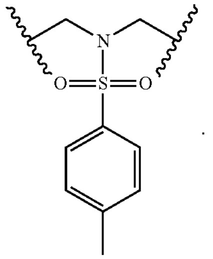 [SMILES: *CN(C*)S(=O)(=O)c1ccc(C)cc1]

In embodiments, $R^A$ is —C(O)—$C_{6-10}$ aryl, and $L^1$ and $L^2$ are each independently $C_{1-6}$ alkylene, or $C_{2-6}$alkenylene, and wherein the aryl of $R^A$ is optionally substituted with —$C_{1-6}$ alkyl. In embodiments, X is

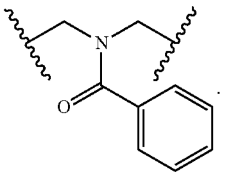 [SMILES: *CN(C*)C(=O)c1ccccc1]

In embodiments, the compound of formula (I), (I-1), (I-2), (I-3), or (I-4) (bifunctional) is:

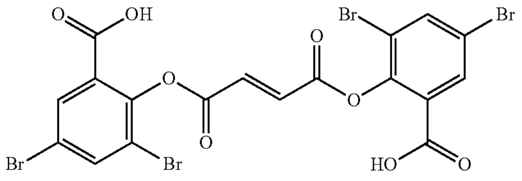 [SMILES: O=C(/C=C/C(=O)Oc1c(Br)cc(Br)cc1C(=O)O)Oc1c(Br)cc(Br)cc1C(=O)O]

(bis(3,5-dibromosalicyl)fumarate; “DBSF”),
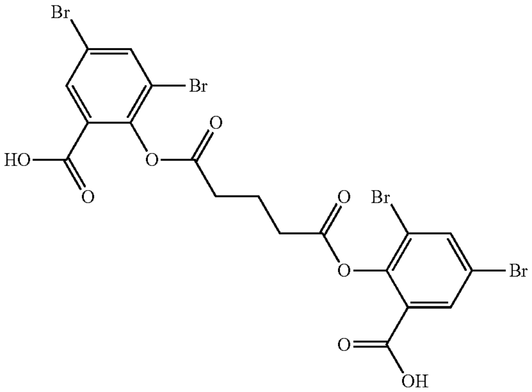 [SMILES: O=C(CCCC(=O)Oc1c(Br)cc(Br)cc1C(=O)O)Oc1c(Br)cc(Br)cc1C(=O)O]
(bis(3,5-dibromosalicyl)glutarate; “DBSG”),
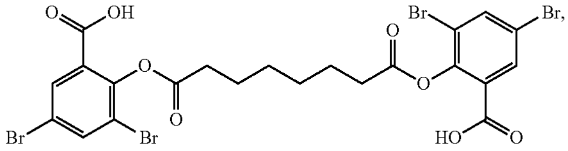
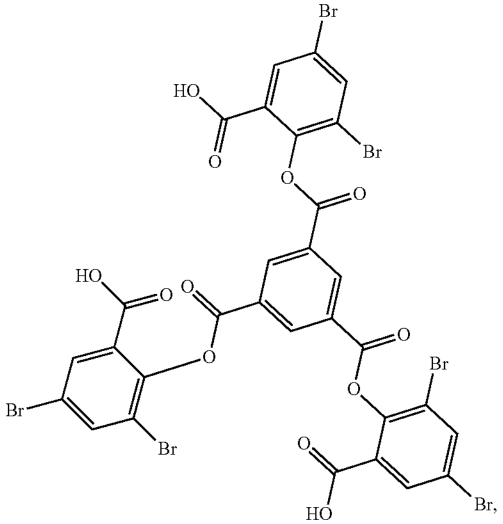
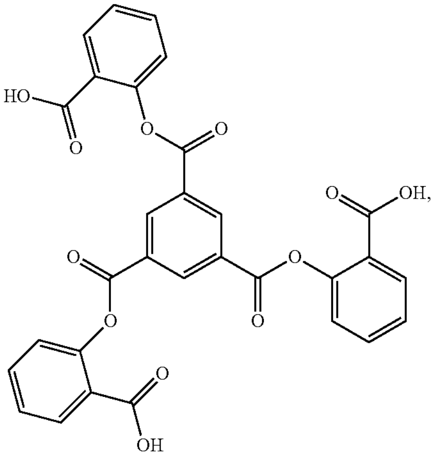
-continued
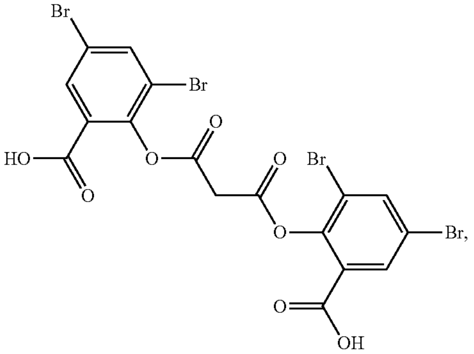
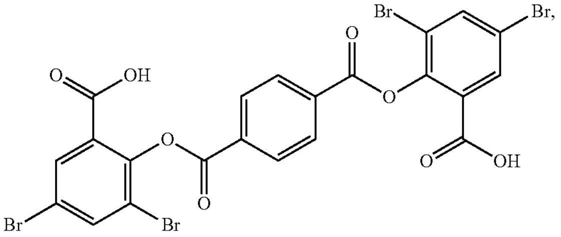
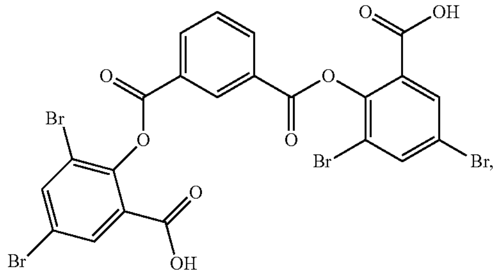
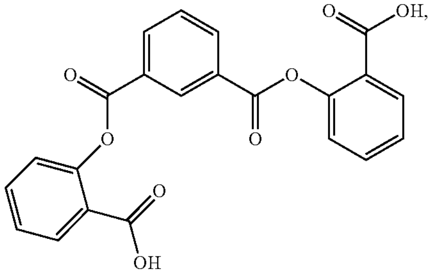
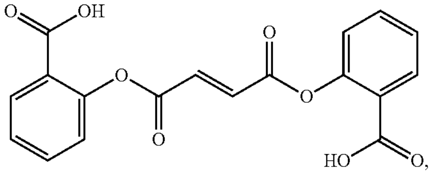
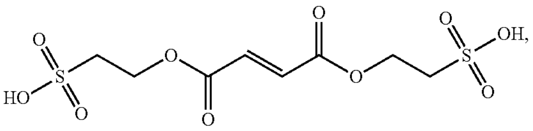
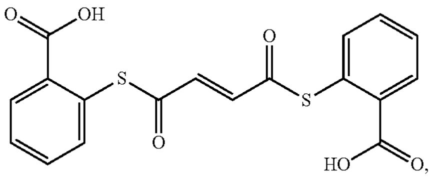

-continued

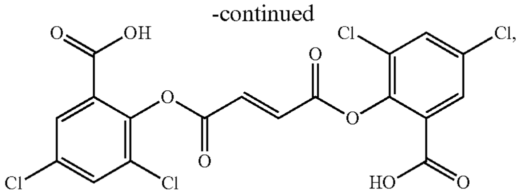

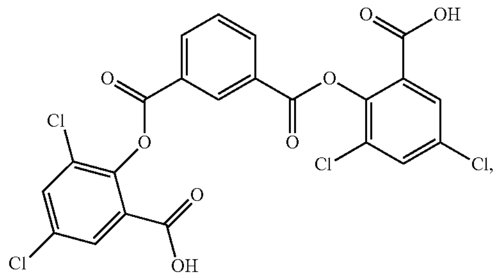

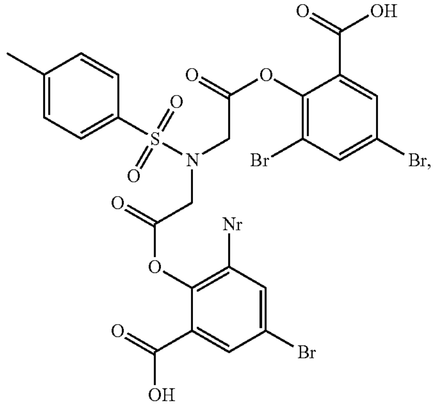

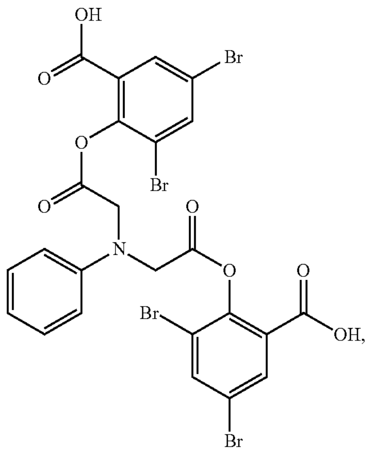

or

-continued

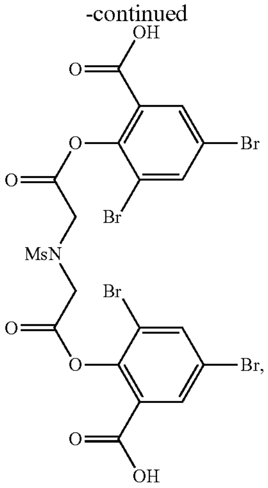

or a salt, a stereoisomer, or a deuterated form thereof, wherein DBS represents

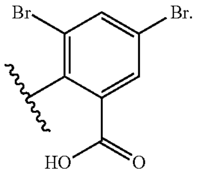 [SMILES: *c1c(Br)cc(Br)cc1C(=O)O]

In embodiments, the compound of formula (I) or (I-3) (bifunctional) is DBSG or DBSF. In embodiments, the compound of formula (I) or (I-3) (bifunctional) is DBSG.

A non-limiting example of a modified Hb (an intramolecularly crosslinked Hb) comprising amino groups of Lys-81 and Lys-81 of the beta subunits (SEQ ID NO: 2) intramolecularly crosslinked with a compound of formula (I) is shown below, wherein X is defined previously:

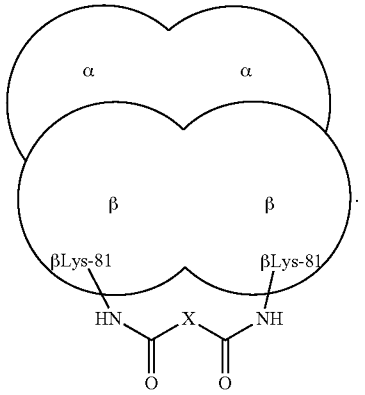

In embodiments, X is

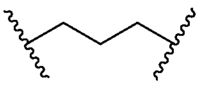

or

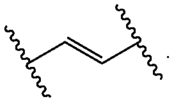

In embodiments, X is

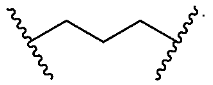 [SMILES: *CCC*]

In embodiments, the compound of formula (I) is DBSG or DBSF. In embodiments, the compound of formula (I) is DBSG.

A non-limiting example of a modified Hb (an intramolecularly crosslinked Hb) comprising amino groups of Lys-81 and Lys-81 of the beta subunits (SEQ ID NO: 2) intramolecularly crosslinked with a compound of formula (I-3) is shown below, wherein $X^3$ is defined previously:

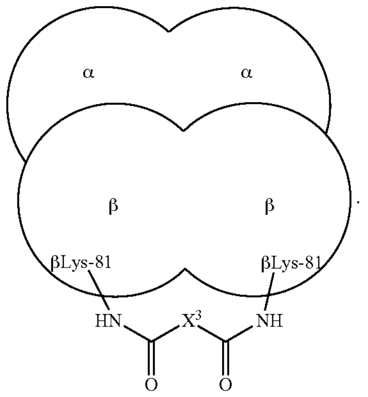

In embodiments, $X^3$ is

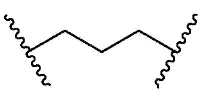
or
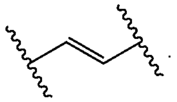

In embodiments, $X^3$ is

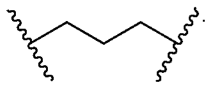 [SMILES: *CCC*]

In embodiments, the compound of formula (I-3) is DBSG or DBSF. In embodiments, the compound of formula (I-3) is DBSG.

B. Multimerization

In embodiments, the multimerized Hb composition comprises a reaction product of: a first modified Hb comprising a first residue functionalized with a first reactive group for a click reaction; and a reactant molecule comprising a second reactive group that is complementary to the first reactive group for the click reaction.

In embodiments, the first reactive group is azido, and the second reactive group is cycloalkynyl; or the first reactive group is cycloalkynyl, and the second reactive group is azido. In embodiments, the first reactive group is azido, and the second reactive group is propargyl; or the first reactive group is propargyl, and the second reactive group is azido.

In embodiments, the first reactive group is tetrazine, and the second reactive group is TCO; or the first reactive group is TCO, and the second reactive group is tetrazine.

In embodiments, at least one of the modified Hb has two, three, or four of the first reactive groups.

Multimerization of Modified Hbs Using Scaffold Compounds

In one embodiment, the reactant molecule is a scaffold compound comprising the second reactive group. In embodiments, the scaffold compound has two, three, or four of the second reactive groups.

In embodiments, at least one of the modified Hb has two, three, or four of the first reactive groups.

In embodiments, the first modified Hb comprising a first residue functionalized with a first reactive group for a click reaction comprises at least one azido or at least one cycloalkynyl that is covalently linked to alpha and/or beta subunits of the Hb. In embodiments, the first modified Hb comprising a first residue functionalized with a first reactive group for a click reaction comprises at least one azido or at least one cycloalkynyl that is covalently linked to alpha subunits of the Hb.

In embodiments, the first reactive group is azido, and the second reactive group is cycloalkynyl; or the first reactive group is cycloalkynyl, and the second reactive group is azido.

In embodiments, the first reactive group is azido, and the second reactive groups are cycloalkynyl. In embodiments, the cycloalkynyl is a $C_{6-9}$ heterocycloalkynyl, or a $C_{7-8}$ heterocycloalkynyl. In embodiments, the first modified Hb comprising a first residue functionalized with the first reactive group for a click reaction is obtained by: reacting the compound of formula (I), (I-1), (I-2), (I-3), or (I-4) and a Hb to form a crosslinked Hb, and reacting the crosslinked Hb and an azido compound; or reacting an azido compound and a Hb to form an azido-functionalized Hb, and reacting the azido-functionalized Hb and the compound of formula (I), (I-1), (I-2), (I-3), or (I-4), wherein the azido compound is 4-azidophenylglyoxal (4-APG), 6-azidomethyl pyridine carboxaldehyde (6-AMPC), or a compound of formula (II) or (III)

(II)

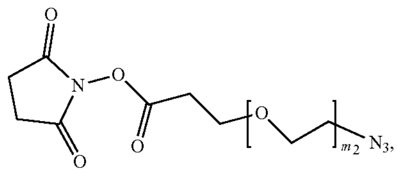

(III)

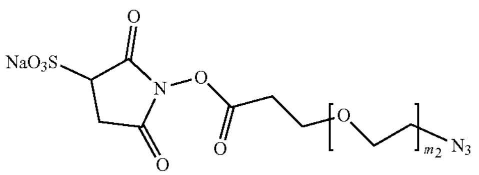

wherein $m_2$ and $m_3$ are each independently an integer of 1-5000, 2-4000, 3-3000, 4-2000, 5-1500, 6-1250, 7-1000, 8-900, 9-900, 10-800, 11-700, 12-600, 13-500, 14-400, 15-300, 16-250, 17-200, 18-175, 19-150, 20-125, 21-110, 22-100, 23-90, 24-80, 25-75, 26-70, 27-65, 28-60, 29-55, 30-50, or 35-40. In embodiments, $m_2$ and $m_3$ are each independently 4, or 12. In embodiments, $m_2$ and $m_3$ are each independently 1-15, 1-10, 2-8, 3-6, or 4-5. In embodiments, $m_2$ and $m_3$ are each 4. In embodiments, the compound of formula (I) or (I-3) is DBSG or DBSF. In embodiments, the compound of formula (I) or (I-3) is DBSG.

Non-limiting examples of a modified Hb that is azido-functionalized obtained by reacting the compound of formula (II) and a Hb are illustrated below, wherein X, $X^3$, and $m_2$ are defined previously:

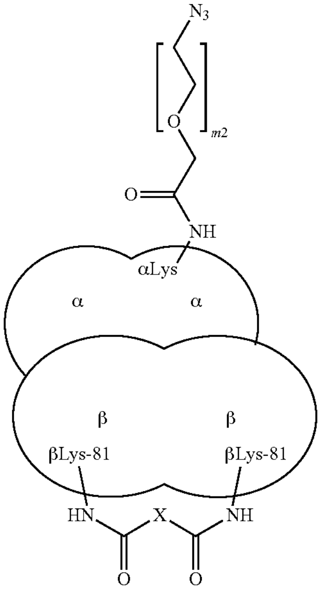

,

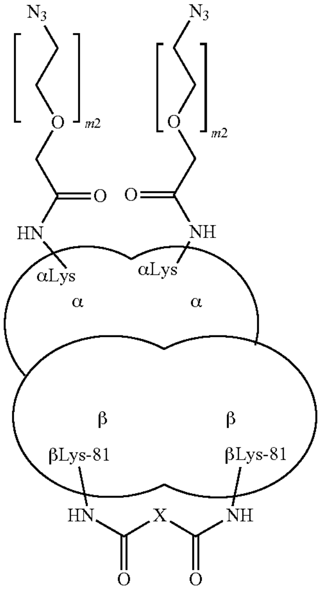

,

-continued

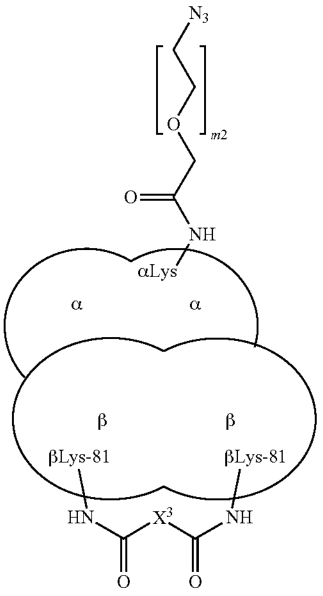

,

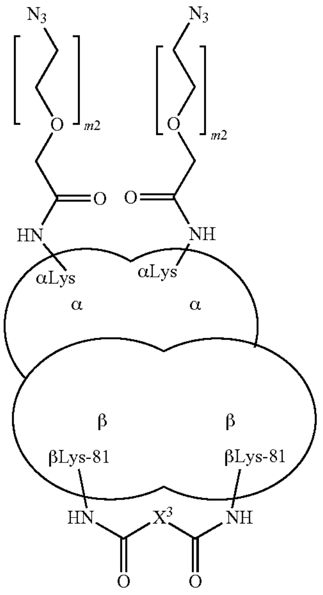

,

In embodiments, the azide functionality is attached to one or more lysine residues on an alpha subunit of the Hb (e.g., as shown above). In embodiments, the azide functionality is attached to one or more lysine residues on a beta subunit of the Hb. In embodiments, each $m_2$ is independently an integer of 1-15, 1-10, 2-8, 3-6, or 4-5. In embodiments, $m_2$ is 4. In embodiments, X or $X^3$ is

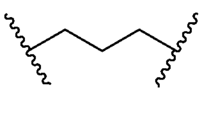

or

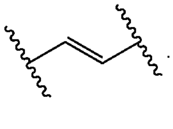

.

In embodiments, X or $X^3$ is

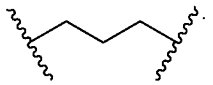

In embodiments, the compound of formula (I) or (I-3) is DBSG or DBSF. In embodiments, the compound of formula (I) or (I-3) is DBSG.

In embodiments, the scaffold compound is a compound of formula (IV) or (V)

(IV)

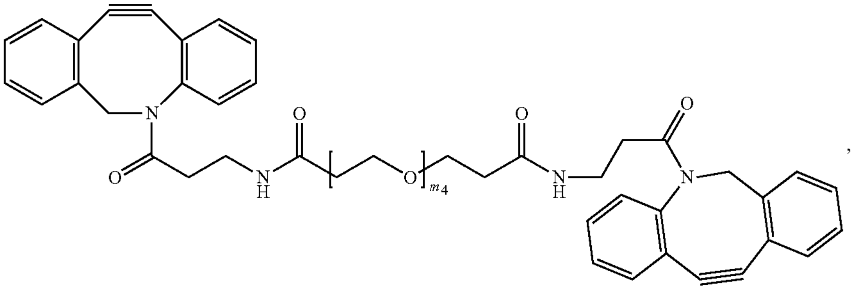

, (V)

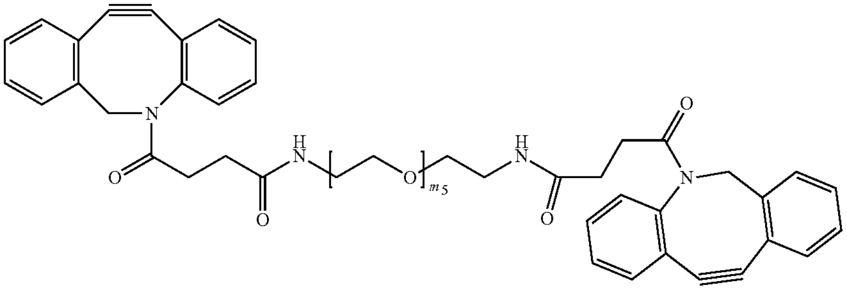

wherein $m_4$ and $m_5$ are each independently an integer of 1-5000, 2-4000, 3-3000, 4-2000, 5-1500, 6-1250, 7-1000, 8-900, 9-900, 10-800, 11-700, 12-600, 13-500, 14-400, 15-300, 16-250, 17-200, 18-175, 19-150, 20-125, 21-110, 22-100, 23-90, 24-80, 25-75, 26-70, 27-65, 28-60, 29-55, 30-50, or 35-40. In embodiments, $m_4$ and $m_5$ are each independently 1-20, 1-12, 2-10, 3-8, 4-7, or 5-6. In embodiments, $m_4$ and $m_5$ are each independently 4, or 35-55. In embodiments, $m_4$ and $m_5$ are each 5.

A non-limiting example of a multimerized Hb composition comprising a reaction product of: a first modified Hb comprising a first residue functionalized with one or more azido reactive groups for a click reaction, and the scaffold compound of formula (V) is illustrated below, wherein X, $m_2$, $m_5$ are defined previously, and Z is an integer of 0-100, 1-75, 2-50, 3-40, 4-30, 5-25, 6-20, 7-15, 8-12, or 9-10:

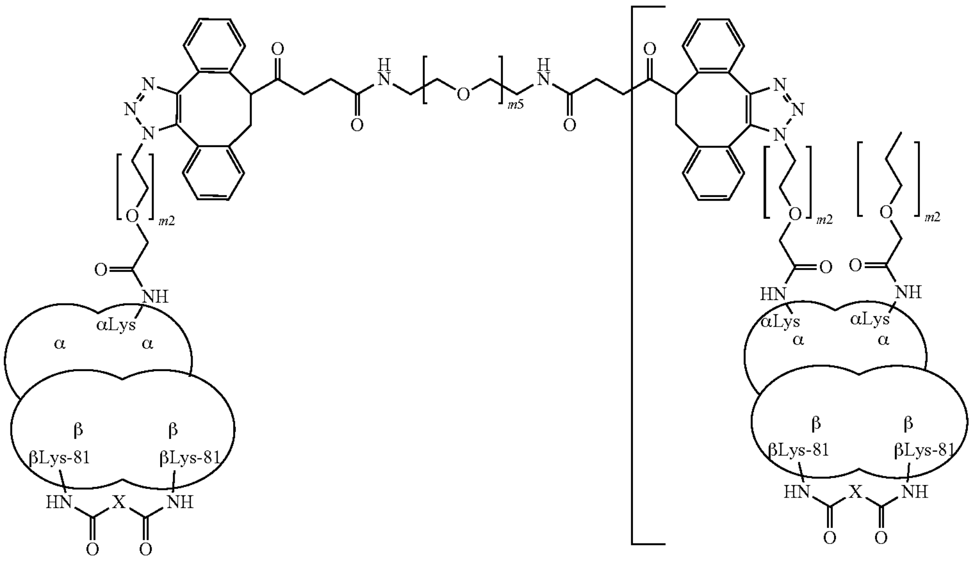

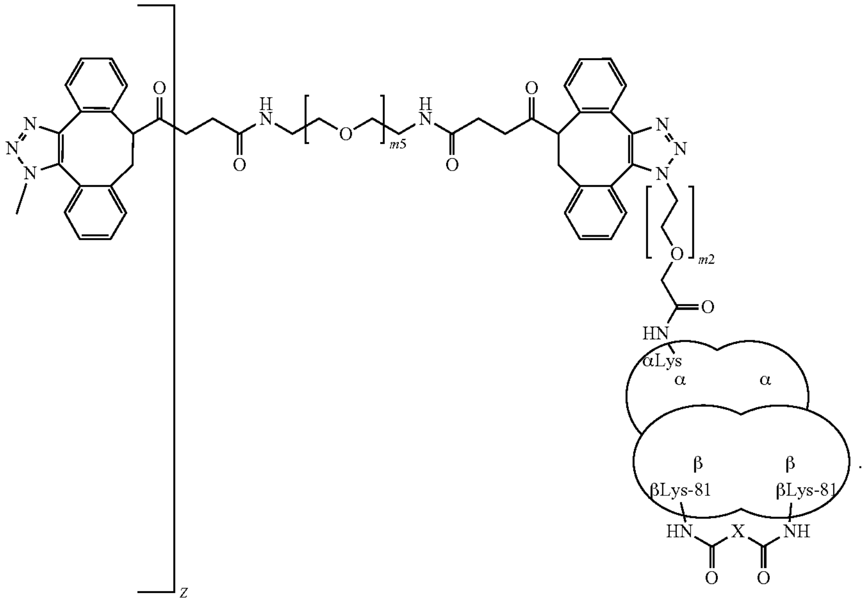

In embodiments, each X is the same or different. In embodiments, each X is the same. In embodiments, X is $X^3$ of formula (I-3). In embodiments, each X is

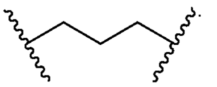 [SMILES: *CCC*]

In embodiments, $m_2$ is an integer of 1-15, 1-10, 2-8, 3-6, or 4-5. In embodiments, $m_2$ is 4. In embodiments, $m_5$ is an integer of 1-20, 1-12, 2-10, 3-8, 4-7, or 5-6. In embodiments, $m_5$ is 5. In embodiments, Z is an integer of 1-20, 2-15, 3-12, 4-10, 5-9, or 6-8. In embodiments, Z is an integer of 1-9.

In embodiments, the first reactive group is cycloalkynyl, and the second reactive groups are azido. In embodiments, the first modified Hb comprising a first residue functionalized with the first reactive group for a click reaction is obtained by:

reacting the compound of formula (I), (I-1), (I-2), (I-3), or (I-4) and a Hb to form a crosslinked Hb, and reacting the crosslinked Hb and a cycloalkynyl compound; or reacting a cycloalkynyl compound and a Hb to form an alkynyl-functionalized Hb, and reacting the alkynyl-functionalized Hb and the compound of formula (I), (I-1), (I-2), (I-3), or (I-4), wherein the cycloalkynyl compound is a compound of formula (VI), (VII), (VIII), or (IX)

(VI)

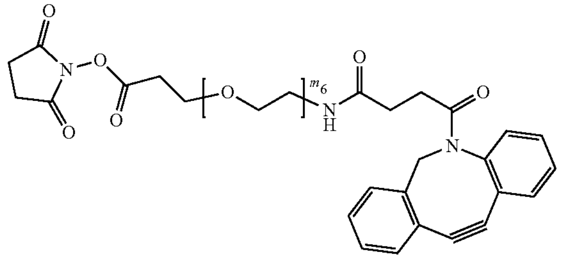

, (VII)

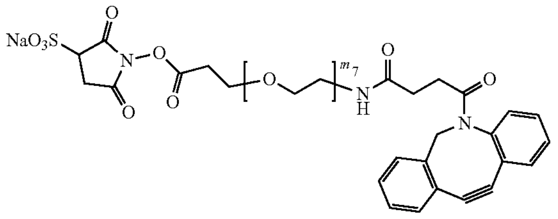

, (VIII)

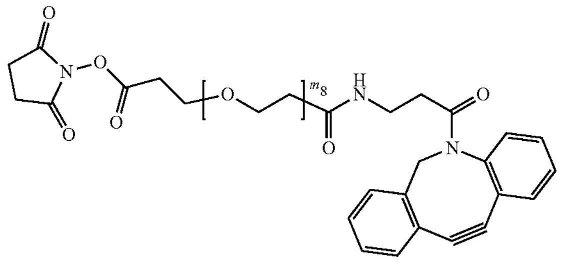

, (IX)

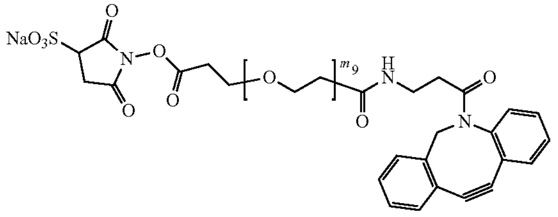

, wherein $m_6$, $m_7$, $m_8$, and $m_9$ are each independently an integer of 1-5000, 2-4000, 3-3000, 4-2000, 5-1500, 6-1250, 7-1000, 8-900, 9-900, 10-800, 11-700, 12-600, 13-500, 14-400, 15-300, 16-250, 17-200, 18-175, 19-150, 20-125, 21-110, 22-100, 23-90, 24-80, 25-75, 26-70, 27-65, 28-60, 29-55, 30-50, or 35-40. In embodiments, $m_6$, $m_7$, $m_8$, and $m_9$ are each independently 4, or 12. In embodiments, the compound of formula (I) or (I-3) is DBSG or DBSF. In embodiments, the compound of formula (I) or (I-3) is DBSG.

Non-limiting examples of a modified Hb that is alkynyl-functionalized obtained by reacting the compound of formula (VI) and a Hb are illustrated below, where X, $X^3$, and $m_6$ are defined previously:

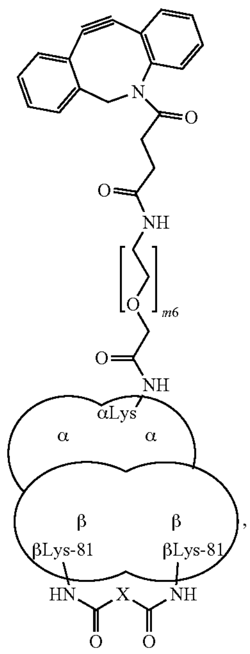

,

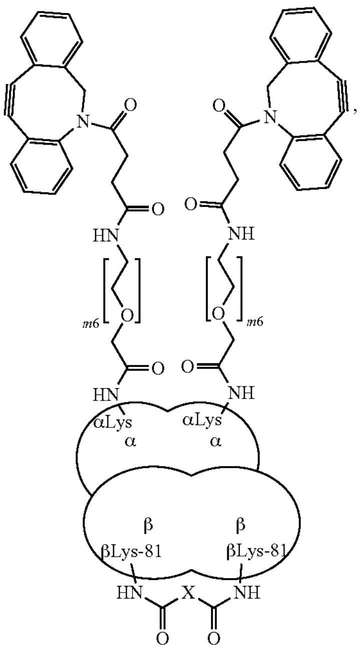

,

-continued

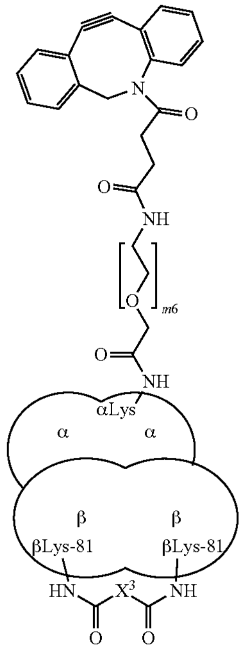

, and

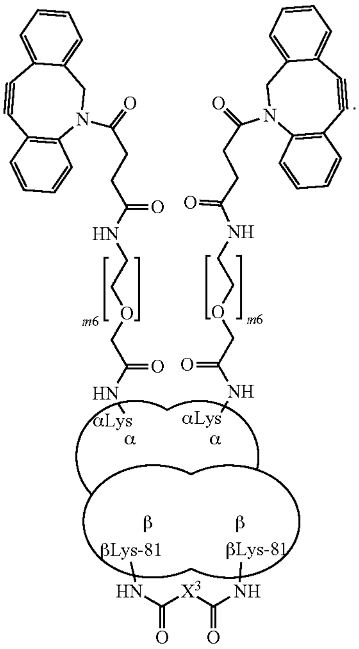

In embodiments, X or $X^3$ is

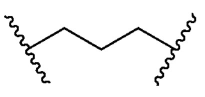

or

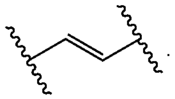

In embodiments, X or $X^3$ is

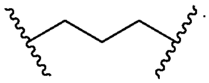 [SMILES: *CCC*]

In embodiments, the compound of formula (I) or (I-3) is DBSG or DBSF. In embodiments, the compound of formula (I) or (I-3) is DBSG.

In embodiments, the scaffold compound is a compound of formula (X) or (XI)

(X)

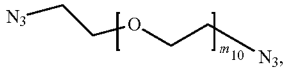

or (XI)

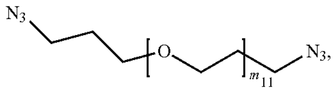

wherein $m_{10}$ and $m_{11}$ are each independently an integer of 1-5000, 2-4000, 3-3000, 4-2000, 5-1500, 6-1250, 7-1000, 8-900, 9-900, 10-800, 11-700, 12-600, 13-500, 14-400, 15-300, 16-250, 17-200, 18-175, 19-150, 20-125, 21-110, 22-100, 23-90, 24-80, 25-75, 26-70, 27-65, 28-60, 29-55, 30-50, or 35-40. In embodiments, $m_{10}$ and $m_{11}$ are each independently 5, or 23.

A non-limiting example of a multimerized Hb composition comprising a reaction product of: a first modified Hb comprising a first residue functionalized with one or more alkynyl reactive groups for a click reaction, and the scaffold compound of formula (X) is illustrated below, wherein X, $m_6$, $m_{10}$ are defined previously, and Z is an integer of 0-100, 1-75, 2-50, 3-40, 4-30, 5-25, 6-20, 7-15, 8-12, or 9-10:

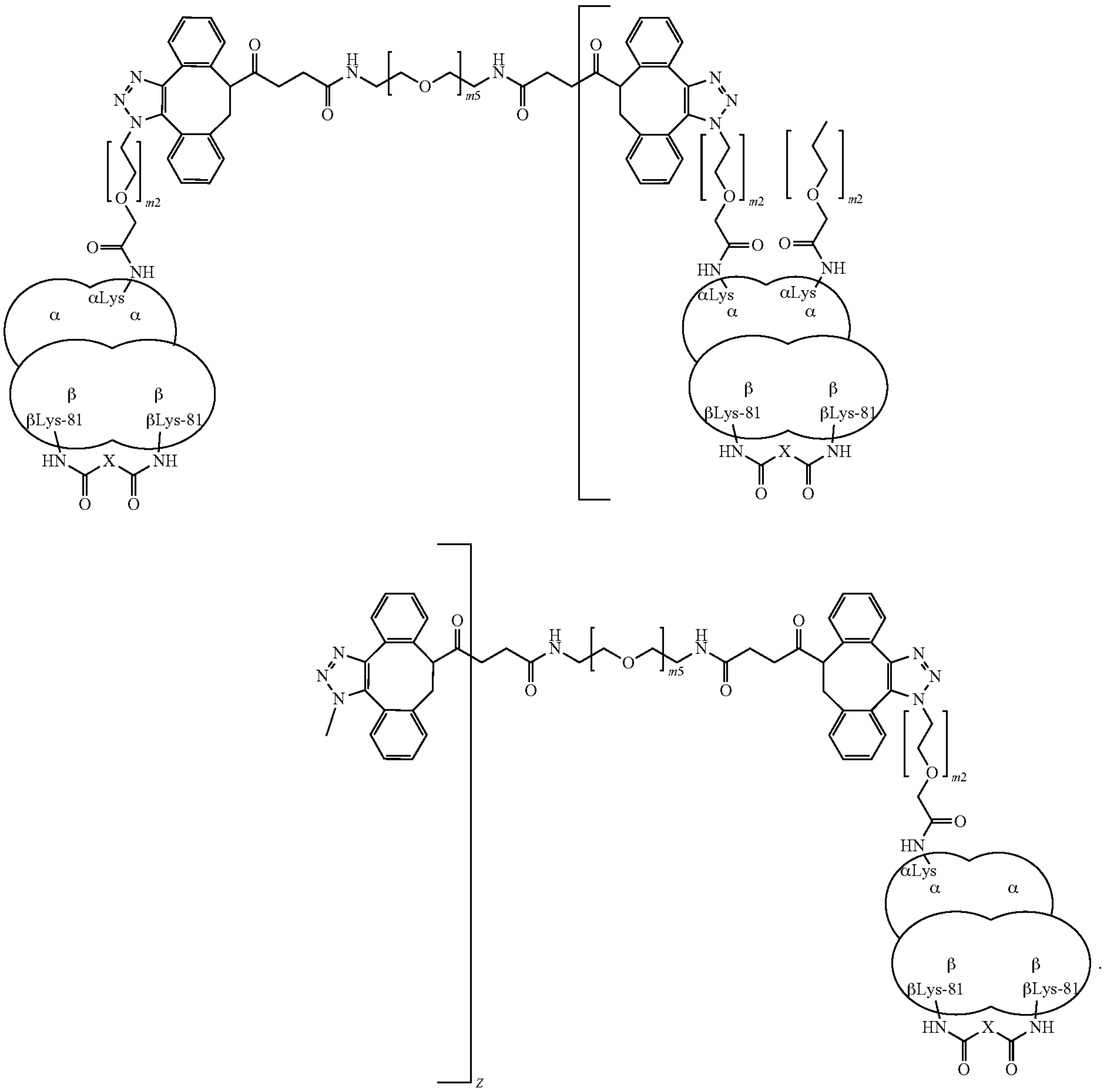

In embodiments, each X is the same or different. In embodiments, each X is the same. In embodiments, X is $X^3$. In embodiments, each X is

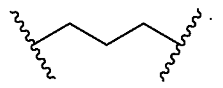 [SMILES: *CCC*]

Multimerization of Modified Hbs

In another embodiment, the reactant molecule is a second modified Hb comprising a second residue functionalized with the second reactive group. The multimerized Hb composition comprises a reaction product of: a first modified Hb comprising a first residue functionalized with one or more first reactive groups for a click reaction, and the second modified Hb comprising a second residue functionalized with one or more second reactive groups.

In embodiments, the first reactive group is azido, and the second reactive group is cycloalkynyl; or the first reactive group is cycloalkynyl, and the second reactive group is azido. In embodiments, the first reactive group is azido, and the second reactive group is propargyl; or the first reactive group is propargyl, and the second reactive group is azido. In embodiments, the first reactive group is tetrazine, and the second reactive group is TCO; or the first reactive group is TCO, and the second reactive group is tetrazine. In embodiments, the first reactive group is azido, and the second reactive group is cycloalkynyl; or the first reactive group is cycloalkynyl, and the second reactive group is azido. In embodiments, at least one of the modified Hb has two, three, or four reactive groups.

Non-limiting examples of a modified Hb that (i) is crosslinked with a compound of formula (I), and (ii) has one or two azido reactive groups using the compound of formula (II) are illustrated below, where X and $m_2$ are defined previously:

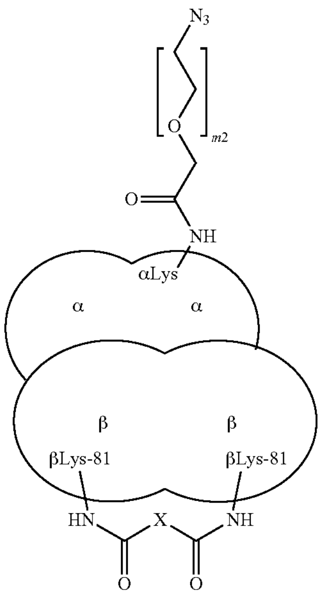

, and

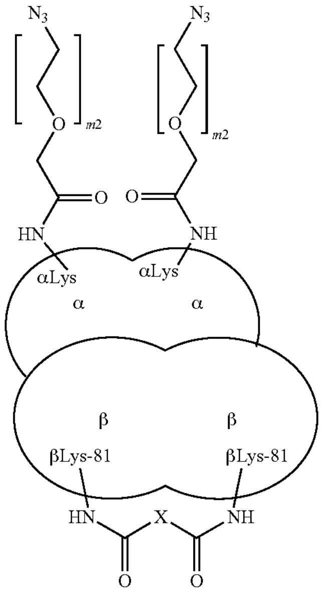

.

In embodiments, each $m_2$ is independently an integer of 1-15, 1-10, 2-8, 3-6, or 4-5. In embodiments, $m_2$ is 4. In embodiments, X is

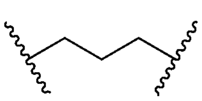

or

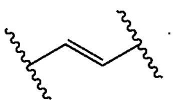

.

In embodiments, X is

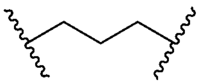

.

In embodiments, the compound of formula (I) is DBSG or DBSF. In embodiments, the compound of formula (I) is DBSG.

Non-limiting examples of a modified Hb that (i) is cross-linked with a compound of formula (I-3), and (ii) has one or two azido reactive groups using the compound of formula (II) are illustrated below, where $X^3$ and $m_2$ are defined previously.

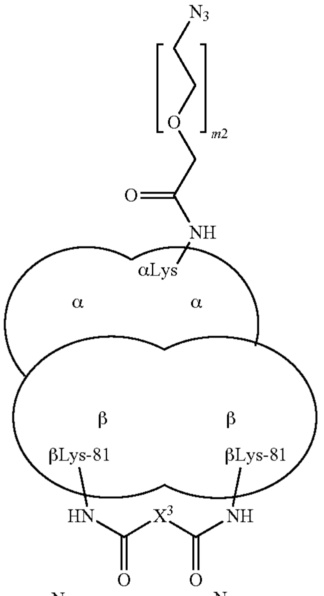

, and

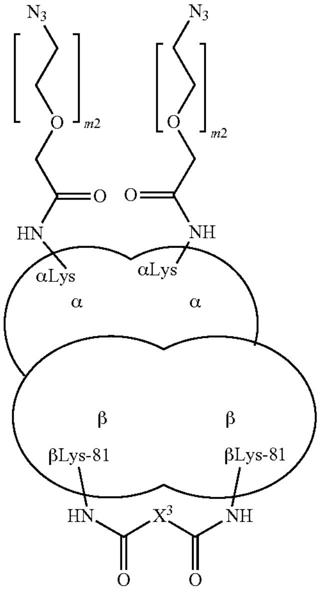

.

In embodiments, each $m_2$ is independently an integer of 1-15, 1-10, 2-8, 3-6, or 4-5. In embodiments, $m_2$ is 4. In embodiments, $X^3$ is

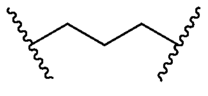

or

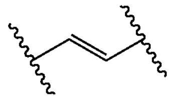

.

In embodiments, $X^3$ is

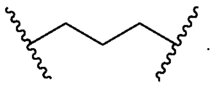 [SMILES: *CCC*]

In embodiments, the compound of formula (I-3) is DBSG or DBSF. In embodiments, the compound of formula (I-3) is DBSG.

Non-limiting examples of a modified Hb that (i) is cross-linked with a compound of formula (I) and (ii) has one or two alkynyl reactive groups using the compound of formula (VI) are illustrated below, where X and $m_6$ are defined previously:

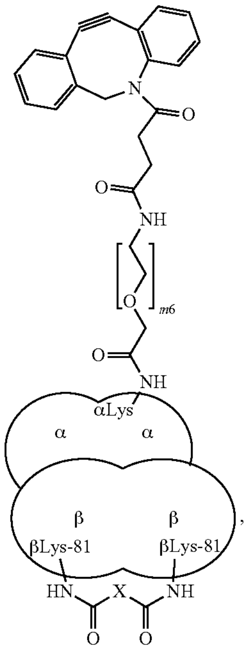

, and

-continued

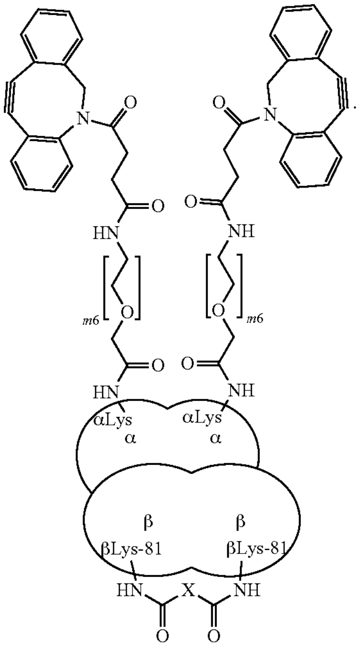

In embodiments, X is

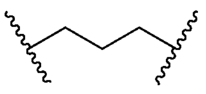

or

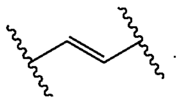

In embodiments, X is

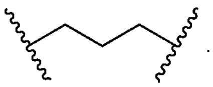 [SMILES: *CCC*]

In embodiments, the compound of formula (I) is DBSG or DBSF. In embodiments, the compound of formula (I) is DBSG.

Non-limiting examples of a modified Hb that (i) is cross-linked with a compound of formula (I-3) and (ii) has one or two alkynyl reactive groups using the compound of formula (VI) are illustrated below, where X and $m_6$ are defined previously:

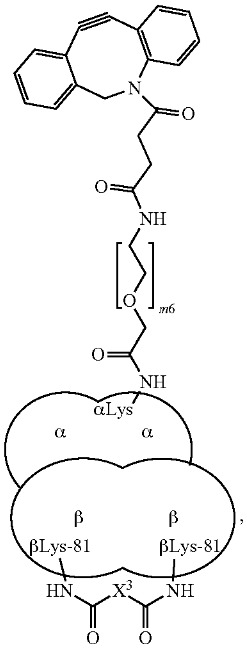

, and

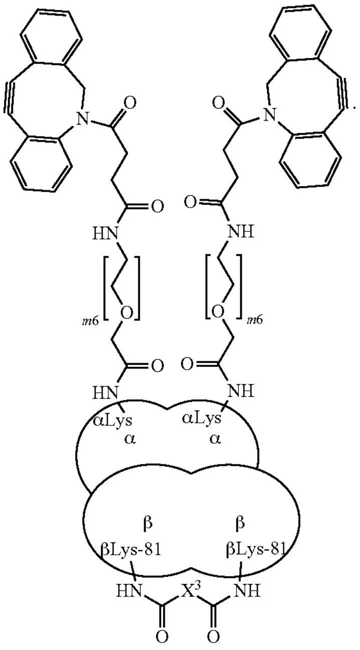

In embodiments, $X^3$ is

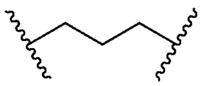

or

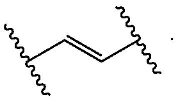

In embodiments, $X^3$ is

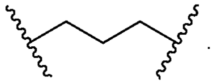 [SMILES: *CCC*]

In embodiments, the compound of formula (I-3) is DBSG or DBSF. In embodiments, the compound of formula (I-3) is DBSG.

Multimerization of Modified Hbs Using Bifunctional Linkers

In another embodiment, the two or more modified Hb are connected by a bifunctional or multifunctional linker, e.g., a linker having two or more glyoxal groups. In embodiments, the modified Hb is not functionalized with any reactive group for e.g., a click reaction.

In embodiments, the bifunctional linker is selected from 1,4-bis-phenylglyoxal (1,4-PBG) and $(PEG)_{m12}$-bis-phenylglyoxal:

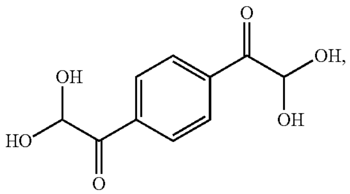

(1,4-PBG)

-continued

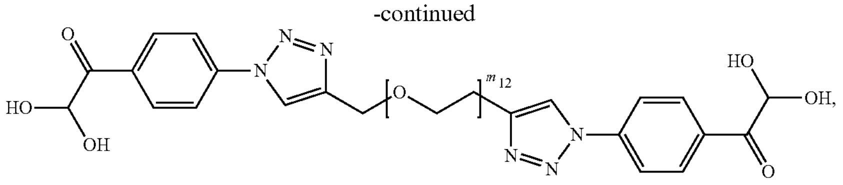

((PEG)$_{m12}$-bis-phenylglyoxal)

wherein $m_{12}$ is an integer of 1-5000, 2-4000, 3-3000, 4-2000, 5-1500, 6-1250, 7-1000, 8-900, 9-900, 10-800, 11-700, 12-600, 13-500, 14-400, 15-300, 16-250, 17-200, 18-175, 19-150, 20-125, 21-110, 22-100, 23-90, 24-80, 25-75, 26-70, 27-65, 28-60, 29-55, 30-50, or 35-40. In embodiments, $m_{12}$ is an integer of 1-10, 3-8, or 2-5. In embodiments, $m_{12}$ is 3.

In embodiments, arginine (Arg) residues of the two or more modified Hb are connected by the bifunctional linker. In embodiments, arginine (Arg) residues of the beta subunits of the two or more modified Hb are connected by the bifunctional or multifunctional'linker.

In embodiments, the multimerized Hb composition is obtained by reacting the compound of formula (I), (I-1), (I-2), (I-3), or (I-4) and a Hb to form a crosslinked Hb, and reacting the crosslinked Hb and the bifunctional or multifunctional linker.

A non-limiting example of a multimerized Hb composition that (i) is crosslinked with compound DBSF (i.e., a compound of formula (I) or (I-3)) and (ii) connected by 1,4-PBG is illustrated below:

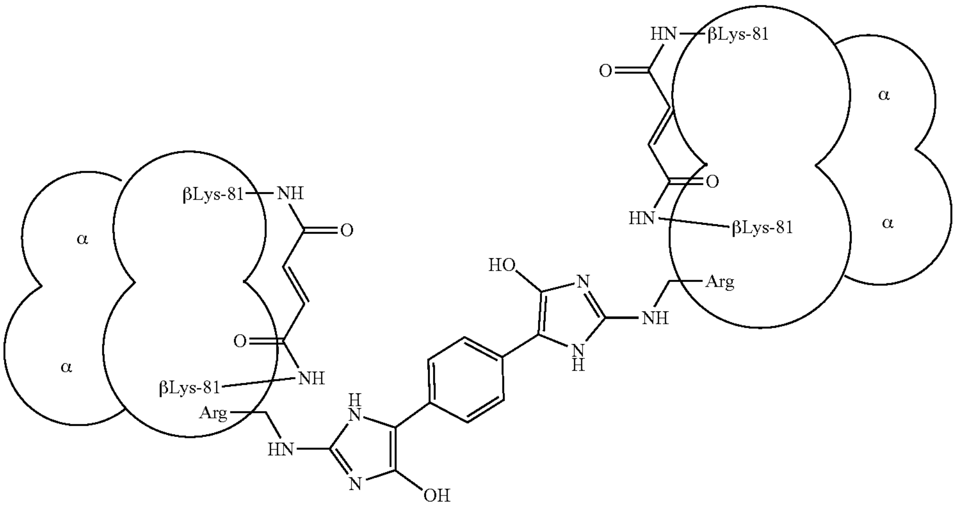
.

Multimerization of Hbs Modified with Trifunctional Cross-linkers

In a further aspect, the modified Hb is obtained with a trifunctional linker. As such, the present disclosure provides a multimerized Hb composition, comprising a reaction product of: a modified Hb comprising a residue functionalized with a first reactive group for a click reaction; and a reactant molecule comprising a second reactive group that is complementary to the first reactive group for the click reaction, wherein the modified Hb comprises:

at least two subunits of a Hb intramolecularly crosslinked with a compound of formula (I), which is a trifunctional linker:

(I)

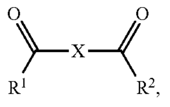

or a salt, a stereoisomer, or a deuterated form thereof, wherein:

X is $C_{1-24}$ alkylene, $C_{2-24}$ alkenylene, $C_{2-24}$ alkynylene, $C_{3-9}$ cycloalkylene, $C_{3-9}$ cycloalkenylene, 5-12 membered heterocyclylene containing 1 or 2 heteroatoms selected from N, S, or O, arylene, heteroarylene, or $-L^1-NR^A-L^2-$, wherein X is optionally substituted with 1-6 $R^3$ as permitted by valency;

$R^1$ and $R^2$ are each independently —OH, halogen, or a leaving group;

each $R^3$ is independently $-(C_{1-12}$ alkylene$)-N_3$, $-(C_{1-12}$ alkylene$)-(OCH_2CH_2)_m-(CH_2)_n-N_3$, $-C(O)NH-(C_{1-12}$ alkylene$)-(OCH_2CH_2)_m-(CH_2)_n-N_3$, $-NHC(O)-(C_{1-12}$ alkylene$)-(OCH_2CH_2)_m-(CH_2)_n-N_3$, $-O-(C_{1-12}$ alkylene$)-(OCH_2CH_2)_m-(CH_2)_n-N_3$, or $-S-(C_{1-12}$ alkylene$)-(OCH_2CH_2)_m-(CH_2)_n-N_3$, wherein each alkylene is optionally and independently substituted with $-C_{1-6}$ alkyl, —OH, —CN, $-NO_2$, or halogen;

$R^A$ is $-(C_{1-6}$ alkylene$)-(OCH_2CH_2)_m-(CH_2)_n-N_3$, wherein each alkylene is optionally and independently substituted with $-C_{1-6}$ alkyl, —OH, —CN, $-NO_2$, or halogen;

$L^1$ and $L^2$ are each independently $C_{1-12}$ alkylene, $C_{2-12}$ alkenylene, $C_{2-12}$ alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each m is independently an integer of 1-200; and each n is independently an integer of 0-50.

In embodiments, the modified Hb has two subunits of the Hb intramolecularly crosslinked with the trifunctional compound of formula (I). As such, the modified Hb has one extra reactive group such as azido suitable for reacting with a reactant molecule via click chemistry.

In embodiments, the reactant molecule is a scaffold compound comprising two or more second reactive groups, which are cycloalkynyl. In embodiments, the scaffold compound comprises two, three, or four second reactive groups, which are cycloalkynyl. In embodiments, the scaffold compound is a compound of formula (IV) or (V)

(IV)

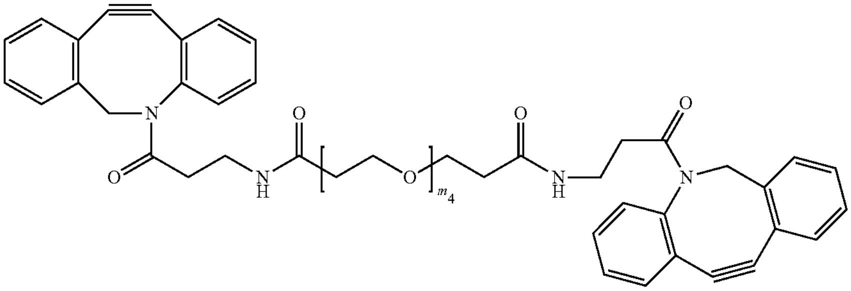

, (V)

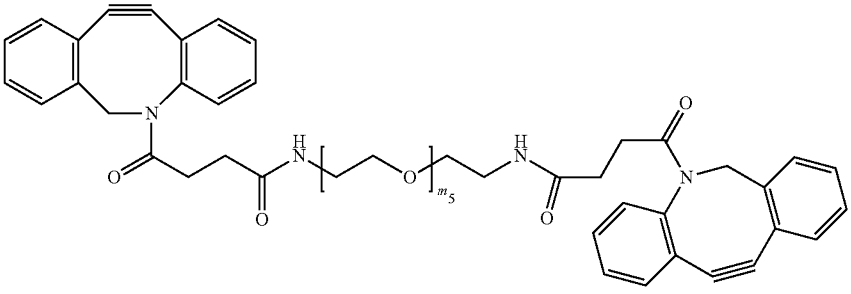

wherein $m_4$ and $m_5$ are each independently an integer of 1-5000.

In embodiments, the reactant molecule is a scaffold compound comprising two or more second reactive groups, which are cycloalkynyl, such as a $C_{6-9}$ heterocycloalkynyl, or a $C_{7-8}$ heterocycloalkynyl. In embodiments, the scaffold compound comprises two, three, or four second reactive groups, which are cycloalkynyl. In embodiments, the scaffold compound is a compound of formula (IV) or (V)

pound of formula (I). In embodiments, the lysine residues of the beta subunits are Lys-81 and Lys-81 of SEQ ID NO: 2, Lys-81 and Lys-94 of SEQ ID NO: 2, or Lys-75 and Lys-81 of SEQ ID NO: 2. In embodiments, the lysine residues of the beta subunits are Lys-81 and Lys-81 of SEQ ID NO: 2.

In embodiments, the two alpha subunits of the Hb are intramolecularly crosslinked by the compound of formula (I). In embodiments, amino groups of lysine residues or N-terminus of the alpha subunits are intramolecularly cross- (IV)

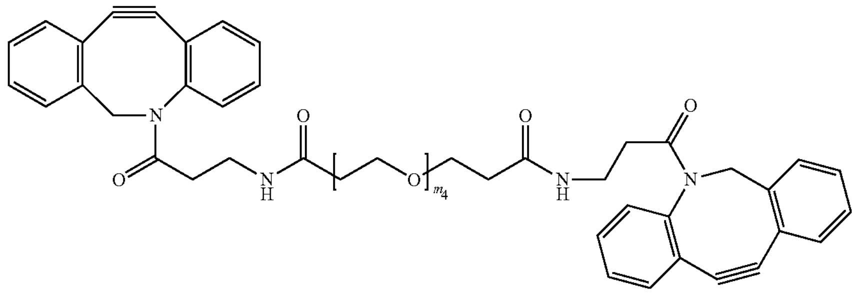

, (V)

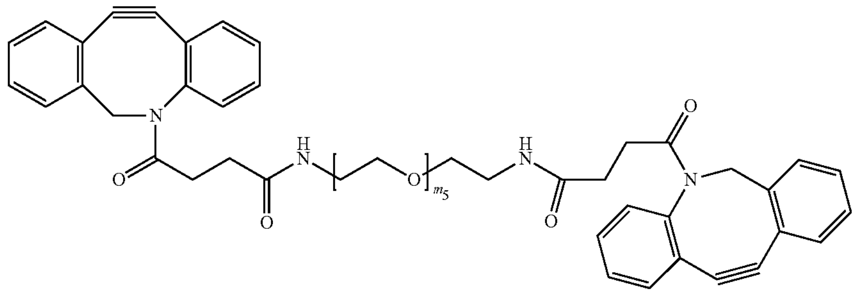

wherein $m_4$ and $m_5$ are each independently an integer of 1-5000, 2-4000, 3-3000, 4-2000, 5-1500, 6-1250, 7-1000, 8-900, 9-900, 10-800, 11-700, 12-600, 13-500, 14-400, 15-300, 16-250, 17-200, 18-175, 19-150, 20-125, 21-110, 22-100, 23-90, 24-80, 25-75, 26-70, 27-65, 28-60, 29-55, 30-50, or 35-40. In embodiments, $m_4$ and $m_5$ are each independently 4, or 35-55.

In embodiments, the Hb intramolecularly crosslinked with the compound of formula (I) comprises:

(I-A)

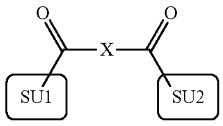

wherein SU1 is a residue on a first subunit of the Hb, and SU2 is a residue on a second subunit of the Hb.

In embodiments, at least two subunits of each modified Hb are intramolecularly crosslinked with the compound of formula (I) at a residue selected from the group consisting of Lys, Cys, Arg, and an N-termini. In embodiments, at least two subunits are intramolecularly crosslinked at residues Lys.

In embodiments, the two beta subunits of the Hb are intramolecularly crosslinked by the compound of formula (I). In embodiments, amino groups of lysine residues of the beta subunits are intramolecularly crosslinked by the comlinked by the compound of formula (I). In embodiments, the lysine residues of the alpha subunits are Lys-99 and Lys-99 of SEQ ID NO: 1, Lys-7 and Lys-139 of SEQ ID NO: 1, Lys-90 and Lys-139 of SEQ ID NO: 1, or Lys-90 and Lys-127 of SEQ ID NO: 1.

In embodiments, the alpha and the beta subunits of the Hb are intramolecularly crosslinked by the compound of formula (I). In embodiments, amino groups of lysine residues of the alpha and the beta subunits are intramolecularly crosslinked by the compound of formula (I). In embodiments, the lysine residues of the alpha and the beta subunits are Lys-99 of SEQ ID NO: 1 and Lys-103 of SEQ ID NO: 2, respectively.

In embodiments, the Hb is bovine, human, equine, porcine, ovine, simian, or fish hemoglobin. In embodiments, the Hb is bovine hemoglobin (bHb).

In embodiments, the compound of formula (I), or a or a salt, a stereoisomer, or a deuterated form thereof, is a trifunctional linker. In embodiments, $R^1$ and $R^2$ of formula (I) are a leaving group, and the leaving group is

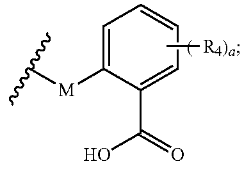

M is O or S;

each $R^4$ is independently halogen or $-C_{1-6}$ alkyl; and a is an integer of 0-4.

In embodiments, the leaving group is

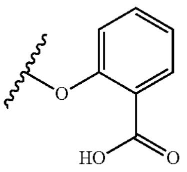

or

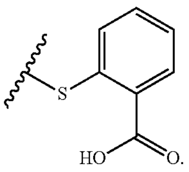

In embodiments, a is 1, 2, or 3. In embodiments, each $R^4$ is halogen. In embodiments, each $R^4$ is independently —F, —Cl, or —Br.

In embodiments, the leaving group is

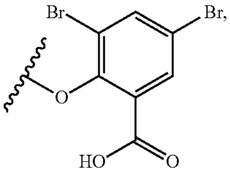

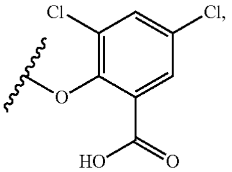

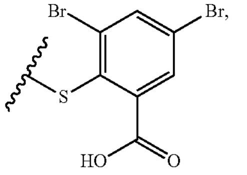

or

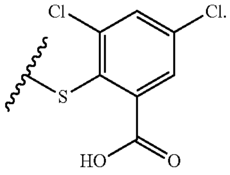

In embodiments, X is $C_{1-6}$ alkylene optionally substituted with 1 or 2 $R^3$ as permitted by valency.

In embodiments, X is $C_{1-6}$ alkylene substituted with $-S-(C_{1-6}$ alkylene)-$(OCH_2CH_2)_m-(CH_2)_n-N_3$, and wherein m is an integer of 1-50, and n is an integer of 0-25.

In embodiments, X is

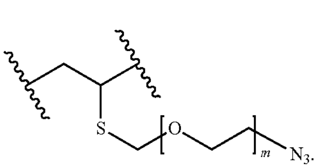

and wherein m is an integer of 1-25. In embodiments, X is

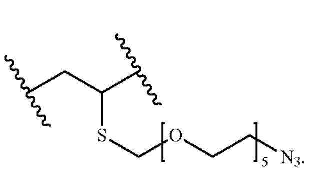

In embodiments, X is $C_{3-7}$ cycloalkenylene optionally substituted with 1 or 2 $R^3$ as permitted by valency. In embodiments, X is $C_{3-7}$ cycloalkenylene substituted with $-(C_{1-6}$ alkylene)-$N_3$. In embodiments, X is

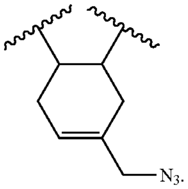 [SMILES: *C1CC=C(CN=[N+]=[N-])CC1*]

In embodiments, X is a 5-12 membered heterocyclylene containing a heteroatom which is S or O, and wherein the heterocyclylene is substituted with $-(C_{1-6}$ alkylene)-$N_3$. In embodiments, X is

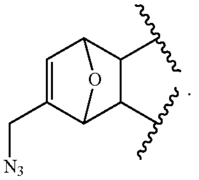 [SMILES: *C1C2C=C(CN=[N+]=[N-])C(O2)C1*]

In embodiments, X is $C_{6-10}$ arylene substituted with $-C(O)NH-(C_{1-12}$ alkylene)-$(OCH_2CH_2)_m-(CH_2)_n-N_3$, or $-NHC(O)-(C_{1-2}$ alkylene)-$(OCH_2CH_2)_m-(CH_2)_n-N_3$, and wherein each m is independently an integer of 1-200, and each n is independently an integer of 0-100. In embodiments, X is $C_{6-10}$ arylene substituted with $-C(O)NH-(C_{1-6}$ alkylene)-$(OCH_2CH_2)_m-N_3$, and wherein m is an integer of 2-50. In embodiments, X is

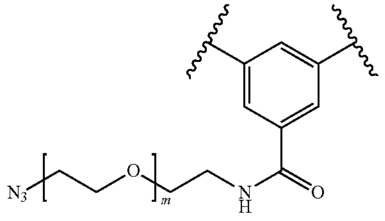

, and wherein m is 4 or 9. In embodiments, X is $C_{6-10}$ arylene substituted with $-NHC(O)-(C_{1-6}$ alkylene)-$(OCH_2CH_2)_m-N_3$, and wherein m is an integer of 2-50. In embodiments, X is

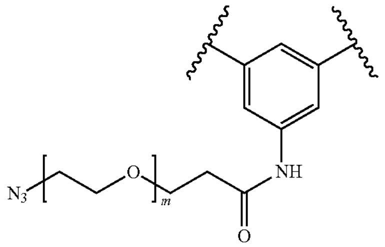

, and wherein m is 4 or 9.

In embodiments, X is $-L^1-NR^A-L^2-$, and wherein: $R^A$ is $-(C_{1-12}$ alkylene)-$(OCH_2CH_2)_m-(CH_2)_n-N_3$, wherein m is an integer of 1-50, n is an integer of 0-25, and each alkylene is optionally substituted with $-C_{1-6}$ alkyl; and $L^1$ and $L^2$ are each independently $C_{1-6}$ alkylene, $C_{2-6}$ alkenylene, $C_{2-6}$alkynylene, $C_{3-6}$cycloalkylene, $C_{3-6}$ cycloalkenylene, arylene, or heteroarylene, wherein $L^1$ and $L^2$ are optionally and independently substituted with 1-3 $R^3$. In embodiments, $R^4$ is —($C_{1-6}$ alkylene)-($OCH_2CH_2$)$_m$—($CH_2$)$_n$—$N_3$, and $L^1$ and $L^2$ are each independently $C_{1-6}$ alkylene, or $C_2$-6 alkenylene, wherein m is an integer of 1-50, and n is an integer of 0-25. In embodiments, X is

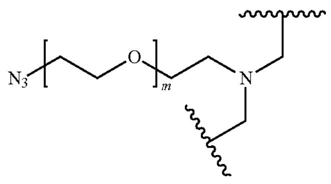

, and m is 3.

In embodiments, X of formula (I) is $C_{1-6}$ alkylene substituted with —($CH_2$)$_n$—$N_3$, wherein n is an integer of 0-25. In embodiments, wherein n is 7, and X is

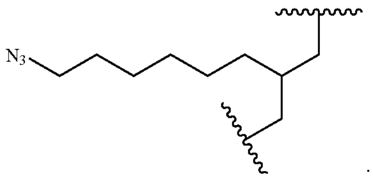 [SMILES: *CC(C*)CCCCCCN=[N+]=[N-]]

.

In embodiments, the compound of formula (I) as a tri-functional linker is:

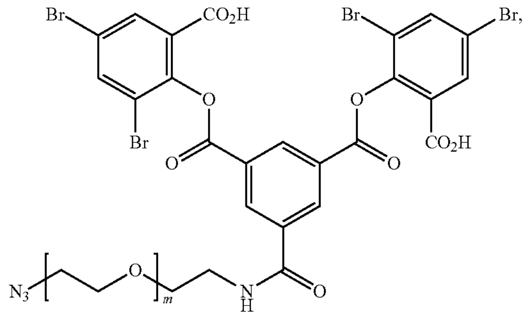

m = 4

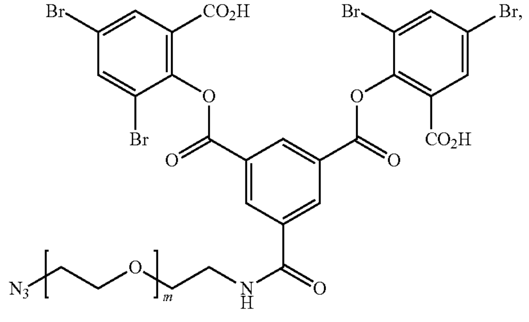

m = 9

-continued

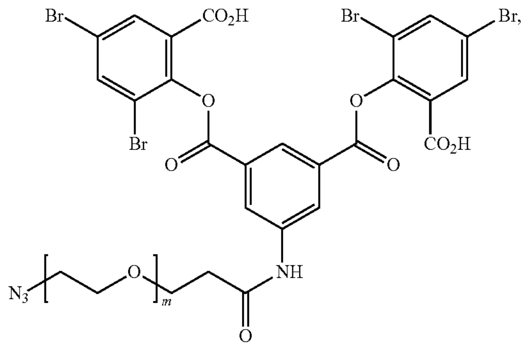

m = 4

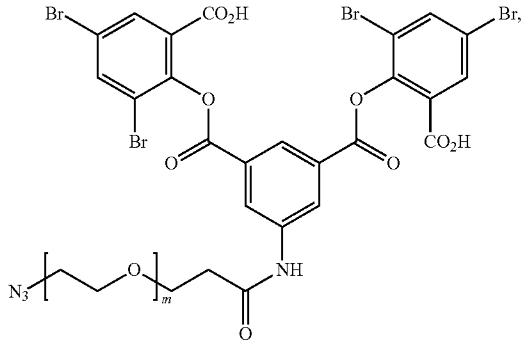

m = 9

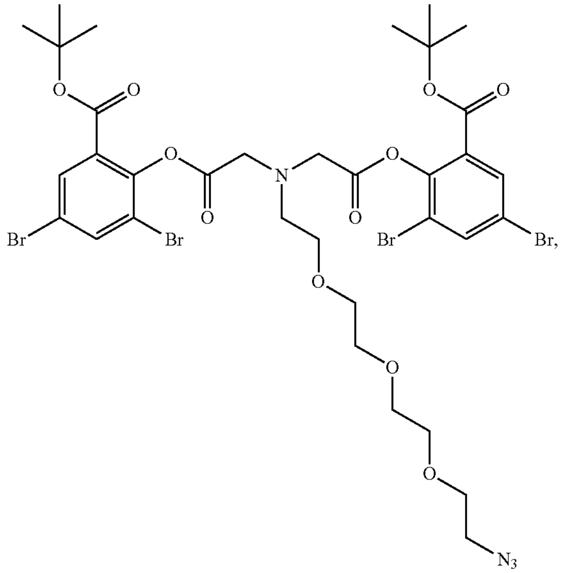

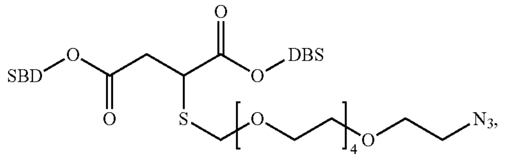

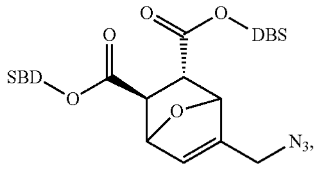

or

-continued

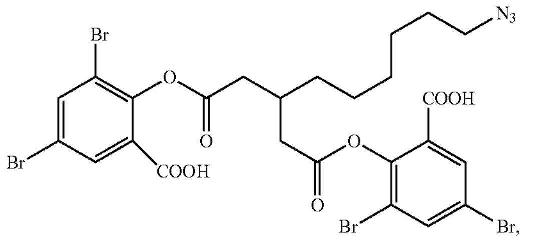

or a salt, a stereoisomer, or a deuterated form thereof, wherein DBS represents

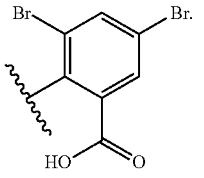 [SMILES: *c1c(Br)cc(Br)cc1C(=O)O]

In embodiments, the compound of formula (I) as a trifunctional linker is:

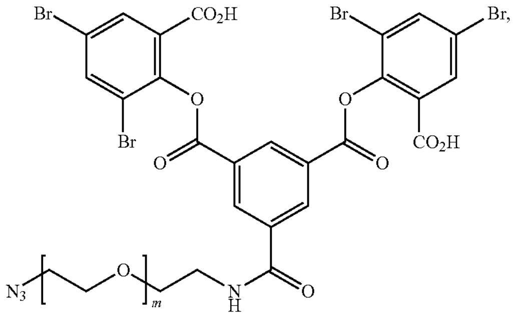

m = 4

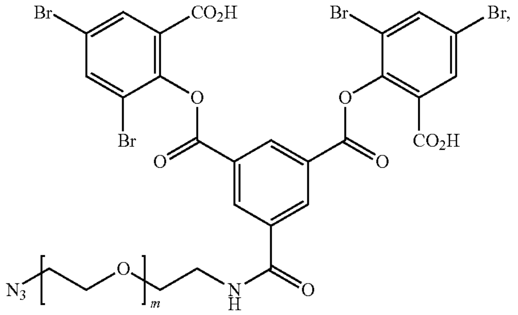

m =9

-continued

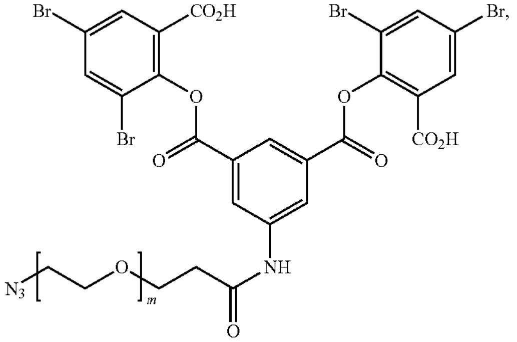

m = 4

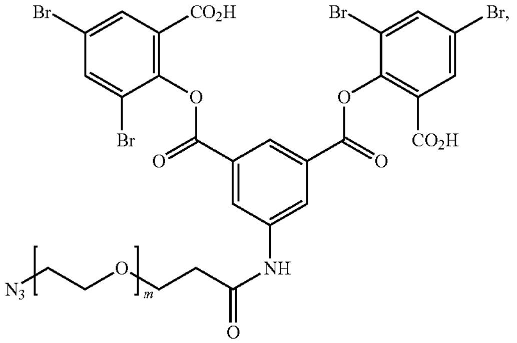

m =9

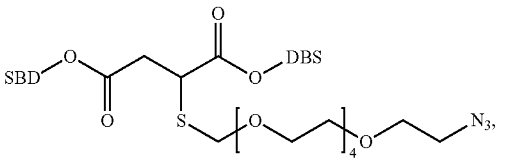

or

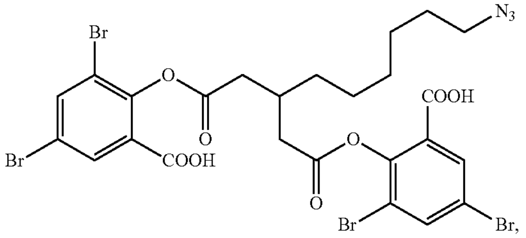

wherein DBS represents

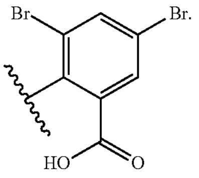 [SMILES: *c1c(Br)cc(Br)cc1C(=O)O]

In embodiments, the multimerized Hb composition is obtained by reacting the trifunctional compound of formula (I) and a Hb to form a crosslinked Hb, and reacting the crosslinked Hb and the scaffold compound of formula (IV) or (V).

A non-limiting example of a modified Hb with a trifunctional linker

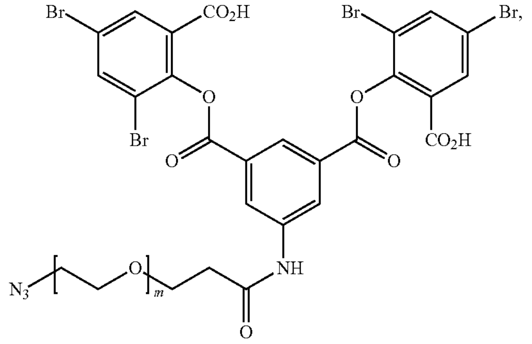
m = 4 or 9
is illustrated below:
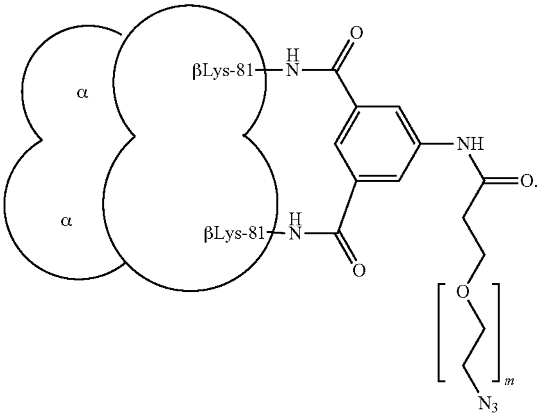
A non-limiting example of multimerized Hb composition prepared using the trifunctional compound of formula (I),
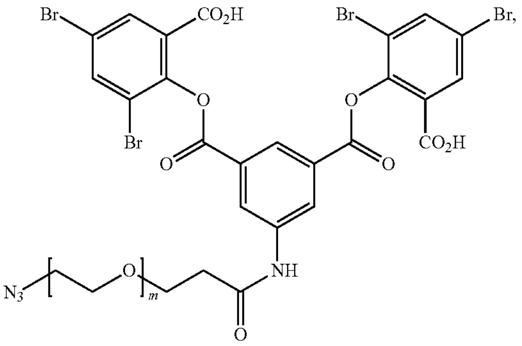
m = 4 or 9
and the scaffold compound of formula (V) are illustrated below, where $m_5$ is defined previously:
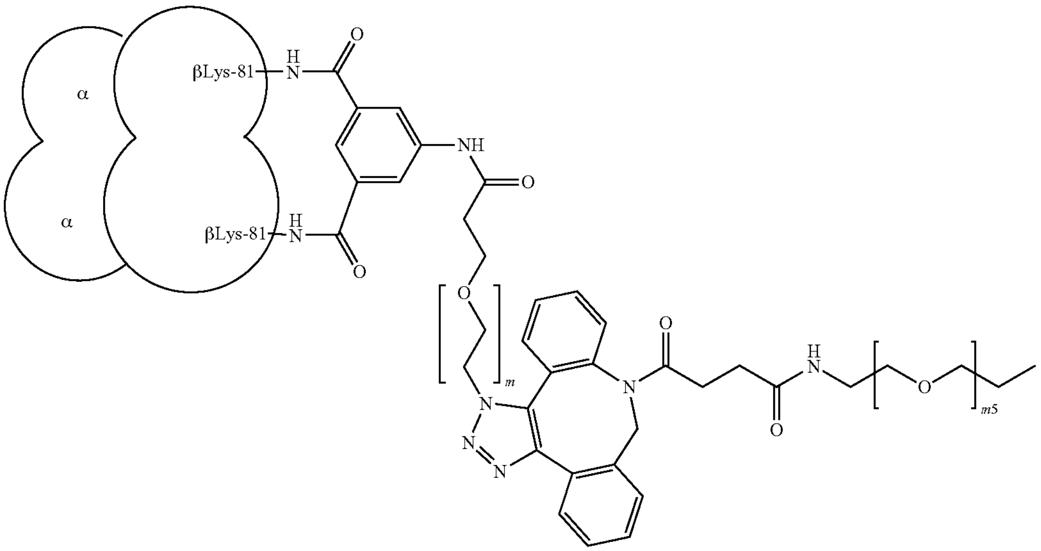

-continued
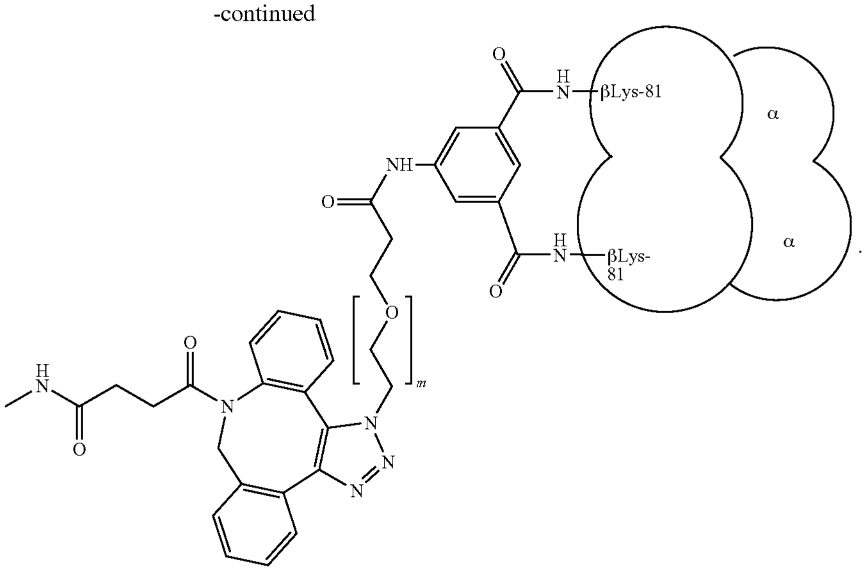
Additional examples of multimerized Hb composition prepared using the trifunctional compound of formula (I),
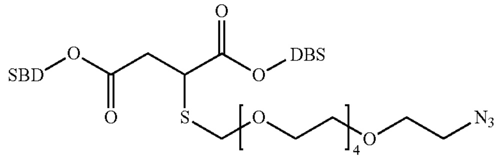
or
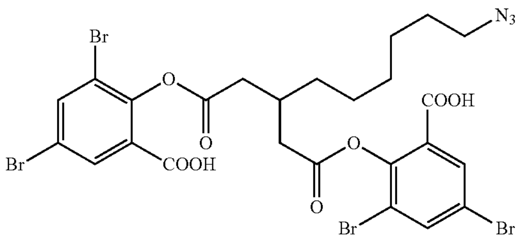
and the scaffold compound of formula (V) are illustrated below, where $m_5$ is defined previously:
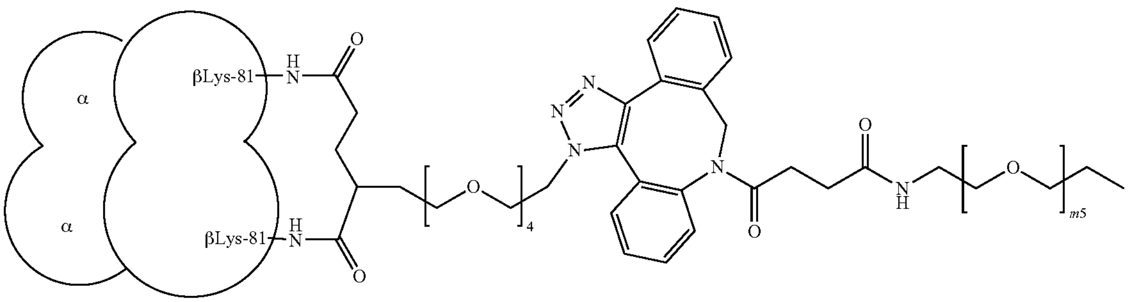

-continued

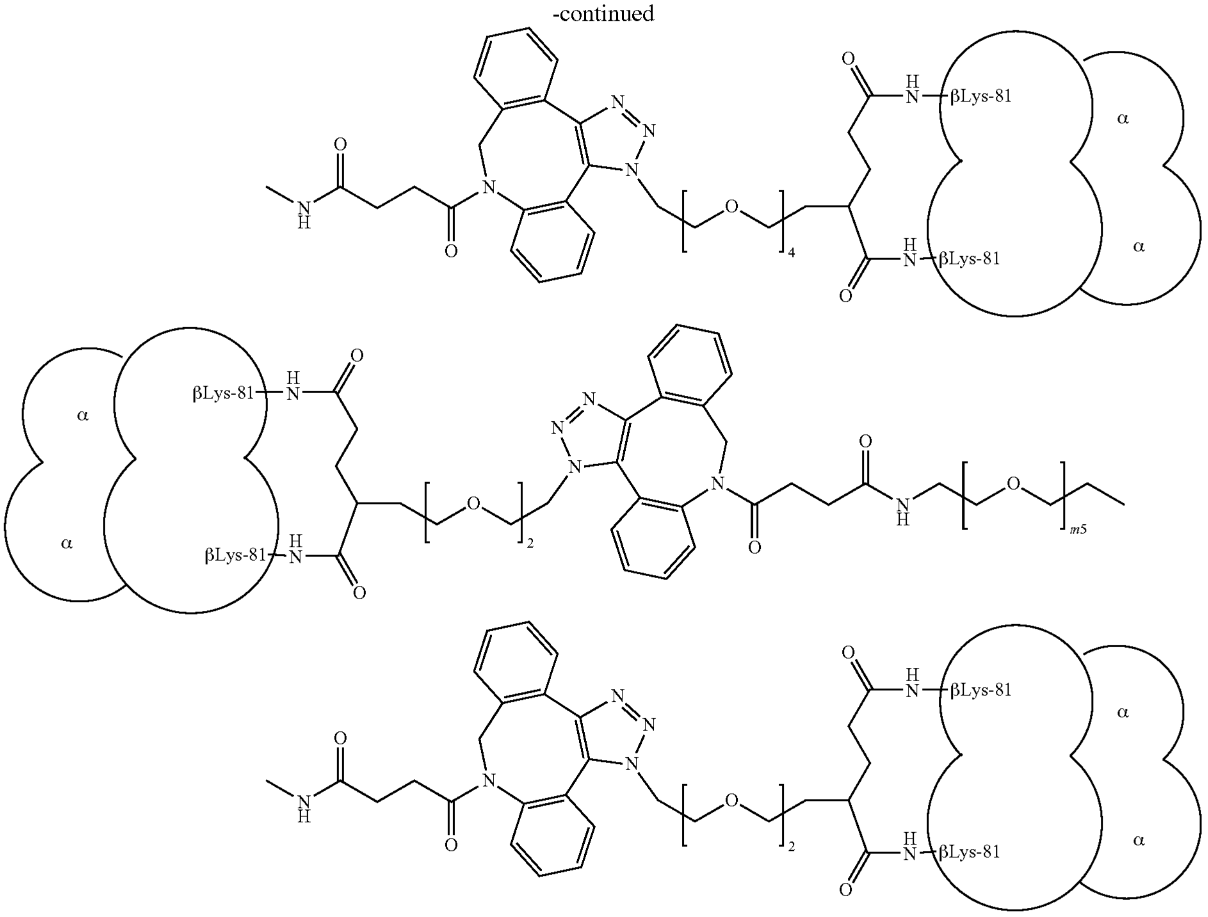

In embodiments, the multimerized Hb composition in any of the above embodiments has a molecular weight of about 50 kDa to about 20 MDa, about 60 kDa to about 15 MDa, about 64 kDa to about 10 MDa, about 66 kDa to about 9 MDa, about 68 kDa to about 8 MDa, about 70 kDa to about 7 MDa, about 75 kDa to about 6 MDa, about 80 kDa to about 5 MDa, about 85 kDa to about 4 MDa, about 90 kDa to about 3 MDa, about 95 kDa to about 2 MDa, about 100 kDa to about 1.5 MDa, about 200 kDa to about 1 MDa, about 300 kDa to about 900 kDa, about 400 kDa to about 800 kDa, about 500 kDa to about 700 kDa, or about 600 kDa to about 650 kDa.

In embodiments, the multimerized Hb composition has the following structure (XII):

(XII)

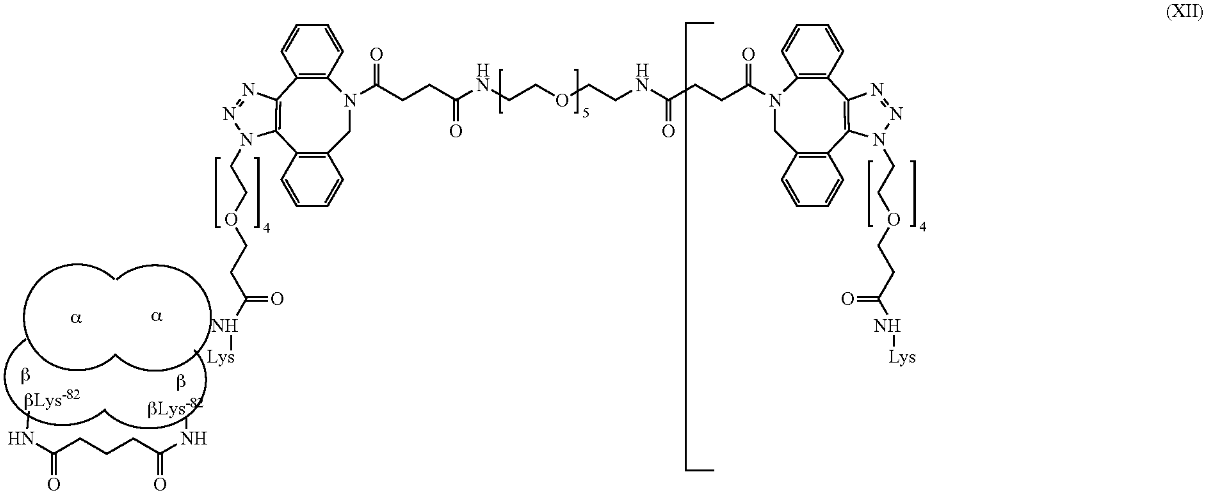

-continued

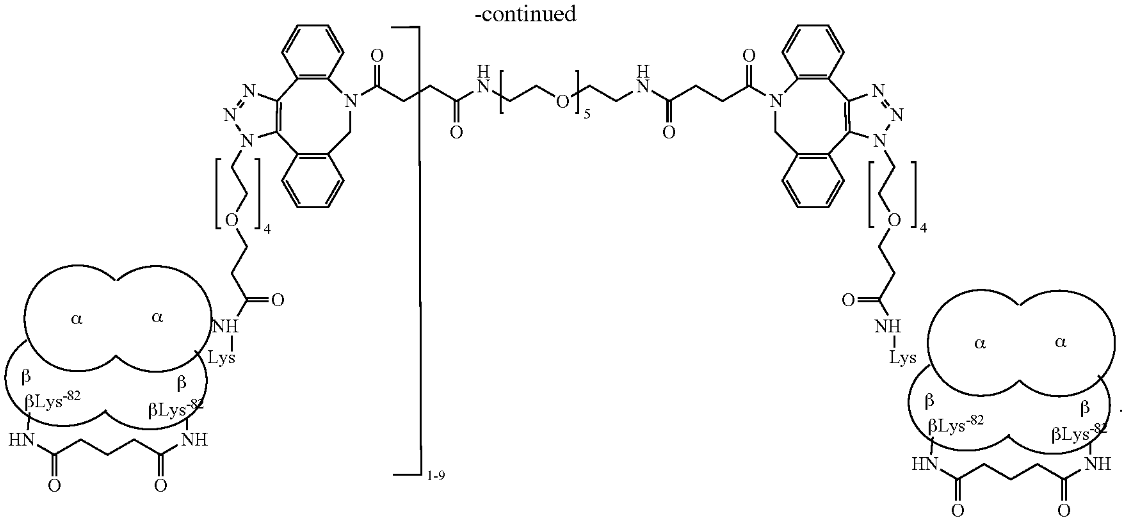

.

In embodiments, the multimerized Hb composition of (XII) has a molecular weight of about 90 kDa to about 2 MDa, about 100 kDa to about 1.8 MDa, about 120 kDa to about 1.6 MDa, about 140 kDa to about 1.5 MDa, about 160 kDa to about 1.4 MDa, about 180 kDa to about 1.3 MDa, about 190 kDa to about 1.2 MDa, about 200 kDa to about 1.1 MDa, about 300 kDa to about 1 MDa, about 400 kDa to about 900 kDa, about 500 kDa to about 800 kDa, or about 600 kDa to about 700 kDa. In embodiments, the multimerized Hb composition has a molecular weight of about 192 kDa to about 800 kDa. In embodiments, the multimerized Hb composition has a molecular weight of about 190 kDa to about 500 kDa.

In embodiments, the multimerized Hb composition in any of the above embodiments comprises one or more modified Hb with unreacted pendant functionalities (e.g., unreacted azido groups, unreacted cycloalkynyl groups).

In embodiments, the multimerized Hb composition of the present disclosure may be prepared by the methods set forth below. The following methods are provided for illustrative purposes and not intended to limit the scope of the disclosure.

In embodiments, the multimerized Hb composition of structure (XII) may be prepared by a method comprising: (i) mixing a Hb and bis(3,5-dibromosalicyl)glutarate (DBSG) to form a crosslinked Hb; (ii) mixing the crosslinked Hb and an azido compound of formula (II)

(II)

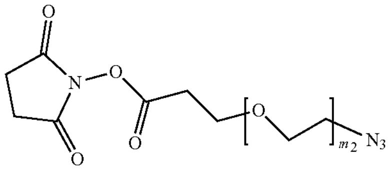

to form a modified Hb; and (iii) mixing the modified Hb and a scaffold compound of formula (V), (V)

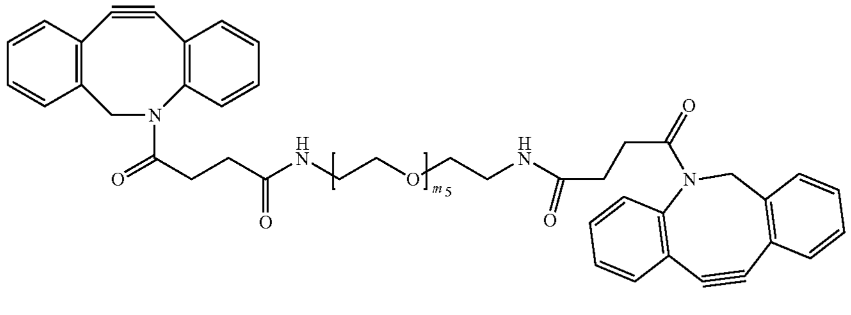

thereby forming the multimerized Hb composition, wherein $m_2$ is 4, and $m_5$ is 5.

In embodiments, the Hb is bovine, human, equine, porcine, ovine, simian, or fish hemoglobin. In embodiments, the Hb is a bovine hemoglobin (bHb).

In embodiments, a molar ratio of DBSG to the Hb in the mixing (i) is greater than 1:1, greater than 3:2, greater than 2:1, greater than 3:1, or greater than 7:2. In embodiments, a molar ratio of DBSG to the Hb in the mixing (i) is 3:2 to 15:1, 2:1 to 10:1, 2:1 to 8:1, 3:1 to 7:1, 7:2 to 6:1, or 4:1 to 5:1. In embodiments, the mixing (i) is performed at a temperature of about 15° C. to about 40° C., about 20° C. to about 37° C., or about 30° C. to about 35° C. for 6-60 hours, 8-48 hours, 12-36 hours, or 16-24 hours.

Prior to the mixing (i), the method disclosed herein may further comprise dissolving the Hb in a buffer and/or dissolving the DBSG in an organic solvent. In embodiments, the buffer has a pH of 7-8.6, 7.2-8.4, 7.4-8.2, 7.6-8, or about 7.8. In embodiments, the buffer has a basic pH. In embodiments, the buffer is MOPS. Additional exemplary buffers include, but are not limited to HEPES, TAPS, Bicine, Glycylglycine, Tris, HEPPSO, EPPS, HEPPS, POPSO, N-ethylmorpholine, TEA (Triethanolamine), Tricine, TAPSO, DIPSO, TES, BES, phosphoric acid, imidazole PIPES and the like. Exemplary organic solvents include, but are not limited to, methanol, ethanol, n-propanol, iso-propanol, n-butanol, iso-butanol, tert-butanol, ethyl acetate, acetone, dichloromethane (DCM), dimethyl sulfoxide (DMSO), dimethyl acetate (DMA), dimethyl formamide (DMF), isopropyl ether, acetonitrile, toluene, N-methylpyrrolidone (NMP), tetrahydrofuran (THF). In embodiments, the organic solvent is DMSO.

In embodiments, a molar ratio of the azido compound of formula (II) to the crosslinked Hb in the mixing (ii) is greater than 1:1, greater than 3:2, greater than 2:1, greater than 3:1, greater than 7:2, greater than 4:1, or greater than 9:2. In embodiments, a molar ratio of the azido compound of formula (II) to the crosslinked Hb in the mixing (ii) is 3:2 to 18:1, 2:1 to 15:1, 2:1 to 10:1, 2:1 to 8:1, 3:1 to 7:1, 7:2 to 6:1, or 4:1 to 5:1. In embodiments, the mixing (ii) is performed at a temperature of about −6° C. to about 20° C., about −4° C. to about 10° C., or about 0° C. to about 5° C. for 1-36 hours, 1-18 hours, 3-12 hours, or 6-8 hours.

Prior to the mixing (ii), the method disclosed herein may further comprise dissolving the azido compound of formula (II) in water or an aqueous solution.

In embodiments, a molar ratio of the scaffold compound of formula (V) to the modified Hb in the mixing (iii) is greater than 1:1, greater than 3:2, or greater than 2:1. In embodiments, a molar ratio of the scaffold compound of formula (V) to the modified Hb in the mixing (iii) is 1.1:1 to 10:1, 1.2:1 to 8:1, 3:2 to 6:1, 2:1 to 5:1, 2.1:1 to 4:1, 2.2:1 to 3:1, 2.3:1 to 5:2. In embodiments, the mixing (iii) is performed at a temperature of about 0° C. to about 40° C., about 5° C. to about 30° C., or about 10° C. to about 20° C. for 12-144 hours, 12-120 hours, 24-60 hours, or 36-48 hours.

In embodiments, the method further comprises (iv) mixing the multimerized Hb composition with a reducing agent. Exemplary reducing agents include, but are not limited to, sodium dithionite, sodium citrate, ascorbates (e.g., sodium ascorbate), sodium borohydride, and elemental hydrogen. In embodiments, the reducing agent is sodium dithionite or sodium ascorbate. In embodiments, the reducing agent is sodium dithionite. In embodiments, the mixing (iv) is performed at a temperature of about −4° C. to about 15° C., about 0° C. to about 10° C., or about 1° C. to about 4° C. for 6-60 hours, 8-48 hours, 12-36 hours, or 16-24 hours. In embodiments, the mixing (iv) is performed at a basic pH level. In embodiments, the mixing (iv) is performed at a pH of about 6.5-8, 6.8-7.8, 7-7.6, or 7.2-7.4.

In embodiments, the multimerized Hb composition of the present disclosure may be prepared by the methods disclosed in Examples 16, 16A, 17, 17A, 17B, 18, 18A, 18B, 18C, 19, 20, and 20A.

EXAMPLES

The present disclosure is further illustrated by reference to the following Examples. However, it should be noted that these Examples, like the embodiments described above, are illustrative and are not to be construed as restricting the scope of the disclosure in any way.

In embodiments, compounds of the present disclosure can be synthesized using the following methods. General reaction conditions are given, and reaction products can be purified by generally known methods including silica gel chromatography using various organic solvents such as hexane, dichloromethane, ethyl acetate, methanol and the like or preparative reverse phase high pressure liquid chromatography.

Synthesis of HBOCs Via Crosslinking, Functionalization, and Multimerization in Separate Steps: (A) Intramolecular Crosslinking First, Followed by Functionalization and Multimerization

Example 1: Determination of NHS-Ester Linker Lengths and Bis-Click Reagents Linker Length for Multimer Formation

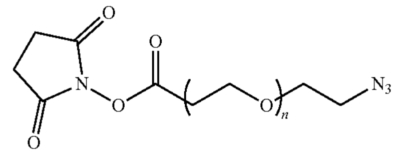

or

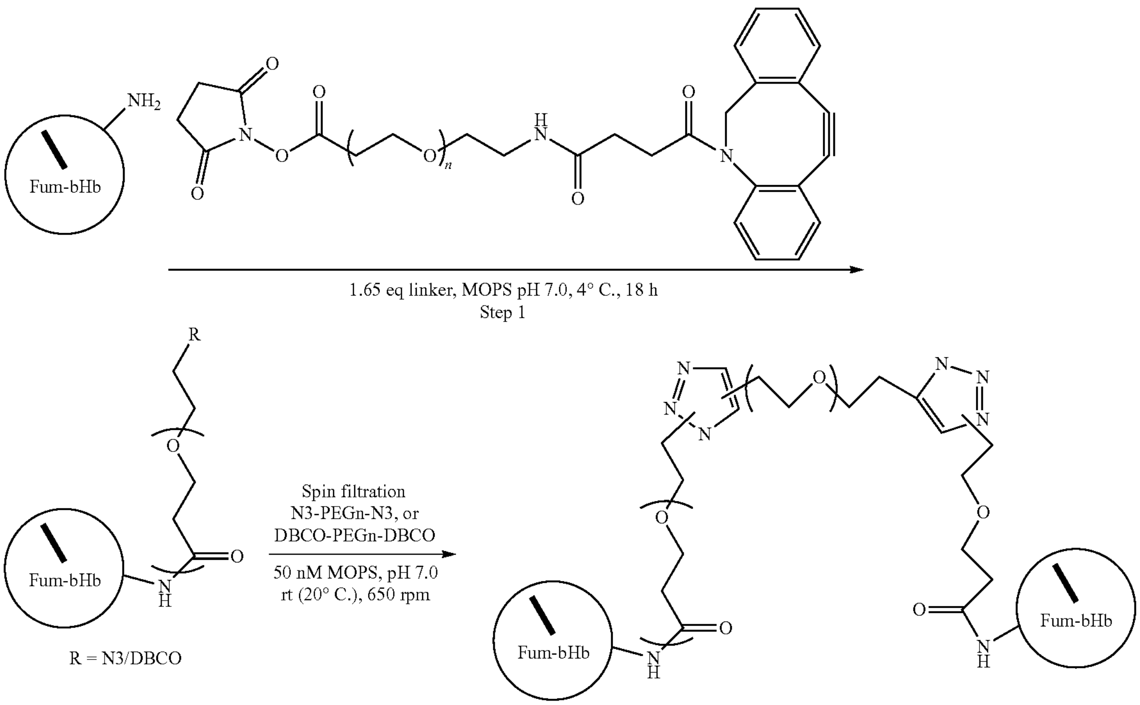

Objective and Background

To determine the optimum NHS-ester linker lengths and bis-click reagents linker lengths for multimer formation, a set of experiments were carried out as set forth in Table 1.

Four different NHS esters were separately tested for functionalizing modified Hb: two containing terminal DBCO functionality and two containing terminal azide functionality.

1) NHS-PEG4-DBCO (

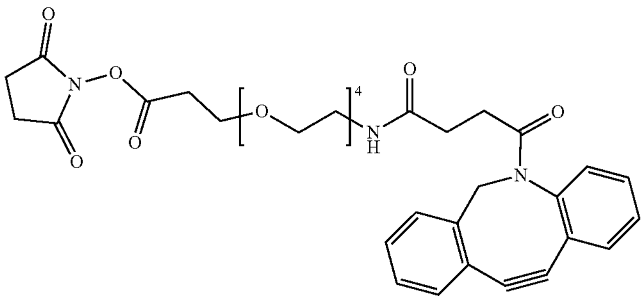

, sNHS-PEG4-DBCO"),

-continued

1) PEG12-DBCO ( 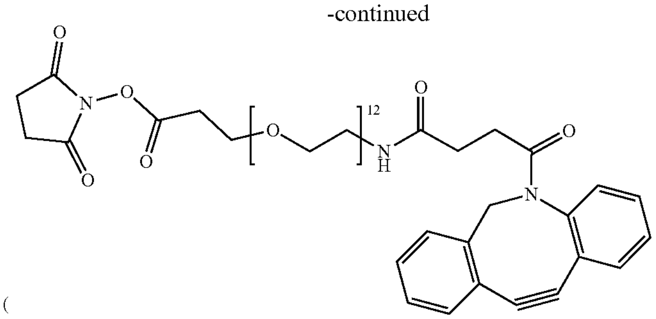 , sNHS-PEG12-DBCO),

3) NHS-PEG4-azide ( 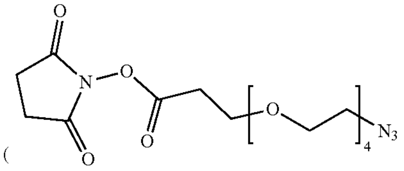 , sNHS-PEG4-azide), and

3) NHS-PEG12-azide ( 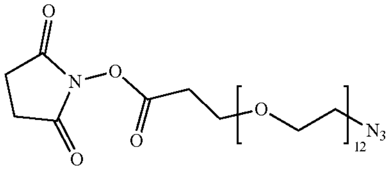 , sNHS-PEG12-azide).

The DBCO functionalized, modified Hb was reacted with two different-length bis-azide-linkers:

1) short-bis-azide-PEG5 ( 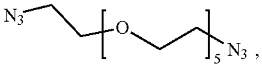 , azide-PEG5-azide), and

2) Long-bis-azide-PEG23 ( 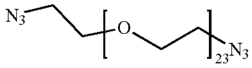 , azide-PEG23-azide).

The azide functionalized, modified Hb was reacted with two different-length bis-DBCO-linkers:

1) bis-DBCO-PEG4 ( 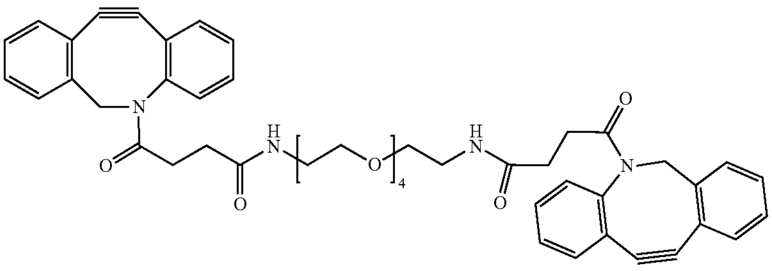 , DBCO-PEG4-DBCO), and 2) bis-azide-PEG2K ( 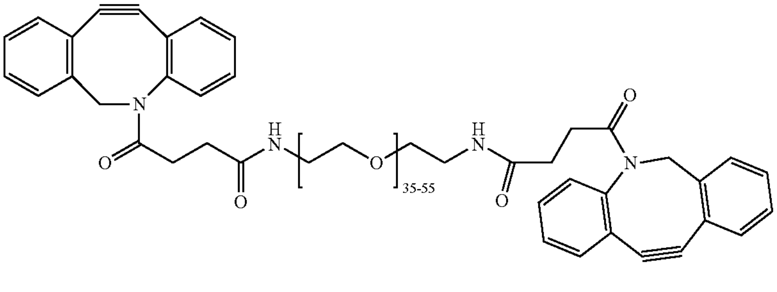 , DBCO-PEG2K-DBCO).

Materials

The modified hemoglobin starting material was Hemoglobin which had been intramolecularly crosslinked with DBSF (HbX) and dissolved in 50 mM MOPS buffer, pH 7.0. The functionalizing reagents were the following, all obtained from Broadpharm: NHS-PEH4-DBCO (#75), 2) NHS-PEG12-DBCO (#81), 3) short-NHS-PEH4-azide (#82), 4) Long-NHS-PEH12-azide (#83), 5) short-bis-azide-PEG5 (#95), 6) Long-bis-azide-PEG23 (#96), 7) short-bis-DBCO-PEG4 (#93), 8) Long-bis-azide-PEG2K (#97).

Step 1: NHS Ester Reaction

Scale 500 uL, Hb, 65 g/l=1 mM, 50 mM MOPS pH 7.0, 1.65 eq NHS ester-DBCO/azide, 1.5 mL Eppendorf, 650 rpm, 4° C., 18 h.

NHS ester functionalization reactions were performed with 500 uL of DBSF crosslinked Hemoglobin (HbX) in a 500 uL Eppendorf tube. Prior to starting reactions, the final buffer concentration was adjusted to 50 mM MOPS, pH 7.0. The reaction was carried out by adding 8.25 ul (1.65 equivalent), from a 100 mM stock solution in DMSO to the solution of a 1 mM HbX. The reaction mixtures were shaken at 650 rpm with the temperature maintained at 4° C. After 18 hours of reaction time, the reaction mixtures were analyzed by HPLC. Unreacted and hydrolyzed NHS ester reagents were removed from all 10 reactions using 10 KDa molecular weight cut-off spin filtration, and protein concentration was adjusted to 1 mM for use in the next reactions.

From analysis by HPLC on a $C_4$ reverse phase column up to 45% alpha sub-unit modification was observed.

Step 2: Multimer Formation

Scale 200 uL, Hb, 65 g/l=1 mM, 50 mM MOPS pH 7.0. The reactions were initiated by the addition of 0.5 eq of bis-DBCO or bis-azide linker. An additional 05 equivalent of bis-DBCO or bis-azide linker was added after 4 days of reaction time. The reactions were carried out in 1.5 mL Eppendorf tubes shaken at 650 rpm at room temperature.

TABLE 1

| Exp. No. | Crosslinker | Introduction of azide/DBCO | Scaffold | Multimer |
|---|---|---|---|---|
| 1 | DBSF | sNHS-PEG4-DBCO | azide-PEG5-azide | 43% |
| 2 | DBSF | sNHS-PEG4-DBCO | azide-PEG23-azide | 44% |
| 3 | DBSF | sNHS-PEG12-DBCO | azide-PEG5-azide | 37% |
| 4 | DBSF | sNHS-PEG12-DBCO | azide-PEG23-azide | 32% |
| 5 | DBSF | sNHS-PEG4-azide | DBCO-PEG4-DBCO | 42% |
| 6 | DBSF | sNHS-PEG4-azide | DBCO-PEG2K-DBCO | 36% |
| 7 | DBSF | sNHS-PEG12-azide | DBCO-PEG4-DBCO | 40% |
| 8 | DBSF | sNHS-PEG12-azide | DBCO-PEG2K-DBCO | 36% |

Click reactions were performed with 200 uL of fumarate crosslinked DBCO or azide labelled Hemoglobin (HbXL) in a 1.5 mL Eppendorf tube. The reaction was initiated with 0.5 equivalent of bis-azide or bis-DBCO linker added from a 100 mM stock solution in DMSO. Particularly, 1 uL (0.5 equivalent) of bis-DBCO or bis-azide linker was added from 100 mM stock solutions in DMSO to 200 uL of the solution of 1 mM HbX in 50 mM MOPS, pH 7.0. The reaction mixtures were shaken at 650 rpm at room temperature. The reactions were analyzed by native gel and HPLC after 4 days of reaction time. An additional 0.5 equivalents additional bis-azide or bis-DBCO linker was added, and all reactions were monitored again with HPLC and native gel after 4 additional days of reaction time. The % multimer formation was determined by gel-densitometry and is reported in Table 1.

Example 2: Test the Effect of a Higher Amount of Azide Functionalization on Multimer Formation Materials and Methods (1) 1.35 mM native-bovine Hemoglobin dissolved in 50 mM MOPS buffer, pH7.0. (2) NHS ester-PEG4-Azide obtained from Broadpharm.

To 20 mL solutions of bovine Hb, 88 g/l (1.35 mM) in 50 mM MOPS buffer pH 7.0, was added three different amounts of NHS-ester-PEG4-azide: 1a) 4 equivalents; 1b) 5 equivalents; 1c) 6 equivalents 50 mL falcon tube, rocker, NHS ester-PEG4-Azide reactions were performed with 20 mL of native Hb in a 50 mL falcon tube mixed on a rocker at 4° C. for 5 hours. Three separate reactions were carried out using 4, 5, and 6 equivalents of NHS-ester added from 100 mM DMSO stock solutions. The reaction mixtures were shaken at 4° C. analyzed by HPLC at the 4 hour time point.

Results

There was formation of multiple alpha-modified, and beta modified new peaks up to 4 azide functionalizations per tetramer based on analysis by reverse phase HPLC using a $C_4$ column.

Example 3: Crosslinking of Azide-Functionalized Hb Using DBSF

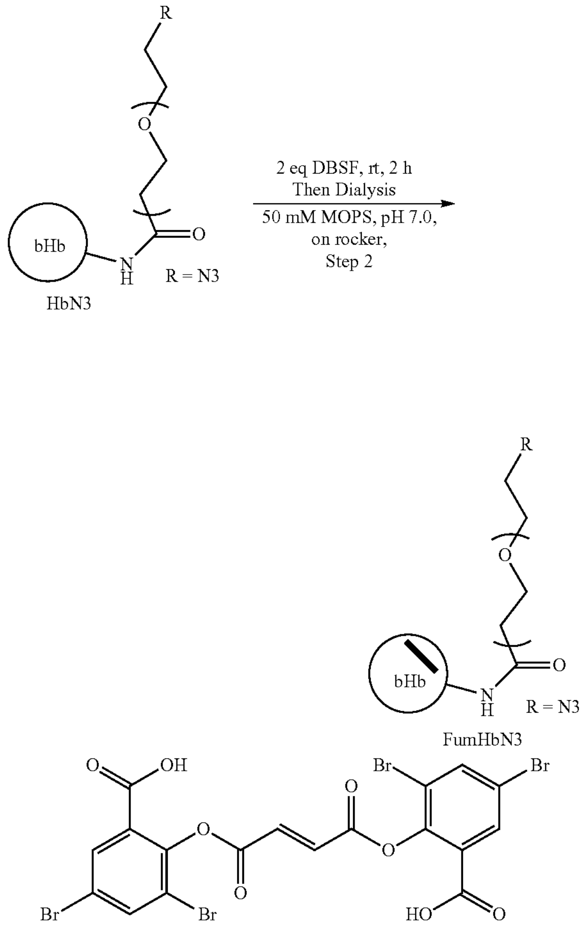

HbN3

FumHbN3

(DBSF)

Objective and Background

Crosslinking of azide-functionalized bovine Hb was carried out using DBSF as the crosslinker, creating a fumarate cross-linked, azide-functionalized modifed Hb product.

Materials and Methods (1) Azide labeled Hb dissolved in 50 mM MOPS, pH 7.0. (2) DBSF Step 2

To 20 mL of 1.35 mM solution of azide-functionalized bovine hemoglobin (HbN3) (in 50 mM MOPS pH 7.0 was added 2 equivalents of DBSF (added from a freshly prepared 200 mM stock solution in DMSO). The reaction was stirred for 2 hours at room temperature. The reaction mixture was analyzed by HPLC at the 2 hour time point. The reaction mixture was dialyzed against 3×1000 mL of 50 mM MOPS pH 7.0 using 10K cut-off dialysis bag with stirring for 24 hours.

Example 4: Multimer Formation Using Click Chemistry

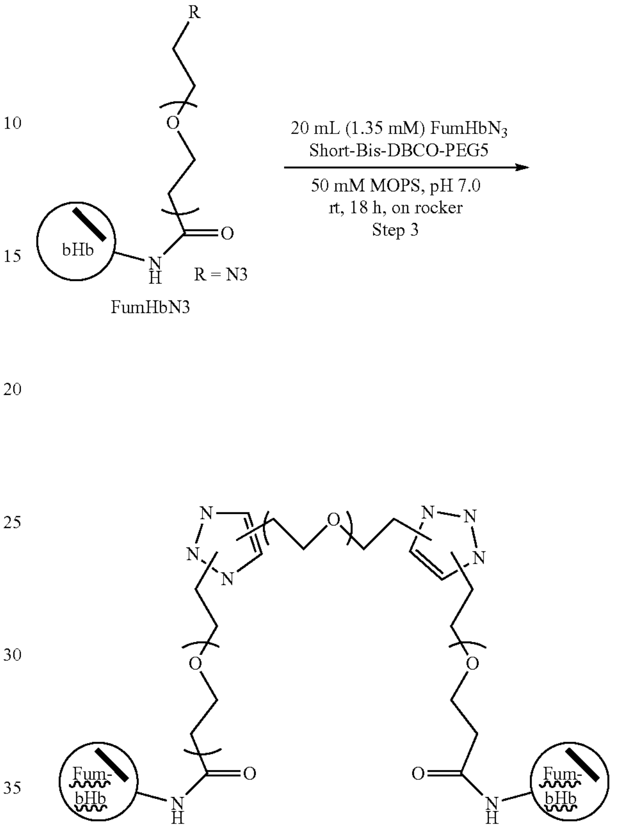

FumHbN3

Objective and Background

To increase the amount of higher molecular weight multimer formed by using more highly functionalized HbN3-X (azide-functionalized, intramolecularly crosslinked hemoglobin) and Bis-DBCO-PEG5.

Materials and Methods (1) Hb-N3-X. (2) bis-DBCO-PEG5

Step 3

To 20 mL of a 1.35 mM solution of Hb-N3-X 3 in 50 mM MOPS pH 7.0 was added 2 equivalents of bis-DBCO-PEG5.

Reactions were performed in a falcon tube at room temperature. Linkers were added from 100 mM stock solutions in DMSO. The reaction was analyzed by native gel electrophoresis (4-20% Tris-Glycine Gel (Invitrogen) run in Tris-Glycine native running buffer. Samples were prepared for this gel by first diluting 1:10 with water and then adding 1 μL of the diluted sample to 24 μL of a 1× native loading dye. Gels were loaded with 20 uL of this mixture. Molecular Weight Standards used for this gel were obtained from Invitrogen: native mark unstained protein standard, 5 μL of which was loaded onto the gel.

Based on analysis by native gel electrophoresis, up to 93% total multimer formation was achieved, of which up to 82% was of molecular weight 190 KDa and higher.

Synthesis of HBOCs Via Crosslinking, Functionalization, and Multimerization in Separate Steps: (B) Functionalization First, Followed by Intramolecular Crosslinking and Multimerization

Example 5: Functionalization of bHb Followed by Crosslinking (Switching Reaction Sequence)

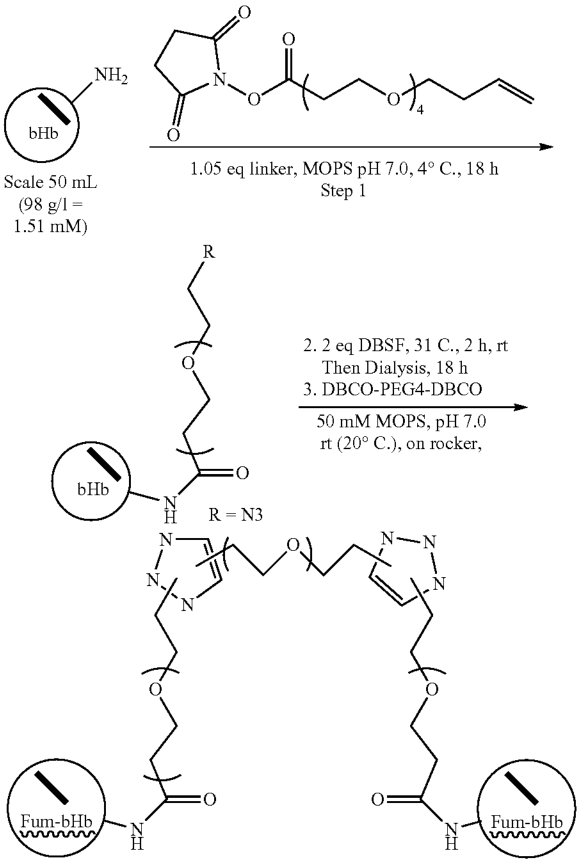

Objective and Background

In previous examples intramolecular crosslinking was carried out first, followed by functionalization. However, it is also possible that functionalization can be carried out first, followed by intramolecular crosslinking.

Step 1: Azide Labelling

Materials: Purified Bovine Hb and NHS Ester-PEG4-Azide

Set up: Hb, 98 g/l=1.51 mM, Scale 50 mL, 50 mM MOPS pH 7.0, 1.05 eq NHS ester-PEG4-azide, 2x50 mL falcon tube, rocker, 4° C., 18 h.

NHS ester-PEG4-azide reactions were performed with 50 mL of native Hb using two 50 mL falcon tubes. Prior to starting reactions, the final buffer concentration was adjusted to 50 mM MOPS, pH 7.0. The reaction was carried out using 1.05 equivalent of NHS-ester. Specifically, 791 uL of NHS ester-PEG4-azide (1.05 equivalent) was added from 100 mM stock in DMSO to a solution of a 1.51 mM native purified bovine Hb in 50 mM MOPS, pH 7.0. The reaction mixtures were shaken at 4° C. on a rocker and analyzed by HPLC after 18 hours.

Analysis by HPLC using a reverse phase $C_4$ column indicated 71% azide functionalization.

Step 2: Intramolecular Crosslinking of Azide Functionalized Bovine Hb Using DBSF Intramolecular crosslinking of functionalized bovine Hb was carried out using DBSF as the crosslinker.

Materials: (1) 1.5 mM Functionalized Bovine Hb in 50 mM MOPS, pH 7.0. (2) DBSF

Set up: Scale 50 mL, 2 eq DBSF (from 200 mM fresh stock in DMSO), room temperature, then dialysis, and concentration adjustment to 2 mM.

To 50 mL of a 1.5 mM solution of azide-functionalized bovine Hb in 50 mM MOPS buffer, pH 7.0 was added 2 equivalents of DBSF from a freshly prepared 200 mM stock solution in DMSO. The reaction as caried out in 2 falcon tubes with mixing on rocker at room temperature for 18 hours. The reaction mixture was analyzed by HPLC and dialyzed against 3x1000 mL 50 mM MOPS buffer, pH 7.0 for 24 hours. The concentration of the crosslinked, functionalized bovine hemoglobin was then adjusted to 2 mM.

HPLC analysis suggested 96% beta-subunit depletion, indicating high specificity of beta0subunit crosslinking.

The efficiency of reaction step switching was also analyzed by Native and denaturing gels and compared with DBSF crosslinked Hb.

Native gel: The gel used was an Invitrogen 4-20% Tris-Glycine Gel run in Tris-Glycine native Running Buffer. Samples were prepared for this gel by first diluting 1:10 with water and then adding 1 μL of that diluted sample to a 25 μL reaction mixture (24 μL of a 1x native loading dye, and 20 ul of which was loaded onto the gel). Molecular Weight Standard for this gel was Invitrogen native mark unstained protein standard of which 5 μL was loaded onto the gel.

Denaturing gel: The gel used was an Invitrogen 4-20% Tris-Glycine Gel run in Tris-Glycine SDS Running Buffer. Samples were prepared for this gel by first diluting 1:10 with water and then adding 2 μL of that diluted sample to a 25 μL reaction mixture (23 μL of a 1x loading dye (2x Bio-Rad Laemmli sample buffer containing 50 uL Beta-mercapto-ethanol), and 20 ul of which was loaded onto the gel. Molecular Weight Standards for this gel were SeeBlue Plus2 Protein Standards, of which 5 μL was loaded onto the gel.

The HPLC and Gel analysis results suggested that changing the order of the reaction sequences doesn't significantly affect the degree of crosslinking.

Example 6: Test on the Effect of Sulfo-NHS Ester-DBCO on the Functionalization Reaction

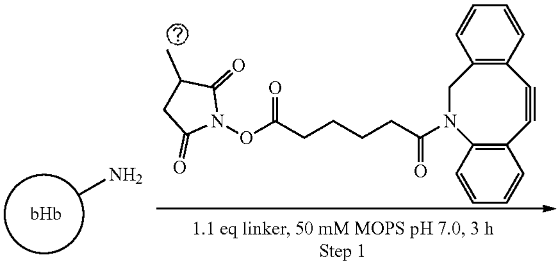

-continued

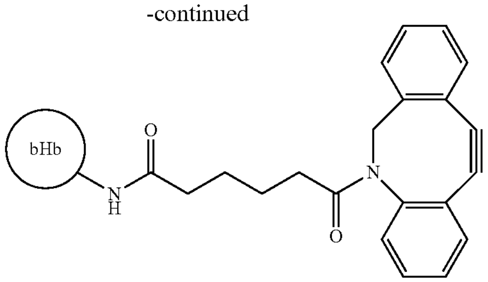

R1A: RT; R1B: 4° C.

Objective and Background

This Example is designed to test the effect of a more reactive on acylation reagent. Accordingly, the Sulfo-NHS ester-DBCO was evaluated for the functionalization reaction.

Materials and Methods (1) 1.5 mM native-Hemoglobin in 50 mM MOPS, pH 7.0.
(2) Sulfo-NHS ester-DBCO (obtained from Broadpharm)

Step 1

To 2.5 mL of purified native bovine Hb dissolved in 50 mM MOPS buffer, pH 7.0 in a 15 mL falcon tube was added Sulfo-NHS ester (41.44 uL drawn from a 100 mM in DMSO stock solution (1.1 equivalent). Two separate reactions were carried out at room temperature and 4° C. The reaction mixtures were shaken on a rocker and analyzed by HPLC at 1 hour and 4 hour time points Results and Discussion Formation of a major single alpha-modified peak was observed at 8.25 min, and minor beta-modified peak was observed at 11.75 using a reverse phase $C_4$ column. The reaction carried out at room temperature reaction achieved 51% acylation and a 63:37% alpha selectivity. The reaction carried out at 4° C. achieved ~72% DBCO functionalization and a 82:18% alpha: beta selectivity.

It was concluded that the acylation reaction to functionalize hemoglobin with DBCO works efficiently at 4° C. while achieving a more selective alpha:beta modification ratio.

Example 7: Crosslinking of DBCO-Functionalized Bovine Hb Using DBSF

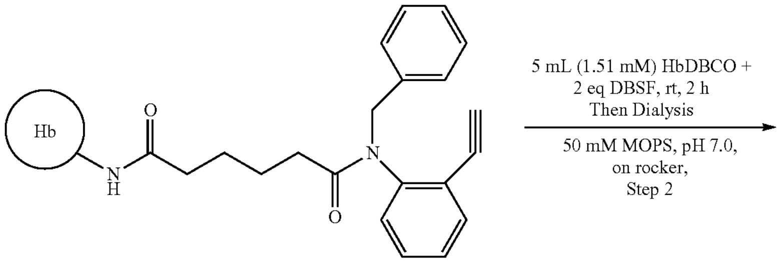

Hb-DBCO

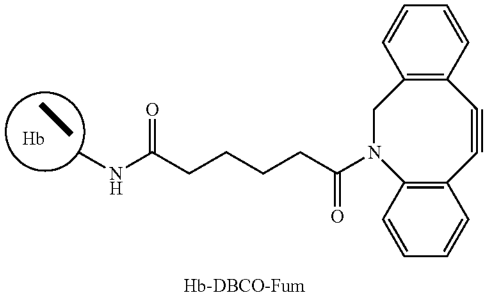

Hb-DBCO-Fum

Materials and Methods 1) 1.5 mM DBCO labeled Hb in 50 mM MOPS, pH 7.0. (2) DBSF.

Setup: Step 2: Scale 5 mL, Hb, 98 g/L=1.51 mM, 50 mM MOPS pH 7.0, 2.2 eq DBSF, 15 mL falcon tube, rocker, room temperature, 2 hours, then dialysis 3×500 mL buffer 24 hours. The reaction mixture analyzed by HPLC at 2 h time point.

Step 2

The reaction was carried out with DBCO-functionalized bovine Hb at a concentration of 98 g/L (1.51 mM) in 50 mM MOPS buffer, pH 7.0. The crosslinking reaction was initiated by the addition of 2.2 equivalents of DBSF to 5 mL of with DBCO-functionalized bovine Hb in a 15 mL falcon tube. The reaction was mixed on a rocker at room temperature for 2 hours. After this time, the reaction mixture was dialyzed against 3×500 mL of 50 mM MOPS buffer, pH 7.0. The reaction mixture analyzed by HPLC at the 2 hour time point.

HPLC analysis shows that 96% beta-subunit was consumed in 2 hours, indicating a high degree of beta0-beta selectivity for the crosslinking.

Example 8: Multimerization Via an Intermolecular Click Reaction

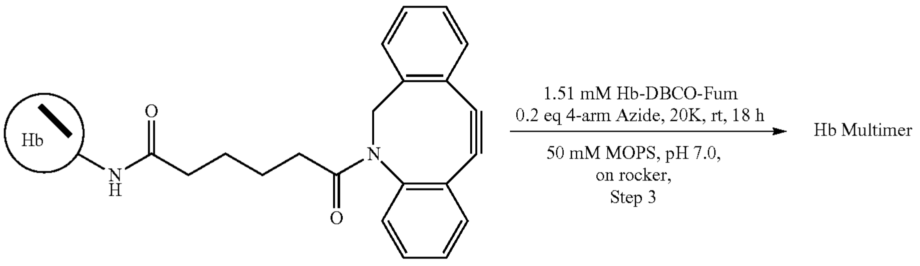

Hb-DBCO-Fum

Objective and Background

This Example tests the intermolecular click reaction of DBCO labelled DBSF-crosslinked, DBCO-functionalized bovine hemoglobin Hb (DBCO-Hb-X) using bis-PEG-azide and a 4-arm PEG-azide.

Materials and Methods (1) 1.5 mM Hb-DBCO-X in 50 mM MOPS, pH 7.0. (2) 4-arm PEG-Azide 20K molecular weight; Source: Creative PEGWorks.

Step 3

Scale: 0.5 mL, 1.5 mM Hb-DBCO-X, 50 mM MOPS pH 7.0, 0.2 eq 4-arm Azide, 20K, 1.5 mL Eppendorf, room temperature Reactions were performed with 500 uL of Hb-DBCO-X in a 1.5 mL Eppendorf tube stirred at 650 rpm at room temperature. The reaction was initiated by the addition of 0.2 equivalents of 4-arm azide added from a 100 mM stock solution in DMSO. After stirring for 40 hours, and an additional 0.1 equivalent of 4-arm azide was added. The reaction mixture was vortexed at 650 rpm at room temperature and analyzed by native gel electrophoresis. The gel used was an invitrogen 4-20% Tris-Glycine Gel run in Tris-Glycine native Running Buffer. Samples were prepared for this gel by first diluting 1:10 with water and then adding 1 μL of that diluted sample to a 25 μL reaction mixture (24 μL of a 1× native loading dye, and 20 uL of which was loaded onto the gel. Molecular Weight Standards for this gel were Invitrogen native mark unstained protein standard of which 5 μL was loaded onto the gel.

Native gel analysis showed 46% formation of 258 KDa and higher multimers of tetrameric hemoglobin.

Synthesis of HBOCs Via Multimerization with Trifunctional Crosslinkers: (A) Diels-Alder-Based Tri-Functional Crosslinkers Example 9: Synthesis of Furan-3-Mesylate A 100 mL round bottom flask was charged with a stir bar, 1 g of furan-3-methanol, and 10 mL of dry DCM. To this solution was added 2.1 mL triethylamine (1.5 eq) and the solution was cooled to 0° C. in an ice bath and capped with a septum. After approximately 20 minutes, 1 mL of mesyl chloride was added via syringe dropwise taking care not to raise the temperature of the solution. After stirring for 30 minutes, the ice bath was removed, and the solution was stirred at room temperature for a further 2 hours. The solution was then washed with 1N HCl, water, saturated sodium bicarbonate solution, and brine, and then evaporated on a rotary evaporator without the use of heating because the mesylate product is thermally sensitive (temperature maintained below 25° C. The reaction afforded 1.59 g of furan-3-mesylate product (83% yield) that was not further characterized before moving to the next step.

Example 10: Synthesis of Furan-S-PEG-Azide

To a 50 mL round bottom was added 250 mg thiol-PEG3-azide, 4 mL of dry DMF, and 346 mg cesium carbonate. This mixture was stirred at room temperature for 30 minutes. Furan-3-mesylate (200 mg, 1.08 eq) was then added dropwise to the suspension. The suspension was stirred overnight at room temperature capped with a septum. After overnight stirring, the mixture was filtered and the DMF was removed in vacuo. The mixture was diluted with dichloromethane and washed with water, saturated sodium bicarbonate solution, and brine. The organic layer was dried and evaporated to a crude oil that was separated on column (10% MeOH/DCM) to afford the product furan-S-PEG3-azide as a viscous oil (second band off column, 276 mg, 77% yield).

Example 11: Synthesis of DAS

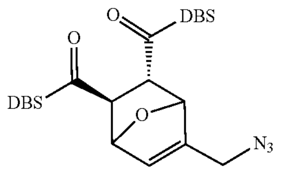

DAS

A 10 mL round bottom was charged with a stir bar and 142 mg of DBSF dissolved in 3 mL of dry tetrahydrofuran (THF) was added, followed by the addition of 66.6 mg of furan-S-PEG3-azide from Example 10 dissolved in 1 mL THF. The solution was heated to 50° C. with stirring for 48 hours capped with a septum. THF was then removed in vacuo and the trifunctional crosslinker product DAS was purified on column as the second band (10% MeOH/DCM). Yield was 50%, giving 105 mg of a reddish residue.

Synthesis of HBOCs Via Multimerization with Trifunctional Crosslinkers: (B) Crosslinking and Multimerization

Example 12: Crosslinking and Multimerization of Bovine Hemoglobin with DAS

A stock solution containing 99 mM DAS in DMSO was generated. To a solution of 500 uL of 1 mM native bovine Hb in 150 mM MOPS buffer, pH 6.8 was added 6 equivalents of DAS (30 uL of 99 mM DAS stock solution) and the reaction mixture shaken in an Eppendorf tube overnight at 4° C. Analysis by gel electrophoresis showed a yield of 52.7% crosslinked hemoglobin. This sample was then subjected to dialysis using a 50 kDa MW cut-off membrane to remove all unreacted crosslinker. Additional equivalents of crosslinker could be added to consume more native hemoglobin at the expense of generating more side-products. These solutions were then reacted further by adding 100 mM stocks of bis-DBCO PEG linkers (0.5 eq) or 4-arm DBCO PEG scaffolds (0.25 eq) to produce multimerize tetrameric bovine hemoglobin.

Example 13: Synthesis of HBOCs Via Direct Multimerization of Crosslinked Hb with 1,4-PBG

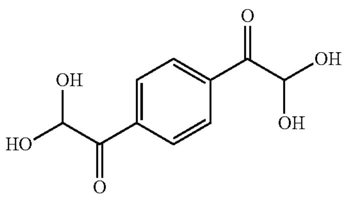

1,4-bis-phenylglyoxal (1,4-PBG)

1,4-PBG formed multimeric crosslinked hemoglobin species when added to aqueous preparations of crosslinked bovine hemoglobin (bHb). A standard reaction involved the addition of 0.5 equivalents of 1,4-PBG dissolved in DMSO (typically 99 mM) to a 1 mM stock solution of crosslinked bovine hemoglobin in 150 mM sodium phosphate buffer at pH 8. Such a reaction produced a 2-10% yield of multimeric products over the course of 24 hours as judged by densitometry from gel electrophoresis.

In a standard reaction, a small aliquot of concentrated 1,4-PBG dissolved in DMSO was added at half an equivalent to one equivalent of DBSF-crosslinked hemoglobin at 1 mM in a high salt concentration buffer (150 mM MOPS or $Na_2PO_4$) near pH 8 and was shaken/stirred for several days under argon and under protection from light. A highly concentrated stock of 1,4-PBG, at about 99 mM, was necessary to keep the overall DMSO concentration low in the reaction mixture. At hemoglobin concentrations lower than 1 mM, the reaction appeared to be proceeding detrimentally slower, whereas increasing the hemoglobin concentration produced viscous gels which were less practical for reactions. Hemoglobin with a concentration at up to 3.75 mM was successfully used which slightly increased the initial yield of the reaction. Reactions run with 3.75 mM hemoglobin likely represented a limit on the concentration as these solutions tend to yield precipitates and appear to oxidize more easily than 1 mM hemoglobin solutions.

Reactions to form multimeric products proceed at room temperature. However, heating the reaction mixtures to up to 35° C. was necessary to reach completeness of the reaction. At temperatures above 35° C., reaction mixtures had a greater propensity to form methemoglobin, especially if not properly purged with inert gas and sealed. It was therefore desirable to purge the crosslinked hemoglobin reactant solution with nitrogen or argon prior to running the reaction and ensure that the reaction vessel is properly sealed and protected from light. For a reaction that will only take place over the course of a few days, shaking on a heated shaker in an Eppendorf tube is adequate, but for longer reaction times magnetic stirring in a round bottom flask sealed with a septum and argon balloon is preferred.

The buffered reaction media in which the multimerization reaction takes place appeared to be rather flexible for the reaction with 1,4-PBG. As buffers, both MOPS and sodium phosphate at concentrations from 50 mM to 150 mM are sufficient for bis-tetramer formation. Perhaps more interestingly, multimerization using 1,4-PBG could proceed over a wide range of pH values. Bis-tetramer product was observed at a range of pHs from 6.5 to 8.2, with a slight preference for pH ~8.

Figure 14:
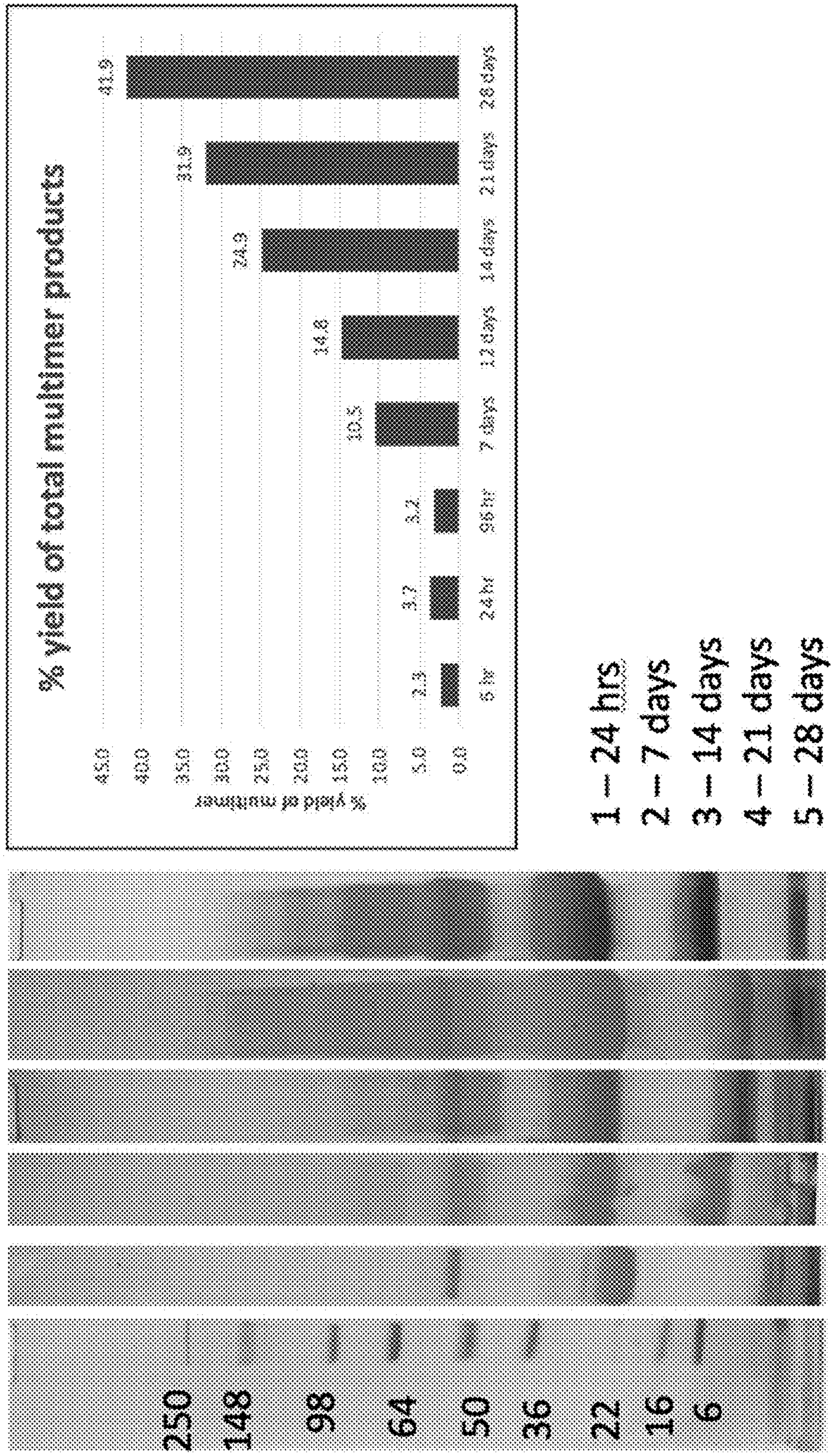
FIG. 14 are SDS-PAGE analysis of the reaction in Example 13, which shows yield increases (~10%) per week from shaking reaction between DBSF-crosslinked bHb and 0.5 eq. 1,4-PBG.

The yield of total multimeric product using the 1,4-PBG agent was typically around 2-10% after reacting overnight. If the reaction was continued with stirring/shaking at 32° C., for extended periods of time, the total multimeric product yield=increased approximately ~10% per week (see e.g., FIG. 14). At 4 weeks, about 40% of the total reaction mixture was transformed into multimeric product, of which, a significant portion was bis-tetramer.

Example 14: Synthesis of HBOCs Via Direct Multimerization of Crosslinked Hb with PEGn-Bis-PG The conditions of the reaction with 1,4-PBG (Example 13) were repeated by substituting $(PEG)_3$-bis-phenylglyoxal for 1,4-PBG.

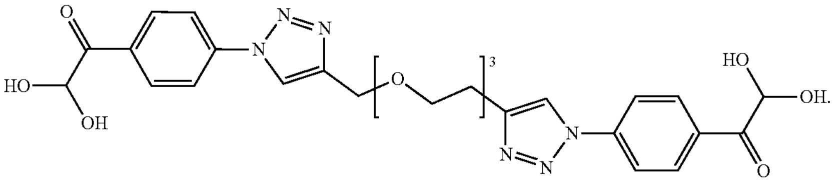

((PEG)$_3$-bis-phenylglyoxal)

Example 15: Crosslinking of Hemoglobin with Isophthalate-PEG4-Type 2 Crosslinker A 140 mL solution of 1 mM Hb (65 g/L) was made in 150 mM 3-(N-morpholino)propanesulfonic buffer (MOPS) with a pH of 6.8. This solution was charged into a 1.6 L reaction vessel. A 19.8 mM solution of Isophthalate-PEG4-Type 2 Crosslinker was prepared in DMSO, and 1.4 mL of this solution was added in a single bolus to the 140 mL solution of hemoglobin. This reaction mixture was gently mixed at 160 RPM at 31° C. overnight on a Benchmark Incu-ShakerMini. After 16 hours of mixing, the reaction was stopped, and 10 uL of the crosslinked solution diluted to 1 g/L and compared against a native hemoglobin standard on RP-HPLC. Crosslinking was estimated using a denaturing SDS-PAGE gel.

Example 16: Intramolecular Crosslinking of Carbonylated Bovine Hemoglobin

Acellular tetrameric bovine hemoglobin can dissociate into αβ dimers, and further into monomers with loss of heme, causing toxicity. To stabilize the hemoglobin and prevent loss of heme, the two b subunits are covalently linked with a crosslinking reagent, stabilizing the tetramer against dissociation. The crosslinking reaction can be carried out using the reagent bis-(3,5-dibromosalicyl)glutarate (DBSG, i.e.,

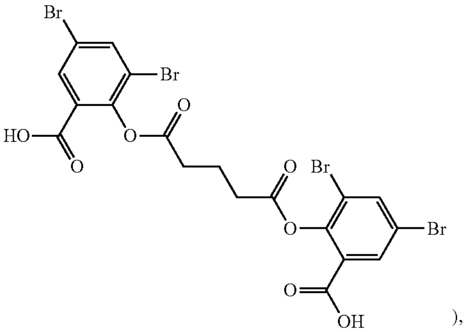

), which is selective in forming a covalent crosslink via a glutaryl residue between two lysines on adjacent β subunits, resulting in a highly stabilized, intramolecularly crosslinked bovine hemoglobin tetramer. In a typical crosslinking reaction, a solution of 100 grams (1.56 mMoles) of purified carbonylated (Maria Celiana P. Lima and Cristina T. Andrade, Artificial Cells, Blood Substitutes, and Biotechnology, 35: 431-447, 2007, incorporated herein by reference in its entirety) bovine hemoglobin dissolved in 1 liter of 50 mM MOPS buffer, pH 7.8, was warmed to 35° C. Four equivalents of DBSG (6.25 mMoles, 4.3 grams) was dissolved in 30 mL of DMSO and sterile filtered, and the sterile filtered DBSG solution was added via syringe to the bovine hemoglobin solution. The reaction mixture was stirred for 16 hours with the temperature maintained at 35° C. The crosslinking reaction was monitored using reversed-phase high-performance liquid chromatography (HPLC) for the disappearance of beta subunits, which were consumed as the crosslinking reaction progressed. At the end of the 16-hour reaction time, the consumption of beta subunits was found to be >95%. This reaction mixture was used for the subsequent functionalization step without further processing.

Example 16A: Intramolecular Crosslinking of Non-Carbonylated Bovine Hemoglobin

Acellular tetrameric bovine hemoglobin can dissociate into cp dimers, and further into monomers with loss of heme, causing toxicity. To stabilize the hemoglobin and prevent loss of heme, the two P subunits are covalently linked with a crosslinking reagent, stabilizing the tetramer against dissociation. The intramolecular crosslinking reaction of non-carbonylated bovine hemoglobin was carried out similarly to that for carbonylated bovine hemoglobin. In a typical crosslinking reaction, a solution of 100 grams (1.56 mMoles) of purified bovine hemoglobin dissolved in 1 liter of 50 mM MOPS buffer, pH 7.8, was warmed to 35° C. Four equivalents of DBSG (6.25 mMoles, 4.3 grams) was dissolved in 30 mL of DMSO and sterile filtered, and the sterile filtered DBSG solution was added via syringe to the bovine hemoglobin solution. The reaction mixture was stirred for 16 hours with the temperature maintained at 35° C. The crosslinking reaction was monitored using reversed-phase high-performance liquid chromatography (HPLC) for the disappearance of beta subunits, which were consumed as the crosslinking reaction progressed. At the end of the 16-hour reaction time, the consumption of beta subunits was found to be >95%. This reaction mixture was used for the subsequent functionalization step without further processing.

Example 17: Functionalization of Intramolecularly Crosslinked Carbonylated Bovine Hemoglobin with Azide The reaction mixture from Example 16 was cooled to 5° C. and to this cooled solution was added 10 mL of a 500 mM solution of sodium ascorbate. After stirring for 30 minutes, an aqueous solution of 5 equivalents (3.02 grams) of N-hydroxysuccinimidyl ester of ω-azido-polyethyleneglycol-4 carboxylate (NHS-PEG-4-azide, i.e.,

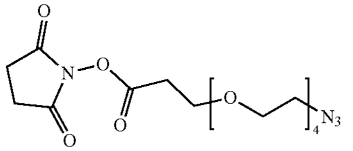

)

was sterile filtered and then added to the crosslinked hemoglobin solution with stirring. The reaction mixture was stirred at 5° C. for 6 hours. After this time, the reaction mixture was filtered to remove solids that had precipitated. Low molecular weight compounds were removed from the filtrate by tangential flow filtration using a 10 kDa molecular weight cut-off membrane.

Example 17A: Functionalization of Intramolecularly Crosslinked Non-Carbonylated Bovine Hemoglobin with Azide The reaction mixture from Example 16A was cooled to 5° C. and to this cooled solution was added 10 mL of a 500 mM solution of sodium ascorbate. After stirring for 30 minutes, an aqueous solution of 5 equivalents (3.02 grams) of N-hydroxysuccinimidyl ester of ω-azido-polyethyleneglycol-4 carboxylate (NHS-PEG-4-azide) was sterile filtered and then added to the crosslinked hemoglobin solution with stirring. The reaction mixture was stirred at 5° C. for 6 hours. After this time, the reaction mixture was filtered to remove any solids that had precipitated. Low molecular weight compounds were removed from the filtrate by tangential flow filtration using a 10 kDa molecular weight cut-off membrane. The final concentration of hemoglobin was 1.55 mM.

Example 17B: Functionalization of Intramolecularly Crosslinked Bovine Hemoglobin with DBCO The functionalization of intramolecularly-crosslinked, tetrameric bovine hemoglobin (either carbonylated or non-carbonylated) with DBCO was carried out using the N-hydroxysuccinimidyl ester of carboxy-polyethyleneglycol-DBCO (NHS-PEGn-DBCO). The polyethyleneglycol segment can vary in length from PEG4 to PEG 45. In a typical reaction, 1.65 equivalents of NHS-PEG4-DBCO was stirred with intramolecularly crosslinked bovine hemoglobin (either carbonyolated or non-carbonylated) in MOPS buffer at pH 7.0 for 18 hours at 4° C. After this time, the reaction mixture was filtered to remove any solids that had precipitated. Low molecular weight compounds were removed from the filtrate by tangential flow filtration using a 10 kDa molecular weight cut-off membrane.

Example 18: Multimerization of Azide-Functionalized Carbonylated Tetrameric Bovine Hemoglobin The multimerization of azide-functionalized intramolecularly-crosslinked, carbonylated tetrameric bovine hemoglobin was accomplished via a strain-promoted azide-alkyne cycloaddition (SPAAC) reaction, commonly referred to as click chemistry. The strained alkyne was introduced as a polyethylene glycol carrying dibenzocyclooctyne groups at each terminus (bis-DBCO-polyethyleneglycol). In a typical reaction, DBCO-PEG5-DBCO, i.e.,

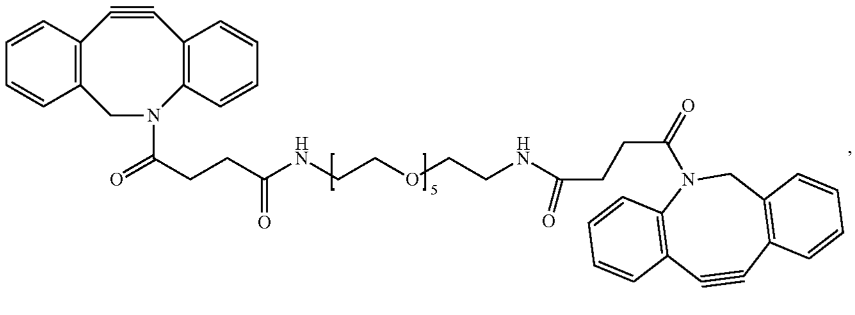

, was added to the functionalized crosslinked carbonylated bovine hemoglobin solution as produced in Example 17 at a final concentration of 3.57 mMoles per liter (2.3 equivalents per equivalent of hemoglobin). The reaction mixture was stirred at 20° C. for 48 hours. The reaction was analyzed by native gel. When the reaction was complete, residual lower molecular weight species (1-2 bovine Hb units) were filtered out of the product mixture using tangential flow filtration (TFF) using a 100 kDa molecular weight cut-off membrane. The resulting retentate solution contained stable multimers of bovine hemoglobin tetramers ranging in molecular weight from 192-800 kilodaltons (3-11 tetramers) as analyzed by native gel.

Example 18A: Multimerization of Azide-Functionalized Non-Carbonylated Tetrameric Bovine Hemoglobin The multimerization of azide-functionalized intramolecularly-crosslinked, non-carbonylated tetrameric bovine hemoglobin was carried out similarly to the reaction with the carbonylated form of crosslinked, functionalized hemoglobin (Example 18). In a typical reaction, DBCO-PEG5-DBCO was added to the functionalized crosslinked non-carbonylated bovine hemoglobin solution at a final concentration of 3.57 mMoles per liter (2.3 equivalents per equivalent of hemoglobin). The reaction mixture was stirred at 20° C. for 48 hours. The reaction was analyzed by native gel. When the reaction was complete, residual lower molecular weight species (1-2 bovine Hb units) were filtered out of the product mixture using tangential flow filtration (TFF) using a 100 kDa molecular weight cut-off membrane. The resulting retentate solution contained stable multimers of bovine hemoglobin tetramers ranging in molecular weight from 192-800 kilodaltons (3-11 tetramers) as analyzed by native gel.

Example 18B: Multimerization of Azide-Functionalized Tetrameric Bovine Hemoglobin Using Different Length PEG Versions of bis-DBCO-PEG The multimerization of azide-functionalized intramolecularly-crosslinked, tetrameric bovine hemoglobin (either carbonylated or non-carbonylated) can be carried out using bis-DBCO PEG molecules having different lengths of PEG chains. In a typical reaction, bis-DBCO-PEG2000 (PEG chain is approximately 45 units in length) was added to the functionalized crosslinked non-carbonylated bovine hemoglobin solution at a final concentration of 3.57 mMoles per liter (2.3 equivalents per equivalent of hemoglobin). The reaction mixture was stirred at 20° C. for 48 hours. The reaction was analyzed by native gel. When the reaction was complete, residual lower molecular weight species (1-2 bovine Hb units) were filtered out of the product mixture using tangential flow filtration (TFF) using a 100 kDa molecular weight cut-off membrane. The resulting retentate solution contained stable multimers of bovine hemoglobin tetramers ranging in molecular weight from 192-800 kilodaltons (3-11 tetramers) as analyzed by native gel.

Example 18C: Multimerization of DBCO-Functionalized Tetrameric Bovine Hemoglobin Using bis Azido-polyethyleneglycol The multimerization of DBCO-functionalized intramolecularly-crosslinked, tetrameric bovine hemoglobin (either carbonylated or non-carbonylated) was carried out using bis-azido PEG (azide-PEGn-azide). In a typical reaction, $N_3$—PEGn-$N_3$ was stirred with DBCO-functionalized crosslinked tetrameric bovine hemoglobin in MOPS buffer, pH 7.0, for 48 hours at 20° C. The reaction was analyzed by native gel. When the reaction was complete, residual lower molecular weight species (1-2 bovine Hb units) were filtered out of the product mixture using tangential flow filtration (TFF) using a 100 kDa molecular weight cut-off membrane. The resulting retentate solution contained stable multimers of bovine hemoglobin tetramers ranging in molecular weight from 192-800 kilodaltons (3-11 tetramers) as analyzed by native gel.

Example 19: Removal of Carbon Monoxide from Carbonylated Hemoglobin Multimers The CO that bound Hb was removed by oxidizing hemoglobin (heme $Fe^{2+}$) to Methemoglobin (heme $Fe^{3+}$) by the addition of sodium nitrite ($NaNO_2$) at a final concentration of 10 mM at pH 7.7. The reaction mixture was stirred for 16 h at 35° C. At the end of the reaction time, the Hb carbonylation content was analyzed using a co-oximeter and found to be <5% of the total hemoglobin.

Example 20: Reduction of metHemoglobin

Methemoglobin (heme Fe+++) which had been formed during the previous multi-step process (e.g., Examples 16-19) was reduced to functionally active hemoglobin (heme Fe++) by the addition of sodium dithionite added at a final concentration of (2 eq) 3.1 mM. The pH was maintained at 7.528, and the reaction mixture was stirred for 10 min at 20° C. At the end of the reaction time, the methemoglobin content was analyzed using a co-oximeter and found to be <5% of the total hemoglobin.

Example 20A: Alternative Reduction of metHemoglobin Using Sodium Ascorbate

Methemoglobin (heme Fe+++) which had been formed during the previous multi-step process (e.g., Examples 16-19) was reduced to functionally active hemoglobin (heme Fe++) by the addition of sodium ascorbate added at a final concentration of 8 mM. The pH was maintained at 7.5, and the reaction mixture was stirred for 18 hours at 4° C. At the end of the reaction time, the methemoglobin content was analyzed using a co-oximeter and found to be <5% of the total hemoglobin.

The publications discussed herein are provided solely for their disclosure prior to the filing date of the present application. Nothing herein is to be construed as an admission that the present invention is not entitled to antedate such publication by virtue of prior invention.

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A multimerized hemoglobin (Hb) composition, comprising two or more modified Hb, wherein each modified Hb independently comprises:

at least two subunits of a Hb intramolecularly crosslinked with a compound of formula (I)

(I)

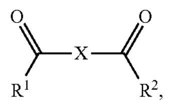

or a salt, a stereoisomer, or a deuterated form thereof, wherein:

X is $C_{1-24}$ alkylene, $C_{2-24}$ alkenylene, $C_{2-24}$ alkynylene, $C_{3-9}$ cycloalkylene, $C_{3-9}$ cycloalkenylene, 5-12 membered heterocyclylene containing 1 or 2 heteroatoms selected from N, S, or O, heteroarylene, or $-L^1-NR^A-L^2-$, wherein X is optionally substituted with 1-6 $R^3$ as permitted by valency;

$R^1$ and $R^2$ are each independently —OH, halogen, or a leaving group;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), —($C_{1-12}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$ $(CH_2)_n$—$N_3$, —NHC(O)—($C_{1-12}$ alkylene)-$(OCH_2CH_2)_m$—$(CH_2)_n$—$N_3$, —O—($C_{1-12}$ alkylene)-$(OCH_2CH_2)_m$—$(CH_2)_n$—$N_3$, —S—($C_{1-12}$ alkylene)-$(OCH_2CH_2)_m$—$(CH_2)_n$—$N_3$, or —C(O)—$R^1$, wherein each alkyl or alkylene is optionally and independently substituted with —$C_{1-6}$ alkyl, —OH, —CN, —$NO_2$, or halogen;

$R^A$ is H, —$C_{1-6}$ alkyl, aryl, —C(O)-aryl, —$SO_2$($C_{1-6}$ alkyl), —$SO_2$-aryl, or —($C_{1-6}$ alkylene)-$(OCH_2CH_2)_m$—$(CH_2)_n$—$N_3$, wherein each alkyl, aryl, or alkylene is optionally and independently substituted with —$C_{1-6}$ alkyl, —OH, —CN, —$NO_2$, or halogen;

$L^1$ and $L^2$ are each independently $C_{1-12}$ alkylene, $C_{2-12}$ alkenylene, $C_{2-12}$ alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each m is independently an integer of 1-200; and each n is independently an integer of 0-50.

2. The multimerized Hb composition of claim 1, wherein the Hb intramolecularly crosslinked with the compound of formula (I) comprises:

(I-A)

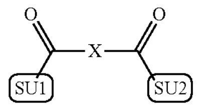

wherein SU1 is a residue on a first subunit of the Hb, and SU2 is a residue on a second subunit of the Hb.

3. The multimerized Hb composition of claim 2, comprising a reaction product of:

a first modified Hb comprising a first residue functionalized with a first reactive group for a click reaction; and a reactant molecule comprising a second reactive group that is complementary to the first reactive group for the click reaction.

4. The multimerized Hb composition of claim 3, wherein the reactant molecule is a second modified Hb comprising a second residue functionalized with the second reactive group.

5. The multimerized Hb composition of claim 3, wherein the reactant molecule is a scaffold compound comprising the second reactive group.

6. The multimerized Hb composition of claim 3, wherein:

the first reactive group is azido, and the second reactive group is cycloalkynyl; or the first reactive group is cycloalkynyl, and the second reactive group is azido.

7. The multimerized Hb composition of claim 3, wherein:

the first reactive group is azido, and the second reactive group is propargyl; or the first reactive group is propargyl, and the second reactive group is azido.

8. The multimerized Hb composition of claim 3, wherein:

the first reactive group is tetrazine, and the second reactive group is TCO; or the first reactive group is TCO, and the second reactive group is tetrazine.

9. The multimerized Hb composition of claim 1, wherein the at least two subunits of each modified Hb are intramolecularly crosslinked with the compound of formula (I) at a residue selected from the group consisting of Lys, Cys, Arg, and an N-termini.

10. The multimerized Hb composition of claim 1, wherein the two beta subunits of the Hb are intramolecularly cross-linked by the compound of formula (I).

11. The multimerized Hb composition of claim 10, wherein amino groups of lysine residues of the beta subunits are intramolecularly crosslinked by the compound of formula (I).

12. The multimerized Hb composition of claim 11, wherein the lysine residues of the beta subunits are Lys-81 and Lys-81 of SEQ ID NO: 2, Lys-81 and Lys-94 of SEQ ID NO: 2, or Lys-75 and Lys-81 of SEQ ID NO: 2.

13. The multimerized Hb composition of claim 1, wherein the Hb is bovine, human, equine, porcine, ovine, simian, or fish hemoglobin.

14. The multimerized Hb composition of claim 3, wherein the first reactive group is azido, and the second reactive groups are cycloalkynyl, and wherein the first modified Hb comprising a first residue functionalized with the first reactive group for a click reaction is obtained by:

reacting the compound of formula (I) and a Hb to form a crosslinked Hb, and reacting the crosslinked Hb and an azido compound; or reacting an azido compound and a Hb to form an azido-functionalized Hb, and reacting the azido-functionalized Hb and the compound of formula (I), wherein the azido compound is 4-azidophenylglyoxal (4-APG), 6-azidomethyl pyridine carboxaldehyde (6-AMPC), or a compound of formula (II) or (III)

(II)

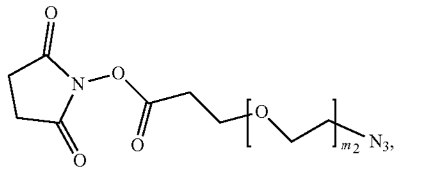

(III)

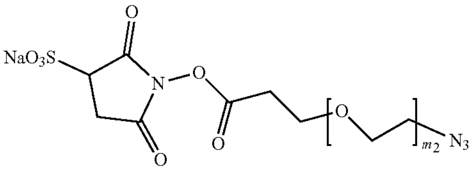

wherein $m_2$ and $m_3$ are each independently an integer of 1-5000.

15. The multimerized Hb composition of claim 14, wherein the reactant molecule is a scaffold compound comprising the second reactive group, and the scaffold compound is a compound of formula (IV) or (V)

(IV)

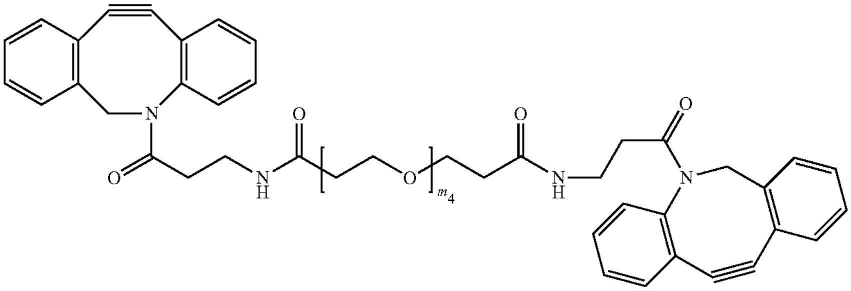

, (V)

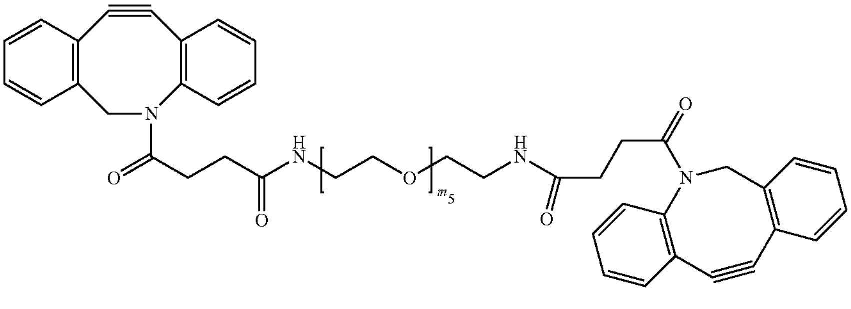

wherein $m_4$ and $m_5$ are each independently an integer of 1-5000.

16. The multimerized Hb composition of claim 3, wherein the first reactive group is cycloalkynyl, and the second reactive groups are azido, and wherein the first modified Hb comprising a first residue functionalized with the first reactive group for a click reaction is obtained by:

reacting the compound of formula (I) and a Hb to form a crosslinked Hb, and reacting the crosslinked Hb and a cycloalkynyl compound; or reacting a cycloalkynyl compound and a Hb to form an alkynyl-functionalized Hb, and reacting the alkynyl-functionalized Hb and the compound of formula (I), wherein the cycloalkynyl compound is a compound of formula (VI), (VII), (VIII), or (IX)

(VI)

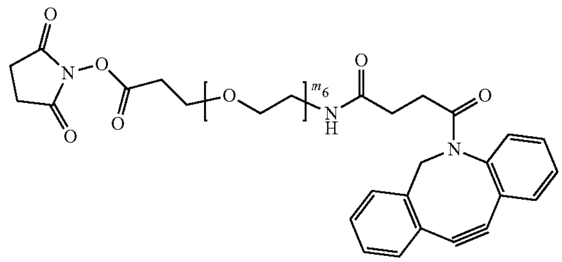

, (VII)

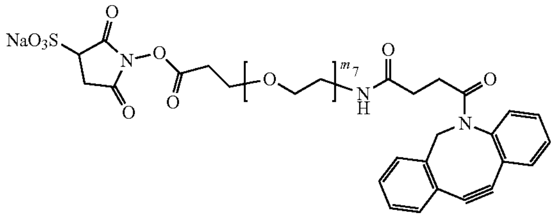

, (VIII)

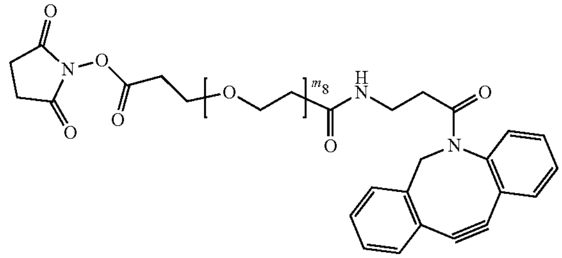

,

-continued (IX)

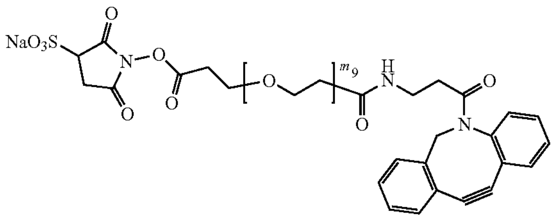

, wherein $m_6$, $m_7$, $m_8$, and $m_9$ are each independently an integer of 1-5000.

17. The multimerized Hb composition of claim 16, wherein the reactant molecule is a scaffold compound comprising the second reactive group, and the scaffold compound is a compound of formula (X) or (XI)

(X)

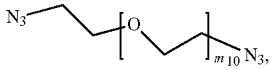

or (XI)

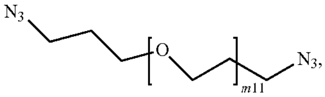

wherein $m_{10}$ and $m_{11}$ are each independently an integer of 1-5000.

18. The multimerized Hb composition of claim 1, wherein the two or more modified Hb are connected by a bifunctional linker selected from 1,4-bis-phenylglyoxal (1,4-PBG) and $(PEG)_{m12}$-bis-phenylglyoxal:

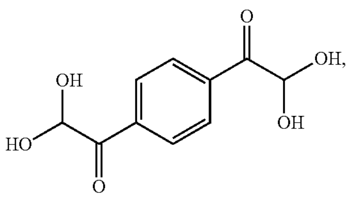

(1,4-PBG)

-continued

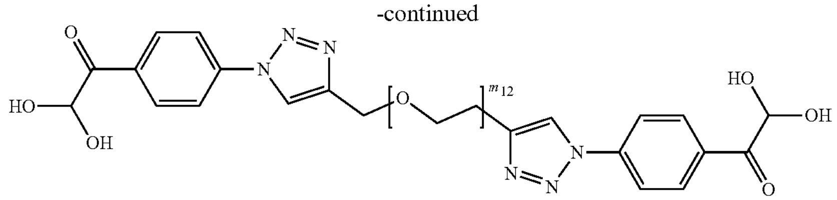

((PEG)$_{m12}$-bis-phenylglyoxal)

wherein $m_{12}$ is an integer of 1-5000.

19. The multimerized Hb composition of claim 1, wherein:

X is $C_{1-24}$ alkylene, $C_{2-24}$ alkenylene, $C_{2-24}$ alkynylene, $C_{3-9}$ cycloalkylene, $C_{3-9}$ cycloalkenylene, 5-12 membered heterocyclylene containing 1 or 2 heteroatoms selected from N, S, or O, heteroarylene, or $-L^1-NR^A-L^2-$, wherein X is optionally substituted with 1-6 $R^3$ as permitted by valency;

$R^1$ and $R^2$ are each independently —OH, halogen, or a leaving group;

each $R^3$ is independently —OH, —CN, —$NO_2$, halogen, oxo, —$C_{1-6}$ alkyl, —$C_{1-6}$ haloalkyl, —O($C_{1-6}$ alkyl), —S($C_{1-6}$ alkyl), —SO($C_{1-6}$ alkyl), —$SO_2$($C_{1-6}$ alkyl), or —C(O)—$R^1$, wherein each alkyl or alkylene is optionally and independently substituted with —$C_{1-6}$ alkyl, —OH, —CN, —$NO_2$, or halogen;

$R^A$ is H, —$C_{1-6}$ alkyl, aryl, —C(O)-aryl, —$SO_2$($C_{1-6}$ alkyl), or —$SO_2$-aryl, wherein each alkyl, aryl, or alkylene is optionally and independently substituted with —$C_{1-6}$ alkyl, —OH, —CN, —$NO_2$, or halogen;

$L^1$ and $L^2$ are each independently $C_{1-12}$ alkylene, $C_{2-12}$ alkenylene, $C_{2-12}$ alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each m is independently an integer of 1-200; and each n is independently an integer of 0-50.

20. The multimerized Hb composition of claim 19, wherein $R^1$ and $R^2$ of formula (I) are a leaving group, and wherein:

the leaving group is

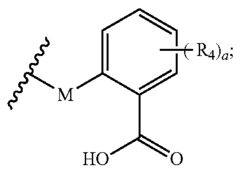

M is O or S;

each $R^4$ is independently halogen or —$C_{1-6}$ alkyl; and a is an integer of 0-4.

21. The multimerized Hb composition of claim 19, wherein X of formula (I) is $C_{1-6}$ alkylene, $C_{2-6}$ alkenylene, or $C_{2-6}$ alkynylene, each of which is optionally substituted with 1 or 2 $R^3$ as permitted by valency.

22. The multimerized Hb composition of claim 19, wherein the compound of formula (I) is:

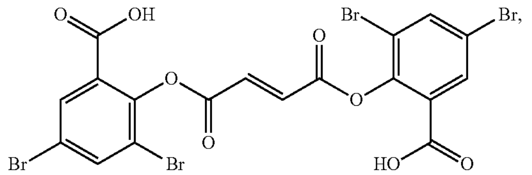

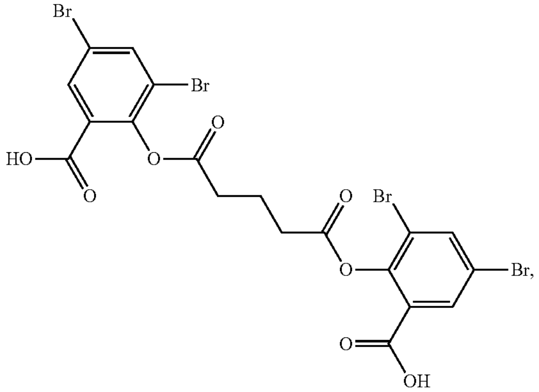

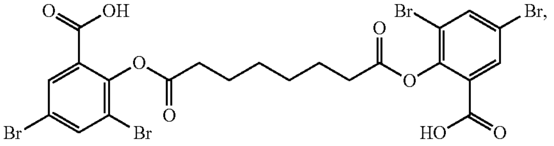

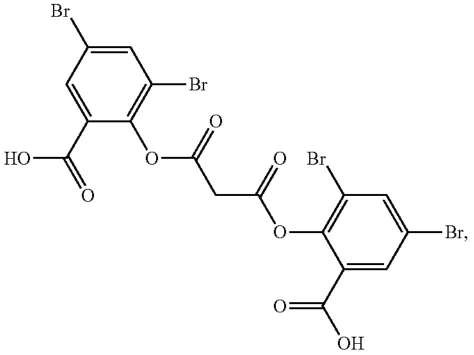

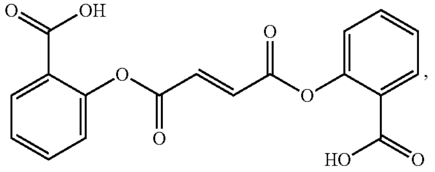

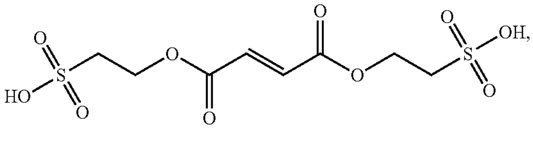

-continued

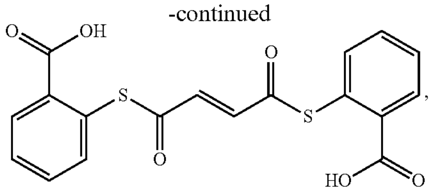

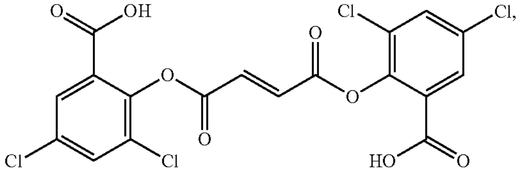

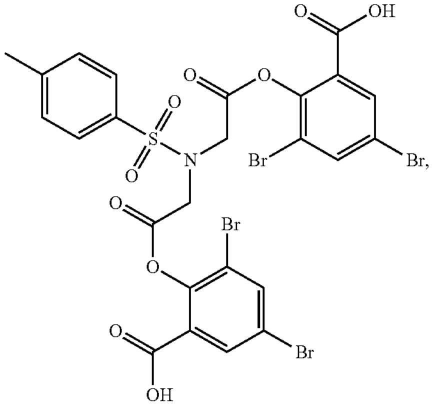

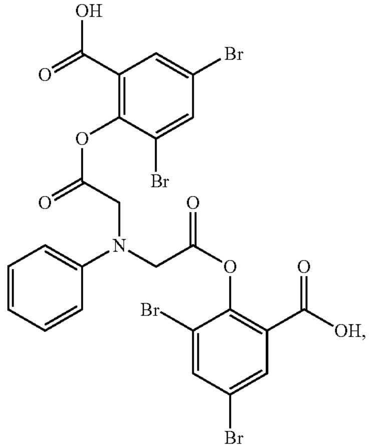

or

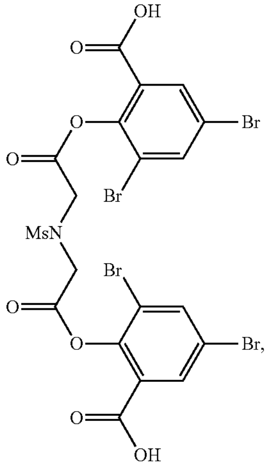

or a salt, a stereoisomer, or a deuterated form thereof, wherein DBS represents

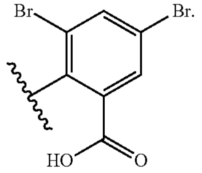 [SMILES: *c1c(Br)cc(Br)cc1C(=O)O]

23. A multimerized Hb composition, comprising a reaction product of:

a modified Hb comprising a residue functionalized with a first reactive group for a click reaction; and a reactant molecule comprising a second reactive group that is complementary to the first reactive group for the click reaction, wherein the modified Hb comprises:

at least two subunits of a Hb intramolecularly crosslinked with a compound of formula (I)

(I)

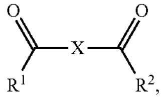

or a salt, a stereoisomer, or a deuterated form thereof, wherein:

X is $C_{1-24}$ alkylene, $C_{2-24}$ alkenylene, $C_{2-24}$ alkynylene, $C_{3-9}$ cycloalkylene, $C_{3-9}$ cycloalkenylene, 5-12 membered heterocyclylene containing 1 or 2 heteroatoms selected from N, S, or O, heteroarylene, or $-L^1-NR^A-L^2-$, wherein X is optionally substituted with 1-6 $R^3$ as permitted by valency;

$R^1$ and $R^2$ are each independently —OH, halogen, or a leaving group;

each $R^3$ is independently —($C_{1-12}$ alkylene)-$N_3$, —($C_{1-12}$ alkylene)-$(OCH_2CH_2)_m$—$(CH_2)_n$—$N_3$, —C(O)NH—($C_{1-12}$ alkylene)-$(OCH_2CH_2)_m$—$(CH_2)_n$—$N_3$, —NHC(O)—($C_{1-12}$ alkylene)-$(OCH_2CH_2)_m$—$(CH_2)$~-$N_3$, —O—($C_{1-12}$ alkylene)-$(OCH_2CH_2)_m$—$(CH_2)_n$—$N_3$, or —S—($C_{1-12}$ alkylene)-$(OCH_2CH_2)_m$—$(CH_2)_n$—$N_3$, wherein each alkylene is optionally and independently substituted with —$C_{1-6}$ alkyl, —OH, —CN, —$NO_2$, or halogen;

$R^A$ is —($C_{1-6}$ alkylene)-$(OCH_2CH_2)_m$—$(CH_2)_n$—$N_3$, wherein each alkylene is optionally and independently substituted with —$C_{1-6}$ alkyl, —OH, —CN, —$NO_2$, or halogen;

$L^1$ and $L^2$ are each independently $C_{1-12}$ alkylene, $C_{2-12}$ alkenylene, $C_{2-12}$ alkynylene, $C_{3-9}$ cycloalkylene, $C_{3-9}$ cycloalkenylene, arylene, or heteroarylene, wherein $L^1$ and $L^2$ are optionally and independently substituted with 1-3 $R^3$ as permitted by valency;

each m is independently an integer of 1-200; and each n is independently an integer of 0-50.

24. The multimerized Hb composition of claim 23, wherein the compound of formula (I) is:

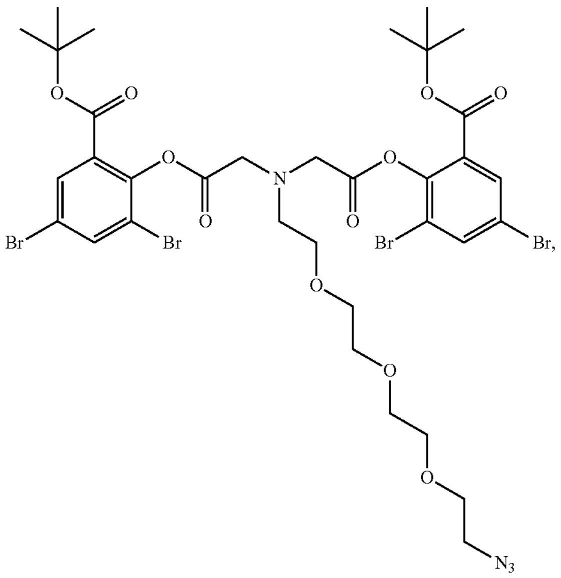
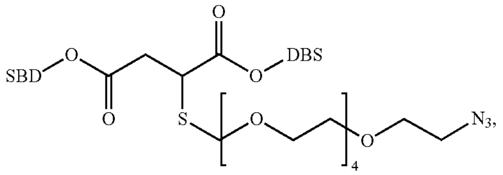
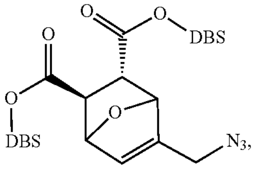 or
-continued
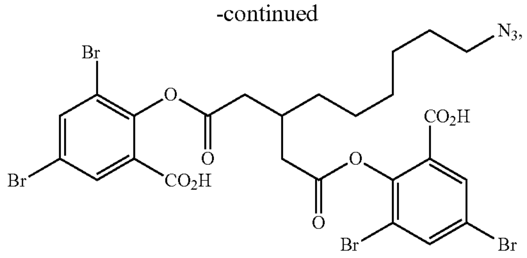
or a salt, a stereoisomer, or a deuterated form thereof, wherein DBS represents
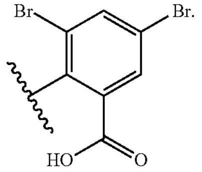 [SMILES: *c1c(Br)cc(Br)cc1C(=O)O]
25. The multimerized Hb composition of claim 15, wherein:
the azido compound is a compound of formula (II)
(II)
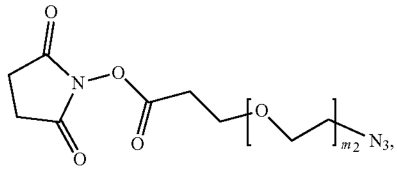
and
the scaffold compound is a compound of formula (V)
(V)
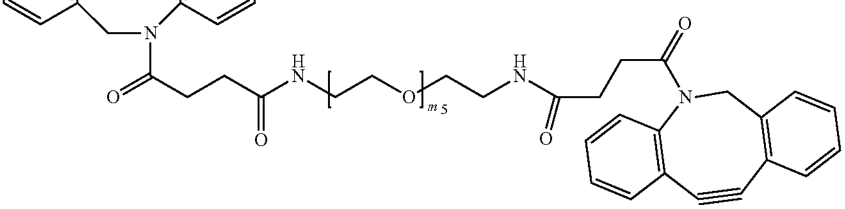
, wherein $m_2$ is an integer of 1-10, and $m_5$ is an integer of 1-12.
26. The multimerized Hb composition of claim 25, wherein $m_2$ is 4, and $m_5$ is 5.
27. The multimerized Hb composition of claim 25, wherein X of the compound of formula (I) is
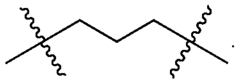 [SMILES: *CCC*]
28. The multimerized Hb composition of claim 15, wherein the multimerized Hb composition has a molecular weight of about 192 kDa to about 800 kDa.
* * * * *